US012655182B2

(12) United States Patent
Liu et al.

(10) Patent No.: US 12,655,182 B2
(45) Date of Patent: Jun. 16, 2026

(54) EVOLVED BOTULINUM NEUROTOXINS AND USES THEREOF

(71) Applicants:President and Fellows of Harvard College, Cambridge, MA (US); The Broad Institute, Inc., Cambridge, MA (US)

(72) Inventors: David R. Liu, Cambridge, MA (US); Travis R. Blum, Cambridge, MA (US)

(73) Assignees: President and Fellows of Harvard College, Cambridge, MA (US); The Broad Institute, Inc., Cambridge, MA (US)

( * ) Notice: Subject to any disclaimer, the term of this patent is extended or adjusted under 35 U.S.C. 154(b) by 911 days.

(21) Appl. No.: 17/627,035

(22) PCT Filed: Jul. 14, 2020

(86) PCT No.: PCT/US2020/042016
§ 371 (c)(1),
(2) Date: Jan. 13, 2022

(87) PCT Pub. No.: WO2021/011579
PCT Pub. Date: Jan. 21, 2021

(65) Prior Publication Data
US 2022/0259269 A1     Aug. 18, 2022

Related U.S. Application Data

(60) Provisional application No. 62/874,443, filed on Jul. 15, 2019.

(51) Int. Cl.
*C07K 14/33*     (2006.01)
*C12N 9/52*     (2006.01)
*A61K 38/00*     (2006.01)

(52) U.S. Cl.
CPC ................ *C07K 14/33* (2013.01); *C12N 9/52* (2013.01); *A61K 38/00* (2013.01); *C12Y 304/24069* (2013.01)

(58) Field of Classification Search
None
See application file for complete search history.

(56) References Cited

U.S. PATENT DOCUMENTS

| | | | |
|---|---|---|---|
| 5,057,432 A | 10/1991 | Wangersky et al. | |
| 5,223,409 A | 6/1993 | Ladner et al. | |
| 5,658,727 A | 8/1997 | Barbas et al. | |
| 5,712,089 A | 1/1998 | Borrebaeck et al. | |
| 5,821,047 A | 10/1998 | Garrard et al. | |
| 5,880,275 A | 3/1999 | Fischhoff et al. | |
| 5,965,124 A | 10/1999 | Feinberg et al. | |
| 6,033,874 A | 3/2000 | Baum et al. | |
| 6,156,509 A | 12/2000 | Schellenberger | |
| 6,429,298 B1 | 8/2002 | Ellington et al. | |
| 6,713,063 B1 | 3/2004 | Malvar et al. | |
| 6,815,194 B2 | 11/2004 | Honjo et al. | |
| 6,884,870 B2 | 4/2005 | Bruce et al. | |
| 6,962,705 B2 | 11/2005 | Malvar et al. | |
| 6,969,731 B1 | 11/2005 | Tang et al. | |
| 7,064,249 B2 | 6/2006 | Corbin et al. | |
| 7,070,982 B2 | 7/2006 | Malvar et al. | |
| 9,023,594 B2 | 5/2015 | Liu et al. | |
| 9,228,207 B2 | 1/2016 | Liu et al. | |
| 9,267,127 B2 | 2/2016 | Liu et al. | |
| 9,340,799 B2 | 5/2016 | Liu et al. | |
| 9,340,800 B2 | 5/2016 | Liu et al. | |
| 9,359,599 B2 | 6/2016 | Liu et al. | |
| 9,394,537 B2 | 7/2016 | Liu et al. | |
| 9,526,784 B2 | 12/2016 | Liu et al. | |
| 9,567,589 B2 | 2/2017 | Jin et al. | |
| 9,737,604 B2 | 8/2017 | Jin et al. | |
| 9,766,216 B2 | 9/2017 | Wada et al. | |
| 9,771,574 B2 | 9/2017 | Liu et al. | |

(Continued)

FOREIGN PATENT DOCUMENTS

| | | |
|---|---|---|
| EP | 0289479 A2 | 11/1988 |
| EP | 3115457 A1 | 1/2017 |

(Continued)

OTHER PUBLICATIONS

Agarwal et al. ('Structural analysis of botulinum neurotoxin serotype F light chain: implications on substrate binding and inhibitor design' Biochemistry v44 2005 pp. 11758-11765) (Year: 2005).*
GenBank accession No. X18714 (retrieved from https://www.ncbi. nlm.nih.gov/nuccore/x81714 on Jan. 23, 2025, 3 pages) (Year: 2025).*
Extended European Search Report for EP 09812363, mailed Mar. 30, 2012.
Extended European Search Report for EP 16 20 3684, mailed May 26, 2017.
International Search Report and Written Opinion for PCT/US2009/ 056194 mailed Jun. 21, 2010.

(Continued)

*Primary Examiner* — Ronald T Niebauer
(74) *Attorney, Agent, or Firm* — Wolf, Greenfield & Sacks, P.C.

(57)     ABSTRACT

The disclosure provides amino acid sequence variants of Botulinum neurotoxin F (BoNT F) proteases that cleave SNARE proteins (e.g., VAMP1, VAMP7, etc.) and methods of evolving the same. In some embodiments, proteases described by the disclosure are useful for cleaving proteins found in a cell, that is in an intracellular environment. In some embodiments, proteases described by the disclosure are useful for treating diseases associated with increased or aberrant VAMP7 expression or activity, for example, cancer, transplantation rejection, graft-versus-host disease, and neurological disorders. Some aspects of this disclosure provide methods for generating BoNT protease variants by continuous directed evolution.

20 Claims, 69 Drawing Sheets

Specification includes a Sequence Listing.

(56)        References Cited

U.S. PATENT DOCUMENTS

| | | |
|---|---|---|
| 9,849,163 B2 | 12/2017 | Chaddock et al. |
| 10,179,911 B2 | 1/2019 | Liu et al. |
| 10,227,581 B2 | 3/2019 | Liu et al. |
| 10,336,997 B2 | 7/2019 | Liu et al. |
| 10,392,674 B2 | 8/2019 | Liu et al. |
| 10,597,679 B2 | 3/2020 | Liu et al. |
| 10,612,011 B2 | 4/2020 | Liu et al. |
| 10,682,410 B2 | 6/2020 | Liu et al. |
| 10,920,208 B2 | 2/2021 | Liu et al. |
| 11,046,948 B2 | 6/2021 | Liu et al. |
| 11,078,469 B2 | 8/2021 | Liu et al. |
| 11,104,967 B2 | 8/2021 | Liu et al. |
| 11,214,792 B2 | 1/2022 | Liu et al. |
| 11,447,809 B2 | 9/2022 | Bryson, Jr. et al. |
| 11,524,983 B2 | 12/2022 | Badran et al. |
| 11,624,130 B2 | 4/2023 | Liu et al. |
| 11,760,986 B2 | 9/2023 | Liu et al. |
| 11,905,623 B2 | 2/2024 | Liu et al. |
| 11,913,040 B2 | 2/2024 | Liu et al. |
| 11,913,044 B2 | 2/2024 | Liu et al. |
| 12,060,553 B2 | 8/2024 | Packer et al. |
| 12,366,009 B2 | 7/2025 | Liu et al. |
| 12,398,390 B2 | 8/2025 | Liu et al. |
| 2002/0132327 A1 | 9/2002 | Hay et al. |
| 2003/0119764 A1 | 6/2003 | Loeb et al. |
| 2003/0167533 A1 | 9/2003 | Yadav et al. |
| 2003/0186292 A1 | 10/2003 | MacNeil et al. |
| 2003/0203480 A1 | 10/2003 | Kovesdi et al. |
| 2005/0019753 A1 | 1/2005 | Kukolj et al. |
| 2005/0100973 A1 | 5/2005 | Steward et al. |
| 2006/0112447 A1 | 5/2006 | Bogdanova et al. |
| 2006/0160222 A1 | 7/2006 | Rozwadowski et al. |
| 2006/0166319 A1 | 7/2006 | Chan et al. |
| 2008/0220502 A1 | 9/2008 | Schellenberger et al. |
| 2009/0215110 A1 | 8/2009 | Gibson et al. |
| 2009/0227463 A1 | 9/2009 | Reif et al. |
| 2009/0300777 A1 | 12/2009 | Nakayama |
| 2010/0297180 A1 | 11/2010 | Shone |
| 2011/0177495 A1 | 7/2011 | Liu et al. |
| 2011/0318385 A1 | 12/2011 | Jackson et al. |
| 2012/0128649 A1 | 5/2012 | Chaddock et al. |
| 2012/0190825 A1 | 7/2012 | Neumann et al. |
| 2012/0196322 A1 | 8/2012 | Siurkus et al. |
| 2013/0059931 A1 | 3/2013 | Petersen-Mahrt et al. |
| 2013/0117869 A1 | 5/2013 | Duchateau et al. |
| 2013/0345064 A1 | 12/2013 | Liu et al. |
| 2013/0345065 A1 | 12/2013 | Liu et al. |
| 2014/0201858 A1 | 7/2014 | Ostertag et al. |
| 2015/0056177 A1 | 2/2015 | Liu et al. |
| 2015/0259721 A1 | 9/2015 | Brunt et al. |
| 2015/0275202 A1 | 10/2015 | Liu et al. |
| 2016/0002301 A1 | 1/2016 | Je et al. |
| 2016/0201040 A1 | 7/2016 | Liu et al. |
| 2016/0348096 A1 | 12/2016 | Liu et al. |
| 2017/0009224 A1 | 1/2017 | Liu et al. |
| 2017/0029844 A1 | 2/2017 | Ball et al. |
| 2017/0044520 A1 | 2/2017 | Liu et al. |
| 2017/0233708 A1 | 8/2017 | Liu et al. |
| 2018/0057545 A9 | 3/2018 | Liu et al. |
| 2018/0087046 A1 | 3/2018 | Liu et al. |
| 2018/0237758 A1 | 8/2018 | Liu et al. |
| 2019/0219575 A1 | 7/2019 | Gray et al. |
| 2019/0256842 A1 | 8/2019 | Liu et al. |
| 2019/0276816 A1 | 9/2019 | Liu et al. |
| 2019/0276873 A1 | 9/2019 | Dong et al. |
| 2020/0071722 A1 | 3/2020 | Liu et al. |
| 2020/0216833 A1 | 7/2020 | Liu et al. |
| 2020/0255868 A1 | 8/2020 | Liu et al. |
| 2020/0277587 A1 | 9/2020 | Liu et al. |
| 2020/0323984 A1 | 10/2020 | Liu et al. |
| 2021/0163924 A1 | 6/2021 | Packer et al. |
| 2021/0238569 A1 | 8/2021 | Liu et al. |
| 2021/0261938 A1 | 8/2021 | Liu et al. |
| 2021/0403887 A1 | 12/2021 | Liu et al. |
| 2022/0073887 A1 | 3/2022 | Liu et al. |
| 2022/0154237 A1 | 5/2022 | Liu et al. |
| 2022/0195418 A1 | 6/2022 | Liu et al. |
| 2022/0267754 A1 | 8/2022 | Liu et al. |
| 2023/0220016 A1 | 7/2023 | Liu et al. |
| 2024/0052331 A1 | 2/2024 | Liu et al. |
| 2024/0124863 A1 | 4/2024 | Liu et al. |
| 2024/0200044 A1 | 6/2024 | Liu et al. |
| 2024/0209338 A1 | 6/2024 | Liu et al. |
| 2024/0271119 A1 | 8/2024 | Liu et al. |
| 2024/0287491 A1 | 8/2024 | Liu et al. |
| 2025/0109177 A1 | 4/2025 | Liu et al. |
| 2025/0195627 A1 | 6/2025 | Liu et al. |

FOREIGN PATENT DOCUMENTS

| | | |
|---|---|---|
| JP | H0937764 A | 2/1997 |
| JP | 2011-081011 | 4/2011 |
| WO | WO 90/02809 A1 | 3/1990 |
| WO | WO 91/17271 A1 | 11/1991 |
| WO | WO 92/01047 A1 | 1/1992 |
| WO | WO 92/09690 A2 | 6/1992 |
| WO | WO 92/15679 A1 | 9/1992 |
| WO | WO 92/18619 A1 | 10/1992 |
| WO | WO 92/20791 A1 | 11/1992 |
| WO | WO 93/01288 A1 | 1/1993 |
| WO | WO 94/18316 A2 | 8/1994 |
| WO | WO 96/04403 A1 | 2/1996 |
| WO | WO 98/32845 A1 | 7/1998 |
| WO | WO 99/23116 A1 | 5/1999 |
| WO | WO 00/71694 A1 | 11/2000 |
| WO | WO 01/05950 A2 | 1/2001 |
| WO | WO 2001/038547 A2 | 5/2001 |
| WO | WO 01/61049 A1 | 8/2001 |
| WO | WO 2005/081632 A2 | 9/2005 |
| WO | WO 2007/066923 A1 | 6/2007 |
| WO | WO 2008/005529 A2 | 1/2008 |
| WO | WO 2009/066964 A1 | 5/2009 |
| WO | WO 2009/082488 A2 | 7/2009 |
| WO | WO 2009/108180 A2 | 9/2009 |
| WO | WO 2010/028347 A2 | 3/2010 |
| WO | WO 2011/039518 A2 | 4/2011 |
| WO | WO 2011/066747 A1 | 6/2011 |
| WO | WO 2011/125015 A2 | 10/2011 |
| WO | WO 2011/147590 A2 | 12/2011 |
| WO | WO 2012/088381 A2 | 6/2012 |
| WO | WO 2012/123370 A1 | 9/2012 |
| WO | WO 2012/138927 A2 | 10/2012 |
| WO | WO 2013/047844 A1 | 4/2013 |
| WO | WO 2014/039585 A2 | 3/2014 |
| WO | WO 2014/086494 A1 | 6/2014 |
| WO | WO 2014/157820 A1 | 10/2014 |
| WO | WO 2014/158593 A1 | 10/2014 |
| WO | WO 2015/134121 A2 | 9/2015 |
| WO | WO 2015/193897 A1 | 12/2015 |
| WO | WO 2016/077052 A9 | 5/2016 |
| WO | WO 2016/168631 A1 | 10/2016 |
| WO | WO 2017/015559 A2 | 1/2017 |
| WO | WO 2017/070632 A2 | 4/2017 |
| WO | WO 2017/136792 A2 | 8/2017 |
| WO | WO 2018/009903 A2 | 1/2018 |
| WO | WO 2018/027078 A1 | 2/2018 |
| WO | WO 2018/039438 A1 | 3/2018 |
| WO | WO 2018/109447 A1 | 6/2018 |
| WO | WO 2018/119042 A1 | 6/2018 |
| WO | WO 2018/136939 A1 | 7/2018 |
| WO | WO 2019/040935 A1 | 2/2019 |
| WO | WO 2019/067815 A1 | 4/2019 |
| WO | WO 2019/089592 A1 | 5/2019 |
| WO | WO 2019/118362 A1 | 6/2019 |
| WO | WO 2020/204836 A1 | 10/2020 |
| WO | WO 2020/252455 A1 | 12/2020 |
| WO | WO 2021/011579 A1 | 1/2021 |
| WO | WO 2021/080427 A1 | 4/2021 |
| WO | WO 2021/188286 A2 | 9/2021 |
| WO | WO 2022/109421 A1 | 5/2022 |

US 12,655,182 B2

Page 3

(56) References Cited

FOREIGN PATENT DOCUMENTS

WO    WO 2023/081805 A1    5/2023
WO    WO 2024/050007 A1    3/2024

OTHER PUBLICATIONS

International Preliminary Report on Patentability for PCT/US2009/056194 mailed Mar. 17, 2011.
Extended European Search Report for EP 17 16 0955, mailed May 16, 2017.
Invitation to Pay Additional Fees for PCT/US2011/066747, mailed Aug. 30, 2012.
International Search Report and Written Opinion for PCT/US2011/066747, mailed Oct. 30, 2012.
International Preliminary Report on Patentability for PCT/US2011/066747, mailed Jul. 4, 2013.
International Search Report and Written Opinion, mailed Dec. 4, 2014, in connection with Application No. PCT/US2014/052231.
International Preliminary Report on Patentability, mailed Mar. 3, 2016, in connection with Application No. PCT/US2014/052231.
International Search Report and Written Opinion for PCT/US2015/012022, mailed Sep. 25, 2015.
International Preliminary Report on Patentability for PCT/US2015/012022, mailed Aug. 4, 2016.
Invitation to Pay Additional Fees for PCT/US/2016/043559, mailed Jan. 12, 2017.
International Search Report and Written Opinion for PCT/US/2016/043559, mailed Mar. 10, 2017.
International Preliminary Report on Patentability for PCT/US/2016/043559, mailed Feb. 1, 2018.
International Search Report and Written Opinion for PCT/US2015/057012, mailed Jun. 10, 2016.
International Preliminary Report on Patentability for PCT/US2015/057012, mailed May 4, 2017.
International Search Report and Written Opinion for PCT/US2016/027795, mailed Aug. 11, 2016.
International Preliminary Report on Patentability for PCT/US2016/027795, mailed Oct. 26, 2017.
Invitation to Pay Additional Fees for PCT/US2016/044546, mailed Oct. 12, 2016.
International Search Report and Written Opinion for PCT/US2016/044546, mailed Dec. 28, 2016.
International Preliminary Report on Patentability for PCT/US2016/044546, mailed Feb. 8, 2018.
International Search Report and Written Opinion for PCT/US2016/043513, mailed Nov. 30, 2016.
International Preliminary Report on Patentability for PCT/US2016/043513, mailed Feb. 1, 2018.
Invitation to Pay Additional Fees for PCT/US2018/14867, mailed Apr. 5, 2018.
International Search Report and Written Opinion for PCT/US2018/14867, mailed May 23, 2018.
International Preliminary Report on Patentability for PCT/US2018/14867 mailed Aug. 1, 2019.
Invitation to Pay Additional Fees, mailed Sep. 12, 2018, in connection with Application No. PCT/US2018/040692.
International Search Report and Written Opinion, mailed Nov. 15, 2018, in connection with Application No. PCT/US2018/040692.
International Preliminary Report on Patentability for PCT/US2018/040692 mailed Jan. 16, 2020.
Invitation to Pay Additional Fees, mailed Jan. 4, 2019, in connection with Application No. PCT/US2018/051557.
International Search Report and Written Opinion for PCT/US2018/051557, mailed Feb. 25, 2019.
International Preliminary Report on Patentability, mailed Apr. 2, 2020, in connection with Application No. PCT/US2018/051557.
International Search Report and Written Opinion for PCT/US2018/044242, mailed Nov. 21, 2018.
International Search Report and Written Opinion for Application No. PCT/US2019/037216 mailed Sep. 4, 2019.

International Preliminary Report on Patentability, mailed Dec. 24, 2020, in connection with Application No. PCT/US2019/037216.
Partial European Search Report for Application No. 18847527.1, mailed Apr. 21, 2021.
Extended European Search Report for Application No. 18847527.1, mailed Aug. 2, 2021.
Invitation to Pay Additional Fees, mailed Nov. 19, 2018, in connection with Application No. PCT/US18/48134.
International Search Report and Written Opinion, mailed Jan. 22, 2019, in connection with Application No. PCT/US18/48134.
International Preliminary Report on Patentability, mailed Mar. 5, 2020, in connection with Application No. PCT/US18/48134.
Invitation to Pay Additional Fees, mailed Oct. 13, 2020, in connection with Application No. PCT/US2020/042016.
International Search Report and Written Opinion, mailed Dec. 10, 2020, in connection with Application No. PCT/US2020/042016.
International Preliminary Report on Patentability mailed Jan. 27, 2022, in connection with Application No. PCT/US2020/042016.
[No Author Listed] Genbank Submission. NCBI; Accession No. WP_010869888, version WP_010869888.1. tyrosine—tRNA ligase [Methanocaldococcus jannaschii]. Jun. 1, 2019.
[No Author Listed] NCBI Accession No. XP_015843220.1. C →U editing enzyme APOBEC-1 [Peromyscus maniculatus bairdii], XP002793540.
[No Author Listed] NCBI Accession No. XP_021505673.1. C →U editing enzyme APOBEC-1 [Meriones unguiculatus], XP002793541.
Agarwal et al., Mode of VAMP substrate recognition and inhibition of Clostridium botulinum neurotoxin F. Nat Struct Mol Biol. Jul. 2009;16(7):789-94. doi: 10.1038/nsmb.1626.Epub Jun. 21, 2009.
Ahluwalia et al., Hypermutability and error catastrophe due to defects in ribonucleotide reductase. Proc Natl Acad Sci U S A. Nov. 12, 2013;110(46):18596-601. doi: 10.1073/pnas.1310849110. Epub Oct. 28, 2013.
Akopian et al., Chimeric recombinases with designed DNA sequence recognition. Proc Natl Acad Sci U S A. Jul. 22, 2003;100(15):8688-91. Epub Jul. 1, 2003.
Amiram et al., Evolution of translation machinery in recoded bacteria enables multi-site incorporation of nonstandard amino acids. Nat Biotechnol. Dec. 2015;33(12):1272-1279. doi: 10.1038/nbt.3372. Epub Nov. 16, 2015.
Armstrong et al., Chapter 3. Vectors for Phage Display. In: Phage Display of Peptides and Proteins. Kay et al., eds. Academic Press. San Diego, CA. 1996:35-53.
Bade et al., Botulinum neurotoxin type D enables cytosolic delivery of enzymatically active cargo proteins to neurones via unfolded translocation intermediates. J Neurochem. Dec. 2004;91(6):1461-72.
Badran et al., Continuous evolution of Bacillus thuringiensis toxins overcomes insect resistance. Nature. May 5, 2016;533(7601):58-63.
Badran et al., Development of potent in vivo mutagenesis plasmids with broad mutational spectra. Nat Commun. Oct. 7, 2015;6:8425. doi: 10.1038/ncomms9425.
Badran et al., In vivo continuous directed evolution. Curr Opin Chem Biol. Feb. 2015;24:1-10. doi: 10.1016/j.cbpa.2014.09.040. Epub Nov. 7, 2014.
Baker et al., Chemical complementation: a reaction-independent genetic assay for enzyme catalysis. Proc Natl Acad Sci U S A. Dec. 24, 2002;99(26):16537-42. Epub Dec. 13, 2002.
Barbas et al., Assembly of combinatorial antibody libraries on phage surfaces: the gene III site. Proc Natl Acad Sci U S A. Sep. 15, 1991;88(18):7978-82.
Bennet et al., Unlocking of the filamentous bacteriophage virion during infection is mediated by the C domain of pIII. J Mol Biol. Feb. 17, 2006;356(2):266-73. Epub Dec. 9, 2005.
Binz et al., Clostridial neurotoxins: mechanism of SNARE cleavage and outlook on potential substrate specificity reengineering. Toxins. Apr. 2010;2(4):665-82. Epub Apr. 13, 2010.
Birling et al., Site-specific recombinases for manipulation of the mouse genome. Methods Mol Biol. 2009;561:245-63. doi: 10.1007/978-1-60327-019-9_16.
Bloom et al., Evolving strategies for enzyme engineering. Curr Opin Struct Biol. Aug. 2005;15(4):447-52.

(56)        References Cited

OTHER PUBLICATIONS

Blum et al., Phage-assisted evolution of botulinum neurotoxin proteases with reprogrammed specificity. Science. Feb. 19, 2021;371(6531):803-810. doi: 10.1126/science.abf5972.

Boch et al., Breaking the code of DNA binding specificity of TAL-type III effectors. Science. Dec. 11, 2009;326(5959):1509-12. doi: 10.1126/science.1178811.

Boeke et al., Effects of bacteriophage f1 gene III protein on the host cell membrane. Mol Gen Genet. 1982;186(2):185-92.

Boersma et al., Selection strategies for improved biocatalysts. FEBS J. May 2007;274(9):2181-95.

Bolusani et al., Evolution of variants of yeast site-specific recombinase Flp that utilize native genomic sequences as recombination target sites. Nucleic Acids Res. 2006;34(18):5259-69. Epub Sep. 26, 2006.

Box et al., A multi-domain protein system based on the HC fragment of tetanus toxin for targeting DNA to neuronal cells. J Drug Target. Jul. 2003;11(6):333-43. doi: 10.1080/10611860310001634667.

Braun et al., Immunogenic duplex nucleic acids are nuclease resistant. J Immunol. Sep. 15, 1988;141(6):2084-9.

Breaker et al., Emergence of a replicating species from an in vitro RNA evolution reaction. Proc Natl Acad Sci U S A. Jun. 21, 1994;91(13):6093-7.

Brieba et al., Role of T7 RNA polymerase His784 in start site selection and initial transcription. Biochemistry. Apr. 23, 2002;41(16):5144-9.

Buchholz et al., Alteration of Cre recombinase site specificity by substrate-linked protein evolution. Nat Biotechnol. Nov. 2001;19(11):1047-52.

Caldwell et al., Randomization of Genes by PCR Mutagenesis. PCR Methods Applic. 1992;2:28-33.

Camps et al., Targeted gene evolution in *Escherichia coli* using a highly error-prone DNA polymerase I. Proc Natl Acad Sci U S A. Aug. 19, 2003;100(17):9727-32. Epub Aug. 8, 2003.

Canitrot et al., Overexpression of DNA polymerase beta in cell results in a mutator phenotype and a decreased sensitivity to anticancer drugs. Proc Natl Acad Sci U S A. Oct. 13, 1998;95(21):12586-90. doi: 10.1073/pnas.95.21.12586.

Cao et al., Characterization of the transgenic rice event TT51-1 and construction of a reference plasmid. J Agric Food Chem. Aug. 24, 2011;59(16):8550-9. doi: 10.1021/jf201699s. Epub Jul. 21, 2011.

Carlson et al., Negative selection and stringency modulation in phage-assisted continuous evolution. Nat Chem Biol. Mar. 2014;10(3):216-22. doi: 10.1038/nchembio.1453. Epub Feb. 2, 2014. With Supplementary Results.

Cattaneo et al., SEL1L affects human pancreatic cancer cell cycle and invasiveness through modulation of PTEN and genes related to cell-matrix interactions. Neoplasia. 2005;7(11):1030-1038.

Chaddock et al., Inhibition of vesicular secretion in both neuronal and nonneuronal cells by a retargeted endopeptidase derivative of Clostridium botulinum neurotoxin type A. Infect. Immun. May 2000;68(5):2587-93.

Chaineau et al., Multiple roles of the vesicular-SNARE TI-VAMP in post-Golgi and endosomal trafficking. FEBS Letters. Oct. 2009;583:3817-26.

Chasteen et al., Eliminating helper phage from phage display. Nucleic Acids Res. 2006;34(21):e145. Epub Nov. 6, 2006.

Chaturvedi et al., Stabilization of triple-stranded oligonucleotide complexes: use of probes containing alternating phosphodiester and stereo-uniform cationic phosphoramidate linkages. Nucleic Acids Res. Jun. 15, 1996;24(12):2318-23.

Cheetham et al., Structural basis for initiation of transcription from an RNA polymerase-promoter complex. Nature. May 6, 1999;399(6731):80-3.

Chen et al., Engineering botulinum neurotoxin to extend therapeutic intervention. PNAS. Jun. 2009;106(23):9180-4.

Chen et al., Information theory based T7-like promoter models: classification of bacteriophages and differential evolution of promoters and their polymerases. Nucleic Acids Res. Oct. 31, 2005;33(19):6172-87. Print 2005.

Chen et al., SNARE-mediated membrane fusion. Nat Rev Mol Cell Biol. Feb. 2001;2(2):98-106.

Chen et al., VAMP8 facilitates cellular proliferation and temozolomide resistance in human glioma cells. Neuro-Oncology. 2015; 17(3):407-18. Epub Sep. 10, 2014.

Chen, Clinical uses of botulinum neurotoxins: current indications, limitations and future developments. Toxins (Basel). 2012;4(10):913-939.

Chin, Expanding and reprogramming the genetic code of cells and animals. Annu Rev Biochem. 2014;83:379-408. doi: 10.1146/annurev-biochem-060713-035737. Epub Feb. 10, 2014.

Chylinski et al., The tracrRNA and Cas9 families of type II CRISPR-Cas immunity systems. RNA Biol. May 2013;10(5):726-37. doi: 10.4161/rna.24321. Epub Apr. 5, 2013.

Clackson et al., Making antibody fragments using phage display libraries. Nature. Aug. 15, 1991;352(6336):624-8.

Click et al., Filamentous phage infection: required interactions with the To1A protein. J Bacteriol. Oct. 1997;179(20):6464-71.

Cobb et al., Directed evolution: an evolving and enabling synthetic biology tool. Curr Opin Chem Biol. Aug. 2012;16(3-4):285-91. doi: 10.1016/j.cbpa.2012.05.186. Epub Jun. 4, 2012.

Cong et al., Multiplex genome engineering using CRISPR/Cas systems. Science. 2013; 339: 819-23.

Corey et al., Trypsin display on the surface of bacteriophage. Gene. Jun. 15, 1993;128(1):129-34.

Craik et al., Proteases as therapeutics. Biochem J. Apr. 2011;435(1):16 pages.

Crameri et al., Display of biologically active proteins on the surface of filamentous phages: a cDNA cloning system for selection of functional gene products linked to the genetic information responsible for their production. Gene. Dec. 27, 1993;137(1):69-75.

Cwirla et al., Peptides on phage: a vast library of peptides for identifying ligands. Proc Natl Acad Sci U S A. Aug. 1990;87(16):6378-82.

Das et al., Viral evolution as a tool to improve the tetracycline-regulated gene expression system. J Biol Chem. Apr. 30, 2004;279(18):18776-82. Epub Feb. 2, 2004.

Datsenko et al., One-step inactivation of chromosomal genes in *Escherichia coli* K-12 using PCR products. Proc Natl Acad Sci U S A. Jun. 6, 2000;97(12):6640-5.

Davis et al., Viral mutagenesis as a means for generating novel proteins. J Virol. Feb. 2010;84(3):1625-30. Epub Nov. 11, 2009.

De Haard et al., A large non-immunized human Fab fragment phage library that permits rapid isolation and kinetic analysis of high affinity antibodies. J Biol Chem. Jun. 25, 1999;274(26):18218-30.

Deltcheva et al., CRISPR RNA maturation by trans-encoded small RNA and host factor RNase III. Nature. Mar. 31, 2011;471(7340):602-7. doi: 10.1038/nature09886.

Deribe, Mechanistic insights into the role of truncating PREX2 mutations in melanoma. Mol Cell Oncol. 2016;3(3):e1160174.

Deussing, Targeted mutagenesis tools for modelling psychiatric disorders. Cell Tissue Res. Oct. 2013;354(1):9-25. doi: 10.1007/s00441-013-1708-5. Epub Sep. 10, 2013.

DiCarlo et al., Genome engineering in *Saccharomyces cerevisiae* using CRISPR-Cas systems. Nucleic Acids Res. Apr. 2013;41(7):4336-43. doi: 10.1093/nar/gkt135. Epub Mar. 4, 2013.

Dickinson et al., A system for the continuous directed evolution of proteases rapidly reveals drug-resistance mutations. Nat Commun. Oct. 30, 2014;5:5352. doi: 10.1038/ncomms6352.

Dickinson et al., Experimental interrogation of the path dependence and stochasticity of protein evolution using phage-assisted continuous evolution. Proc Natl Acad Sci USA. May 2013;110(22):9007-12.

Dove et al., Conversion of the omega subunit of *Escherichia coli* RNA polymerase into a transcriptional activator or an activation target. Genes Dev. Mar. 1, 1998;12(5):745-54.

Doyon et al., Directed evolution and substrate specificity profile of homing endonuclease I-SceI. J Am Chem Soc. Feb. 22, 2006;128(7):2477-84.

Drake, A constant rate of spontaneous mutation in DNA-based microbes. Proc Natl Acad Sci USA. Aug. 15, 1991;88(16):7160-4.

Duggan et al., Inhibition of Release of Neurotransmitters from Rat Dorsal Root Ganglia by a Novel Conjugate of a Clostridium

(56) References Cited

OTHER PUBLICATIONS botulinum Toxin A Endopeptidase Fragment and Erythrina cristagalli Lectin. The Journal of Biological Chemistry. Sep. 2002;277(38):34846-52.

Durai et al., A bacterial one-hybrid selection system for interrogating zinc finger-DNA interactions. Comb Chem High Throughput Screen. May 2006;9(4):301-11.

Durniak et al., The structure of a transcribing T7 RNA polymerase in transition from initiation to elongation. Science. Oct. 24, 2008;322(5901):553-7.

Esvelt et al., A system for the continuous directed evolution of biomolecules. Nature. Apr. 28, 2011;472(7344):499-503. Epub Apr. 10, 2011.

Fan et al., Rationally evolving tRNAPyl for efficient incorporation of noncanonical amino acids. Nucleic Acids Res. Dec. 15, 2015;43(22):e156. doi: 10.1093/nar/gkv800. Epub Aug. 6, 2015.

Feng et al., Exo1: A new chemical inhibitor of the exocytic pathway. PNAS. May 2003;100(11):6469-74.

Ferretti et al., Complete genome sequence of an M1 strain of *Streptococcus pyogenes*. Proc Natl Acad Sci U S A. Apr. 10, 2001;98(8):4658-63. doi: 10.1073/pnas.071559398.

Fijalkowska et al., Mutants in the Exo I motif of *Escherichia coli* dnaQ: defective proofreading and inviability due to error catastrophe. Proc Natl Acad Sci U S A. Apr. 2, 1996;93(7):2856-61.

Foster et al., Re-engineering the target specificity of Clostridial neurotoxins—A route to novel therapeutics. Neurotoxicity Research. May 2006;9(2,3):101-7.

Foster et al., Targeted Secretion Inhibitors—Innovative Protein Therapeutics. Toxins. Dec. 2010;2:2795-815.

Fowlkes et al., Multipurpose vectors for peptide expression on the M13 viral surface. Biotechniques. Sep. 1992;13(3):422-8.

Friedberg et al., Error-prone DNA polymerases: novel structures and the benefits of infidelity. Cell. Oct. 5, 2001;107(1):9-12.

Fu et al., Promises and Pitfalls of Intracellular Delivery of Proteins. Bioconjugate Chemistry. Aug. 2014;25:1602-8.

Fuchs et al., Targeting Recombinant Antibodies to the Surface of *Escherichia coli*: Fusion to a Peptidoglycan Associated Lipoprotein. Bio/Technology. 1991;9:1370-72.

Gaj et al., Expanding the scope of site-specific recombinases for genetic and metabolic engineering. Biotechnol Bioeng. Jan. 2014;111(1):1-15. doi: 10.1002/bit.25096. Epub Sep. 13, 2013.

Garrard et al., Fab assembly and enrichment in a monovalent phage display system. Biotechnology (N Y). Dec. 1991;9(12):1373-7.

Genbank Submission. NCBI; Accession No. WP_011033391, version WP_011033391.1. pyrrolysine—tRNA(Pyl) ligase [Methanosarcina mazei].Polycarpo et al.; Nov. 29, 2019.

Genbank Submission. NCBI; Accession No. WP_011305865, version WP_011305865.1. pyrrolysine—tRNA(Pyl) ligase [Methanosarcina barkeri]. Polycarpo et al.; Nov. 29, 2019.

Gibson et al., Enzymatic assembly of DNA molecules up to several hundred kilobases. Nat Methods. May 2009;6(5):343-5. Epub Apr. 12, 2009.

Gill, Bacterial Toxins: a Table of Letal Amounts. Microbiological Reviews. Mar. 1982;46(1):86-94.

Goodnough et al., Development of a delivery vehicle for intracellular transport of botulinum neurotoxin antagonists. FEBS Lett. Feb. 27, 2002;513(2-3):163-8.

Gordley et al., Evolution of programmable zinc finger-recombinases with activity in human cells. J Mol Biol. Mar. 30, 2007;367(3):802-13. Epub Jan. 12, 2007.

Gram et al., In vitro selection and affinity maturation of antibodies from a naive combinatorial immunoglobulin library. Proc Natl Acad Sci U S A. Apr. 15, 1992;89(8):3576-80.

Griffiths et al., Human anti-self antibodies with high specificity from phage display libraries. EMBO J. Feb. 1993;12(2):725-34.

Guilinger et al., Broad specificity profiling of TALENs results in engineered nucleases with improved DNA-cleavage specificity. Nat Methods. Apr. 2014;11(4):429-35. doi: 10.1038/nmeth.2845. Epub Feb. 16, 2014.

Guilinger et al., Fusion of catalytically inactive Cas9 to FokI nuclease improves the specificity of genome modification. Nat. Biotechnol. 2014; 32(6): 577-82. doi: 10.1038/nbt.2909. Epub Apr. 25, 2014.

Guo et al., Evolution of amber suppressor tRNAs for efficient bacterial production of proteins containing nonnatural amino acids. Angew Chem Int Ed Engl. 2009;48(48):9148-51. doi: 10.1002/anie.200904035.

Guo et al., Polyspecific pyrrolysyl-tRNA synthetases from directed evolution. Proc Natl Acad Sci U S A. Nov. 25, 2014;111(47):16724-9. doi: 10.1073/pnas.1419737111. Epub Nov. 10, 2014.

Guzman et al., Tight regulation, modulation, and high-level expression by vectors containing the arabinose PBAD promoter. J Bacteriol. 1995;177(14):4121-4130.

Harris et al., Measurement of enzyme activity. Methods Enzymol. 2009;463:57-71.

Hart et al., Directed Evolution to Investigate Steric Control of Enzymatic Oxidosqualene Cyclization. An Isoleucine-to-Valine Mutation in Cycloartenol Synthase Allows Lanosterol and Parkeol Biosynthesis. J Am Chem Soc. 1999;121:9887-88.

Hawkins et al., Selection of phage antibodies by binding affinity. Mimicking affinity maturation. J Mol Biol. Aug. 5, 1992;226(3):889-96.

Hay et al., Bacteriophage cloning and *Escherichia coli* expression of a human IgM Fab. Hum Antibodies Hybridomas. Apr. 1992;3(2):81-5.

Hedstrom et al., Converting trypsin to chymotrypsin: the role of surface loops. Science. Mar. 1992;255(5049):1249-53.

Hendricks et al., The S. cerevisiae Mag1 3-methyladenine DNA glycosylase modulates susceptibility to homologous recombination. DNA Repair (Amst). 2002;1(8):645-659.

Herring et al., The amino-terminal domain of pyrrolysyl-tRNA synthetase is dispensable in vitro but required for in vivo activity. FEBS Lett. Jul. 10, 2007;581(17):3197-203. doi: 10.1016/j.febslet.2007.06.004. Epub Jun. 12, 2007.

Ho et al., Recombinant botulinum neurotoxin A heavy chainbased delivery vehicles for neuronal cell targeting. Protein Engineering, Design & Selection. 2011;24(3):247-53. Epub Nov. 4, 2010.

Hoogenboom et al., Antibody phage display technology and its applications. Immunotechnology. Jun. 1998;4(1):1-20.

Hoogenboom et al., Multi-subunit proteins on the surface of filamentous phage: methodologies for displaying antibody (Fab) heavy and light chains. Nucleic Acids Res. Aug. 11, 1991;19(15):4133-7.

Hoogenboom et al., Natural and designer binding sites made by phage display technology. Immunol Today. Aug. 2000;21(8):371-8.

Houshmand et al., Use of Bateriophage T7 Displayed Peptides for Determination of Monoclonal Anitbody Specificity and Biosensor Analysis of the Binding Reaction. Anal Biochem. 1999;268:363-70.

Hu et al., *Escherichia coli* one- and two-hybrid systems for the analysis and identification of protein-protein interactions. Methods. Jan. 2000;20(1):80-94.

Hubbard et al., Continuous directed evolution of DNA-binding proteins to improve TALEN specificity. Nat Methods. Oct. 2015;12(10):939-42. doi: 10.1038/nmeth.3515. Epub Aug. 10, 2015. With Supplementary Information.

Huse et al., Generation of a large combinatorial library of the immunoglobulin repertoire in phage lambda. Science. Dec. 8, 1989;246(4935):1275-81.

Husimi et al., Cellstat—a continuous culture system of a bacteriophage for the study of the mutation rate and the selection process of the DNA level. Rev Sci Instrum. Apr. 1982;53(4):517-22.

Husimi, Selection and evolution of bacteriophages in cellstat. Adv Biophys. 1989;25:1-43.

Hwang et al., Efficient genome editing in zebrafish using a CRISPR-Cas system. Nat Biotechnol. Mar. 2013;31(3):227-9. doi: 10.1038/nbt.2501. Epub Jan. 29, 2013.

Ichetovkin et al., Substrate recognition by the leucyl/phenylalanyl-tRNA-protein transferase. Conservation within the enzyme family and localization to the trypsin-resistant domain. J Biol Chem. Dec. 26, 1997;272(52):33009-14.

Ikeda et al., In vivo and in vitro activities of point mutants of the bacteriophage T7 RNA polymerase promoter. Biochemistry. Sep. 22, 1992;31(37):9073-80.

(56)            References Cited

OTHER PUBLICATIONS

Ikeda et al., Selection and characterization of a mutant T7 RNA polymerase that recognizes an expanded range of T7 promoter-like sequences. Biochemistry. Sep. 7, 1993;32(35):9115-24.

Imburgio et al., Studies of promoter recognition and start site selection by T7 RNA polymerase using a comprehensive collection of promoter variants. Biochemistry. Aug. 29, 2000;39(34):10419-30.

Irion et al., Identification and targeting of the ROSA26 locus in human embryonic stem cells. Nat Biotechnol. Dec. 2007;25(12): 1477-82. Epub Nov. 25, 2007.

Jankovic et al., Direct selection and phage display of a Gram-positive secretome. Genome Biology. Dec. 13, 2007; 8(266):1-15.

Jiang et al., PylSn and the homologous N-terminal domain of pyrrolysyl-tRNA synthetase bind the tRNA that is essential for the genetic encoding of pyrrolysine. J Biol Chem. Sep. 21, 2012;287(39):32738-46. doi: 10.1074/jbc.M112.396754. Epub Jul. 31, 2012.

Jiang et al., RNA guided editing of bacterial genomes using CRISPR-Cas systems. Nat Biotechnol. Mar. 2013;31(3):233-9. doi: 10.1038/nbt.2508. Epub Jan. 29, 2013.

Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.

Jinek et al., RNA-programmed genome editing in human cells. Elife. Jan. 29, 2013;2:e00471. doi: 10.7554/eLife.00471.

Johns et al., The promise and peril of continuous in vitro evolution. J Mol Evol. Aug. 2005;61(2):253-63. Epub Jun. 27, 2005.

Joho et al., Identification of a region of the bacteriophage T3 and T7 RNA polymerases that determines promoter specificity. J Mol Biol. Sep. 5, 1990;215(1):31-9.

Joung et al., A bacterial two-hybrid selection system for studying protein-DNA and protein-protein interactions. Proc Natl Acad Sci U S A. Jun. 20, 2000;97(13):7382-7.

Karpinsky et al., Directed evolution of a recombinase that excises the provirus of most HIV-1 primary isolates with high specificity. Nat Biotechnol. Apr. 2016;34(4):401-9. doi: 10.1038/nbt.3467. Epub Feb. 22, 2016.

Kasai et al., Distinct initial SNARE configurations underlying the diversity of exocytosis. Physiol Rev. Oct. 2012;92(4):1915-64. doi: 10.1152/physrev.00007.2012.

Kavran et al., Structure of pyrrolysyl-tRNA synthetase, an archaeal enzyme for genetic code innovation. Proc Natl Acad Sci U S A. Jul. 3, 2007;104(27):11268-73. doi: 10.1073/pnas.0704769104. Epub Jun. 25, 2007.

Kawarasaki et al., Enhanced crossover SCRATCHY: construction and high-throughput screening of a combinatorial library containing multiple non-homologous crossovers. Nucleic Acids Res. Nov. 1, 2003;31(21):e126.

Khlebnikov et al., Modulation of gene expression from the arabinose-inducible araBAD promoter. J Ind Microbiol Biotechnol. Jul. 2002;29(1):34-7.

Kim et al., DJ-1, a novel regulator of the tumor suppressor PTEN. Cancer Cell. 2005;7(3):263-273.

Kim et al., Increasing the genome-targeting scope and precision of base editing with engineered Cas9-cytidine deaminase fusions. Nature Biotechnology; Feb. 13, 2007; 35(4): 371-376.

Klement et al., Discrimination between bacteriophage T3 and T7 promoters by the T3 and T7 RNA polymerases depends primarily upon a three base-pair region located 10 to 12 base-pairs upstream from the start site. J Mol Biol. Sep. 5, 1990;215(1):21-9.

Köhler, A yeast-based growth assay for the analysis of site-specific proteases. Nucleic Acids Res. 2003;31(4):e16. 5 pages.

Komor et al., Programmable editing of a target base in genomic DNA without double-stranded DNA cleavage. Nature. May 19, 2016;533(7603):420-4. doi: 10.1038/nature17946. Epub Apr. 20, 2016.

Kozak et al., Structural features in eukaryotic mRNAs that modulate the initiation of translation. J Biol Chem. Oct. 25, 1991;266(30):19867-70.

Kuzmine et al., Binding of the priming nucleotide in the initiation of transcription by T7 RNA polymerase. J Biol Chem. Jan. 31, 2003;278(5):2819-23. Epub Nov. 9, 2002.

Laskowska et al., IbpA and IbpB, the new heat-shock proteins, bind to endogenous *Escherichia coli* proteins aggregated intracellularly by heat shock. Biochimie. 1996;78(2):117-22.

Latimer et al., Specificity of monoclonal antibodies produced against phosphorothioate and ribo modified DNAs. Mol Immunol. Oct. 1995;32(14-15):1057-64.

Lebeda et al., The Zinc-Dependent Protease Activity of the Botulinum Neurotoxins. Toxins. May 2010;2:978-97.

Leconte et al., A population-based experimental model for protein evolution: effects of mutation rate and selection stringency on evolutionary outcomes. Biochemistry. Feb. 26, 2013; 52(8): 1490-1499.

Lei et al., Efficient targeted gene disruption in Xenopus embryos using engineered transcription activator-like effector nucleases (TALENs). PNAS Oct. 23, 2012;109(43):17484-17489; https://doi.org/10.1073/pnas.1215421109.

Lincoln et al., Self-sustained replication of an RNA enzyme. Science. Feb. 27, 2009;323(5918):1229-32. Epub Jan. 8, 2009.

Lindemann et al., Evolution of bacteriophage in continuous culture: a model system to test antiviral gene therapies for the emergence of phage escape mutants. J Virol. Jun. 2002;76(11):5784-92.

Liu et al., Adding new chemistries to the genetic code. Annu Rev Biochem. 2010;79:413-44. doi: 10.1146/annurev.biochem.052308.105824.

Liu et al., PTEN deletion enhances the regenerative ability of adult corticospinal neurons. Nat Neurosci. Sep. 2010;13(9):1075-81. doi: 10.1038/nn.2603. Epub Aug. 8, 2010.

Lu, The destructive effect of botulinum neurotoxins on the SNARE protein: SNAP-25 and synaptic membrane fusion. PeerJ. 2015;3:e1065. Published Jun. 30, 2015.

Lundquist et al., Site-directed mutagenesis and characterization of uracil-DNA glycosylase inhibitor protein. Role of specific carboxylic amino acids in complex formation with *Escherichia coli* uracil-DNA glycosylase. J Biol Chem. Aug. 22, 1997;272(34):21408-19. doi: 10.1074/jbc.272.34.21408.

Lutz et al., Creating multiple-crossover DNA libraries independent of sequence identity. Proc Natl Acad Sci U S A. Sep. 25, 2001;98(20):11248-53. Epub Sep. 18, 2001.

Maeder et al., Robust, synergistic regulation of human gene expression using TALE activators. Nat Methods. Mar. 2013;10(3):243-5. doi: 10.1038/nmeth.2366. Epub Feb. 10, 2013.

Makeyev et al., Evolutionary potential of an RNA virus. J Virol. Feb. 2004;78(4):2114-20.

Mali et al., RNA-guided human genome engineering via Cas9. Science. 2013; 339:823-26.

Malmborg et al., Selective phage infection mediated by epitope expression on F pilus. J Mol Biol. Oct. 31, 1997;273(3):544-51.

Marcet-Palacios et al., Vesicle-associated membrane protein 7 (VAMP-7) is essential for target cell killing in a natural killer cell line. Biochem Biophys Res Commun. Feb. 15, 2008;366(3):617-23. doi: 10.1016/j.bbrc.2007.11.079. Epub Nov. 26, 2007.

Martin et al., Kinetic analysis of T7 RNA polymerase-promoter interactions with small synthetic promoters. Biochemistry. May 19, 1987;26(10):2690-6.

Masuyer et al., Engineered botulinum neurotoxins as new therapeutics. Annu Rev Pharmacol Toxicol. 2014;54:27-51.

McCafferty et al., Phage antibodies: filamentous phage displaying antibody variable domains. Nature. Dec. 6, 1990;348(6301):552-4.

McConnell et al., Constrained peptide libraries as a tool for finding mimotopes. Gene. Dec. 30, 1994;151(1-2):115-8.

McNaughton et al., Mammalian cell penetration, siRNA transfection, and DNA transfection by supercharged proteins. Proc Natl Acad Sci U S A. Apr. 14, 2009;106(15):6111-6. doi: 10.1073/pnas.0807883106. Epub Mar. 23, 2009.

Meng et al., Role of SNARE proteins in tumourigenesis and their potential as targets for novel anti-cancer therapeutics. Biochim Biophys Acta. Aug. 2015;1856(1):1-12. doi: 10.1016/j.bbcan.2015.04.002. Epub May 5, 2015.

(56)　　　　　References Cited

OTHER PUBLICATIONS

Mihai et al., PTEN inhibition improves wound healing in lung epithelia through changes in cellular mechanics that enhance migration. Am J Physiol Lung Cell Mol Physiol. 2012;302(3):L287-L299.

Miller et al., A Tale nuclease architecture for efficient genome editing. Nat Biotechnol. Feb. 2011;29(2):143-8. doi:10.1038/nbt. 1755. Epub Dec. 22, 2010.

Milligan et al., Oligoribonucleotide synthesis using T7 RNA polymerase and synthetic DNA templates. Nucleic Acids Res. Nov. 11, 1987;15(21):8783-98.

Mills et al., An extracellular Darwinian experiment with a self-duplicating nucleic acid molecule. Proc Natl Acad Sci U S A. Jul. 1967;58(1):217-24.

Mussolino et al., TALE nucleases: tailored genome engineering made easy. Curr Opin Biotechnol. Oct. 2012;23(5):644-50. doi: 10.1016/j.copbio.2012.01.013. Epub Feb. 17, 2012.

Nelson et al., Filamentous phage DNA cloning vectors: a noninfective mutant with a nonpolar deletion in gene III. Virology. Jan. 30, 1981;108(2):338-50.

Nern et al., Multiple new site-specific recombinases for use in manipulating animal genomes. Proc Natl Acad Sci U S A. Aug. 23, 2011;108(34):14198-203. doi: 10.1073/pnas.1111704108. Epub Aug. 9, 2011.

Nicholson-Fish et al., VAMP4 is an Essential Cargo Molecule for Activity-Dependent Bulk Endocytosis. Neuron. Dec. 2, 2015;88(5):973-984. doi: 10.1016/j.neuron.2015.10.043. Epub Nov. 19, 2015.

Nozawa et al., Pyrrolysyl-tRNA synthetase-tRNA(Pyl) structure reveals the molecular basis of orthogonality. Nature. Feb. 26, 2009;457(7233):1163-7. doi: 10.1038/nature07611. Epub Dec. 31, 2008.

O'Maille et al., Structure-based combinatorial protein engineering (SCOPE). J Mol Biol. Aug. 23, 2002;321(4):677-91.

O'Donoghue et al., Upgrading protein synthesis for synthetic biology. Nat Chem Biol. Oct. 2013;9(10):594-8. doi: 10.1038/nchembio. 1339.

Oeemig et al., Solution structure of DnaE intein from Nostoc punctiforme: structural basis for the design of a new split intein suitable for site-specific chemical modification. FEBS Lett. May 6, 2009;583(9):1451-6.

Opperman et al., A model for a umuDC-dependent prokaryotic DNA damage checkpoint. Proc Natl Acad Sci U S A. Aug. 3, 1999;96(16):9218-23.

Ostendorf et al., Characterization of a dam mutant of Serratia marcescens and nucleotide sequence of the dam region. J Bacteriol. Jul. 1999;181(13):3880-5.

Ostermeier et al., A combinatorial approach to hybrid enzymes independent of DNA homology. Nat Biotechnol. Dec. 1999;17(12):1205-9.

Peyrottes et al., Oligodeoxynucleoside phosphoramidates (P-NH2): synthesis and thermal stability of duplexes with DNA and RNA targets. Nucleic Acids Res. May 15, 1996;24(10):1841-8.

Pickett et al., Towards New Uses of Botulinum Toxin as a Novel Therapeutic Tool. Toxins. Jan. 2011;3:63-81.

Pogson et al., Engineering Next Generation Proteases. Curr Opin Biotechnol. Aug. 2009;20(4):390-7.

Pu et al., Evolution of a split RNA polymerase as a versatile biosensor platform. Nat Chem Biol. Apr. 2017;13(4):432-438. doi: 10.1038/nchembio.2299. Epub Feb. 13, 2017.

Putnam et al., Protein mimicry of DNA from crystal structures of the uracil-DNA glycosylase inhibitor protein and its complex with *Escherichia coli* uracil-DNA glycosylase. J Mol Biol. Mar. 26, 1999;287(2):331-46. doi: 10.1006/jmbi.1999.2605.

Radany et al., Increased spontaneous mutation frequency in human cells expressing the phage PBS2-encoded inhibitor of uracil-DNA glycosylase. Mutat Res. Sep. 15, 2000;461(1):41-58. doi: 10.1016/s0921-8777(00)00040-9.

Raingo et al., VAMP4 directs synaptic vesicles to a pool that selectively maintains asynchronous neurotransmission. Nat Neurosci. Mar. 11, 2012;15(5):738-45. doi: 10.1038/nn.3067.

Rakonjac et al., Filamentous phage are released from the bacterial membrane by a two-step mechanism involving a short C-terminal fragment of pIII. J Mol Biol. Jun. 25, 1999;289(5):1253-65.

Rakonjac et al., Filamentous phage infection-mediated gene expression: construction and propagation of the gIII deletion mutant helper phage R408d3. Gene. Oct. 1, 1997;198(1-2):99-103.

Rakonjac et al., Roles of pIII in filamentous phage assembly. J Mol Biol. Sep. 11, 1998;282(1):25-41.

Raskin et al., Substitution of a single bacteriophage T3 residue in bacteriophage T7 RNA polymerase at position 748 results in a switch in promoter specificity. J Mol Biol. Nov. 20, 1992;228(2):506-15.

Raskin et al., T7 RNA polymerase mutants with altered promoter specificities. Proc Natl Acad Sci U S A. Apr. 15, 1993;90(8):3147-51.

Rawlings et al., MEROPS: the database of proteolytic enzymes, their substrates and inhibitors. Nucleic Acids Res. Jan. 2014;42(Database issue):D503-9.

Rebar et al., Phage display methods for selecting zinc finger proteins with novel DNA-binding specificities. Methods Enzymol. 1996;267:129-49.

Reidhaar-Olson et al., Random mutagenesis of protein sequences using oligonucleotide cassettes. Methods Enzymol. 1991;208:564-86.

Reuven et al., Lesion bypass by the Escherichia coli DNA polymerase V requires assembly of a RecA nucleoprotein filament. J Biol Chem. Feb. 23, 2001;276(8):5511-7. Epub Nov. 17, 2000.

Riechmann et al., The C-terminal domain of To1A is the coreceptor for filamentous phage infection of *E. coli*. Cell. Jul. 25, 1997;90(2):351-60.

Ringquist et al., Translation initiation in *Escherichia coli*: sequences within the ribosome-binding site. Mol Microbiol. May 1992;6(9):1219-29.

Rosenberg et al.,T7 Select® Phage Display System: A Powerful new protein display system based on bacteriophage T7. Innovations. 1996;6:1-6.

Rossetto et al., Botulinum neurotoxins: genetic, structural and mechanistic insights. Nat Rev Microbiol. Aug. 2014;12(8):535-49. doi: 10.1038/nrmicro3295. Epub Jun. 30, 2014.

Ruiz-Martinez et al., YKT6 expression, exosome release, and survival in non-small cell lung cancer. Oncotarget. Aug. 9, 2016;7(32):51515-51524. doi: 10.18632/oncotarget.9862.

Santini et al., Efficient display of an HCV cDNA expression library as C-terminal fusion to the capsid protein D of bacteriophage lambda. J Mol Biol. Sep. 11, 1998;282(1):125-35.

Santoro et al., Directed evolution of the site specificity of Cre recombinase. Proc Natl Acad Sci U S A. Apr. 2, 2002;99(7):4185-90. Epub Mar. 19, 2002.

Schultz et al., Oligo-2'-fluoro-2'-deoxynucleotide N3'→P5' phosphoramidates: synthesis and properties. Nucleic Acids Res. Aug. 1, 1996;24(15):2966-73.

Scott et al., Searching for peptide ligands with an epitope library. Science. Jul. 27, 1990;249(4967):386-90.

Sices et al., A genetic screen for the isolation and characterization of site-specific proteases. Proc Natl Acad Sci U S A. Mar. 17, 1998;95(6):2828-33.

Sices et al., Rapid genetic selection of inhibitor-resistant protease mutants: clinically relevant and novel mutants of the HIV protease. AIDS Res Hum Retroviruses. Sep. 1, 2001;17(13):1249-55.

Sieber et al., Libraries of hybrid proteins from distantly related sequences. Nat Biotechnol. May 2001;19(5):456-60.

Sikorra et al., Substrate Recognition Mechanism of VAMP/Synaptobrevin-cleaving Clostridial Neurotoxins. Journal of Biological Chemistry. 2008;283:21145-52. Epub May 29, 2008.

Silva et al., Selective disruption of the DNA polymerase III α-β complex by the umuD gene products. Nucleic Acids Res. Jul. 2012;40(12):5511-22. doi: 10.1093/nar/gks229. Epub Mar. 9, 2012.

Smith, Filamentous fusion phage: novel expression vectors that display cloned antigens on the virion surface. Science. Jun. 14, 1985;228(4705):1315-7.

Somm et al., A botulinum toxin-drived targeted secretion inihibitor downregulates the GH/IGF1 axis. The Journal of Clinical Investigation. Sep. 2012;122(9):3295-306.

(56)　　　　　References Cited

OTHER PUBLICATIONS

Steffen et al., MT1-MMP-Dependent Invasion is Regulated by TI-VAMP/VAMP7. Current Biology. Jun. 2008;18:926-31.
Stemmer, Rapid evolution of a protein in vitro by DNA shuffling. Nature. Aug. 4, 1994;370(6488):389-91.
Sutter et al., Non-replicating vaccinia vector efficiently expresses bacteriophage T7 RNA polymerase. FEBS Lett. Aug. 28, 1995;371(1):9-12.
Torres et al., Non-integrative lentivirus drives high-frequency cre-mediated cassette exchange in human cells. PLoS One. 2011;6(5):e19794. doi: 10.1371/journal.pone.0019794. Epub May 23, 2011.
Tracewell et al., Directed enzyme evolution: climbing fitness peaks one amino acid at a time. Curr Opin Chem Biol. Feb. 2009;13(1):3-9. doi: 10.1016/j.cbpa.2009.01.017. Epub Feb. 25, 2009.
Tsai et al., Targeting botulinum neurotoxin persistence by the ubiquitin-proteasome system. PNAS. Sep. 2010;107(38):16554-9.
Tsuji et al., Random multi-recombinant PCR for the construction of combinatorial protein libraries. Nucleic Acids Res. Oct. 15, 2001;29(20):E97.
Turner et al., Structural plasticity of an aminoacyl-tRNA synthetase active site. Proc Natl Acad Sci U S A. Apr. 25, 2006;103(17):6483-8. doi: 10.1073/pnas.0601756103. Epub Apr. 17, 2006.
Tzagoloff et al., The Initial Steps In Infection With Coliphage M13. Virology. Nov. 1964;24:372-80.
Umehara et al., N-acetyl lysyl-tRNA synthetases evolved by a CcdB-based selection possess N-acetyl lysine specificity in vitro and in vivo. FEBS Lett. Mar. 23, 2012;586(6):729-33. doi: 10.1016/j.febslet.2012.01.029. Epub Jan. 28, 2012.
Varadarajan et al., Engineering of protease variants exhibiting high catalytic activity and exquisite substrate selectivity. PNAS. May 2005;102(19):6855-60.
Varadarajan et al., Highly active and selective endopeptidases with programmed substrate specificities. Nat Chem Biol. May 2008;4(5):290-4.
Vidal et al., Yeast forward and reverse 'n'-hybrid systems. Nucleic Acids Res. Feb. 15, 1999;27(4):919-29.
Vidal-Aroca et al., One-step high-throughput assay for quantitative detection of beta- galactosidase activity in intact gram-negative bacteria, yeast, and mammalian cells. Biotechniques. Apr. 2006;40(4):433-4, 436, 438 passim.
Voigt et al., Rational evolutionary design: the theory of in vitro protein evolution. Adv Protein Chem. 2000;55:79-160.
Voytek et al., Emergence of a fast-reacting ribozyme that is capable of undergoing continuous evolution. Proc Natl Acad Sci U S A. Sep. 25, 2007;104(39):15288-93. Epub Sep. 18, 2007.
Wang et al., Continuous directed evolutions of proteins with improved soluble expression. Nature Chemical Biology. Nat Publishing Group. Aug. 20, 2018; 14(10):972-980.
Wang et al., Evolution of new nonantibody proteins via iterative somatic hypermutation. Proc Natl Acad Sci U S A. Nov. 30, 2004;101(48):16745-9. Epub Nov. 19, 2004.
Wang et al., Programming cells by multiplex genome engineering and accelerated evolution. Nature. Aug. 13, 2009;460(7257):894-8. Epub Jul. 26, 2009.
Wang et al., Syntaxin Requirement for Ca2+-Triggered Exocytosis in Neurons and Endocrine Cells Demonstrated with an Engineered Neurotoxin. Boiochemistry. Apr. 2011;50(14):2711-3.
Webb et al., Production of catalytically inactive BoNT/A1 holoprotein and comparison with BoNT/A1 subunit vaccines against toxin subtypes A1, A2, and A3. Vaccine. 2009;27(33):4490-4497.
Wharton et al., A new-specificity mutant of 434 repressor that defines an amino acid-base pair contact. Nature. Apr. 30-May 6, 1987;326(6116):888-91.
Wharton et al., Changing the binding specificity of a repressor by redesigning an alpha-helix. Nature. Aug. 15-21, 1985;316(6029):601-5.
Williams et al., SNAP23, Syntaxin4, and vesicle-associated membrane protein 7 (VAMP7) mediate trafficking of membrane type 1-matrix metalloproteinase (MT1-MMP) during invadopodium formation and tumor cell invasion. MBoC. Jul. 2014;25:2061-70.
Wright et al., Continuous in vitro evolution of catalytic function. Science. Apr. 25, 1997;276(5312):614-7.
Yamamoto et al., Virological and immunological bases for HIV-1 vaccine design. Uirusu 2007;57(2):133-139. https://doi.org/10.2222/jsv.57.133.
Yanagisawa et al., Crystallographic studies on multiple conformational states of active-site loops in pyrrolysyl-tRNA synthetase. J Mol Biol. May 2, 2008;378(3):634-52. doi: 10.1016/j.jmb.2008.02.045. Epub Feb. 29, 2008.
Yanagisawa et al., Multistep engineering of pyrrolysyl-tRNA synthetase to genetically encode N(epsilon)-(o-azidobenzyloxycarbonyl) lysine for site-specific protein modification. Chem Biol. Nov. 24, 2008;15(11):1187-97. doi: 10.1016/j.chembiol.2008.10.004.
Yeh et al., Retargeted Clostridial neurotoxins as Novel Agents for Treating Chronic Diseases. Biochemistry. Nov. 2011;50:10419-21.
Yi et al., Engineering of TEV protease variants by yeast ER sequestration screening (YESS) of combinatorial libraries. PNAS. Apr. 2013;110(18):7229-34.
Yuan et al., Laboratory-directed protein evolution. Microbiol Mol Biol Rev. Sep. 2005;69(3):373-92.
Zhang et al., Identification and characterization of a novel botulinum neurotoxin. Nat Commun. Aug. 3, 2017;8:14130. doi: 10.1038/ncomms14130.
Zhou et al., Optimization of the Tet-On system for regulated gene expression through viral evolution. Gene Ther. Oct. 2006;13(19):1382-90. Epub May 25, 2006.
Ziemann et al., Gene name errors are widespread in the scientific literature. Genome Biol. Aug. 23, 2016;17(1):177. doi: 10.1186/s13059-016-1044-7.
Burland et al., Analysis of the *Escherichia coli* genome VI: DNA sequence of the region from 92.8 through 100 minutes. Nucleic Acids Res. Jun. 25, 1995;23(12):2105-19. doi: 10.1093/nar/23.12.2105.
Chappell et al., Generation and characterization of proteolytically active and highly stable truncated and full-length recombinant West Nile virus NS3. Protein Expr Purif. May 2007;53(1):87-96. doi: 10.1016/j.pep.2006.10.022. Epub Nov. 7, 2006.
Chen et al., Mechanism of substrate recognition by botulinum neurotoxin serotype A. J Biol Chem. Mar. 30, 2007;282(13):9621-9627. doi: 10.1074/jbc.M611211200. Epub Jan. 23, 2007.
Chen et al., Multiple pocket recognition of SNAP25 by botulinum neurotoxin serotype E. J Biol Chem. Aug. 31, 2007;282(35):25540-7. doi: 10.1074/jbc.M701922200. Epub Jul. 3, 2007.
Chibani-Chennoufi et al., Phage-host interaction: an ecological perspective. J Bacterial. Jun. 2004; 186(12):3677-86. doi: 10.1128/JB.186.12.3677-3686.2004.
Dong et al., Using fluorescent sensors to detect botulinum neurotoxin activity in vitro and in living cells. Proc Natl Acad Sci U S A. Oct. 12, 2004;101(41):14701-6. doi: 10.1073/pnas.0404107101. Epub Oct. 1, 2004.
Hendel et al., Directed evolution in mammalian cells. Nat Methods. Apr. 2021;18(4):346-357. doi: 10.1038/s41592-021-01090-x. Epub Apr. 7, 2021.
Jan et al., Reversible On- and Off-switch chimeric antigen receptors controlled by lenalidomide. Sci Transl Med. Jan. 6, 2021;13(575):eabb6295. doi: 10.1126/scitranslmed.abb6295.
Jan et al., Reversible On- and Off-switch chimeric antigen receptors controlled by lenalidomide. Sci Transl Med. 2021. Supplemental info. 12 pages.
Jeruzalmi et al., Structure of T7 RNA polymerase complexed to the transcriptional inhibitor T7 lysozyme. EMBO J. Jul. 15, 1998;17(14):4101-13. doi: 10.1093/emboj/17.14.4101.
Jones et al., Phage-Assisted Continuous Evolution and Selection of Enzymes for Chemical Synthesis. ACS Cent Sci. Sep. 22, 2021;7(9):1581-1590. doi: 10.1021/acscentsci.1c00811. Epub Sep. 13, 2021.
Latremoliere et al., Reduction of Neuropathic and Inflammatory Pain through Inhibition of the Tetrahydrobiopterin Pathway. Neuron. Jun. 17, 2015;86(6):1393-406. doi: 10.1016/j.neuron.2015.05.033.

(56)          References Cited

OTHER PUBLICATIONS

Lee et al., Enhanced production of human full-length immunoglobulin G1 in the periplasm of *Escherichia coli*. Appl Microbiol Biotechnol. Feb. 2014;98(3):1237-46. doi: 10.1007/s00253-013-5390-z. Epub Nov. 26, 2013.

Manta et al., Disulfide Bond Formation in the Periplasm of *Escherichia coli*. EcoSal Plus. Feb. 2019;8(2). doi: 10.1128/ecosalplus.ESP-0012-2018.

Mayrhofer et al., Mutation-oriented profiling of autoinhibitory kinase conformations predicts RAF inhibitor efficacies. Proc Natl Acad Sci USA. Dec. 8, 2020;117(49):31105-31113. doi: 10.1073/pnas.2012150117. Epub Nov. 23, 2020.

McCreary et al., Reprogramming protease specificity using phage-assisted evolution. Poster. Harvard University. CCB Department G1 Poster Session. Presented Aug. 25, 2022.

Mccreary, Evolution of a procaspase-1 cleaving protease. Presentation. 2021. 10 pages.

Miller et al., Phage-assisted continuous and non-continuous evolution. Nat Protoc. Dec. 2020; 15(12):4101-4127. doi: 10.1038/s41596-020-00410-3. Epub Nov. 16, 2020.

Morrison et al., Chapter 4: Future directions and potential applications of this work. Thesis for Harvard University. 2021. 29 pages.

Morrison et al., Disulfide-compatible phage-assisted continuous evolution in the periplasmic space. Author Manuscript with Supplementary information. Broad Institute of Harvard and MIT and Harvard University. 2022. 75 pages.

Morrison et al., Disulfide-compatible phage-assisted continuous evolution in the periplasmic space. Nat Commun. Oct. 13, 2021;12(1):5959. doi: 10.1038/s41467-021-26279-8.

Packer et al., Phage-assisted continuous evolution of proteases with altered substrate specificity. Nat Commun. Oct. 16, 2017;8(1):956. doi: 10.1038/s41467-017-01055-9.

Popa et al., Phage-Assisted Continuous Evolution (PACE): A Guide Focused on Evolving Protein-DNA Interactions. ACS Omega. Oct. 16, 2020;5(42):26957-26966. doi: 10.1021/acsomega.0c03508. eCollection Oct. 27, 2020.

Romanini et al., A Heritable Recombination system for synthetic Darwinian evolution in yeast. ACS Synth Biol. Dec. 21, 2012;1(12):602-9. doi: 10.1021/sb3000904.

Sikorra et al., Identification and Characterization of Botulinum Neurotoxin A Substrate Binding Pockets and Their Re-Engineering for Human SNAP-23. J Mol Biol. Jan. 29, 2016;428(2 Pt A):372-384. doi: 10.1016/j.jmb.2015.10.024. Epub Oct. 30, 2015.

Sikorra et al., Identification of the amino acid residues rendering TI-VAMP insensitive toward botulinum neurotoxin B. J Mol Biol. Mar. 24, 2006;357(2):574-82. doi: 10.1016/j.jmb.2005.12.075. Epub Jan. 18, 2006.

Xie et al., Contingency and chance erase necessity in the experimental evolution of ancestral proteins. Elife. Jun. 1, 2021:10:e67336. doi: 10.7554/eLife.67336.

Ngo et al., Computational Complexity, Protein Structure Prediction, and the Levinthal Paradox in the Protein Folding Problem and Tertiary Structure Prediction. Merz et al., Eds. 1994. pp. 433 and 492-495.

Vincenzeti et al., Functional properties of subunit interactions in human cytidine deaminase. Protein Engi. Dec. 2003;16(12):1055-61. doi: 10.1093/protein/gzg117.

Vincenzeti et al., Possible role of two phenylalanine residues in the active site of human cytidine deaminase. Protein Eng. Nov. 2000;13(11):791-9. doi: 10.1093/protein/13.11.791.

[No Author Listed] Genbank Submission. NCBI; Accession No. AEA29692, version AEA29692.1. cadherin [Trichoplusia ni]. Oct. 18, 2011.

[No Author Listed] Genbank Submission. NCBI; Accession No. AY730621, version AY730621.1. Bacillus thuringiensis plasmid Cry1Ac (cry1Ac) gene, complete cds. Jul. 26, 2016.

[No Author Listed] Genbank Submission. NCBI; Accession No. NP_001166953, version NP_001166953.1. protein cereblon isoform 2 [Homo sapiens]. May 29, 2022.

[No Author Listed] Genbank Submission. NCBI; Accession No. NP_057386, version NP_057386.2. protein cereblon isoform 1 [Homo sapiens]. Jun. 8, 2022.

Adang et al., Characterized full-length and truncated plasmid clones of the crystal protein of *Bacillus thuringiensis* subsp. *kurstaki* HD-73 and their toxicity to Manduca sexta. Gene. 1985;36(3):289-300. doi: 10.1016/0378-1119(85)90184-2.

Altschul et al., Basic local alignment search tool. J Mol Biol. Oct. 5, 1990;215(3):403-10. doi: 10.1016/S0022-2836(05)80360-2.

Altschul et al., Gapped BLAST and PSI-BLAST: a new generation of protein database search programs. Nucleic Acids Res. Sep. 1, 1997;25(17):3389-402. doi: 10.1093/nar/25.17.3389.

Blum, Continuous evolution of bacterial neurotoxins for intracellular protease therapy. Gordon Research Conference (GRC) Synthetic Biology. Presented Jul. 15, 2019. Waterville Valley, New Hampshire, United States. Poster. 1 page.

Brayer et al., Keep your fingers off my DNA: protein-protein interactions mediated by C2H2 zinc finger domains. Cell Biochem Biophys. 2008;50(3):111-31. doi: 10.1007/s12013-008-9008-5. Epub Feb. 6, 2008.

Chen et al., Recognition of DNA by single-chain derivatives of the phage 434 repressor: high affinity binding depends on both the contacted and non-contacted base pairs. Nucleic Acids Res. Jun. 1, 1997;25(11):2047-54. doi: 10.1093/nar/25.11.2047.

Dong et al., Molecular Glues for Targeted Protein Degradation: From Serendipity to Rational Discovery. J Med Chem. Aug. 12, 2021;64(15):10606-10620. doi: 10.1021/acs.jmedchem.1c00895. Epub Jul. 28, 2021.

Jurat-Fuentesa et al., Specificity determinants for Cry insecticidal proteins: Insights from their mode of action. J Invertebr Pathol. Jan. 2017:142:5-10. doi: 10.1016/j.jip.2016.07.018. Epub Jul. 29, 2016.

Karlin et al., Applications and statistics for multiple high-scoring segments in molecular sequences. Proc Natl Acad Sci U S A. Jun. 15, 1993;90(12):5873-7. doi: 10.1073/pnas.90.12.5873.

Karlin et al., Methods for assessing the statistical significance of molecular sequence features by using general scoring schemes. Proc Natl Acad Sci U S A. Mar. 1990;87(6):2264-8. doi: 10.1073/pnas.87.6.2264.

Lucena et al., Molecular approaches to improve the insecticidal activity of Bacillus thuringiensis Cry toxins. Toxins (Basel). Aug. 13, 2014;6(8):2393-423. doi: 10.3390/toxins6082393.

Mercer et al., Continuous evolution of compact protein degradation tags regulated by selective molecular glues. Science. Mar. 15, 2024;383(6688):eadk4422. doi: 10.1126/science.adk4422. Epub Mar. 15, 2024.

Meyer et al., Molecular evolution picks up the PACE. Nat Biotechnol. Jun. 7, 2011;29(6):502-3. doi: 10.1038/nbt.1884.

Myers et al., Optimal alignments in linear space. Comput Appl Biosci. Mar. 1988;4(1):11-7. doi: 10.1093/bioinformatics/4.1.11.

Nakahira et al., Theophylline-dependent riboswitch as a novel genetic tool for strict regulation of protein expression in Cyanobacterium Synechococcus elongatus PCC 7942. Plant Cell Physiol. Oct. 2013;54(10):1724-35. doi: 10.1093/pcp/pct115. Epub Aug. 21, 2013.

Pardo-Lopez et al., Strategies to improve the insecticidal activity of Cry toxins from Bacillus thuringiensis. Peptides. Mar. 2009;30(3):589-95. doi: 10.1016/j.peptides.2008.07.027. Epub Aug. 19, 2008.

Pigott et al., Role of receptors in Bacillus thuringiensis crystal toxin activity. Microbial Mol Biol Rev. Jun. 2007;71(2):255-81. doi: 10.1128/MMBR.00034-06.

Polyak et al., Overview: Gene Structure. Holland-Frei Cancer Medicine. 6th edition. 2003. Accessed at: www.ncbi.nlm.nih.gov/books/NBK12983.

Ptashne et al., Autoregulation and Function of a Repressor in Bacteriophage Lambda. Science. Oct. 8, 1976;194(4261):156-61. doi: 10.1126/science.959843.

Sauer et al., The lambda and P22 phage repressors. J Biomol Struct Dyn. Dec. 1983;1(4):1011-22. doi: 10.1080/07391102.1983.10507499.

Sievers et al., Defining the human C2H2 zinc finger degrome targeted by thalidomide analogs through CRBN. Science. Nov. 2, 2018;362(6414):eaat0572. doi: 10.1126/science.aat0572.

(56)     References Cited

OTHER PUBLICATIONS

Xie et al., Methods for the directed evolution of biomolecular interactions. Trends Biochem Sci. May 2022;47(5):403-416. doi: 10.1016/j.tibs.2022.01.001.

Yamamoto et al., ARID2 is a pomalidomide-dependent CRL ACRBN substrate in multiple myeloma cells. Nat Chem Biol. Nov. 2020;16(11):1208-1217. doi: 10.1038/s41589-020-0645-3. Epub Sep. 21, 2020.

Invitation to Pay Additional Fees for Application No. PCT/US2025/ 028625, mailed Sep. 24, 2025.

Lemmon et al., Pleckstrin homology (PH) domains and phosphoinositides. Biochem Soc Symp. Author manuscript; available in PMC: Sep. 19, 2013. Published in final edited form as: Biochem Soc Symp. 2007;(74):81-93. doi: 10.1042/BSS0740081.

Vande Walle et al., Snapshot of a Deadly Embrace: The Caspase-1-GSDMD Interface. Immunity. Jul. 14, 2020;53(1):6-8. doi: 10.1016/ j.immuni.2020.06.019.

* cited by examiner

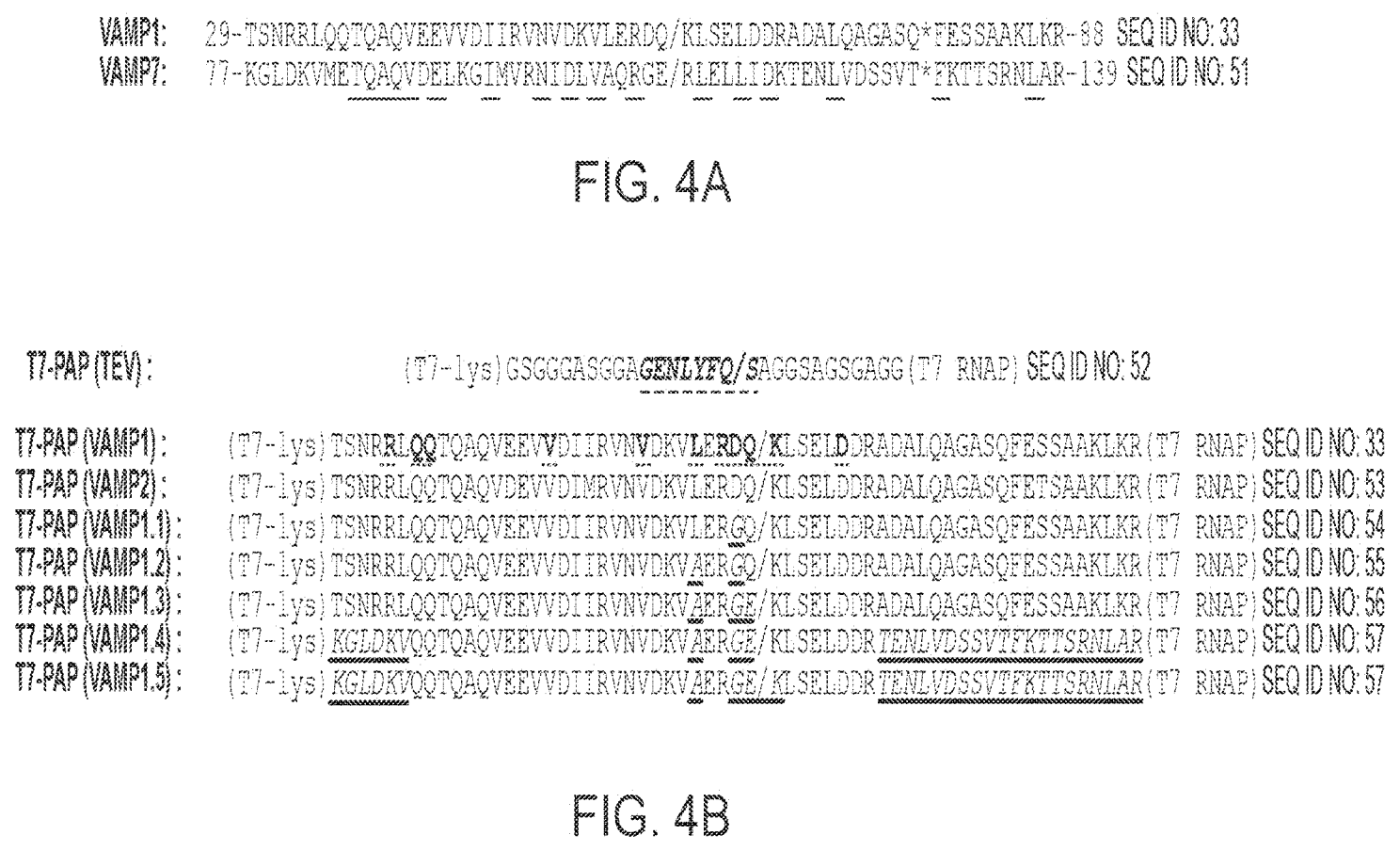

VAMP1:    29-TSNRRLQQTQAQVEEVVDIIRVNVDKVLERDQ/KLSEILDRADAIQAGASQ*FESSAAKLKR--98 SEQ ID NO: 33
VAMP2:    77--KGLDKVMETQAQVDEVKGIMVRNIDLVAQRGE/RLELLDKFENLVDSSVT*KTTSRMLAR--139 SEQ ID NO: 51

FIG. 4A

T7-RAP (TEV):    (T7-lys)GSGGGASGGAGENLYFQ/SAGGSAGSGAGG(T7 RNAP)SEQ ID NO: 52

T7-RAP (VAMP1):     (T7-lys)TSNRRLQQTQAQVEEVVDIIRVNVDKVLERDQ/KLSEILDRADAIQAGASQFESSAAKLKR(T7 RNAP)SEQ ID NO: 33
T7-RAP (VAMP2):     (T7-lys)TSNRRLQQTQAQVDEVVDIMRVNVDKVIERDQ/KLSEILDRADAIQAGASQFBTSAAKLKR(T7 RNAP)SEQ ID NO: 53
T7-RAP (VAMP1.1):   (T7-lys)TSNRRLQQTQAQVEEVVDIIRVNVDKVLERGQ/KLSEILDRADAIQAGASQFESSAAKLKR(T7 RNAP)SEQ ID NO: 54
T7-RAP (VAMP1.2):   (T7-lys)TSNRRLQQTQAQVEEVVDIIRVNVDKVAERGQ/KLSEILDRADAIQAGASQFESSAAKLKR(T7 RNAP)SEQ ID NO: 55
T7-RAP (VAMP1.3):   (T7-lys)TSNRRLQQTQAQVEEVVDIIRVNVDKVAERGE/KLSEILDRADAIQAGASQFESSAAKLKR(T7 RNAP)SEQ ID NO: 56
T7-RAP (VAMP1.4):   (T7-lys)KGLDKVQQTQAQVEEVVDIIRVNVDKVAERGE/KLSEILDBRTENLVDSSVTKTTSRMLAR(T7 RNAP)SEQ ID NO: 57
T7-RAP (VAMP1.5):   (T7-lys)KGLDKVQQTQAQVEEVVDIIRVNVDKVAERGE/KLSEILDBRTENLVDSSVTKTTSRMLAR(T7 RNAP)SEQ ID NO: 57

FIG. 4B

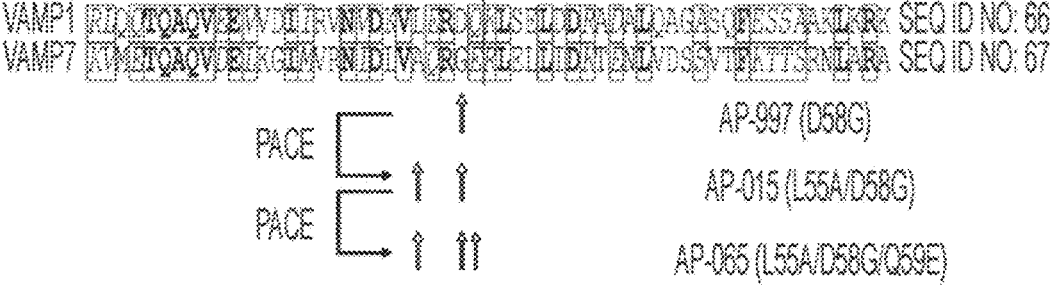
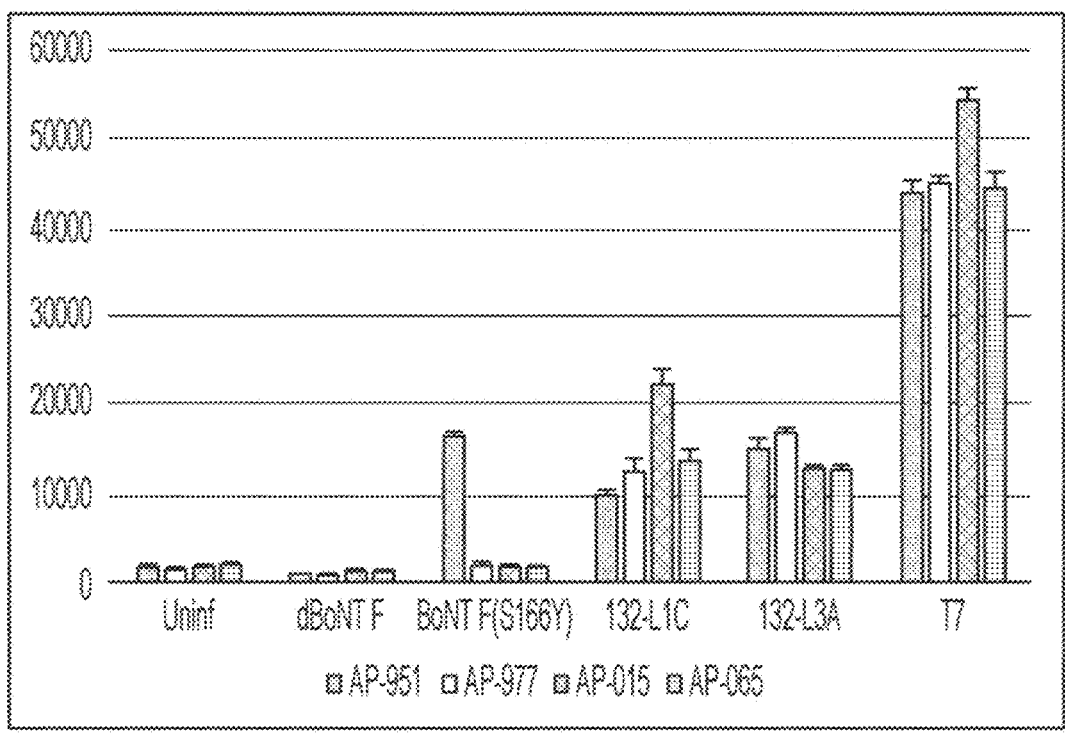
FIG. 19

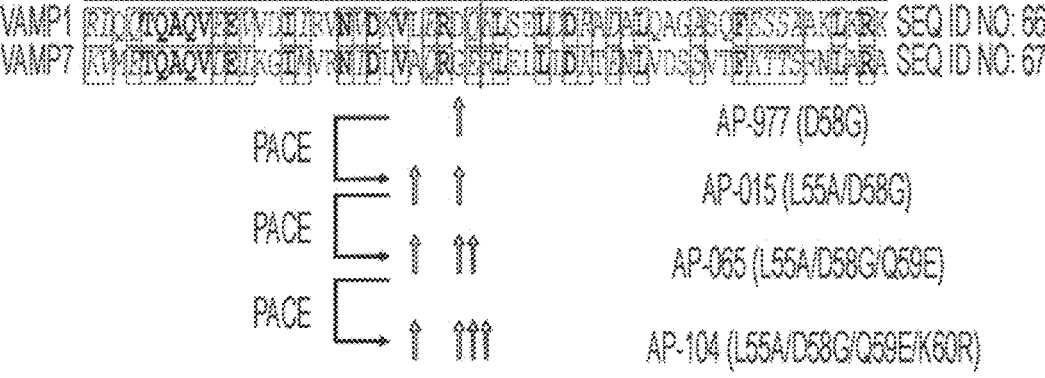
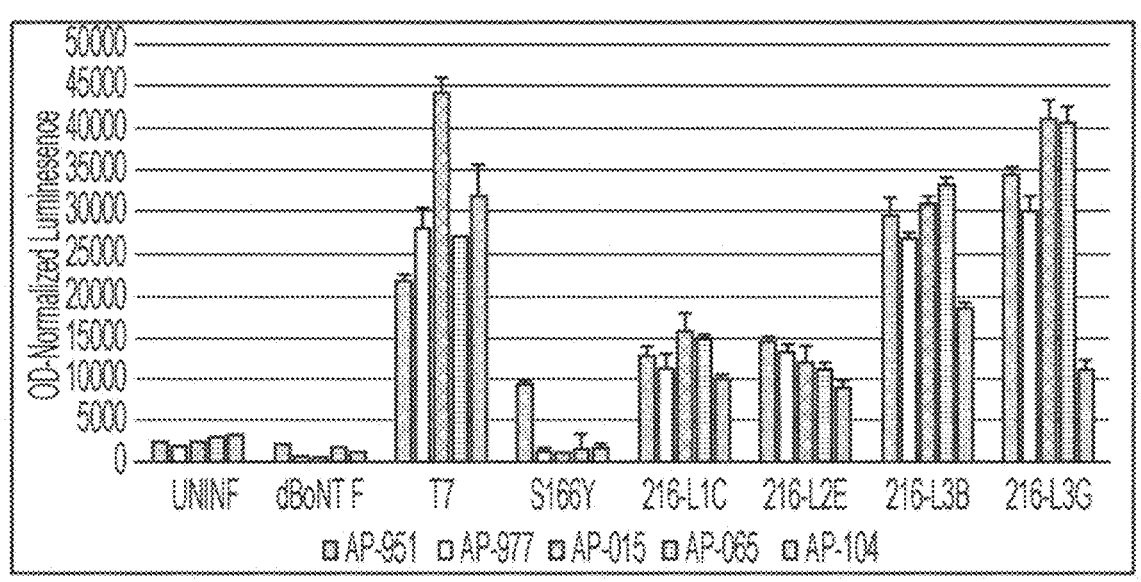
FIG. 20

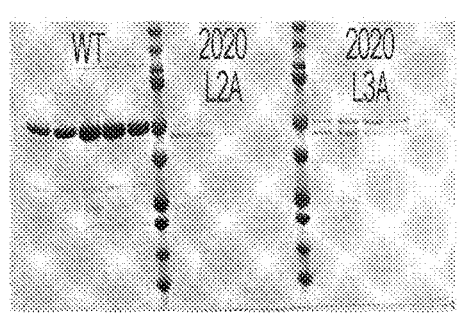

C-term His6 tag literature isolation conditions
(detergent lysis + 5x protease inhibitors)

N-terminal MBP solubility tag,
isolated by metal affinity, literature isolation conditions
(detergent lysis + 5x protease inhibitors)

FIG. 24

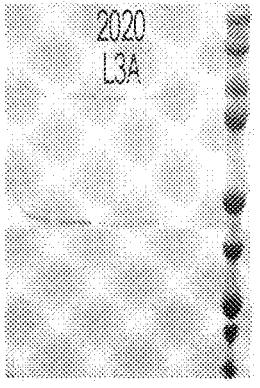

VAMP1   TSNRRLQQTQAQVEEVVDIIRVNVDKVLERDQKLSELDDRADALQAGASQFESSAAKLKRK SEQ ID NO: 74
VAMP8   GSNRRLQQTQAQVDEVVDIMRVNVDKVLERDQKLSELDDRADALQAGASQFETSAAKLKRK SEQ ID NO: 75

VAMP1     Q39E V44K     D58G     VAMP8

AP-951:VAMP1 [R32-R87]     AP-074:VAMP1 [T36-R67]
AP-977 (D58G)    A38S E42G    K60N    AP-176 (D58G)
AP-110 (D58G/A38S)     AP-178 (D58G/A38S)
AP-112 (D58G/Q39E)     AP-180 (D58G/Q39E)
AP-113 (D58G/E42G)     AP-181 (D58G/E42G)
AP-115 (D58G/V44K)     AP-182 (D58G/V44K)
AP-121 (D58G/K60N)     AP-183 (D58G/K60N)

FIG. 25

VAMP1 ...DSNRRLQQTQAQVDEVVDIMRVNVDKVLERDQKLSELDDRADALQAGASQFESSAAKLKRK SEQ ID NO: 74
VAMP8 ...GSNRRLQQTQNQVDEVVDIMRVNVDKVLERDQKLSELGERADQLEQGASQFEQQAGKLKRK SEQ ID NO: 75

AP-951 (VAMP1)
AP-977 (VAMP1 D58G)
AP-174 (VAMP1 D58G/Q59E/K60N)
AP-287 (VAMP8-tethered D58G/Q59E/K60N)

AP-291 (VAMP8-tethered
V44K/R48T/N49Q/E56A/D58G/Q59E/K60N)

Advanced VAMP7-evolved
proteases are active on
VAMP 8 substrates

| Protease | WT | L2F | L2B | | WT | L2F | L2B |
|---|---|---|---|---|---|---|---|
| Substrate | | | | GST-PTEN | GST-PTEN | GST-PTEN | GST-PTEN |

- L2F (before neg. selection)
- L2B (after neg. selection)
- Red-Anti-PTEN C-terminus
- Green Anti-PTEN N-terminus 250kDa
150kDa 100kDa
75kDa                    GST-PTEN (76kDa)

Expected N-terminal fragment 65kDa?

50kDa
                         Off-target N-terminal fragment?
37kDa

25kDa
15kDa                    Expected C-terminal fragment 11kDa?
10kDa m2020-L2A BoNT proteases (BoNT F) are
PACE compatible, and show
activity-dependent circuit activation Evolution of BoNT F on VAMP1
enriches for a point mutation (S166Y)

BoNT F is evolvable

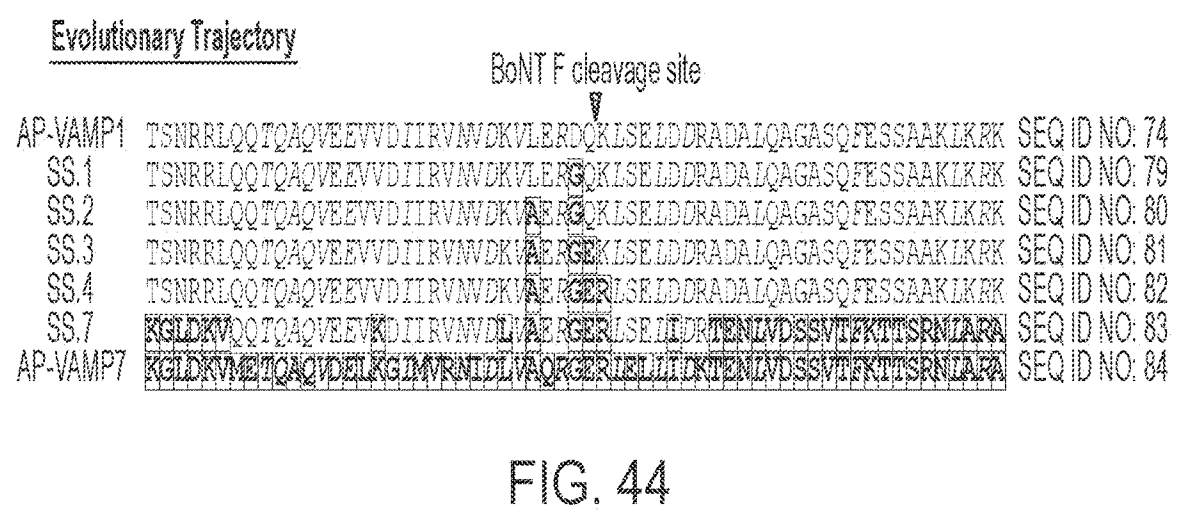

Evolutionary Trajectory

BoNT F cleavage site

AP-VAMP1  TSNRRLQQTQAQVEENVDIIRVNVDKVLERDQKLSELDDRADALQAGASQFESSAAKLKRK  SEQ ID NO. 74
SS.1      TSNRRLQQTQAQVEENVDIIRVNVDKVLERDQKLSELDDRADALQAGASQFESSAAKLKRK  SEQ ID NO. 79
SS.2      TSNRRLQQTQAQVEENVDIIRVNVDKVLERDQKLSELDDRADALQAGASQFESSAAKLKRK  SEQ ID NO. 80
SS.3      TSNRRLQQTQAQVEENVDIIRVNVDKVRELSEKLSELDDRADALQAGASQFESSAAKLKRK  SEQ ID NO. 81
SS.4      TSNRRLQQTQAQVEENVDIIRVNVDKVRELSEKLSELDDRADALQAGASQFESSAAKLKRK  SEQ ID NO. 82
SS.7      TSNRRLQQTQAQVEVKDIIRVNVDKVRELSEKLSELDDRADALQAGASQFESSAAKLKRK   SEQ ID NO. 83
AP-VAMP7  KGLDRNVETQAQVDELKGIMVRNLDLVEETDENLDRVEGRLSELDRTNLLVDSSNTKITTSRNTARK  SEQ ID NO. 84

FIG. 44

| Protease | F7.2[A6] | F7N[1.3] |
|---|---|---|
| Kм (µM) | 48.3 (±36.5) | 5.84 (±1.09) |
| Vmax | $1.7 \times 10^{-3}$ µM*s$^{-1}$ | $1.2 \times 10^{-3}$ µM*s$^{-1}$ |
| | Positive selection | w/Negative selection |

FIG. 45E

| Target | Relative Rate F7N[1.3] |
|---|---|
| VAMP1 | < 1% |
| VAMP2 | < 1% |
| VAMP3 | < 1% |
| VAMP4 | < 1% |
| VAMP5 | 0.015 |
| VAMP7 | 1.000 |
| VAMP8 | 0.034 |
| Ykt6 | < 1% |
| Sec22b | 0.044 |

FIG. 45F

| | | |
|---|---|---|
| AP-VAMP1 | TSNRRLQQTQAQVDEVVDIMRVNVDKVLERDQKLSELDDRADALQAGASQFETSSAAKLKRK | SEQ ID NO: 74 |
| SS.1 | TSNRRLQQTQAQVDEVVDIMRVNVDKVLERDQKLSELDDRADALQAGASQFETSSAAKLKRK | SEQ ID NO: 79 |
| SS.2 | TSNRRLQQTQAQVDEVVDIMRVNVDKVLERDQKLSELDDRADALQAGASQFETSSAAKLKRK | SEQ ID NO: 80 |
| SS.3 | TSNRRLQQTQAQVDEVVDIMRVNVDKVLERDQKLSELDDRADALQAGASQFETSSAAKLKRK | SEQ ID NO: 81 |
| SS.4 | TSNRRLQQTQAQVDEVVDIMRVNVDKVLERDQKLSELDDRADALQAGASQFETSSAAKLKRK | SEQ ID NO: 82 |
| SS.7 | TSNRRLQQTQAQVDEVVDIMRVNVDKVLERDQKLSELDDRADALQAGASQFETSSAAKLKRK | SEQ ID NO: 83 |
| AP-VAMP7 | KRLDKNVQTQAQVDEVVDIMRVNVDKVAEGSRLSELDDRADALQAGASQFETSSAAKLKRK | SEQ ID NO: 84 |

FIG. 47

Residue Number

FIG. 48

F7N[1.3] Protease

AP-VAMP1  TSNRRLQQTQAQVDEVVDIMRVNVDKVLERDQKLSELDDRADALQAGASQFESSAAKLKRK  SEQ ID NO: 74
AP-VAMP7  KSLDYNPYMSPVSSNRRLSLMRTQQCEIQLKNNPPPLIATSTLSPSSRLVAAP  SEQ ID NO: 84

Combined Reversion Analysis

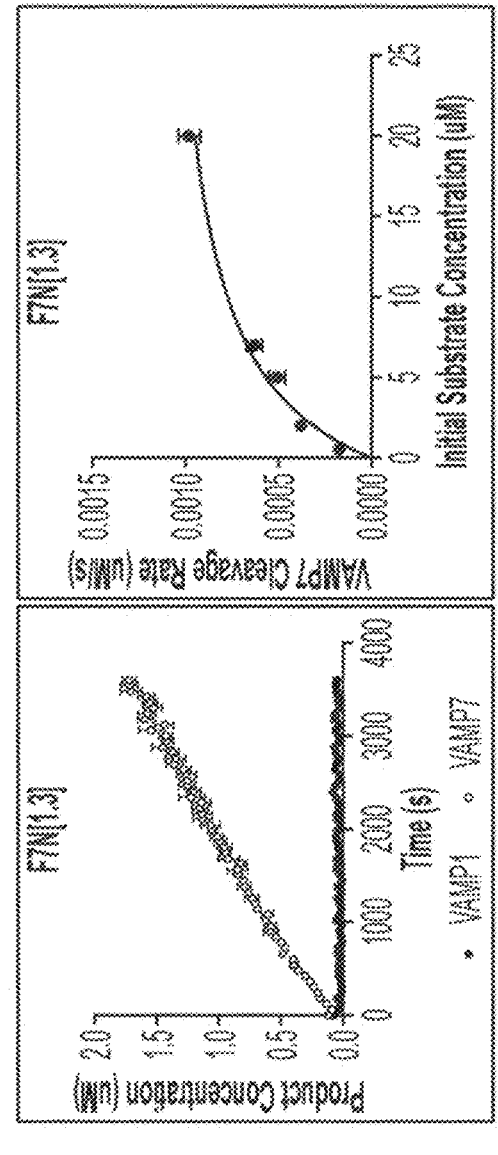
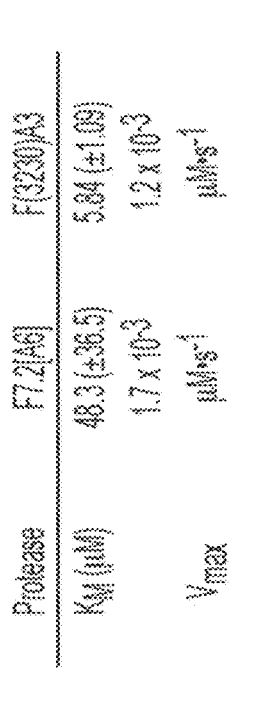
FIG. 54C

AP-VAMP1  L E R G E K L D D L V S K S E V L
AP-Ykt6   L E R D K L S E L D D R A D A L

SEQ ID NO: 85    VAMP1 negative selection

SEQ ID NO: 86    Ykt6 positive selection

| Position | 68 | 98 | 113 | 150 | 166 | 280 | 405 | 435 |
|---|---|---|---|---|---|---|---|---|
| Wild Type | E | V | E | Q | A | S | S | R |
| a | E | G | K | Q | E | L | S | R |
| b | E | V | E | Q | E | S | S | R |
| c | E | V | E | Q | E | S | L | L |
| d | A | V | E | Q | E | S | S | R |
| e | E | V | E | Q | E | S | R | R |
| f | E | V | E | Q | E | S | S | R |
| g | E | V | E | Q | E | S | S | L |
| h | E | G | K | Q | E | S | S | L |

BoNT X(LC), A166 in blue

Position: 23 98 100 113 133 143 144 148 166 167 175 169 216 225 241 257 267 268 279 285 314 322 341 345 349 364 391 413 416 425    434

| | 23 | 98 | 100 | 113 | 133 | 143 | 144 | 148 | 166 | 167 | 175 | 169 | 216 | 225 | 241 | 257 | 267 | 268 | 279 | 285 | 314 | 322 | 341 | 345 | 349 | 364 | 391 | 413 | 416 | 425 | | 434 |
|---|---|---|---|---|---|---|---|---|---|---|---|---|---|---|---|---|---|---|---|---|---|---|---|---|---|---|---|---|---|---|---|---|
| Wild Type | R | V | E | E | D | N | N | A | T | | I | G | A | L | N | R | L | L | S | K | Y | Q | T | V | S | L | S | S | L | R | YRNSKN | SEQ ID NO: 89 |
| A2 | R | V | E | E | D | N | N | L | E | | I | G | A | L | N | R | L | L | S | K | S | Q | T | V | S | L | S | S | L | R | KLINSKN | SEQ ID NO: 48 |
| A3 | R | V | E | E | D | N | N | E | L | | I | G | A | L | N | R | L | L | S | K | Y | Q | T | V | S | F | L | R | | | YRNSKN | SEQ ID NO: 89 |
| A4 | R | V | E | E | D | N | N | E | | | I | G | A | L | N | C | L | L | S | K | Y | K | T | V | S | L | S | S | L | R | YRNSKN | SEQ ID NO: 89 |
| A6 | R | V | E | E | D | N | N | E | | | W | G | A | L | N | C | L | L | S | K | Y | K | T | V | S | F | L | R | | | YRNSKN | SEQ ID NO: 89 |
| B1 | R | V | E | E | D | T | N | E | T | | I | G | A | L | N | R | L | L | S | K | N | Q | T | V | S | L | S | S | L | R | *424* | SEQ ID NO: 49 |
| B2 | R | V | E | E | D | N | N | E | | | I | G | A | L | N | R | L | L | S | K | V | K | T | V | S | W | S | S | L | R | YLINSKN | SEQ ID NO: 49 |
| B3 | R | V | E | E | D | D | N | E | T | | I | G | A | L | N | R | L | L | S | K | C | Q | T | V | S | L | S | S | L | R | YRNSKN | SEQ ID NO: 89 |
| B4 | R | G | E | K | D | D | N | E | | | I | G | A | L | N | R | L | L | S | K | Y | T | E | S | S | L | S | S | L | R | YRNSKN | SEQ ID NO: 89 |
| B5 | R | S | E | G | E | N | N | E | | | I | G | A | L | N | R | L | L | S | K | Y | T | | V | S | L | S | S | L | R | YRNSKN | SEQ ID NO: 89 |
| B6 | R | V | E | E | E | N | S | E | | | W | G | A | L | N | R | L | L | P | K | Y | Q | T | V | S | L | S | S | L | R | KLINSKN | SEQ ID NO: 48 |
| B7 | R | V | E | E | D | N | N | E | | | I | G | A | L | N | R | L | L | S | K | Y | Q | T | V | S | L | S | S | L | R | YRNSKN | SEQ ID NO: 89 |
| B8 | R | G | E | D | D | N | T | E | T | | I | G | A | L | N | R | L | L | P | K | Y | Q | T | V | S | L | S | S | F | R | KLINSKN | SEQ ID NO: 48 |
| C1 | R | V | E | E | D | N | N | E | T | | I | G | A | L | N | R | L | L | S | K | Y | Q | T | V | S | L | S | S | L | R | YRNSKN | SEQ ID NO: 89 |
| C2 | R | V | E | E | D | N | N | E | T | | I | G | A | L | N | R | L | L | S | K | Y | Q | T | V | S | L | S | S | L | R | AFTATQKSNNGFQHSLAQP | SEQ ID NO: 50 |
| C3 | R | V | E | E | D | N | N | E | T | | I | G | A | L | N | R | L | L | S | K | Y | Q | T | V | S | L | S | S | L | R | YRNSKN | SEQ ID NO: 89 |
| C4 | R | V | E | E | D | N | N | E | T | | I | G | A | W | N | R | L | L | S | K | Y | Q | P | V | F | S | S | L | | | AFTATQKSNNGFQHSLAQP | SEQ ID NO: 50 |
| C5 | R | V | E | E | D | N | N | E | | | I | G | A | W | L | R | L | L | S | K | Y | Q | T | V | S | L | S | S | L | R | YRNSKN | SEQ ID NO: 89 |
| C6 | R | V | E | E | D | N | N | T | E | | I | G | A | W | L | R | L | L | S | K | N | Y | Q | T | V | S | L | S | S | L | R | YRNSKN | SEQ ID NO: 89 |
| C7 | R | V | E | E | D | D | N | E | T | | I | R | A | L | N | R | L | L | S | K | Y | Q | T | V | S | L | S | S | L | R | YRNSKN | SEQ ID NO: 89 |
| C8 | R | V | E | E | D | D | N | E | T | | I | G | A | L | N | | L | L | S | K | Y | Q | T | V | F | S | L | S | S | L | R | AFTATQKSNNGFQHSLAQP | SEQ ID NO: 50 |

*Note* X(A130)R1* variant used in subsequent assays was cloned such that it does not contain the C-terminus indicated in orange, and instead contains the wild-type C-terminus (top line).

FIG. 56B

PANCE-X(4253)

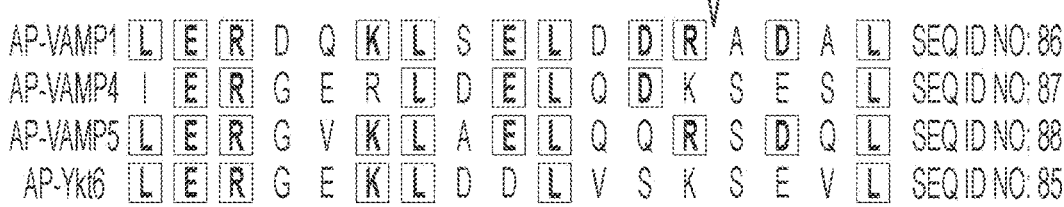

| | | | | | | | | | | | | | | | | | |
|---|---|---|---|---|---|---|---|---|---|---|---|---|---|---|---|---|---|
| AP-VAMP1 | L | E | R | D | Q | K | L | S | E | L | D | D | R | A | D | A | L | SEQ ID NO: 86 |
| AP-VAMP4 | I | E | R | G | E | R | L | D | E | L | Q | D | K | S | E | S | L | SEQ ID NO: 87 |
| AP-VAMP5 | L | E | R | G | V | K | L | A | E | L | Q | Q | R | S | D | Q | L | SEQ ID NO: 88 |
| AP-Ykt6 | L | E | R | G | E | K | L | D | D | L | V | S | K | S | E | V | L | SEQ ID NO: 85 |

|  | | Positive Selection AP | Negative Selection AP | Starting Phage |
|---|---|---|---|---|
| Highest stringency | 4130-X(122) | T3pos-sd5-VAMP4-proB | T7neg-sd8-VAMP1-proD | |
| | 4130-X(720) | T3pos-sd5-VAMP4-proB | T7neg-sd5-VAMP1-proD | SP-BoNT/X (expanded with mutagenesis) |
| | 4130-X(721) | T3pos-sd5-VAMP4-proB | T7neg-sd2-VAMP1-proD | |
| Lowest stringency | 4130-X(722) | T3pos-sd5-VAMP4-proB | T7neg-sd4U-VAMP1-proD | |

FIG. 57C

| | Very High | High | Med. | Low | Very High | High | Med. | Low | Very High | High | Med. | Low | Dilution Coefficient |
|---|---|---|---|---|---|---|---|---|---|---|---|---|---|
| 1 | 6.9 | 6.7 | 6.6 | 6 | 6.4 | 6.6 | 6.5 | 6.7 | 6.6 | 6.5 | 6.6 | 6.6 | 100 |
| 2 | 0 | 0 | 3 | 43 | 0 | 0 | 26 | 4 | 0 | 0 | 3 | 48 | 200 |
| 3 | 0 | 0 | 0 | 35 | 0 | 0 | 0 | 29 | 0 | 0 | 0 | 3 | 200 |
| 4 | 0 | 0 | 0 | 28 | 0 | 0 | 0 | 25 | 0 | 0 | 0 | 23 | 250 |
| 5 | 0 | 0 | 0 | 0 | 0 | 0 | 0 | 18 | 0 | 0 | 0 | 0 | 200 |
| 6 | 0 | 0 | 0 | 0 | 0 | 0 | 0 | 3 | 0 | 0 | 0 | 0 | 100 |
| 7 | 0 | 0 | 0 | 3 | 0 | 0 | 0 | 37 | 0 | 0 | 0 | 53 | 100 |
| 8 | 0 | 0 | 0 | 4 | 0 | 0 | 0 | 8 | 0 | 0 | 0 | 15 | 100 |
| 9 | 0 | 0 | 0 | 14 | 0 | 0 | 0 | 64 | 0 | 0 | 0 | 6 | 100 |

FIG. 57D

| Position | | 143 | 150 | 164 | 168 | 174 | 222 | 224 | 240 | 313 | 322 | 339 |
|---|---|---|---|---|---|---|---|---|---|---|---|---|
| Wild Type | | N | Q | N | Y | P | A | T | S | K | Q | L |
| A | a | D | Q | S | Y | H | A | T | S | K | Q | L |
| A | b | D | Q | S | C | H | A | T | S | K | Q | L |
| B | a | D | Q | S | Y | T | S | I | N | R | Q | L |
| B | b | D | Q | S | Y | T | S | I | N | R | Q | L |
| B | c | D | Q | S | Y | T | S | I | N | R | Q | L |
| C | a | N | K | D | Y | P | A | T | N | N | E | F |
| C | b | N | Q | D | Y | P | A | T | N | N | E | F |
| C | c | N | Q | D | Y | P | A | T | N | N | E | F |
| C | d | N | Q | D | Y | P | A | T | N | N | E | F |

Figure 57F:
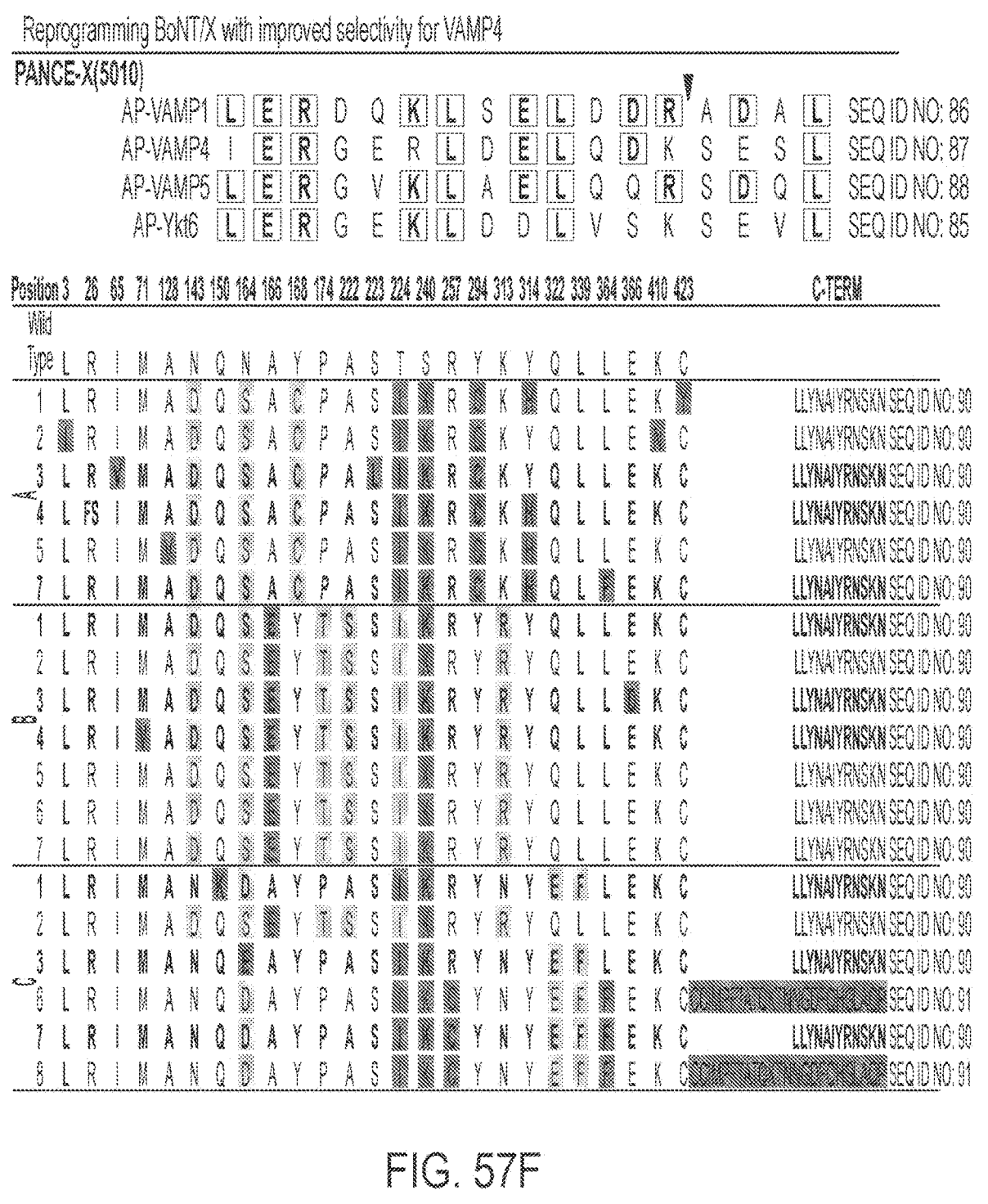

Reprogramming BoNT/X with improved selectivity for VAMP4

PANCE-X(5010)

| | | | | | | | | | | | | | | | | |
|---|---|---|---|---|---|---|---|---|---|---|---|---|---|---|---|---|
| AP-VAMP1 | L | E | R | D | Q | K | L | S | E | L | D | D | R | A | D | A | L | SEQ ID NO: 86 |
| AP-VAMP4 | I | E | R | G | E | R | L | D | E | L | Q | D | K | S | E | S | L | SEQ ID NO: 87 |
| AP-VAMP5 | L | E | R | G | V | K | L | A | E | L | Q | Q | R | S | D | Q | L | SEQ ID NO: 88 |
| AP-Ykt6 | L | E | R | G | E | K | L | D | D | L | V | S | K | S | E | V | L | SEQ ID NO: 85 |

Position 3  26  65  71  128 143 150 164 166 188 174 222 223 224 240 257 294 313 314 322 339 384 386 410 423                    C-TERM Wild Type  L R I M A N Q N A Y P A S T S R Y K Y Q L L E K C

| | Position | | | | | | | | | | | | | | | | | | | | | | | | | C-TERM | |
|---|---|---|---|---|---|---|---|---|---|---|---|---|---|---|---|---|---|---|---|---|---|---|---|---|---|---|---|---|
| 1 | L | R | I | M | A | D | Q | S | A | C | P | A | S | | | R | K | | Q | L | L | E | K | | LLYNAYRNSKN | SEQ ID NO: 90 |
| 2 | | R | I | M | A | D | Q | S | A | C | P | A | S | | | R | K | Y | Q | L | L | E | | C | LLYNAYRNSKN | SEQ ID NO: 90 |
| 3 | L | R | | M | A | D | Q | S | A | C | P | A | | | | R | | K | Y | Q | L | L | E | K | C | LLYNAYRNSKN | SEQ ID NO: 90 |
| 4 | L | FS | I | M | A | D | Q | S | A | C | P | A | S | | | R | | K | | Q | L | L | E | K | C | LLYNAYRNSKN | SEQ ID NO: 90 |
| 5 | L | R | I | M | | D | Q | S | A | C | P | A | S | | | R | | K | | Q | L | L | E | K | C | LLYNAYRNSKN | SEQ ID NO: 90 |
| 7 | L | R | I | M | A | D | Q | S | A | C | P | A | S | | | R | | K | | Q | L | | E | K | C | LLYNAYRNSKN | SEQ ID NO: 90 |
| 1 | L | R | I | M | A | D | Q | S | | | Y | | S | S | | | R | Y | | Y | Q | L | L | E | K | C | LLYNAYRNSKN | SEQ ID NO: 90 |
| 2 | L | R | I | M | A | D | Q | S | | | Y | | S | S | | | R | Y | | Y | Q | L | L | E | K | C | LLYNAYRNSKN | SEQ ID NO: 90 |
| 3 | L | R | I | M | A | D | Q | S | | | Y | | S | S | | | R | Y | | Y | Q | L | L | | K | C | LLYNAYRNSKN | SEQ ID NO: 90 |
| 4 | L | R | I | | A | D | Q | S | | | Y | | S | S | | | R | Y | | Y | Q | L | L | E | K | C | LLYNAYRNSKN | SEQ ID NO: 90 |
| 5 | L | R | I | M | A | D | Q | S | | | Y | | S | S | | | R | Y | | Y | Q | L | L | E | K | C | LLYNAYRNSKN | SEQ ID NO: 90 |
| 6 | L | R | I | M | A | D | Q | S | | | Y | | S | S | | | R | Y | | Y | Q | L | L | E | K | C | LLYNAYRNSKN | SEQ ID NO: 90 |
| 7 | L | R | I | M | A | D | Q | S | | | Y | | S | S | | | R | Y | | Y | Q | L | L | E | K | C | LLYNAYRNSKN | SEQ ID NO: 90 |
| 1 | L | R | I | M | A | N | | D | A | Y | P | A | S | | | R | Y | N | Y | E | | L | E | K | C | LLYNAYRNSKN | SEQ ID NO: 90 |
| 2 | L | R | I | M | A | D | Q | S | | | Y | | S | | | | R | Y | | Y | Q | L | L | E | K | C | LLYNAYRNSKN | SEQ ID NO: 90 |
| 3 | L | R | I | M | A | N | Q | | | A | Y | P | A | S | | | R | Y | N | Y | E | | L | E | K | C | LLYNAYRNSKN | SEQ ID NO: 90 |
| 6 | L | R | I | M | A | N | Q | D | A | Y | P | A | S | | | | Y | N | Y | E | | | E | K | C | | SEQ ID NO: 91 |
| 7 | L | R | I | M | A | N | Q | D | A | Y | P | A | S | | | | Y | N | Y | E | F | | E | K | C | LLYNAYRNSKN | SEQ ID NO: 90 |
| 5 | L | R | I | M | A | N | Q | D | A | Y | P | A | S | | | | Y | N | Y | E | | | E | K | C | | SEQ ID NO: 91 |

Blue: mutations enriched in low stringency selection
Orange: Mutations enriched in second round higher
stringency selection

|  | BoNT/X(wt) | X(5010)A3 | X(5010)B1 | X(5010)C1 |
|---|---|---|---|---|
| $k_{cat}/K_M$ (VAMP1) | $9.82 \times 10^5$ | $1.39 \times 10^4$ | $1.15 \times 10^4$ | $3.16 \times 10^4$ |
| $k_{cat}/K_M$ (VAMP4) | $1.35 \times 10^6$ | $1.57 \times 10^6$ | $3.46 \times 10^6$ | $6.07 \times 10^6$ |
| Fold-change in VAMP4: VAMP1 activity ratio | - | 82 | 219 | 140 |

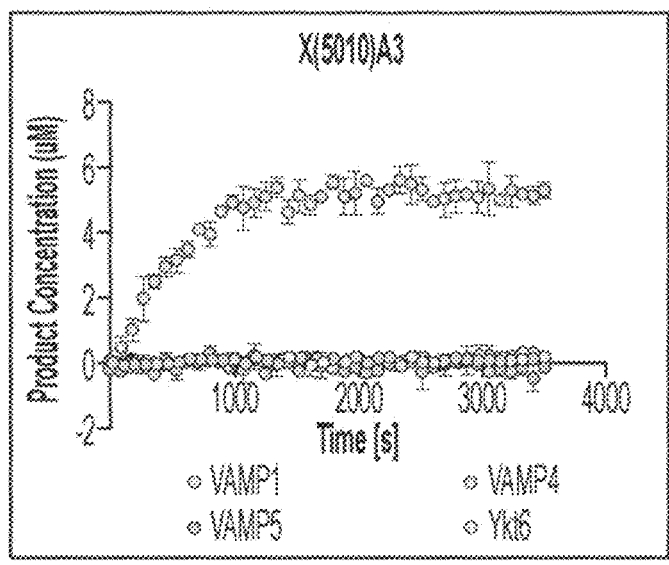
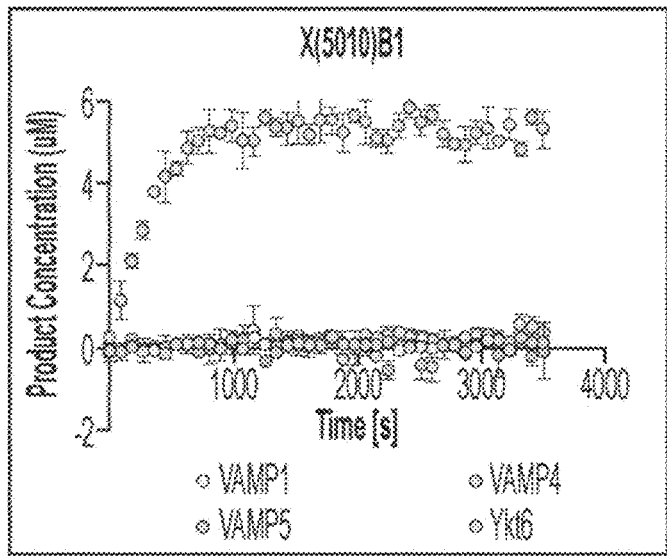
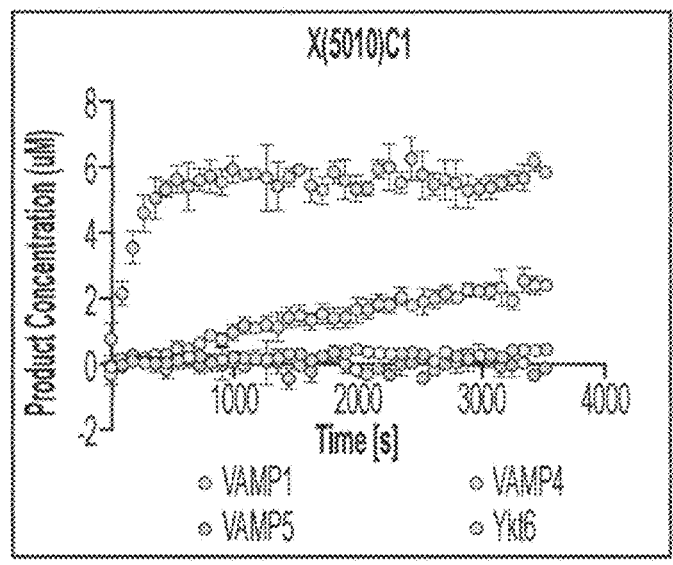
FIG. 58B

Positive Selection Trajectories

Trajectory A

| | | SEQ ID NO: |
|---|---|---|
| AP-SNAP25 | M G N E I D T Q N R Q I D R I M E K A D | SEQ ID NO: 92 |
| SS-E1 | M G N E I D T Q N R Q I D S I M E K A D | SEQ ID NO: 94 |
| SS-E2 | M G N E I D T Q N R Q I D S I M E K A D | SEQ ID NO: 95 |
| SS-E3 | M G S I L C D I D T Q N R Q I C S I M E K A D | SEQ ID NO: 96 |
| SS-E4 | M G S I L C D Q E I I D S I C S I M E K A D | SEQ ID NO: 97 |
| AP-PTEN | M G S I L C D Q E I I D S I C S I R I A D I N | SEQ ID NO: 98 |

Trajectory B

| | | SEQ ID NO: |
|---|---|---|
| AP-SNAP25 | M G N E I D T Q N R Q I D R I M E K A D | SEQ ID NO: 92 |
| SS-E1 | M G N E I D T Q N R Q I C S I M E K A D | SEQ ID NO: 88 |
| SS-E2 | M G N E I D T Q N R Q I C S I M E K A D | SEQ ID NO: 95 |
| SS-E3 | M G S I L C D I D T Q N R Q I C S I M E K A D | SEQ ID NO: 96 |
| SS-E4 | M G S I L C D Q E I I D S I C S I M E K A D | SEQ ID NO: 97 |
| AP-PTEN | M G S I L C D Q E I I D S I C S I R I A D I N | SEQ ID NO: 93 |

PANCE Negative Selection

| Selection | Positive selection (high) | Negative selection |
|---|---|---|
| 4130-E(122) | T3pos-sd5-PTEN-proB | T7neg-sd6-SNAP25-proD |
| 4130-E(720) | T3pos-sd5-PTEN-proB | T7neg-sd5-SNAP25-proD |
| 4130-E(721) | T3pos-sd5-PTEN-proB | T7neg-sd2-SNAP25-proD |
| 4130-E(722) | T3pos-sd5-PTEN-proB | T7neg-sd40-SNAP25-proD |

FIG. 59C

Phage population activity during positive selection

After Negative Selection

| | BoNT E(wt) | E.020617 | E.021317 | E.022717 | E.031017 | E.041917 | E(122)_P15A |
|---|---|---|---|---|---|---|---|
| AP-SNAP25 | 5.69 | 4.58 | 6.71 | 10.80 | 1.00 | 2.57 | 0.57 |
| SS.E1 | 1.29 | 2.51 | 7.31 | 8.79 | 1.05 | 1.09 | 0.50 |
| SS.E2 | 1.07 | 1.90 | 4.87 | 10.74 | 1.51 | 0.85 | 0.60 |
| SS.E3 | 0.81 | 1.31 | 1.56 | 0.75 | 1.32 | 0.88 | 0.61 |
| SS.E4 | 0.89 | 1.11 | 1.00 | 3.42 | 1.15 | 2.13 | 7.06 |
| AP-PTEN | 0.82 | 1.17 | 0.97 | 0.71 | 1.32 | 5.48 | |

FIG. 59D

EVOLVED BOTULINUM NEUROTOXINS AND USES THEREOF

CROSS-REFERENCE TO RELATED APPLICATIONS

This application is a national stage filing under 35 U.S.C. § 371 of International PCT Application PCT/US2020/042016, filed Jul. 14, 2020, which claims priority under 35 U.S.C. § 119(e) to U.S. Provisional Patent Application U.S. Ser. No. 62/874,443, filed on Jul. 15, 2019, each of which is incorporated herein by reference.

FEDERALLY SPONSORED RESEARCH

This invention was made with government support under HG009490, EB022376, GM118062 awarded by the National Institutes of Health. The government has certain rights in the invention.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on Jan. 11, 2022, is named H082470330US01-SEQ-KZM and is 179,520 bytes in size.

BACKGROUND

Over the last few decades, the medical community has witnessed a remarkable shift in the composition of pharmaceutical therapies from traditional small molecules to biomacromolecules (e.g., enzymes; compositions of multiple proteins, peptides, amino acids, polymers, nucleic acids). The growing number of macromolecular therapeutics is a result of their potential for highly specific interactions in biological systems and has been facilitated by improvements in molecular biology and biomolecule engineering. Despite their tremendous success, macromolecular therapies have been limited almost exclusively to extracellular targets due to the significant challenge of their controllable delivery into the cytoplasm. While a number of notable advances have been made in the area of macromolecular delivery, this critical problem remains a major barrier to the development and use of macromolecular therapeutics that address intracellular targets. As an alternative, several natural protein systems are capable of cytoplasmic self-delivery. However, the ability to reengineer these systems to imbue them with the necessary binding or catalytic activities and specificities for therapeutic effect is largely underexplored and underdeveloped.

SUMMARY

The disclosure relates to novel Botulinum neurotoxin (BoNT) protease variants and methods of evolving the same. As described herein, BoNT proteases are attractive candidates for evolution because BoNTs provide a built-in cytosolic delivery mechanism, which allows BoNTs to cleave intracellular targets. In some embodiments, evolved BoNT protease variants that cleave a desired substrate (e.g., a disease-associated intracellular protein (e.g., Vamp 7, PTEN, etc.)) are described herein. The disclosure is based, in part, on the discovery that BoNT protease variants that cleave target proteins lacking canonical BoNT cleavage substrates can be produced by phage-assisted continuous evolution (PACE), for example, as described in U.S. Pat. No. 9,023,594, issued May 5, 2015; U.S. Pat. No. 9,771,574, issued Sep. 26, 2017; U.S. patent application Ser. No. 15/713,403, filed Sep. 22, 2017 (now abandoned); International PCT Application PCT/US2009/056194, filed Sep. 8, 2009, published as WO 2010/028347 on Mar. 11, 2010; U.S. Provisional Patent Application Ser. No. 61/426,139, filed Dec. 22, 2010; U.S. Pat. No. 9,394,537, issued Jul. 19, 2016; U.S. Pat. No. 10,336,997, issued Jul. 2, 2019; U.S. patent application Ser. No. 16/410,767, filed May 13, 2019; International PCT Application PCT/US2011/066747, filed Dec. 22, 2011, published as WO 2012/088381 on Jun. 28, 2012; U.S. Provisional Patent Application Ser. No. 61/929,378 filed Jan. 20, 2014; U.S. Pat. No. 10,179,911, issued Jan. 15, 2019; U.S. patent application Ser. No. 16/238,386, filed Jan. 2, 2019; International PCT Application PCT/US2015/012022, filed Jan. 20, 2015; U.S. Provisional Patent Application Ser. No. 62/158,982, filed May 8, 2015; U.S. Provisional Patent Application Ser. No. 62/187,669, filed Jul. 1, 2015; U.S. Provisional Patent Application Ser. No. 62/067,194, filed Oct. 22, 2014; U.S. patent application Ser. No. 15/518,639, filed Apr. 12, 2017; and International PCT Application PCT/US2018/048134, filed Aug. 27, 2018; U.S. patent application Ser. No. 13/922,812, filed Jun. 20, 2013; International PCT Application PCT Application, PCT/US2015/057012, filed Oct. 22, 2015, published as WO 2016/077052; and International PCT Application PCT/US2016/027795, filed Apr. 15, 2016, published as WO 2016/168631, the entire contents of each of which are incorporated herein by reference.

In some embodiments, evolved BoNT protease variants as described herein may be expressed as a part of a full-length protein comprising a BoNT light chain (LC) and a BoNT heavy chain (HC). Typically, the catalytic protease domain is located in the light chain (LC) of the BoNT. The BoNT HC encodes a domain which generally enables the BoNT protease variant to cross cellular membranes, where the LC may cleave target proteins in the intracellular environment, making them useful for treating diseases associated with aberrant activity of intracellular proteins (e.g., cancer, neurological disorders, etc.), such as Soluble NSF Attachment Protein Receptors (SNARE) proteins (e.g., VAMP7, etc.). It should be appreciated that evolved BoNT protease variants described herein may comprise an evolved BoNT LC, or both an evolved BoNT LC and HC. In some embodiments, an evolved BoNT protease variant comprises a wild-type BoNT HC. In some embodiments, an evolved BoNT protease variant comprises a BoNT HC having one or more amino acid mutations relative to a wild-type BoNT HC. In some embodiments, an evolved BoNT protease variant comprises a wild-type BoNT LC. In some embodiments, an evolved BoNT protease variant comprises a BoNT LC having one or more amino acid mutations relative to a wild-type BoNT LC. In some embodiments, the receptor-binding domain of the BoNT HC has been replaced by a protein domain capable of binding to a cell surface receptor or ligand. In some embodiments, this protein domain may take the form of an antibody, lectin, monobody, single-chain variable fragment (scFv), hormone, signaling factor, or other targeting moiety.

Accordingly, in some aspects, the disclosure provides a protein that is evolved from a wild-type Botulinum neurotoxin serotype F (e.g., an evolved BoNT F protease variant, also referred to as a "BoNT F variant") to cleave a non-canonical (i.e., non-native) BoNT F substrate, for example, VAMP7. In some embodiments, the disclosure provides a protein that is evolved from or evolved to cleave the canonical BoNT F substrate VAMP1 with lower efficiency than wild-type BoNT F. In some embodiments, the disclosure provides a protein that is evolved from a wild-type BoNT F evolved to not cleave the canonical BoNT F substrate, VAMP1. In some embodiments, the disclosure provides a protein that is evolved from a wild-type BoNT F that does not cleave VAMP1.

In some aspects, the disclosure provides a protein that is evolved from a wild-type Botulinum neurotoxin serotype X (e.g., an evolved BoNT X protease variant, also referred to as a "BoNT X variant") to cleave a non-canonical (i.e., non-native) BoNT X substrate, for example, VAMP7. In some embodiments, the disclosure provides a protein that is evolved from a BoNT X protein, or evolved to cleave at least one canonical BoNT X substrate (e.g., VAMP1/2/3/4/5, Ykt6) with lower efficiency than wild-type BoNT X. In some embodiments, the disclosure provides a protein that is evolved from a wild-type BoNT X evolved to not cleave at least one canonical BoNT X substrate (e.g., VAMP1/2/3/4/5, Ykt6, etc.). In some embodiments, the disclosure provides a protein that is evolved from a wild-type BoNT X evolved to not cleave not substantially cleave at least one canonical BoNT X substrate (e.g., VAMP1/2/3/4/5, Ykt6). In some embodiments the disclosure provides a protein that is evolved from a wild-type BoNT X evolved to cleave only VAMP4 and not other VAMP proteins.

In some aspects, the disclosure provides a protein that is evolved from a wild-type Botulinum neurotoxin serotype E (e.g., an evolved BoNT E protease variant, also referred to as a "BoNT E variant") to cleave a non-canonical (i.e., non-native) BoNT E substrate, for example, PTEN. In some embodiments, the disclosure provides a protein that is evolved from or evolved to cleave the canonical BoNT E substrate SNAP25 with lower efficiency than wild-type BoNT E. In some embodiments, the disclosure provides a protein that is evolved from a wild-type BoNT E evolved to not cleave the canonical BoNT E substrate, SNAP25. In some embodiments, the disclosure provides a protein that is evolved from a wild-type BoNT E evolved to not cleave not substantially cleave SNAP25.

In some embodiments, wild-type BoNT F comprises the sequence set forth in SEQ ID NO.: 6. In some embodiments, wild-type BoNT X comprises the sequence set forth in SEQ ID NO.: 8. In some embodiments, wild-type BoNT E comprises the sequence set forth in SEQ ID NO: 5.

In some aspects, the disclosure provides a protein comprising an amino acid sequence that is at least 90% (e.g., at least 95%, at least 96%, at least 97%, etc.) identical to SEQ ID NO.: 6 (wild-type BoNT F), SEQ ID NO: 5 (wild-type BoNT E), or SEQ ID NO.: 8 (wild-type BoNT X). In some embodiments, the disclosure relates to a protein comprising an amino acid sequence at least 90% (e.g., at least 95%, at least 96%, at least 97%, etc.) identical to SEQ ID NOs.: 1, wherein the protein comprises at least one of the amino acid mutations set forth in Tables 1A, 6, 7, 8, and/or 9. In some embodiments, the disclosure relates to a protein comprising at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 amino acid mutations as compared to the sequence of SEQ ID NO.: 6. In some embodiments, the disclosure relates to a protein comprising an amino acid sequence at least 90% (e.g., at least 95%, at least 96%, at least 97%, etc.) identical to SEQ ID NOs.: 8, wherein the protein comprises at least one of the amino acid mutations set forth in Table 1B, Tables 10-12, or FIGS. 55D, 56B, 57C, 57E, and 57F. In some embodiments, the disclosure relates to a protein comprising at least 1, at least 2, at least 3, at least 4, at least 5, at least 6, at least 7, or at least 8 amino acid mutations as compared to the sequence of SEQ ID NO.: 8. In some embodiments, the disclosure relates to a protein comprising an amino acid sequence at least 90% (e.g., at least 95%, at least 96%, at least 97%, etc.) identical to SEQ ID NO.: 5, wherein the protein comprises at least one of the amino acid mutations set forth in Tables 13-14, or FIGS. 59A-59G. In some embodiments, the disclosure relates to a protein comprising at least 1, at least 2, at least 3, at least 4, at least 5, at least 6, at least 7, or at least 8 amino acid mutations as compared to the sequence of SEQ ID NO.: 5.

In some aspects, the disclosure relates to evolved BoNT protease variants that cleave intracellular vesicle-associated membrane proteins (VAMPs). VAMPs are members of the SNARE protein family and typically mediate vesicle fusion, such as synaptic vesicle fusion and vesicular secretion. Without wishing to be bound by any particular theory, aberrant function of VAMPs is associated with certain diseases, for example, motor neuron diseases. Thus, evolved BoNT proteases that cleave certain VAMPs, in some embodiments, are useful for reducing VAMP protein activity inside a cell or a subject. In some embodiments, a protein (e.g., a BoNT F variant) cleaves a vesicle-associated membrane (VAMP) protein, for example, a VAMP7 protein. In some embodiments, the VAMP7 protein comprises the sequence set forth in SEQ ID NO.: 35.

In some embodiments, a protein (e.g., a BoNT F variant) cleaves a VAMP1. In some embodiments, the VAMP1 protein comprises the sequence set forth in SEQ ID NO.: 32. In some embodiments, a protein cleaves a target sequence comprising SEQ ID NO.: 33 (TSNRRLQQTQAQVEEVV-DIIRVNVDKVLERDQKLSELDDRADALQAGASQFES-SAAKL KR (SEQ ID NO.: 33)).

In some embodiments, a BoNT F variant protease comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 amino acid mutations set forth in Tables 1A, 6, 7, 8, and/or 9.

In some embodiments, a BoNT X variant protease comprises at least 2, at least 3, at least 4, at least 5, at least 6, at least 7, or at least 8 amino acid mutations set forth in Table 1B, Tables 10-12, or FIGS. 55D, 56B, 57C, 57E, and 57F.

In some embodiments, at least one of the amino acid sequence mutations of a BoNT F variant is introduced at an amino acid position selected from the group consisting of Y72, V106, V131, S141, S166, S167, M174, E200, S224, R240, S350, F360, Y372, N396, P410, and G420.

In some embodiments, at least one of the amino acid sequence mutations of a BoNT F variant is introduced at an amino acid position selected from the group consisting of Y72H, V106A, V131G, S141T, S166Y, S167I, M174T, E200G, S224I, R240L, S350G, F360L, Y372H, N396H, P410L, and GLVEKIVKF*420AWLRKS* (SEQ ID NO: 44). When used herein, "GLVEKIVKF*420AWLRKS*" (SEQ ID NO: 44) shall refer to a mutation of the terminal residues of the variant protease, such that the replaced sequence (e.g., GLVEKIVKF* (SEQ ID NO: 45), or simply G) precedes the first residue in such sequence (e.g., G at position 420) and is replaced by the subsequent sequence (e.g., AWLRKS* (SEQ ID NO: 46)), and the "*" shall represent a stop codon.

In some embodiments, at least one of the amino acid mutations of a BoNT F variant is selected from the group consisting of S69, Y72, V106, S148, 1150, A158, S166, S167, G177, N184, E200, S224, A232, R240, S350, F360, Y372, L381, N396, P410, and G420.

In some embodiments, at least one of the amino acid mutations of a BoNT F variant is selected from the group consisting of S69L, Y72H, V106A, S148N, 1150V, A158P, S166Y, S167I, G177D, N184H, E200G, S224I, A232S, R240L, S350G, F360L, Y372N, L381M, N396H, P410L, GLVEKIVKF*420AWLRKS* (SEQ ID NO: 44).

In some embodiments, a BoNT F variant comprises the following mutation: S166Y.

In some embodiments, a BoNT F variant comprises the following mutations: R41H, K96N, S166Y, R240L/C, Y372H, and D414G.

In some embodiments, a BoNT F variant comprises the following mutations: S166Y, N184H/K, R240L, S350G, F360L, Y372H, P410L, and D414G.

In some embodiments, a BoNT F variant comprises the following mutations: S166Y, N184K, R240L, S350G, F360L, Y372H, N396H, P410L, GLVEKIVKF*420AWLRKS* (SEQ ID NO: 44), and E423K.

In some embodiments, a BoNT F variant comprises the following mutations: V106A, N165S, S166Y, S167I, N184K, R240L, S350G, F360L, Y372H, N396H, P410L, GLVEKIVKF*420AWLRKS* (SEQ ID NO: 44), and E423K.

In some embodiments, a BoNT F variant comprises the following mutations: V106A, Y113D/S, S166Y, S167I, N184H/K/S, E200K, R240L, Y244C, S350G, F360L, Y372H, N396H, P410L, GLVEKIVKF*420AWLRKS* (SEQ ID NO: 44), and E423K.

In some embodiments, a BoNT F variant comprises the following mutations: E66D, V106A, S166Y, S167I, D175G, N184K, E200G, S224I, R240L/F, T335S, S350G, F360L, Y372H, N396H, P410L, D418Y, and GLVEKIVKF*420AWLRKS* (SEQ ID NO: 44).

In some embodiments, a BoNT F variant comprises the following mutations: Y72H, N99S, V106A, V131G, S141T, S166Y, S167I, M174T, N184T, V193M, E200G, S224I, R240L/F, S350G, F360L, Y372H, N396H, P410L, GLVEKIVKF*420AWLRKS* (SEQ ID NO: 44).

In some embodiments, a BoNT F variant comprises the following mutations: Y72H, V106A, V131G, S141T, S166Y, S167I, M174T, E200G, S224I, R240L, S350G, F360L, Y372H, N396H, P410L, and GLVEKIVKF*420AWLRKS* (SEQ ID NO: 44).

In some embodiments, a BoNT F variant comprises the following mutations: S69L, Y72H, V106A, S148N, 1150V, A158P, S166Y, S167I, G177D, N184H, E200G, S224I, A232S, R240L, S350G, F360L, Y372N, L381M, N396H, P410L, and GLVEKIVKF*420AWLRKS* (SEQ ID NO: 44).

In some embodiments, at least one of the amino acid mutations of a BoNT F variant (e.g., a BoNT F variant described in Tables 1A, 6, 7, 8, and/or 9) is selected from the group consisting of R303H, T335S, S350G, I354V, S166Y, S167I, M147T, D175G, E200K, K31N, V106A, Y113D, E200G, R240L, V131G, S141T, N99S, R240C, F360L, G177D, N184H, R240F, Y113S, V131F, N184K, S69L, Y72H, K96N, N184T, S148N, 1150V, A158P, L381M, N396H, P410L, Y372H, I412N, D141G, D418Y, Y372N, E423K, Y244C, V193M, Y372P, N165S, S224I, A281V, E66D, R41H, A232S, V106AWLRKS* (SEQ ID NO: 47), and GLVEKIVKF*420AWLRKS* (SEQ ID NO: 44). In some embodiments, a BoNT F variant comprises the amino acid sequence as set forth in any one of SEQ ID NOs.: 12-30.

In some embodiments, an evolved BoNT protease variant comprises a BoNT heavy chain. Generally, a BoNT heavy chain comprises a neurotoxin HCC domain, and a neurotoxin translocation domain (HCN). Without wishing to be bound by any particular theory, the HCC domain binds to specific receptors typically found on the presynaptic terminal of a cell, and the HCN domain translocates the BoNT LC into the cell, resulting in intracellular delivery of the catalytic domain of the protease. In some embodiments, an evolved BoNT protease variant (e.g., a BoNT F variant) further comprises a neurotoxin HCC domain, and/or a neurotoxin translocation domain (HCN), for example, a Botulinum toxin HCC or HCN domain or a Tetanus toxin HCC or HCN domain. In some embodiments, the HCN domain comprises SEQ ID NO.: 10 (BoNT F HC$_N$, translocation domain). In some embodiments, the HCC domain comprises SEQ ID NO.: 11 (BoNT F HC$_C$, Binding domain).

In some aspects, the disclosure provides a pharmaceutical composition comprising a protein (e.g., a BoNT F variant) as described herein and a pharmaceutically acceptable excipient.

In some aspects, the disclosure provides an isolated nucleic acid encoding a BoNT F variant comprising an amino acid sequence as set forth in any one of SEQ ID NOs.: 12-31. In some aspects, the isolated nucleic acid is contained and expressed in a host cell, for example, a bacterial cell, yeast cell, or mammalian cell (e.g., human cell, primate cell, mouse cell, etc.).

In some aspects, the disclosure provides a method of cleaving an intracellular protein, the method comprising delivering to a cell a BoNT F variant as described herein, wherein the protein contacts and cleaves the intracellular protein in the cell. In some embodiments, the cell is in a subject, for example, a mammalian subject, such as a human or mouse.

In some aspects, the disclosure provides a method for reducing VAMP7 activity in a subject, the method comprising administering to the subject an effective amount of a BoNT F variant as described herein. In some embodiments, the subject has or is suspected of having a disease characterized by increased or aberrant VAMP7 activity, for example, cancer, transplantation rejection, graft-versus-host disease, or a neurological disease.

In some aspects, the disclosure relates to a method of reducing PTEN activity in a subject, the method comprising administering to the subject an effective amount of a BoNT E variant as described herein.

In some aspects, the disclosure relates to methods of producing an evolved BoNT F, E, or X variant using phage-assisted continuous evolution (PACE). The general concept of PACE technology been described, for example, U.S. Pat. No. 9,023,594, issued May 5, 2015; U.S. Pat. No. 9,771,574, issued Sep. 26, 2017; U.S. patent application Ser. No. 15/713,403, filed Sep. 22, 2017 (now abandoned); International PCT Application PCT/US2009/056194, filed Sep. 8, 2009, published as WO 2010/028347 on Mar. 11, 2010; U.S. Provisional Patent Application Ser. No. 61/426, 139, filed Dec. 22, 2010; U.S. Pat. No. 9,394,537, issued Jul. 19, 2016; U.S. Pat. No. 10,336,997, issued Jul. 2, 2019; U.S. patent application Ser. No. 16/410,767, filed May 13, 2019; International PCT Application PCT/US2011/066747, filed 7                                                                                  8

Dec. 22, 2011, published as WO 2012/088381 on Jun. 28, 2012; U.S. Provisional Patent Application Ser. No. 61/929, 378 filed Jan. 20, 2014; U.S. Pat. No. 10,179,911, issued Jan. 15, 2019; U.S. patent application Ser. No. 16/238,386, filed Jan. 2, 2019; International PCT Application PCT/US2015/ 012022, filed Jan. 20, 2015; U.S. Provisional Patent Application Ser. No. 62/158,982, filed May 8, 2015; U.S. Provisional Patent Application Ser. No. 62/187,669, filed Jul. 1, 2015; U.S. Provisional Patent Application Ser. No. 62/067, 194, filed Oct. 22, 2014; U.S. patent application Ser. No. 15/518,639, filed Apr. 12, 2017; and International PCT Application PCT/US2018/048134, filed Aug. 27, 2018; U.S. patent application Ser. No. 13/922,812, filed Jun. 20, 2013; International PCT Application PCT Application, PCT/US2015/057012, filed Oct. 22, 2015, published as WO 2016/077052; and International PCT Application PCT/US2016/027795, filed Apr. 15, 2016, published as WO 2016/168631, the entire contents of each of which are incorporated herein by reference.

In some embodiments, evolved proteases described herein (e.g., proteases evolved using PACE technology described herein) cleave certain substrates (e.g., VAMP1, VAMP7, PTEN, etc.) with higher efficiency and/or specificity relative to previously described BoNT proteases. In some embodiments, evolved proteases described herein (e.g., proteases evolved using PACE technology described herein) cleave certain substrates (e.g., VAMP1, VAMP7, PTEN, etc.) while simultaneously not cleaving other substrates (e.g., VAMP1, VAMP7, etc.).

In some aspects, the present disclosure relates to application of the evolution of protease variants of BoNT X. In some embodiments, a BoNT X variant has mutations at the following positions: V98, E113, A166, and S280. In some embodiments, a BoNT X variant has the following mutations: V98G, E113K, A166E, and S280L. In some embodiments, a BoNT X variant has mutations at the following positions: A166. In some embodiments, a BoNT X variant has the following mutation: A166E. In some embodiments, a BoNT X variant has mutations at the following positions: A166, S405, and R435. In some embodiments, a BoNT X variant has the following mutations: A166E, S405L, and R435L. In some embodiments, a BoNT X variant has mutations at the following positions: E68, Q150, and A166. In some embodiments, a BoNT X variant has the following mutations: E68A, Q150L, and A166E. In some embodiments, a BoNT X variant has mutations at the following positions: A166 and R435. In some embodiments, a BoNT X variant has the following mutations: A166E and R435L. In some embodiments, a BoNT X variant has mutations at the following positions: V98, E113, A166, and R435. In some embodiments, a BoNT X variant has the following mutations: V98G, E113K, A166E, and R435L. In some embodiments, a BoNT X variant has an amino acid sequence comprising a sequence selected from SEQ ID NOs.: 36-43. In some embodiments, a BoNT X variant has at least one mutation at the following positions: E68, V98, E113, Q150, A166, S280, S405, and R435. In some embodiments, a BoNT X variant has at least one mutation selected from the following mutations: E68A, V98G, E113K, Q150L, A166E, S280L, S405L, and R435L.

In some embodiments, a BoNT-X protease has a mutation in at least one of the following positions: N144, A166, T167, and Y314. In some embodiments, a BoNT-X protease has a mutation in at least one of the following positions: A166, T167, R257, Q322, L364, and S413. In some embodiments, the C-terminal region of a BoNT-X protease comprises the amino acid sequence YLNSKN (SEQ ID NO: 48). In some embodiments, a BoNT-X protease has a mutation in at least one of the following positions: A166, T167, R257, and Q322. In some embodiments, a BoNT-X protease has a mutation in at least one of the following positions: A166, T167, R257, Q322, L364, and S413. In some embodiments, a BoNT-X protease has a mutation in at least one of the following positions: N143, N148, A166, T167, Y314, and L364. In some embodiments, a BoNT-X protease has a mutation in at least one of the following positions: A166, T167, Q322, and L364. In some embodiments, the C-terminal region of a BoNT-X protease comprises the amino acid sequence TATQKTNNGDFQHGLARP* (SEQ ID NO: 49). In some embodiments, a BoNT-X protease has a mutation in at least one of the following positions: N143, N148, A166, T167, Y314, and L364. In some embodiments, a BoNT-X protease has a mutation in at least one of the following positions: V98, E113, N143, N148, A166, T167, V345, and L364. In some embodiments, a BoNT-X protease has a mutation in at least one of the following positions: R23, V98, A166, and T167. In some embodiments, a BoNT-X protease has a mutation in at least one of the following positions: D133, N148, A166, T167, and S279. In some embodiments, a BoNT-X protease has a mutation in at least one of the following positions: A166, T167, I175, L364, and S391. In some embodiments, a BoNT-X protease has a mutation in at least one of the following positions: V98, E100, N143, N148, A166, T167, S279, and L416. In some embodiments, a BoNT-X protease has a mutation at position A166. In some embodiments, a BoNT-X protease has a mutation in at least one of the following positions: N143, A166, R257, L267, L268, Q322, S349, and L364. In some embodiments, a BoNT-X protease has a mutation in at least one of the following positions: N143, and A166. In some embodiments, the C-terminal region of a BoNT-X protease comprises the amino acid sequence AFTATQKSNNGDFQHGLAQP* (SEQ ID NO: 50). In some embodiments, a BoNT-X protease has a mutation in at least one of the following positions: N143, A166, L225, R257, L267, L268, T341, S349, L364, and R425. In some embodiments, a BoNT-X protease has a mutation in at least one of the following positions: A166, T167, and A218. In some embodiments, a BoNT-X protease has a mutation in at least one of the following positions: N148, A166, T167, A218, N241, and K285. In some embodiments, a BoNT-X protease has a mutation in at least one of the following positions: N143, A166, and G169. In some embodiments, a BoNT-X protease has a mutation in at least one of the following positions: N143, A166, R257, L267, L268, S349, and L364.

In some embodiments, a BoNT-X protease has at least one of the following mutations: N144L, A166E, T167I, and Y314S. In some embodiments, a BoNT-X protease has at least one of the following mutations: A166E, T167I, R257C, Q322K, L364I, and S413F. In some embodiments, the C-terminal region of a BoNT-X protease comprises the amino acid sequence YLNSKN (SEQ ID NO.: 48). In some embodiments, a BoNT-X protease has at least one of the following mutations: A166E, T167I, R257C, and Q322K. In some embodiments, a BoNT-X protease has at least one of the following mutations: A166E, T167I, R257C, Q322K, L364I, and S413F. In some embodiments, a BoNT X protease has at least one of the following mutations: N143D, N148T, A166E, T167I, Y314N, and L364I.

In some embodiments, a BoNT-X protease has at least one of the following mutations: A166E, T167I, Q322K, and L364V. In some embodiments, the C-terminal region of a BoNT-X protease comprises the amino acid sequence TATQKTNNGDFQHGLARP* (SEQ ID NO.: 49). In some embodiments, a BoNT-X protease has at least one of the following mutations: N143D, N148T, A166E, T167I, Y314C, and L364I. In some embodiments, a BoNT-X protease has at least one of the following mutations: V98G, E113K, N143D, N148T, A166E, T167I, V345E, and L364I. In some embodiments, a BoNT-X protease has at least one of the following mutations: R23S, V98G, A166E, T167I. In some embodiments, a BoNT-X protease has at least one of the following mutations: D133N, N148S, A166E, T167I, and S279P. In some embodiments, a BoNT-X protease has at least one of the following mutations: A166E, T167I, I175V, L364I, and S391G. In some embodiments, a BoNT-X protease has at least one of the following mutations: V98G, E100D, N143D, N148T, A166E, T167I, S279P, and L416F. In some embodiments, a BoNT-X protease has at least one of the following mutations: A166E, and YLNSKN (SEQ ID NO: 48). In some embodiments, a BoNT-X protease has at least one of the following mutations: N143D, A166E, R257C, L267I, L268I, Q322K, S349F, and L364I. In some embodiments, a BoNT-X protease has at least one of the following mutations: N143D, and A166E. In some embodiments, the C-terminal region of a BoNT-X protease comprises the amino acid sequence AFTATQKSNNGDFQHGLAQP* (SEQ ID NO.: 50). In some embodiments, a BoNT-X protease has at least one of the following mutations: N143D, A166E, L225W, R257C, L267I, L268I, T341P, S349F, L364I, and R425L. In some embodiments, a BoNT-X protease has at least one of the following mutations: A166E, T167I, and A218V. In some embodiments, a BoNT-X protease has at least one of the following mutations: N148T, A166E, T167A, A218V, N241I, and K285N. In some embodiments, a BoNT-X protease has at least one of the following mutations: N143D, A166E, and G169R. In some embodiments, a BoNT-X protease has at least one of the following mutations: N143D, A166E, R257C, L267I, L268I, S349F, and L364I.

In some embodiments, a BoNT-X protease has a mutation in at least one of the following positions: V98, E113, Q150, A166, and S280. In some embodiments, a BoNT-X protease has a mutation at position A166. In some embodiments, a BoNT-X protease has a mutation in at least one of the following positions: A166, S405, and R435. In some embodiments, a BoNT-X protease has a mutation in at least one of the following positions: E68, Q150, and A166. In some embodiments, a BoNT-X protease has a mutation in at least one of the following positions: A166, and R435. In some embodiments, a BoNT-X protease has a mutation in at least one of the following positions: V98, E113, A166, and R435.

In some embodiments, a BoNT-X protease has at least one of the following mutations: V98G, E113K, Q150Q, A166E, and S280L. In some embodiments, a BoNT-X protease has at least one of the following mutations: A166E. In some embodiments, a BoNT-X protease has at least one of the following mutations: A166E, S405L, and R435L. In some embodiments, a BoNT-X protease has at least one of the following mutations: E68A, Q150L, and A166E. In some embodiments, a BoNT-X protease has at least one of the following mutations: A166E, and R435L. In some embodiments, a BoNT-X protease has at least one of the following mutations: V98G, E113K, A166E, and R435L.

In some embodiments, a BoNT-X protease has a mutation in at least one of the following positions: N143, N148, A166, T167, R257, L267, L268, Y314, Q322, S349, L364, and S413.

In some embodiments, a BoNT-X protease has at least one of the following mutations: N143N, N148N, A166E, T167I, R257C, L267L, L268L, Y314Y, Q322K, S349S, L364I, and S413F. In some embodiments, a BoNT-X protease has at least one of the following mutations: N143D, N148T, A166E, T167I, R257R, L267L, L268L, Y314N, Q322Q, S349S, L364I, and S413S. In some embodiments, a BoNT-X protease has at least one of the following mutations: N143D, N148N, A166E, T167T, R257C, L267I, L268I, Y314Y, Q322K, S349F, L364I, and S413S.

In some embodiments, a BoNT-X protease has a mutation in at least one of the following positions: N143, N148, A166, T167, Y314, and L364.

In some embodiments, a BoNT-X protease has at least one of the following mutations: N143D, N148T, A166E, T167I, Y314N, and L364I.

In some embodiments, a BoNT-X protease has a mutation in at least one of the following positions: L3, R26, I65, M71, A128, N143, Q150, N164, A166, Y168, P174, A222, S223, T224, S240, R257, Y294, K313, Y314, Q322, L339, L364, E366, K410, and C423.

In some embodiments, a BoNT-X protease has at least one of the following mutations: N143D, N164S, Y168C, T224I, S240K, Y294C, Y314H, and C423Y. In some embodiments, a BoNT-X protease has at least one of the following mutations: L3I, N143D, N164S, Y168C, T224I, S240K, Y294C, and K410N. In some embodiments, a BoNT-X protease has at least one of the following mutations: I65V, N143D, N164S, Y168C, S223L, T224I, S240K, and Y294C. In some embodiments, a BoNT-X protease has at least one of the following mutations: R26F, N143D, N164S, Y168C, T224I, S240K, Y294C, and Y314H. In some embodiments, a BoNT-X protease has at least one of the following mutations: R26S, N143D, N164S, Y168C, T224I, S240K, Y294C, and Y314H. In some embodiments, a BoNT-X protease has at least one of the following mutations: A128V, N143D, N164S, Y168C, T224I, S240K, Y294C, and Y314H. In some embodiments, a BoNT-X protease has at least one of the following mutations: N143D, N164S, Y168C, T224I, S240K, Y294C, Y314H, and L364F. In some embodiments, a BoNT-X protease has at least one of the following mutations: N143D, N164S, A166E, P174T, A222S, T224I, S240K, and K313R. In some embodiments, a BoNT-X protease has at least one of the following mutations: N143D, N164S, A166E, P174T, A222S, T224I, S240K, and K313R. In some embodiments, a BoNT-X protease has at least one of the following mutations: N143D, N164S, A166E, P174T, A222S, T224I, S240K, K313R, and E366D. In some embodiments, a BoNT-X protease has at least one of the following mutations: M71V, N143D, N164S, A166E, P174T, A222S, T224I, S240K, and K313R. In some embodiments, a BoNT-X protease has at least one of the following mutations: N143D, N164S, A166E, P174T, A222S, T224I, S240K, and K313R. In some embodiments, a BoNT-X protease has at least one of the following mutations: N143D, N164S, A166E, P174T, A222S, T224I, S240K, and K313R. In some embodiments, a BoNT-X protease has at least one of the following mutations: N143D, N164S, A166E, P174T, A222S, T224I, S240K, and K313R. In some embodiments, a BoNT-X protease has at least one of the following mutations: Q150K, N164D, T224I, S240K, K313N, Q322E, and L339F. In some embodiments, a BoNT-X protease has at least one of the following mutations: N143D, N164S, A166E, P174T, A222S, T224I, S240K, and K313R. In some embodiments, a BoNT-X protease has at least one of the following mutations: N164E, T224I, S240K, K313N, Q322E, and L339F. In some embodiments, a BoNT-X protease has at least one of the following mutations: N164D, T224I, S240K, R257C, K313N, Q322E, L339F, and L364F. In some embodiments, a BoNT-X protease has at least one of the following mutations: N164D, T224I, S240K, R257C, K313N, Q322E, L339F, and L364F. In some embodiments, a BoNT-X protease has at least one of the following mutations: N164D, T224I, S240K, R257C, K313N, Q322E, L339F, and L364F.

In some embodiments, a BoNT-X protease has a mutation in at least one of the following positions: N143, Q150, N164, Y168, P174, A222, T224, S240, K313, Q322, and L339.

In some embodiments, a BoNT-X protease has at least one of the following mutations: N143D, N164S, and P174I. In some embodiments, a BoNT-X protease has at least one of the following mutations: N143D, N164S, Y168C, and P174I. In some embodiments, a BoNT-X protease has at least one of the following mutations: N143D, N164S, P174T, A222S, T224I, S240N, and K313R. In some embodiments, a BoNT-X protease has at least one of the following mutations: N143D, N164S, P174T, A222S, T224I, S240N, and K313R. In some embodiments, a BoNT-X protease has at least one of the following mutations: N143D, N164S, P174T, A222S, T224I, S240N, and K313R. In some embodiments, a BoNT-X protease has at least one of the following mutations: Q150K, N164D, S240N, K313N, Q322E, and L339F. In some embodiments, a BoNT-X protease has at least one of the following mutations: N164D, S240N, K313N, Q322E, and L339F. In some embodiments, a BoNT-X protease has at least one of the following mutations: N164D, S240N, K313N, Q322E, and L339F. In some embodiments, a BoNT-X protease has at least one of the following mutations: N164D, S240N, K313N, Q322E, and L339F.

In some embodiments, a BoNT-E protease has a mutation in at least one of the following positions: C26, Q27, E28, 135, G49, H56, D65, E79, S99, G101, N118, D156, E159, N161, S162, S163, S166, M172, I203, I232, T242, R244, N248, I262, I263, A313, I316, G353, Q354, Y355, Y357, K359, N365, 5367, N390, G403, and L404.

In some embodiments, a BoNT-E protease has at least one of the following mutations: Q27H, S99A, G101S, N118D, E159L, N161Y, S162Q, S163R, M172K, I232T, Q354R, Y357Y, and L404*. In some embodiments, a BoNT-E protease has at least one of the following mutations: C26Y, Q27H, S99A, G101S, N118D, D156N, E159L, N161Y, S162Q, S163R, M172K, I232T, N248K, Q354R, Y355P, and Y357F. In some embodiments, a BoNT-E protease has at least one of the following mutations: C26Y, Q27H, S99A, G101S, N118D, D156N, E159L, N161Y, S162Q, S163R, M172K, I232T, N248K, I262T, Q354W, Y357F, and N390D. In some embodiments, a BoNT-E protease has at least one of the following mutations: Q27H, S99A, G101S, N118D, E159L, N161Y, S162Q, S163R, M172K, I232T, N248K, G353E, Q354R, Y355P, and Y357F. In some embodiments, a BoNT-E protease has at least one of the following mutations: Q27H, S99A, G101S, N118D, E159L, N161Y, S162Q, S163R, M172K, I232T, N248K, Q354W, Y355P, Y357F, and N390D. In some embodiments, a BoNT-E protease has at least one of the following mutations: C26Y, Q27H, D65G, S99A, G101S, N118D, D156N, E159L, N161Y, S162Q, S163R, M172K, I232T, N248K, Q354R, Y355P, Y357F, and L404*. In some embodiments, a BoNT-E protease has at least one of the following mutations: Q27H, S99A, G101S, N118D, D156N, E159L, N161Y, S162Q, S163R, M172K, I232T, N248K, I316T, Q354W, and Y357F. In some embodiments, a BoNT-E protease has at least one of the following mutations: Q27H, S99T, G101S, N118D, D156N, E159L, N161Y, S162Q, S163R, M172K, I232T, T242A, N248K, Q354R, Y355P, and Y357F. In some embodiments, a BoNT-E protease has at least one of the following mutations: Q27H, S99A, G101S, N118D, E159L, N161Y, S162Q, S163R, M172K, I232T, I316T, Q354R, Y357Y, and L404*. In some embodiments, a BoNT-E protease has at least one of the following mutations: C26Y, Q27H, S99A, G101S, N118D, D156N, E159L, N161Y, S162Q, S163R, S166R, M172K, I232T, N248K, I263V, Q354R, Y355P, Y357F, and S367F. In some embodiments, a BoNT-E protease has at least one of the following mutations: C26Y, Q27H, S99A, G101S, N118D, D156N, E159L, N161Y, S162Q, S163R, M172K, I232T, R244V, N248K, Q354R, Y355P, Y357F, and K359R. In some embodiments, a BoNT-E protease has at least one of the following mutations: C26Y, Q27H, E79D, S99A, G101S, N118D, D156N, E159L, N161Y, S162Q, S163R, M172K, 1203V, I232T, N248K, Q354R, Y355H, and Y357F. In some embodiments, a BoNT-E protease has at least one of the following mutations: C26Y, Q27H, S99A, G101S, N118D, D156N, E159L, N161Y, S162Q, S163R, M172K, I232T, N248K, Q354R, Y355P, and Y357F. In some embodiments, a BoNT-E protease has at least one of the following mutations: C26Y, Q27H, E28K, H56L, S99A, G101S, N118D, D156N, E159L, N161Y, S162Q, S163R, M172K, I232T, N248K, Q354R, Y355P, Y357F, and L404*. In some embodiments, a BoNT-E protease has at least one of the following mutations: Q27H, S99A, G101S, N118D, E159L, N161Y, S162Q, S163R, M172K, I232T, Q354R, and Y357Y. In some embodiments, a BoNT-E protease has at least one of the following mutations: C26Y, Q27H, H56L, S99A, G101S, N118D, D156N, E159L, N161Y, S162Q, S163R, M172K, I232T, N248K, Q354R, Y355P, and Y357F. In some embodiments, a BoNT-E protease has at least one of the following mutations: Q27H, S99A, G101S, N118D, D156N, E159L, N161Y, S162Q, S163R, M172K, I232T, N248K, Q354R, Y355P, Y357F, and L404*. In some embodiments, a BoNT-E protease has at least one of the following mutations: C26Y, Q27H, G49S, S99A, G101S, N118D, D156N, E159L, N161Y, S162Q, S163R, M172K, I232T, N248K, A313V, Q354R, Y355P, Y357F, and G403E. In some embodiments, a BoNT-E protease has at least one of the following mutations: C26Y, Q27H, S99A, G101S, N118D, D156N, E159L, N161Y, S162Q, S163R, M172K, I232T, N248K, Q354R, Y355P, and Y357F. In some embodiments, a BoNT-E protease has at least one of the following mutations: Q27H, H56Y, S99A, G101S, N118D, D156N, E159L, N161Y, S162Q, S163R, M172K, I232T, N248K, Q354R, Y355P, and Y357F. In some embodiments, a BoNT-E protease has at least one of the following mutations: C26Y, Q27H, S99A, G101S, N118D, D156N, E159L, N161Y, S162Q, S163R, M172K, I232T, N248K, Q354R, Y355P, Y357F, and L404*. In some embodiments, a BoNT-E protease has at least one of the following mutations: Q27H, I35V, S99A, G101S, N118D, D156N, E159L, N161Y, S162Q, S163R, M172K, I232T, N248K, Q354W, Y355P, Y357F, N365S, and L404*.

In some embodiments, a BoNT-E protease has a mutation in at least one of the following positions: C26, Q27, S99, G101, N118, D156, E159, N161, S162, S163, M172, I232, N248, Q354, Y355, and Y357.

In some embodiments, a BoNT-E protease has at least one of the following mutations: C26Y, Q27H, S99A, G101S, N118D, D156N, E159L, N161Y, S162Q, S163R, M172K, I232T, N248K, Q354R, Y355P, and Y357F.

The summary above is meant to illustrate and outline, in a non-limiting manner, some of the embodiments, advantages, features, and uses of the technology disclosed herein. The disclosure is, however, not limited to the embodiments described in the summary above. Other embodiments, advantages, features, and uses of the technology disclosed herein will be apparent from the Detailed Description, the Drawings, the Examples, and the Claims.

BRIEF DESCRIPTION OF DRAWINGS

FIGS. 4A-4D show PACE selection for the evolution of BoNT proteases. FIG. 4A shows an alignment of VAMP1 and VAMP7 protein sequences. Bold residues have been experimentally determined to be important for BoNT F cleavage activity. Underlined residues are fully conserved. FIG. 4B shows representative T7-PAP constructs for incorporation into PACE accessory plasmids (APs). FIG. 4C shows analysis of relative cleavage activity for a selection of BoNT-expressing phage on VAMP1- and VAMP2-derived T7-PAP constructs in a luciferase reporter assay. Columns 1-5, as read left to right, of each T7-PAP(VAMP1) and T7-PAP(VAMP2): uninfected, T7 polymerase, BoNT B, BoNT D, and BoNT F. FIG. 4D shows evolution of novel activity in BoNT F phage clones through iterative PACE. BoNT F(1.5) indicates a representative phage clone isolated after PACE selection on the T7-PAP(VAMP71.5) AP. Columns 1-6, as read left to right, of each Uninfected, T7, BoNT F(S166Y, and BoNT F(1.5): T7-PAP(VAMP1), T7-PAP (VAMP1.1.), T7-PAP(VAMP1.2), T7-PAP(VAMP1.3), T7-PAP(VAMP1.4), and T7-PAP(VAMP1.5).

FIG. 6A shows BoNT Light Chain (LC) proteolytic activity in SNARE-derived PA-RNAP constructs. Columns 1-8, as ready left to right, of each Syntaxin1, Syntaxin2, VAMP1, VAMP2, VAMP3, SNAP25, and SNAP23: Positive Control, Negative Control, BoNT A, BoNT B, BoNT C, BoNT D, BoNT E, and BoNT F. FIG. 6B shows comparative data for wild-type BoNT serotypes B and F to PACE evolved clones displaying improved VAMP1 and VAMP2 cleavage activity. Columns 1-2, as read left to right, of each Uninfected, BoNT_B, BoNT_B L2f, BoNT_F, and BoNT_F L3E: VAMP1 and VAMP2.

FIG. 19 shows protease-dependent luciferase assay data indicating that certain BoNT F variants produced by PACE can cleave the triple mutant VAMP1 substrate (L55A/D58G/ Q59E). Columns 1-4, as read left to right, of each grouping of four columns: AP-951, AP-977, AP-015, and AP-065.

FIG. 20 shows protease-dependent luciferase assay data indicating that certain BoNT F variants produced by PACE can cleave the triple mutant VAMP1 substrate (L55A/D58G/ Q59E/K60R). Columns 1-5, as read left to right, of each grouping of five columns: AP-951, AP-977, AP-015, AP-065, and AP-104.

FIG. 24 shows protein blot analysis for protein expression of two BoNT F evolved variants (2020 L2A, 2020 L3A).

FIG. 25 is a schematic diagram of an alignment of VAMP1 and VAMP8 amino acid sequences and double mutant accessory plasmids (APs).

FIG. 29A shows a Western blot of evolved BoNT F protease m2020-L2A ("m" indicates a maltose-binding protein tag on the N-terminus of the protein). FIG. 29B shows a Western blot of Ni-NTA (top) purified BoNT F proteases m2020-L2A and m2020-L3A and subsequent amylose-purification of BoNT F proteases m2020-L2A and m2020-L3A.

FIG. 44 shows another PACE evolution on BoNT on endogenous substrate VAMP 1.

FIGS. 45A-45F show characterizations of two BoNT F variants, F7.2[A6], and F7N[1.3]. In vitro kinetic analysis performed using an adapted version of the commercial BoTest FRET sensor demonstrated that the evolved proteases are indeed active on their target VAMP7 sequence, and have kinetic characteristics within an order of magnitude of naturally-occurring neurotoxins, such as Tetanus neurotoxin (TeNT) (FIGS. 45A-45D). Upper data line: VAMP7, lower data line: VAMP1 (FIGS. 45A and 45C). Comparing selected clones both before and after negative selection suggests selectivity for VAMP7 over VAMP1 is primarily achieved by a decrease in $K_m$ rather than a substrate-dependent modification to catalysis (FIG. 45E). Kinetic parameters and selectivity profile for evolved BoNT F/LC clones are shown (FIG. 45F).

FIG. 47 shows an AP trajectory for BoNT F/LC evolution towards VAMP7.

FIG. 48 shows a mutational cross section of evolving BoNT F/LC populations across the evolutionary trajectory.

FIGS. 54A-54C show that the ability of PACE to accommodate long cleavage sites allows the protease to self-identify optimal cleavage sites during reprogramming. Cleavage site shift after positive selection is shown in FIG. 54A and combined reversion analysis is shown in FIG. 54B. Columns 1-2, as read left to right, of each grouping of two columns: AP-VAMP1 and AP-VAMP7. FIG. 54C shows representative data of evolved BoNT X protease activity on VAMP 1 and VAMP7 substrates. Left panel: upper line, VAMP7, lower line, VAMP1.

FIG. 55A shows the positive and negative selection for the evolution of BoNT X. Selection for cleavage of Ykt6 and negative selection of cleavage of VAMP1. FIG. 55B shows the mutations in evolved proteases of BoNT X (a-h) (left panel), with the BoNT X LC shown in blue (right panel). FIG. 55C shows the resulting evolution of reduction in cleavage of VAMP1 and increased cleavage of Ykt6 in the evolved BoNT X variant (Wild-type, left panel; A166E mutation right panel). Left panel: upper line, VAMP1, lower line Ykt6. Right panel: upper line Ykt6, lower line VAMP1. FIG. 55D: shows an alignment of the amino acid sequences of VAMP1, VAMP4, VAMP5, and Ykt6.

FIGS. 56A-56B show representative data for PANCE parallel negative selection of evolved BoNT proteases. FIG. 56A shows phage titer data for positive selection of VAMP7-cleaving proteases and negative selection of VAMP1-cleaving proteases over two replicates of 15 passages. FIG. 56B shows the evolution over passages of a BoNT X variant.

FIGS. 57A-57G show the characteristics of a PANCE evolved BoNT-X. FIG. 57A shows results of various BoNT serotypes (F and X wt) against various evolved variants, on 4 different substrates, VAMP1, VAMP4, VAMP5, and Ykt6. Columns 1-4, as read left to right, of each group of four columns: VAMP1, VAMP4, VAMP5, and Ykt6. FIG. 57B shows product concentration over time for wt BoNT-X on the four different substrates (left panel), and variant X(4130) B1\* (middle panel). The right panel shows luciferase assay data. Left panel: data lines from top to bottom, VAMP1, VAMP4, Ykt6, and VAMP5. Middle panel: data lines from top to bottom, Ykt6, VAMP4, VAMP5, and VAMP 1. FIG. 57C shows an evolution strategy including positive and negative selection Aps used in a BoNT-X PANCE evolution. FIG. 57D shows phage titer data. FIG. 57E an evolution over passages of different BoNT-X proteases (left panel) and activity of variants on four different substrates (right panel). Columns 1-4, as read left to right, of each grouping of four columns: VAMP1, VAMP4, VAMP5, and Ykt6. FIG. 57F shows the evolution of BoNT-X (5010) over passages. FIG. 57G shows the activity of BoNT-X (5010) on various substrates. Columns 1-4, as read left to right, of each grouping of four columns: VAMP1, VAMP4, VAMP5, and Ykt6.

FIGS. 58A-58B show BoNT-X(5010)B1. FIG. 58A shows a depiction of various mutations and the quantification of activity of each variant on two different substrates. FIG. 58B shows product concentration over time of BoNT-X(5010) on four substrates, BoNT-X(5010)A3 (top panel), top data line VAMP4, bottom data lines VAMP1, VAMP5, and Ykt6; BoNT-X(5010)B1 (middle panel), top data line VAMP4, bottom data lines VAMP1, VAMP5, and Ykt6; and BoNT-X(5010)C1 (bottom panel), top data line VAMP4, middle data line, Ykt6, bottom data lines VAMP1, and VAMP5.

FIGS. 59A-59G show the evolution of BoNT proteases to cleave PTEN (phosphatase and tensin homolog). FIG. 59A shows a cross-reference of a BoNT substrate to a PTEN substrate. FIG. 59B shows an illustration of a PTEN structure and cleavage site. FIG. 59C shows two positive selection trajectories from SNAP-25 substrate to PTEN and a negative selection strategy. FIG. 59D shows the phage populations of substrates throughout the evolution. Positive and negative selection steps are shown. FIG. 59E shows the results of evolved BoNT-E proteases on various substrates, SNAP25 (left panel) and PTEN (right panel). FIG. 59F shows evolution of BoNT-E(122)A2. FIG. 59 G shows the activity of an evolved BoNT-E protease on various substrates. Top column: Columns 1-2, as read left to right, of each grouping of two columns, SNAP35 and PTEN; middle panel (line graph), top data line: PTEN, bottom data line: SNAP25.

DEFINITIONS

Figure 1:
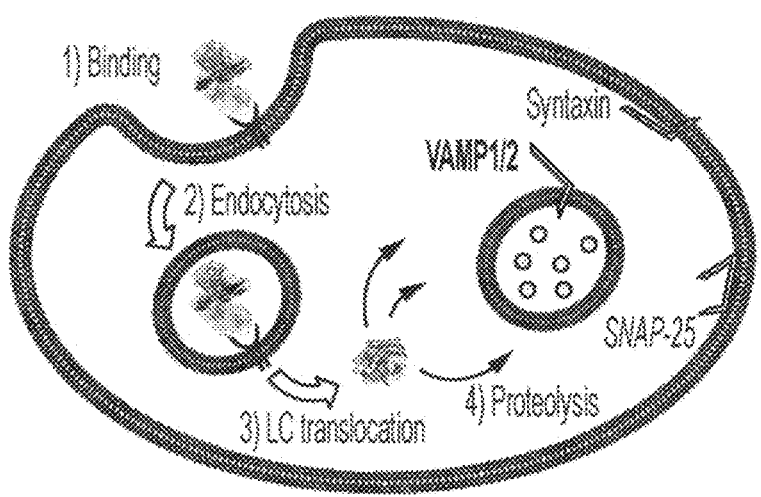
FIG. 1 is a schematic depicting the mechanism of intoxication by Botulinum neurotoxins.

The term "protease," as used herein, refers to an enzyme that catalyzes the hydrolysis of a peptide (amide) bond linking amino acid residues together within a protein. The term embraces both naturally occurring and engineered proteases. Many proteases are known in the art. Proteases can be classified by their catalytic residue, and protease classes include, without limitation, serine proteases (serine alcohol), threonine proteases (threonine secondary alcohol), cysteine proteases (cysteine thiol), aspartate proteases (aspartate carboxylic acid), glutamic acid proteases (glutamate carboxylic acid), and metalloproteases (metal ion, e.g., zinc). The structures in parentheses in the preceding sentence correlate to the respective catalytic moiety of the proteases of each class. Some proteases are highly promiscuous and cleave a wide range of protein substrates, e.g., trypsin or pepsin. Other proteases are highly specific and only cleave substrates with a specific sequence. Some blood clotting proteases such as, for example, thrombin, and some viral proteases, such as, for example, HCV or TEV protease, are highly specific proteases. In another example, Botulinum toxin proteases (BoNTs) generally cleave specific SNARE proteins. Proteases that cleave in a very specific manner typically bind to multiple amino acid residues of their substrate. Suitable proteases and protease cleavage sites, also sometimes referred to as "protease substrates," will be apparent to those of skill in the art and include, without limitation, proteases listed in the MEROPS database, accessible at merops.sanger.ac.uk and described in Rawlings et al., (2014) MEROPS: the database of proteolytic enzymes, their substrates and inhibitors. *Nucleic Acids Res* 42, D503-D509, the entire contents of each of which are incorporated herein by reference.

The term "protein," as used herein, refers to a polymer of amino acid residues linked together by peptide bonds. This term (i.e., protein), as used herein, refers to proteins, polypeptides, and peptides of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature, but that can be incorporated into a polypeptide chain; see, for example, cco.caltech.edu/~dadgrp/Unnatstruct.gif, which displays structures of non-natural amino acids that have been successfully incorporated into functional ion channels) and/or amino acid analogs as are known in the art may alternatively be employed. Also, one or more of the amino acids in an inventive protein may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein may also be a single molecule or may be a multi-molecular complex. A protein may be just a fragment of a naturally occurring protein or peptide. A protein may be naturally occurring, recombinant, synthetic, or any combination of these.

The term "Botulinum neurotoxin (BoNT) protease," as used herein, refers to a protease derived from, or having at least 70% sequence homology to (e.g., at least 70%, at least 80%, at least 85%, at least 90%, at least 95%, at least 96%, at least 97%, at least 98%, at least 99%, at least 99.5%, at least 99.9%, or more identity to) a Botulinum neurotoxin (BoNT), for example, a BoNT derived from a bacterium of the genus *Clostridium* (e.g., *C. botulinum*). Structurally, BoNT proteins comprise two conserved domains, a "heavy chain" (HC) and a "light chain" (LC). The LC comprises a zinc metalloprotease domain responsible for the catalytic activity of the protein. The HC typically comprises an HCC domain, which is responsible for binding to neuronal cells, and an HCN domain, which mediates translocation of the protein into a cell.

There are eight serotypes of BoNTs, denoted BoNT A-G, and X. BoNT serotypes A, C, and E cleave synaptosome-associated protein (SNAP25). BoNT serotype C has also been observed to cleave syntaxin. BoNT serotypes B, D, F, and G cleave vesicle-associated membrane proteins (VAMPs). BoNT X was more recently discovered and seems to show a more promiscuous substrate profile than the other serotypes. BoNT X has the lowest sequence identity with other BoNTs serotypes and is also not recognized by antisera against known BoNT serotypes. BoNT X similar, however in cleaving vesicle-associated membrane proteins (VAMP) 1, 2 and 3, but does so at a novel site (Arg66-Ala67 in VAMP2). Lastly, BoNT X is the only toxin that also cleaves non-canonical substrates VAMP4, VAMP5 and Ykt6 (Nat Commun. 2017 Aug. 3; 8:14130. doi: 10.1038/ncomms14130, www.ncbi.nlm.nih.gov/pubmed/28770820). An example of a VAMP substrate (e.g., VAMP1) that is cleaved by wild-type BoNT proteases (e.g., BoNT F) is represented by the amino acid sequence set forth in SEQ ID NO.: 32.

A wild-type BoNT protease refers to the amino acid sequence of a BoNT protease as it naturally occurs in *Clostridium botulinum* (*C. botulinum*). Examples of wild-type BoNT proteases are represented by the amino acid sequences set forth in SEQ ID NOs.: 1-8, as follows: Botulinum neurotoxin serotype A (BoNT A) (SEQ ID NO.: 1); Botulinum neurotoxin serotype B (BoNT B) (SEQ ID NO.: 2); Botulinum neurotoxin serotype C (BoNT C) (SEQ ID NO.: 3); Botulinum neurotoxin serotype D (BoNT D) (SEQ ID NO.: 4); Botulinum neurotoxin serotype E (BoNT E) (SEQ ID NO.: 5); Botulinum neurotoxin serotype F (BoNT F) (SEQ ID NO.: 6); Botulinum neurotoxin serotype G (BoNT G) (SEQ ID NO.: 7); and Botulinum neurotoxin serotype X (BoNT X) (SEQ ID NO.: 8).

The term "BoNT protease variant," as used herein, refers to a protein (e.g., a BoNT protease) having one or more amino acid variations introduced into the amino acid sequence, e.g., as a result of application of the PACE method or by genetic engineering (e.g., recombinant gene expression, gene synthesis, etc.), as compared to the amino acid sequence of a naturally-occurring or wild-type BoNT protein (e.g., SEQ ID NOs.: 1-8). Amino acid sequence variations may include one or more mutated residues within the amino acid sequence of the protease, e.g., as a result of a change in the nucleotide sequence encoding the protease that results in a change in the codon at any particular position in the coding sequence, the deletion of one or more amino acids (e.g., a truncated protein), the insertion of one or more amino acids, or any combination of the foregoing. In certain embodiments, a BoNT protease variant cleaves a different target peptide (e.g., has broadened or different substrate specificity) relative to a wild-type BoNT protease. For example, in some embodiments, a BoNT F protease variant cleaves a VAMP7 protein or peptide. In some embodiments, a BoNT F variant cleaves a target sequence comprising SEQ ID NO.: 35. In some embodiments, cleavage of the target VAMP7 decreases VAMP7 activity. In some embodiments, cleavage of the target VAMP7 eliminates VAMP7 activity.

The term "VAMP" as used interchangeably herein with the term "Vesicle-associated membrane protein" refers to a family of proteins belonging to the SNARE protein family and share similar structures. Different proteins make up the collection VAMP1-VAMP8 and are mostly involved in vesicle fusion. For example, VAMP1 and VAMP2 proteins are expressed in brain and are constituents of the synaptic vesicles, where they participate in neurotransmitter release; VAMP3 is expressed and participates in regulated and constitutive exocytosis as a constituent of secretory granules and secretory vesicles; VAMP4 is involved in transport out of the Golgi apparatus; VAMP5 and VAMP7 participate in constitutive exocytosis; VAMP5 is a constituent of secretory vesicles; VAMP7 is also found both in secretory granules and endosomes; and VAMP8 is part of endocytosis and is found in early endosomes. VAMP8 is also involved in exocytosis in pancreatic acinar cells.

The term "continuous evolution," as used herein, refers to an evolution procedure, in which a population of nucleic acids is subjected to multiple rounds of: (a) replication, (b) mutation (or modification of the primary sequence of nucleotides of the nucleic acids in the population), and (c) selection to produce a desired evolved product, for example, a novel nucleic acid encoding a novel protein with a desired activity, wherein the multiple rounds of replication, mutation, and selection can be performed without investigator interaction, and wherein the processes (a)-(c) can be carried out simultaneously. Typically, the evolution procedure is carried out in vitro, for example, using cells in culture as host cells. In general, a continuous evolution process provided herein relies on a system in which a gene of interest is provided in a nucleic acid vector that undergoes a life-cycle including replication in a host cell and transfer to another host cell, wherein a critical component of the life-cycle is deactivated and reactivation of the component is dependent upon a desired variation in an amino acid sequence of a protein encoded by the gene of interest.

In some embodiments, the gene of interest (e.g., a gene encoding a BoNT protease) is transferred from cell to cell in a manner dependent on the activity of the gene of interest. In some embodiments, the transfer vector is a virus infecting cells, for example, a bacteriophage or a retroviral vector. In some embodiments, the viral vector is a phage vector infecting bacterial host cells. In some embodiments, the transfer vector is a conjugative plasmid transferred from a donor bacterial cell to a recipient bacterial cell.

In some embodiments, the nucleic acid vector comprising the gene of interest is a phage, a viral vector, or naked DNA (e.g., a mobilization plasmid). In some embodiments, transfer of the gene of interest from cell to cell is via infection, transfection, transduction, conjugation, or uptake of naked DNA, and efficiency of cell-to-cell transfer (e.g., transfer rate) is dependent on an activity of a product encoded by the gene of interest. For example, in some embodiments, the nucleic acid vector is a phage harboring the gene of interest and the efficiency of phage transfer (via infection) is dependent on an activity of the gene of interest in that a protein required for the generation of phage particles (e.g., pIII for M13 phage) is expressed in the host cells only in the presence of the desired activity of the gene of interest.

For example, some embodiments provide a continuous evolution system, in which a population of viral vectors comprising a gene of interest to be evolved replicates in a flow of host cells, e.g., a flow through a lagoon (e.g., evolution vessel), wherein the viral vectors are deficient in a gene encoding a protein that is essential for the generation of infectious viral particles, and wherein that gene is in the host cell under the control of a conditional promoter that can be activated by a gene product encoded by the gene of interest, or a mutated version thereof. In some embodiments, the activity of the conditional promoter depends on a desired function of a gene product encoded by the gene of interest. Viral vectors, in which the gene of interest has not acquired a desired function as a result of a variation of amino acids introduced into the gene product protein sequence, will not activate the conditional promoter, or may only achieve minimal activation, while any mutations introduced into the gene of interest that confers the desired function will result in activation of the conditional promoter. Since the conditional promoter controls an essential protein for the viral life cycle, e.g., pIII, activation of this promoter directly corresponds to an advantage in viral spread and replication for those vectors that have acquired an advantageous mutation.

The term "flow," as used herein in the context of host cells, refers to a stream of host cells, wherein fresh host cells are being introduced into a host cell population, for example, a host cell population in a lagoon, remain within the population for a limited time, and are then removed from the host cell population. In a simple form, a host cell flow may be a flow through a tube, or a channel, for example, at a controlled rate. In other embodiments, a flow of host cells is directed through a lagoon that holds a volume of cell culture media and comprises an inflow and an outflow. The introduction of fresh host cells may be continuous or intermittent and removal may be passive, e.g., by overflow, or active, e.g., by active siphoning or pumping. Removal further may be random, for example, if a stirred suspension culture of host cells is provided, removed liquid culture media will contain freshly introduced host cells as well as cells that have been a member of the host cell population within the lagoon for some time. Even though, in theory, a cell could escape removal from the lagoon indefinitely, the average host cell will remain only for a limited period of time within the lagoon, which is determined mainly by the flow rate of the culture media (and suspended cells) through the lagoon.

Since the viral vectors replicate in a flow of host cells, in which fresh, uninfected host cells are provided while infected cells are removed, multiple consecutive viral life cycles can occur without investigator interaction, which allows for the accumulation of multiple advantageous mutations in a single evolution experiment.

The term "phage-assisted continuous evolution" (also used interchangeably herein with "PACE"), as used herein, refers to continuous evolution that employs phage as viral vectors.

The term "viral vector," as used herein, refers to a nucleic acid comprising a viral genome that, when introduced into a suitable host cell, can be replicated and packaged into viral particles able to transfer the viral genome into another host cell. The term viral vector extends to vectors comprising truncated or partial viral genomes. For example, in some embodiments, a viral vector is provided that lacks a gene encoding a protein essential for the generation of infectious viral particles. In suitable host cells, for example, host cells comprising the lacking gene under the control of a conditional promoter, however, such truncated viral vectors can replicate and generate viral particles able to transfer the truncated viral genome into another host cell. In some embodiments, the viral vector is a phage, for example, a filamentous phage (e.g., an M13 phage). In some embodiments, a viral vector, for example, a phage vector, is provided that comprises a gene of interest to be evolved.

The term "nucleic acid," as used herein, refers to a polymer of nucleotides. The polymer may include natural nucleosides (i.e., adenosine, thymidine, guano sine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, 0(6)-methylguanine, 4-acetylcytidine, 5-(carboxyhydroxymethyl)uridine, dihydrouridine, methylpseudouridine, 1-methyl adenosine, 1-methyl guanosine, N6-methyl adenosine, and 2-thiocytidine), chemically modified bases, biologically modified bases (e.g., methylated bases), intercalated bases, modified sugars (e.g., 2'-fluororibose, ribose, 2'-deoxyribose, 2'-O-methylcytidine, arabinose, and hexose), or modified phosphate groups (e.g., phosphorothioates and 5'-N-phosphoramidite linkages).

The term "gene of interest" or "gene encoding a protease of interest," as used herein, refers to a nucleic acid construct comprising a nucleotide sequence encoding a gene product (e.g., a BoNT protease) of interest (e.g., for its properties, either desirable or undesirable) to be evolved in a continuous evolution process as described herein. The term includes any variations of a gene of interest that are the result of a continuous evolution process according to methods described herein (e.g., increase expression, decreased expression, modulated or changed activity, modulated or changed specificity). For example, in some embodiments, a gene of interest is a nucleic acid construct comprising a nucleotide sequence encoding a protease to be evolved, cloned into a viral vector, for example, a phage genome, so that the expression of the encoding sequence is under the control of one or more promoters in the viral genome. In other embodiments, a gene of interest is a nucleic acid construct comprising a nucleotide sequence encoding a protease to be evolved and a promoter operably linked to the encoding sequence. When cloned into a viral vector, for example, a phage genome, the expression of the encoding sequence of such genes of interest is under the control of the heterologous promoter and, in some embodiments, may also be influenced by one or more promoters in the viral genome.

The term "function of a gene of interest," as interchangeably used with the term "activity of a gene of interest," refers to a function or activity of a gene product, for example, a nucleic acid or a protein, encoded by the gene of interest. For example, a function of a gene of interest may be an enzymatic activity (e.g., proteolytic activity resulting in the generation of cleavage of a desired substrate, proteolytic activity resulting in the generation of non-cleavage of a undesirable substrate, etc.), an ability to modulate transcription (e.g., transcriptional activation activity or inhibition activity targeted to a specific promoter sequence), a bond-forming activity (e.g., an enzymatic activity resulting in the formation of a covalent bond), or a binding activity (e.g., a protein, DNA, or RNA binding activity).

The term "promoter" refers to a nucleic acid molecule with a sequence recognized by the cellular transcription machinery and able to initiate transcription of a downstream gene. A promoter can be constitutively active, meaning that the promoter is always active in a given cellular context, or conditionally active, meaning that the promoter is only active under specific conditions. For example, a conditional promoter may only be active in the presence of a specific protein that connects a protein associated with a regulatory element in the promoter to the basic transcriptional machinery, or only in the absence of an inhibitory molecule. A subclass of conditionally active promoters are inducible promoters that require the presence of a small molecule "inducer" for activity. Examples of inducible promoters include, but are not limited to, arabinose-inducible promoters, Tet-on promoters, and tamoxifen-inducible promoters. A variety of constitutive, conditional, and inducible promoters are well known to the skilled artisan, and the skilled artisan will be able to ascertain a variety of such promoters useful in carrying out the instant invention, which is not limited in this respect.

The term "viral particle," as used herein, refers to a viral genome, for example, a DNA or RNA genome, that is associated with a coat of a viral protein or proteins, and, in some cases, with an envelope of lipids. For example, a phage particle comprises a phage genome packaged into a protein encoded by the wild type phage genome.

The term "infectious viral particle," as used herein, refers to a viral particle able to transport the viral genome it comprises into a suitable host cell. Not all viral particles are able to transfer the viral genome to a suitable host cell. Particles unable to accomplish this are referred to as non-infectious viral particles. In some embodiments, a viral particle comprises a plurality of different coat proteins, wherein one or some of the coat proteins can be omitted without compromising the structure of the viral particle. In some embodiments, a viral particle is provided in which at least one coat protein cannot be omitted without the loss of infectivity. If a viral particle lacks a protein that confers infectivity, the viral particle is not infectious. For example, an M13 phage particle that comprises a phage genome packaged in a coat of phage proteins (e.g., pVIII) but lacks pIII (protein III) is a non-infectious M13 phage particle because pIII is essential for the infectious properties of M13 phage particles.

The term "viral life cycle," as used herein, refers to the viral reproduction cycle comprising insertion of the viral genome into a host cell, replication of the viral genome in the host cell, and packaging of a replication product of the viral genome into a viral particle by the host cell.

In some embodiments, the viral vector provided is a phage. The term "phage," as used herein interchangeably with the term "bacteriophage," refers to a virus that infects bacterial cells. Typically, phages consist of an outer protein capsid enclosing genetic material. The genetic material can be ssRNA, dsRNA, ssDNA, or dsDNA, in either linear or circular form. Phages and phage vectors are well known to those of skill in the art and non-limiting examples of phages that are useful for carrying out the methods provided herein are λ (Lysogen), T2, T4, T7, T12, R17, M13, MS2, G4, P1, P2, P4, Phi X174, N4, Φ6, and Φ29. In certain embodiments, the phage utilized in the present invention is M13. Additional suitable phages and host cells will be apparent to those of skill in the art, and the invention is not limited in this aspect. For an exemplary description of additional suitable phages and host cells, see Elizabeth Kutter and Alexander Sulakvelidze: *Bacteriophages: Biology and Applications*. CRC Press; 1$^{st}$ edition (December 2004), ISBN: 0849313368; Martha R. J. Clokie and Andrew M. Kropinski: *Bacteriophages: Methods and Protocols, Volume 1: Isolation, Characterization, and Interactions (Methods in Molecular Biology)* Humana Press; 1$^{st}$ edition (December, 2008), ISBN: 1588296822; Martha R. J. Clokie and Andrew M. Kropinski: *Bacteriophages: Methods and Protocols, Volume 2: Molecular and Applied Aspects (Methods in Molecular Biology)* Humana Press; 1$^{st}$ edition (December 2008), ISBN: 1603275649; all of which are incorporated herein in their entirety by reference for disclosure of suitable phages and host cells as well as methods and protocols for isolation, culture, and manipulation of such phages).

In some embodiments, the phage is a filamentous phage. In some embodiments, the phage is an M13 phage. M13 phages are well known to those in the art and the biology of M13 phages has extensively been studied. Wild type M13 phage particles comprise a circular, single-stranded genome of approximately 6.4 kb. In certain embodiments, the wild-type genome of an M13 phage includes eleven genes, gI-gXI, which, in turn, encode the eleven M13 proteins, pI-pXI, respectively. gVIII encodes pVIII, also often referred to as the major structural protein of the phage particles, while gIII encodes pIII, also referred to as the minor coat protein, which is required for infectivity of M13 phage particles, whereas gIII-neg encodes and antagonistic protein to pIII.

The M13 life cycle includes attachment of the phage to the sex pilus of a suitable bacterial host cell via the pIII protein and insertion of the phage genome into the host cell. The circular, single-stranded phage genome is then converted to a circular, double-stranded DNA, also termed the replicative form (RF), from which phage gene transcription is initiated. The wild type M13 genome comprises nine promoters and two transcriptional terminators as well as an origin of replication. This series of promoters provides a gradient of transcription such that the genes nearest the two transcriptional terminators (gVIII and IV) are transcribed at the highest levels. In wild-type M13 phage, transcription of all 11 genes proceeds in the same direction. One of the phage-encoded proteins, pII, initiates the generation of linear, single-stranded phage genomes in the host cells, which are subsequently circularized, and bound and stabilized by pV. The circularized, single-stranded M13 genomes are then bound by pVIII, while pV is stripped off the genome, which initiates the packaging process. At the end of the packaging process, multiple copies of pIII are attached to wild-type M13 particles, thus generating infectious phage ready to infect another host cell and concluding the life cycle.

The M13 phage genome can be manipulated, for example, by deleting one or more of the wild type genes, and/or inserting a heterologous nucleic acid construct into the genome. M13 does not have stringent genome size restrictions, and insertions of up to 42 kb have been reported. This allows M13 phage vectors to be used in continuous evolution experiments to evolve genes of interest without imposing a limitation on the length of the gene to be involved.

The term "selection phage," as used herein interchangeably with the term "selection plasmid," refers to a modified phage that comprises a gene of interest to be evolved and lacks a full-length gene encoding a protein required for the generation of infectious phage particles. For example, some M13 selection phages provided herein comprise a nucleic acid sequence encoding a protease to be evolved, e.g., under the control of an M13 promoter, and lack all or part of a phage gene encoding a protein required for the generation of infectious phage particles, e.g., gI, gII, gIII, gIV, gV, gVI, gVII, gVIII, gIX, or gX, or any combination thereof. For example, some M13 selection phages provided herein comprise a nucleic acid sequence encoding a protease to be evolved, e.g., under the control of an M13 promoter, and lack all or part of a gene encoding a protein required for the generation of infective phage particles, e.g., the gIII gene encoding the pIII protein.

The term "helper phage," as used herein interchangeable with the terms "helper phagemid" and "helper plasmid," refers to a nucleic acid construct comprising a phage gene required for the phage life cycle, or a plurality of such genes, but lacking a structural element required for genome packaging into a phage particle. For example, a helper phage may provide a wild-type phage genome lacking a phage origin of replication. In some embodiments, a helper phage is provided that comprises a gene required for the generation of phage particles, but lacks a gene required for the generation of infectious particles, for example, a full-length pIII gene. In some embodiments, the helper phage provides only some, but not all, genes required for the generation of phage particles. Helper phages are useful to allow modified phages that lack a gene required for the generation of phage particles to complete the phage life cycle in a host cell. Typically, a helper phage will comprise the genes required for the generation of phage particles that are lacking in the phage genome, thus complementing the phage genome. In the continuous evolution context, the helper phage typically complements the selection phage, but both lack a phage gene required for the production of infectious phage particles.

The term "replication product," as used herein, refers to a nucleic acid that is the result of viral genome replication by a host cell. This includes any viral genomes synthesized by the host cell from a viral genome inserted into the host cell. The term includes non-mutated as well as mutated replication products.

The term "accessory plasmid," as used herein, refers to a plasmid comprising a gene required for the generation of infectious viral particles under the control of a conditional promoter. In the context of continuous evolution described herein, the conditional promoter of the accessory plasmid is typically activated by a function of the gene of interest to be evolved. Accordingly, the accessory plasmid serves the function of conveying a competitive advantage (in the case of positive selection) to those viral vectors in a given population of viral vectors that carry a gene of interest able to activate the conditional promoter. Only viral vectors carrying an "activating" gene of interest will be able to induce expression of the gene required to generate infectious viral particles in the host cell, and, thus, allow for packaging and propagation of the viral genome in the flow of host cells. Vectors carrying non-activating versions of the gene of interest, on the other hand, will not induce expression of the gene required to generate infectious viral vectors, and, thus, will not be packaged into viral particles that can infect fresh host cells.

In some embodiments, the conditional promoter of the accessory plasmid is a promoter the transcriptional activity of which can be regulated over a wide range, for example, over 2, 3, 4, 5, 6, 7, 8, 9, or 10 orders of magnitude by the activating function, for example, function of a protein encoded by the gene of interest. In some embodiments, the level of transcriptional activity of the conditional promoter depends directly on the desired function of the gene of interest. This allows for starting a continuous evolution process with a viral vector population comprising versions of the gene of interest that only show minimal activation of the conditional promoter. In the process of continuous evolution, any mutation in the gene of interest that increases activity of the conditional promoter directly translates into higher expression levels of the gene required for the generation of infectious viral particles, and, thus, into a competitive advantage over other viral vectors carrying minimally active or loss-of-function versions of the gene of interest.

The stringency of selective pressure imposed by the accessory plasmid in a continuous evolution procedure as provided herein can be modulated. In some embodiments, the use of low copy number accessory plasmids results in an elevated stringency of selection for versions of the gene of interest that activate the conditional promoter on the accessory plasmid, while the use of high copy number accessory plasmids results in a lower stringency of selection. The terms "high copy number plasmid" and "low copy number plasmid" are art-recognized and those of skill in the art will be able to ascertain whether a given plasmid is a high or low copy number plasmid. In some embodiments, a low copy number accessory plasmid is a plasmid exhibiting an average copy number of plasmid per host cell in a host cell population of about 5 to about 100. In some embodiments, a very low copy number accessory plasmid is a plasmid exhibiting an average copy number of plasmid per host cell in a host cell population of about 1 to about 10. In some embodiments, a very low copy number accessory plasmid is a single-copy per cell plasmid. In some embodiments, a high copy number accessory plasmid is a plasmid exhibiting an average copy number of plasmid per host cell in a host cell population of about 100 to about 5000. The copy number of an accessory plasmid will depend to a large part on the origin of replication employed. Those of skill in the art will be able to determine suitable origins of replication in order to achieve a desired copy number.

In some embodiments, the stringency of selective pressure imposed by the accessory plasmid can also be modulated through the use of mutant or alternative conditional transcription factors with higher or lower transcriptional output (e.g., a T7 RNA polymerase comprising a Q649S mutation). In some embodiments, the use of lower transcriptional output results in an elevated stringency of selection for versions of the gene of interest that activate the conditional promoter on the accessory plasmid, while the use of higher transcriptional output machinery results in a lower stringency of selection.

It should be understood that the function of the accessory plasmid, namely to provide a gene required for the generation of viral particles under the control of a conditional promoter the activity of which depends on a function of the gene of interest, can be conferred to a host cell in alternative ways. Such alternatives include, but are not limited to, permanent insertion of a gene construct comprising the conditional promoter and the respective gene into the genome of the host cell, or introducing it into the host cell using an different vector, for example, a phagemid, a cosmid, a phage, a virus, or an artificial chromosome. Additional ways to confer accessory plasmid function to host cells will be evident to those of skill in the art, and the invention is not limited in this respect.

The term "mutagen," as used herein, refers to an agent that induces mutations or increases the rate of mutation in a given biological system, for example, a host cell, to a level above the naturally-occurring level of mutation in that system. Some exemplary mutagens useful for continuous evolution procedures are provided elsewhere herein and other useful mutagens will be evident to those of skill in the art. Useful mutagens include, but are not limited to, ionizing radiation, ultraviolet radiation, base analogs, deaminating agents (e.g., nitrous acid), intercalating agents (e.g., ethidium bromide), alkylating agents (e.g., ethylnitrosourea), transposons, bromine, azide salts, psoralen, benzene, 3-chloro-4-(dichloromethyl)-5-hydroxy-2(5H)-furanone (MX) (CAS no. 77439-76-0), O,O-dimethyl-S-(phthalimidomethyl)phosphorodithioate (phos-met) (CAS no. 732-11-6), formaldehyde (CAS no. 50-00-0), 2-(2-furyl)-3-(5-nitro-2-furyl)acrylamide (AF-2) (CAS no. 3688-53-7), glyoxal (CAS no. 107-22-2), 6-mercaptopurine (CAS no. 50-44-2), N-(trichloromethylthio)-4-cyclohexane-1,2-dicarboximide (captan) (CAS no. 133-06-2), 2-aminopurine (CAS no. 452-06-2), methyl methane sulfonate (MMS) (CAS No. 66-27-3), 4-nitroquinoline 1-oxide (4-NQO) (CAS No. 56-57-5), N4-aminocytidine (CAS no. 57294-74-3), sodium azide (CAS no. 26628-22-8), N-ethyl-N-nitrosourea (ENU) (CAS no. 759-73-9), N-methyl-N-nitrosourea (MNU) (CAS no. 820-60-0), 5-azacytidine (CAS no. 320-67-2), cumene hydroperoxide (CHP) (CAS no. 80-15-9), ethyl methanesulfonate (EMS) (CAS no. 62-50-0), N-ethyl-N-nitro-N-nitrosoguanidine (ENNG) (CAS no. 4245-77-6), N-methyl-N-nitro-N-nitrosoguanidine (MNNG) (CAS no. 70-25-7), 5-diazouracil (CAS no. 2435-76-9), and t-butyl hydroperoxide (BHP) (CAS no. 75-91-2). Additional mutagens can be used in continuous evolution procedures as provided herein, and the invention is not limited in this respect.

Ideally, a mutagen is used at a concentration or level of exposure that induces a desired mutation rate in a given host cell or viral vector population, but is not significantly toxic to the host cells used within the average time frame a host cell is exposed to the mutagen or the time a host cell is present in the host cell flow before being replaced by a fresh host cell.

The term "mutagenesis plasmid," as used herein, refers to a plasmid comprising a gene encoding a gene product that acts as a mutagen. In some embodiments, the gene encodes a DNA polymerase lacking a proofreading capability. In some embodiments, the gene is a gene involved in the bacterial SOS stress response, for example, a UmuC, UmuD', or RecA gene. In some embodiments, the gene is a GATC methylase gene, for example, a deoxyadenosine methylase (dam methylase) gene. In some embodiments, the gene is involved in binding of hemimethylated GATC sequences, for example, a seqA gene. In some embodiments, the gene is involved with repression of mutagenic nucleobase export, for example emrR. In some embodiments, the gene is involved with inhibition of uracil DNA-glycosylase, for example a Uracil Glycosylase Inhibitor (ugi) gene. In some embodiments, the gene is involved with deamination of cytidine (e.g., a cytidine deaminase from *Petromyzon marinus*), for example, cytidine deaminase 1 (CDA1).

The term "host cell," as used herein, refers to a cell that can host a viral vector useful for a continuous evolution process as provided herein. A cell can host a viral vector if it supports expression of genes of viral vector, replication of the viral genome, and/or the generation of viral particles. One criterion to determine whether a cell is a suitable host cell for a given viral vector is to determine whether the cell can support the viral life cycle of a wild-type viral genome that the viral vector is derived from. For example, if the viral vector is a modified M13 phage genome, as provided in some embodiments described herein, then a suitable host cell would be any cell that can support the wild-type M13 phage life cycle. Suitable host cells for viral vectors useful in continuous evolution processes are well known to those of skill in the art, and the invention is not limited in this respect.

In some embodiments, modified viral vectors are used in continuous evolution processes as provided herein. In some embodiments, such modified viral vectors lack a gene required for the generation of infectious viral particles. In some such embodiments, a suitable host cell is a cell comprising the gene required for the generation of infectious viral particles, for example, under the control of a constitutive or a conditional promoter (e.g., in the form of an accessory plasmid, as described herein). In some embodiments, the viral vector used lacks a plurality of viral genes. In some such embodiments, a suitable host cell is a cell that comprises a helper construct providing the viral genes required for the generation of viral particles. A cell is not required to actually support the life cycle of a viral vector used in the methods provided herein. For example, a cell comprising a gene required for the generation of infectious viral particles under the control of a conditional promoter may not support the life cycle of a viral vector that does not comprise a gene of interest able to activate the promoter, but it is still a suitable host cell for such a viral vector. In some embodiments, the viral vector is a phage, and the host cell is a bacterial cell. In some embodiments, the host cell is an *E. coli* cell. Suitable *E. coli* host strains will be apparent to those of skill in the art, and include, but are not limited to, New England Biolabs (NEB) Turbo, Top10F', DH12S, ER2738, ER2267, XL1-Blue MRF', and DH10B. In some embodiments, the strain of *E. coli* used is known as 51030 (available from Addgene). In some embodiments, the strain of *E. coli* use to express proteins is BL21(DE3). These strain names are art recognized, and the genotype of these strains has been well characterized. It should be understood that the above strains are exemplary only, and that the invention is not limited in this respect.

The term "fresh," as used herein interchangeably with the terms "non-infected" or "uninfected" in the context of host cells, refers to a host cell that has not been infected by a viral vector comprising a gene of interest as used in a continuous evolution process provided herein. A fresh host cell can, however, have been infected by a viral vector unrelated to the vector to be evolved or by a vector of the same or a similar type but not carrying the gene of interest. In some embodiments, the host cell is a prokaryotic cell, for example, a bacterial cell, such as an *E. coli* cell.

In some embodiments, the host cell is an *E. coli* cell. In some embodiments of PACE, for example, in embodiments employing an M13 selection phage, the host cells are *E. coli* cells expressing the Fertility factor, also commonly referred to as the F factor, sex factor, or F-plasmid. The F-factor is a bacterial DNA sequence that allows a bacterium to produce a sex pilus necessary for conjugation and is essential for the infection of *E. coli* cells with certain phage, for example, with M13 phage. For example, in some embodiments, the host cells for M13-PACE are of the genotype F'proA⁺B⁺ Δ(lacIZY) zzf::Tn10(TetR)/endA1 recA1 galE15 galK16 nupG rpsL ΔlacIZYA araD139 Δ(ara, leu)7697 mcrA Δ(mrr-hsdRMS-mcrBC) proBA::pir116λ⁻. In some embodiments, the host cells for M13-PACE are of the genotype F'proA+B+ Δ(lacIZY) zzf::Tn10(TetR) lacIQ1PN25-tetR luxCDE/endA1 recA1 galE15 galK16 nupG rpsL(StrR) ΔlacIZYA araD139 Δ(ara,leu)7697 mcrA Δ(mrr-hsdRMS-mcrBC) proBA::pir116 araE201 ΔrpoZ Δflu ΔcsgABCDEFG ApgaC λ–, for example S1030 cells as described in Carlson, J. C., et al. Negative selection and stringency modulation in phage-assisted continuous evolution. *Nat. Chem. Biol.* 10, 216-222(2014). In some embodiments, the host cells for M13-PACE are of the genotype F' proA+B+ Δ(lacIZY) zzf::Tn10 lacIQ1 PN25-tetR luxCDE Ppsp(AR2) lacZ luxR Plux groESL/endA1 recA1 galE15 galK16 nupG rpsL ΔlacIZYA araD139 Δ(ara,leu)7697 mcrA Δ(mrr-hsdRMS-mcrBC) proBA::pir116 araE201 ΔrpoZ Δflu ΔcsgABCDEFG ApgaC λ–, for example 52060 cells as described in Hubbard, B. P. et al. Continuous directed evolution of DNA-binding proteins to improve TALEN specificity. *Nature Methods* 12, 939-942 (2015).

The term "subject," as used herein, refers to an individual organism, for example, an individual mammal. In some embodiments, the subject is a human. In some embodiments, the subject is a non-human mammal. In some embodiments, the subject is a non-human primate. In some embodiments, the subject is a rodent. In some embodiments, the subject is a sheep, a goat, a cattle, a cat, or a dog. In some embodiments, the subject is a vertebrate, an amphibian, a reptile, a fish, an insect, a fly, or a nematode. In some embodiments, the subject is a research animal. In some embodiments, the subject is genetically engineered, e.g., a genetically engineered non-human subject. The subject may be of any sex and at any stage of development. In some embodiments, the subject has a disease characterized by increased activity of an intracellular protein (e.g., a SNARE protein, etc.). In some embodiments, the disease characterized by increased activity of an intracellular protein is cancer, transplantation rejection, graft-versus-host disease, ischemic neuronal injury (stroke), Parkinson's Disease, Huntington's Disease, Alzheimer's Disease, spinal cord injury, diabetes, autoimmune disorders, allergy, or Cushing Disease. In some embodiments, the subject has a disease characterized by increased activity of a SNARE protein (e.g., VAMP1, VAMP7, etc.). In some embodiments, the subject has a disease characterized by increased activity of a VAMP protein (e.g., VAMP7). In some embodiments, the disease characterized by increased VAMP7 activity is cancer, transplantation rejection, graft-versus-host disease, or a neurological disease. In some embodiments, the cancer is metastatic breast cancer. In some embodiments, the disease is a neurological disease.

The term "cell," as used herein, refers to a cell derived from an individual organism, for example, from a mammal. A cell may be a prokaryotic cell or a eukaryotic cell. In some embodiments, the cell is a eukaryotic cell, for example, a human cell, a mouse cell, a pig cell, a hamster cell, a monkey cell, etc. In some embodiments, a cell is characterized by increased VAMP7 expression, such as a neuronal cell. In some embodiments, a cell is obtained from a subject having or suspected of having a disease characterized by increased VAMP7 levels/expression, for example, cancer, transplantation rejection, or graft-versus-host disease, or neurological disease.

The term "intracellular environment," as used herein refers, to the aqueous biological fluid (e.g., cytosol) forming the microenvironment contained by the outer membrane of a cell. For example, in a subject, an intracellular environment may include the cytoplasm of a cell or cells of a target organ or tissue (e.g., the cytosol of neuronal cells in CNS tissue). In another example, a cellular environment is the cytoplasm of a cell or cells surrounded by cell culture growth media housed in an in vitro culture vessel, such as a cell culture plate or flask.

The term "increased activity," as used herein, refers to an increase in activity (e.g., via elevated expression) of a particular molecule in one cell or subject relative to a normal cell or subject that is not characterized by increased activity of that molecule (e.g., a "normal" or "control" cell or subject). In another example, a cell having increased VAMP7 activity is characterized by more VAMP7 activity (e.g., than a control cell expressing a normal (e.g., healthy) amount of VAMP7). Methods of determining relative expression levels of biomolecules (e.g., cytokines, proteins, nucleic acids, etc.) are known to the skilled artisan and include quantitative real-time PCR (q-RT-PCR), western blot, northern blot, protein quantification assays (e.g., BCA assay), biochemical assays, immunochemistry, flow cytometry, etc.

As used herein, "aberrant activity" refers to an altered level of gene product (e.g., protein) activity in a cell or subject relative to a normal, healthy cell or subject. Examples of aberrant activity include but are not limited to increased activity of a gene product due to increased expression of the gene encoding the gene product, loss of activity of a gene product due to deceased expression of the gene encoding the gene product, altered function of a gene product due to epigenetic regulation of the gene encoding the gene product, etc., in a cell or subject relative to a normal, healthy cell or subject.

DETAILED DESCRIPTION

Introduction

Proteases are ubiquitous regulators of protein function in all domains of life and represent approximately one percent of known protein sequences. Substrate-specific proteases have proven useful as research tools and as therapeutics that supplement a natural protease deficiency to treat diseases, such as hemophilia, or that simply perform their native function, such as in the case of botulinum toxin, which catalyzes the cleavage of SNARE proteins (e.g., VAMPs).

Researchers have engineered or evolved proteases for industrial use with enhanced thermostability and solvent tolerance. Similarly, a handful of therapeutic proteases have been engineered with improved kinetics and prolonged activity. The potential of proteases to serve as a broadly useful platform for degrading proteins implicated in disease, however, is greatly limited by the native substrate scope of known proteases. In contrast to the highly successful generation of therapeutic monoclonal antibodies with tailor-made binding specificities, the generation of proteases with novel protein cleavage specificities has proven to be a challenge.

The evolution of a protease that can degrade a target protein of interest often necessitates changing substrate sequence specificity at more than one position, and thus may require many generations of evolution. Continuous evolution strategies, which require little or no researcher intervention between generations, therefore is well-suited to evolve proteases capable of cleaving a target protein that differs substantially in sequence from the preferred substrate of a wild-type protease. In phage-assisted continuous evolution (PACE), a population of evolving selection phage (SP) is continuously diluted in a fixed-volume vessel by an incoming culture of host cells, e.g., *E. coli*. The SP is a modified phage genome in which the evolving gene of interest has replaced gene III (gIII), a gene essential for phage infectivity. If the evolving gene of interest possesses the desired activity, it will trigger expression of gene III from an accessory plasmid (AP) in the host cell, thus producing infectious progeny encoding active variants of the evolving gene. The mutation rate of the SP is controlled using an inducible mutagenesis plasmid (MP), such as MP6 (for example, as described in U.S. Pat. No. 9,023,594, issued May 5, 2015; U.S. Pat. No. 9,771,574, issued Sep. 26, 2017; U.S. patent application Ser. No. 15/713,403, filed Sep. 22, 2017 (now abandoned); International PCT Application PCT/ US2009/056194, filed Sep. 8, 2009, published as WO 2010/ 028347 on Mar. 11, 2010; U.S. Provisional Patent Application Ser. No. 61/426,139, filed Dec. 22, 2010; U.S. Pat. No. 9,394,537, issued Jul. 19, 2016; U.S. Pat. No. 10,336,997, issued Jul. 2, 2019; U.S. patent application Ser. No. 16/410, 767, filed May 13, 2019; International PCT Application PCT/US2011/066747, filed Dec. 22, 2011, published as WO 2012/088381 on Jun. 28, 2012; U.S. Provisional Patent Application Ser. No. 61/929,378 filed Jan. 20, 2014; U.S. Pat. No. 10,179,911, issued Jan. 15, 2019; U.S. patent application Ser. No. 16/238,386, filed Jan. 2, 2019; International PCT Application PCT/US2015/012022, filed Jan. 20, 2015; U.S. Provisional Patent Application Ser. No. 62/158, 982, filed May 8, 2015; U.S. Provisional Patent Application Ser. No. 62/187,669, filed Jul. 1, 2015; U.S. Provisional Patent Application Ser. No. 62/067,194, filed Oct. 22, 2014; U.S. patent application Ser. No. 15/518,639, filed Apr. 12, 2017; and International PCT Application PCT/US2018/ 048134, filed Aug. 27, 2018; U.S. patent application Ser. No. 13/922,812, filed Jun. 20, 2013; International PCT Application PCT Application, PCT/US2015/057012, filed Oct. 22, 2015, published as WO 2016/077052; and International PCT Application PCT/US2016/027795, filed Apr. 15, 2016, published as WO 2016/168631, the entire contents of each of which are incorporated herein by reference.), which upon induction increases the mutation rate of the SP by >300, 000-fold. Because the rate of continuous dilution is slower than phage replication but faster than *E. coli* replication, mutations only accumulate in the SP.

Some aspects of this disclosure are based on the recognition that PACE can be employed for the directed evolution of proteases, in particular the evolution of proteases that cleave intracellular proteins (e.g., VAMP1, VAMP7, PTEN, etc.). In some embodiments, proteases described by the disclosure are evolved from wild-type Botulinum toxin (BoNT) proteases, for example, BoNT F, E, and X. Proteases may require many successive mutations to remodel complex networks of contacts with polypeptide substrates and are thus not readily manipulated by conventional, iterative evolution methods. The ability of PACE to perform the equivalent of hundreds of rounds of iterative evolution methods within days enables complex protease evolution experiments, that are impractical with conventional methods.

This disclosure provides data illustrating the feasibility of PACE-mediated evolution of the BoNT proteases (e.g., BoNT F, E, and X) to cleave intracellular proteins (e.g., VAMP7, PTEN, etc.), as well as the feasibility of evolving BoNT proteases to have activity toward a novel substrate (compared to its native or canonical substrate) while simultaneously losing its activity to its native substrate (e.g., VAMP1, PTEN). As described in the Examples, BoNT F protease, which normally cleaves the consensus substrate sequence of SEQ ID NO.: 33, was evolved by PACE to cleave a target sequence of SEQ ID NO.: 35.

```
                                          (SEQ ID NO.: 33)
TSNRRLQQTQAQVEEVVDIIRVNVDKVLERDQKLSELDDRADALQAGASQ

FESSAAKLKR;

(SEQ ID NO.: 35)
KGLDKVMETQAQVDELKGIMVRNIDLVAQRGERLELLIDKTENLVDSSVT

FKTTSRNLARGGSGGSGGS.
```

It was observed that after constructing a pathway of evolutionary stepping-stones and performing iterative evolutions using PACE, the resulting BoNT protease variants (e.g., BoNT F, E, and X variants) contain up to 21 amino acid substitutions relative to wild-type BoNT proteases (e.g., SEQ ID NO.: 9, 6, and 5) and cleave human VAMP7 at the intended target peptide bond. Together, the work described herein establishes novel peptides resulting from directed evolution with changed substrate specificities and the ability to cleave proteins implicated in human disease. Further provided herein, is shown are novel peptides resulting from directed evolution with changed substrate specificities, in which a non-canonical substrate is cleaved by the evolved protease which no longer cleaves its canonical substrate.

PACE technology has been described previously, for example, in U.S. Pat. No. 9,023,594, issued May 5, 2015; U.S. Pat. No. 9,771,574, issued Sep. 26, 2017; U.S. patent application Ser. No. 15/713,403, filed Sep. 22, 2017 (now abandoned); International PCT Application PCT/US2009/ 056194, filed Sep. 8, 2009, published as WO 2010/028347 on Mar. 11, 2010; U.S. Provisional Patent Application Ser. No. 61/426,139, filed Dec. 22, 2010; U.S. Pat. No. 9,394, 537, issued Jul. 19, 2016; U.S. Pat. No. 10,336,997, issued Jul. 2, 2019; U.S. patent application Ser. No. 16/410,767, filed May 13, 2019; International PCT Application PCT/ US2011/066747, filed Dec. 22, 2011, published as WO 2012/088381 on Jun. 28, 2012; U.S. Provisional Patent Application Ser. No. 61/929,378 filed Jan. 20, 2014; U.S. Pat. No. 10,179,911, issued Jan. 15, 2019; U.S. patent application Ser. No. 16/238,386, filed Jan. 2, 2019; International PCT Application PCT/US2015/012022, filed Jan. 20, 2015; U.S. Provisional Patent Application Ser. No. 62/158, 982, filed May 8, 2015; U.S. Provisional Patent Application Ser. No. 62/187,669, filed Jul. 1, 2015; U.S. Provisional Patent Application Ser. No. 62/067,194, filed Oct. 22, 2014; U.S. patent application Ser. No. 15/518,639, filed Apr. 12, 2017; and International PCT Application PCT/US2018/ 048134, filed Aug. 27, 2018; U.S. patent application Ser. No. 13/922,812, filed Jun. 20, 2013; International PCT Application PCT Application, PCT/US2015/057012, filed Oct. 22, 2015, published as WO 2016/077052; and International PCT Application PCT/US2016/027795, filed Apr. 15, 2016, published as WO 2016/168631, the entire contents of each of which are incorporated herein by reference.

Variant BoNT Proteases and Uses Thereof

This disclosure provides variants of BoNT proteases that are derived from a wild-type BoNT F protease (e.g., SEQ ID NO.: 9) and have at least one amino acid mutation at the positions recited in Tables 1A, 6, 7, 8, and/or 9. In some embodiments, this disclosure provides variants of BoNT proteases that are derived from a wild-type BoNT F protease (e.g., SEQ ID NO.: 9) and have at least one of the amino acid mutations present in Tables 1A, 6, 7, 8, and/or 9. The variation in amino acid sequence generally results from a mutation, insertion, or deletion in a DNA coding sequence. In some embodiments, mutation of a DNA sequence results in a non-synonymous (i.e., conservative, semi-conservative, or radical) amino acid substitution.

In another aspect, this disclosure provides variants of BoNT proteases that are derived from a wild-type BoNT X protease (e.g., SEQ ID NO.: 8) and have at least one amino acid mutation at the positions recited in Table 1B, Tables 10-12, and FIGS. 55D, 56B, 57C, 57E, and 57F. In some embodiments, this disclosure provides variants of BoNT proteases that are derived from a wild-type BoNT X protease (e.g., SEQ ID NO.: 8) and have at least one of the amino acid mutations present in Table 1B, Tables 10-12, and FIGS. 55D, 56B, 57C, 57E, and 57F. The variation in amino acid sequence generally results from a mutation, insertion, or deletion in a DNA coding sequence. In some embodiments, mutation of a DNA sequence results in a non-synonymous (i.e., conservative, semi-conservative, or radical) amino acid substitution.

In another aspect, this disclosure provides variants of BoNT proteases that are derived from a wild-type BoNT E protease (e.g., SEQ ID NO.: 5) and have at least one amino acid mutation at the positions recited in Tables 13-14 and FIGS. 59A-59G. In some embodiments, this disclosure provides variants of BoNT proteases that are derived from a wild-type BoNT E protease (e.g., SEQ ID NO.: 5) and have at least one of the amino acid mutations present in Tables 13-14 and FIGS. 59A-59G. The variation in amino acid sequence generally results from a mutation, insertion, or deletion in a DNA coding sequence. In some embodiments, mutation of a DNA sequence results in a non-synonymous (i.e., conservative, semi-conservative, or radical) amino acid substitution.

Generally, wild-type BoNT protease is encoded by a gene of the microorganism *C. botulinum*. The amount or level of variation between a wild-type BoNT protease and a BoNT protease variant provided herein can be expressed as the percent identity of the nucleic acid sequences or amino acid sequences between the two genes or proteins, respectively.

The "percent identity" of two amino acid sequences may be determined using algorithms or computer programs, for example, the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into various computer programs, for example NBLAST and XBLAST programs (version 2.0) of Altschul, et al. J. Mol. Biol. 215:403-10, 1990. BLAST protein searches can be performed with the XBLAST program, score=50, word length=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used. BLAST nucleotide searches can be performed with the NBLAST nucleotide program parameters set, e.g., for score=100, wordlength=12 to obtain nucleotide sequences homologous to a nucleic acid molecule described herein. BLAST protein searches can be performed with the XBLAST program parameters set, e.g., to score 50, wordlength=3 to obtain amino acid sequences homologous to a protein molecule described herein. To obtain gapped alignments for comparison purposes, Gapped BLAST can be utilized as described in Altschul S F et al., (1997) Nuc Acids Res 25: 3389 3402. Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the world-wide web, ncbi.nlm.nih.gov). Another specific, non-limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

In some embodiments, the amount of variation is expressed as the percent identity at the amino acid sequence level. In some embodiments, a BoNT protease variant and a wild-type BoNT protease are from about 70% to about 99.9% identical, about 75% to about 95% identical, about 80% to about 90% identical, about 85% to about 95% identical, or about 95% to about 99% identical at the amino acid sequence level. In some embodiments, a BoNT protease variant comprises an amino acid sequence that is at least 95%, at least 99%, or at least 99.9% identical to the amino acid sequence of a wild-type BoNT protease.

In some embodiments, a variant BoNT protease is about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 99.9% identical to a wild-type BoNT protease.

Some aspects of the disclosure provide variant BoNT proteases having between about 80% and about 99.9% (e.g., about 80%, about 80.5%, about 81%, about 81.5%, about 82%, about 82.5%, about 83%, about 83.5%, about 84%, about 84.5%, about 85%, about 85.5%, about 86%, about 86.5%, about 87%, about 87.5%, about 88%, about 88.5%, about 89%, about 89.5%, about 90%, about 90.5%, about 91%, about 91.5%, about 92%, about 92.5%, about 93%, about 93.5%, about 94%, about 94.5%, about 95%, about 95.5%, about 96%, about 96.5%, about 97%, about 97.5%, about 98%, about 98.5%, about 99%, about 99.2%, about 99.4%, about 99.6%, about 99.8%, or about 99.9%) identical to a wild-type BoNT protease as set forth in SEQ ID NO.: 1-9. In some embodiments, the variant BoNT protease is no more than 99.9% identical to a wild-type BoNT protease.

Some aspects of the disclosure provide variant BoNT proteases having between 1 and 21 amino acid substitutions (e.g., mutations) relative to a wild-type BoNT protease (e.g., 1, 2, 3, 4, 5, etc.). In some embodiments, a variant BoNT protease has 1, 2, 3, 4, 5, 6, 7, 8, 9, 10, 11, 12, 13, 14, or 15 amino acid substitutions relative to a wild-type BoNT protease (e.g., 1, 2, 3, 4, 5, etc.). The mutations disclosed herein are not exclusive of other mutations which may occur or be introduces. For example, a protease variant may have a mutation as described herein in addition to at least one mutation not described herein (e.g., 1, 2, 3, 4, 5, etc. additional mutations). In some embodiments, a BoNT protease variant has at least one mutation at a position specified in Tables 1A, 6, 7, 8, and/or 9 in addition to at least mutation (e.g., 1, 2, 3, 4, 5, etc.) not described herein. In some embodiments, a BoNT protease variant has at least one of the mutations specified in Tables 1A, 6, 7, 8, and/or 9 in addition to at least one mutation (e.g., 1, 2, 3, 4, 5, etc.) not described herein. In some embodiments, a BoNT protease variant has at least one mutation at a position specified in Table 1B, Tables 10-12, or FIGS. 55D, 56B, 57C, 57E, and 57F in addition to at least mutation (e.g., 1, 2, 3, 4, 5, etc.) not described herein. In some embodiments, a BoNT protease variant has at least one of the mutations specified in Table 1B, Tables 10-12, or FIGS. 55D, 56B, 57C, 57E, and 57F in addition to at least one mutation (e.g., 1, 2, 3, 4, 5, etc.) not described herein.

The amount or level of variation between a wild-type BoNT protease and a variant BoNT protease can also be expressed as the number of mutations present in the amino acid sequence encoding the variant BoNT protease relative to the amino acid sequence encoding the wild-type BoNT protease. In some embodiments, an amino acid sequence encoding a variant BoNT protease comprises between about 1 mutation and about 100 mutations, about 1 mutations and about 80 mutations, about 2 mutations and about 60 mutations, about 3 mutations and about 55 mutations, or about 4 and about 50 mutations relative to an amino acid sequence encoding a wild-type BoNT protease. In some embodiments, an amino acid sequence encoding a variant BoNT protease comprises more than 75 mutations relative to an amino acid sequence encoding a wild-type BoNT protease In some embodiments, the variant BoNT protease comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 amino acid variations selected from the variations (e.g., amino acid substitutions) provided in Tables 1A, 6, 7, 8, and/or 9 or 1B.

TABLE 1A

Unique BoNT F Positions and Specific Mutations

| | | | |
|---|---|---|---|
| R303 | T335 | S350 | I354 |
| S166 | S167 | M147 | D175 |
| E200 | K31 | V106 | Y113 |
| E200 | R240 | V131 | S141 |
| N99 | R240 | F360 | G177 |
| N184 | R240 | Y113 | V131 |
| N184 | S69 | Y72 | K96 |
| N184 | S148 | I150 | A158 |
| L381 | N396 | P410 | Y372 |
| I412 | D141 | D418 | Y372 |
| E423 | Y244 | V193 | Y372 |
| N165 | S224 | A281 | E66 |
| R41 GLVEKIVKF*420 | A232 | V106 | |
| R303H | T335S | S350G | I354V |
| S166Y | S167I | M147T | D175G |
| E200K | K31N | V106A | Y113D |
| E200G | R240L | V131G | S141T |
| N99S | R240C | F360L | G177D |
| N184H | R240F | Y113S | V131F |

TABLE 1A-continued

Unique BoNT F Positions and Specific Mutations

| | | | |
|---|---|---|---|
| N184K | S69L | Y72H | K96N |
| N184T | S148N | I150V | A158P |
| L381M | N396H | P410L | Y372H |
| I412N | D141G | D418Y | Y372N |
| E423K | Y244C | V193M | Y372P |
| N165S | S224I | A281V | E66D |
| R41H | A232S | V106A | |
| GLVEKIVKF*420AWLRKS* (SEQ ID NO: 44) | | | |

TABLE 1B

Unique BoNT X Positions and Specific Mutations

| | | | |
|---|---|---|---|
| E68 | V98 | E113 | Q150 |
| A166 | S280 | S405 | R435 |
| E68A | V98G | E113K | Q150L |
| A166E | S280L | S405L | R435L |

Particular combinations of mutations present in an amino acid sequence encoding a variant BoNT protease can be referred to as the "genotype" of the variant BoNT protease. In some embodiments, a BoNT F variant comprises the following mutations: Y72H, V106A, V131G, S141T, S166Y, S167I, M174T, E200G, S224I, R240L, S350G, F360L, Y372H, N396H, P410L, and GLVEKIVKF*420AWLRKS* (SEQ ID NO: 44). In some embodiments, a BoNT F variant genotype comprises the following mutations: S69L, Y72H, V106A, S148N, I150V, A158P, S166Y, S167I, G177D, N184H, E200G, S224I, A232S, R240L, S350G, F360L,Y372N, L381M, N396H, P410L, and GLVEKIVKF*420AWLRKS* (SEQ ID NO: 44). When used herein, "GLVEKIVKF*420AWLRKS*" (SEQ ID NO: 44) shall refer to a mutation of the terminal residues of the variant protease, such that the replaced sequence (e.g., GLVEKIVKF* (SEQ ID NO: 45), or simply G) precedes the first residue in such sequence (e.g., G at position 420) and is replaced by the subsequent sequence (e.g., AWLRKS* (SEQ ID NO: 46)), and the "*" shall represent a stop codon. In some embodiments, a BoNT F variant genotype comprises the following mutations: S166Y. In some embodiments, a BoNT F variant genotype comprises the following mutations: R41H, K96N, S166Y, R240L/C, Y372H, and D414G. In some embodiments, a BoNT F variant genotype comprises the following mutations: S166Y, N184H/K, R240L, S350G, F360L, Y372H, P410L, and D414G. In some embodiments, a BoNT F variant genotype comprises the following mutations: S166Y, N184K, R240L, S350G, F360L, Y372H, N396H, P410L, GLVEKIVKF*420AWLRKS* (SEQ ID NO: 44), and E423K. In some embodiments, a BoNT F variant genotype comprises the following mutations: V106A, N165S, S166Y, S167I, N184K, R240L, S350G, F360L, Y372H, N396H, P410L, GLVEKIVKF*420AWLRKS* (SEQ ID NO: 44), and E423K. In some embodiments, a BoNT F variant genotype comprises the following mutations: V106A, Y113D/S, S166Y, S167I, N184H/K/S, E200K, R240L, Y244C, S350G, F360L, Y372H, N396H, P410L, GLVEKIVKF*420AWLRKS* (SEQ ID NO: 44), and E423K. In some embodiments, a BoNT F variant genotype comprises the following mutations: E66D, V106A, S166Y, S167I, D175G, N184K, E200G, S224I, R240L/F, T335S, S350G, F360L, Y372H, N396H, P410L, D418Y, and GLVEKIVKF*420AWLRKS* (SEQ ID NO: 44). In some embodiments, a BoNT F variant genotype comprises the following mutations: Y72H, N99S, V106A, V131G, S141T, S166Y, S167I, M174T, N184T, V193M, E200G, S224I, R240L/F, S350G, F360L, Y372H, N396H, P410L, and GLVEKIVKF*420AWLRKS*. In some embodiments, a BoNT F variant genotype comprises the following mutations: Y72H, V106A, V131G, S141T, S166Y, S167I, M174T, E200G, S224I, R240L, S350G, F360L, Y372H, N396H, P410L, and GLVEKIVKF*420AWLRKS* (SEQ ID NO: 44). In some embodiments, a BoNT F variant genotype comprises the following mutations: S69L, Y72H, V106A, S148N, I150V, A158P, S166Y, S167I, G177D, N184H, E200G, S224I, A232S, R240L, S350G, F360L, Y372N, L381M, N396H, P410L, and GLVEKIVKF*420AWLRKS* (SEQ ID NO: 44).

In some embodiments, a variant BoNT protease comprises at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 mutations provided in Tables 1A, 6, 7, 8, and/or 9. In some embodiments, the at least one mutation is selected from the group consisting of: R303H, T335S, S350G, I354V, S166Y, S167I, M147T, D175G, E200K, K31N, V106A, Y113D, E200G, R240L, V131G, S141T, N99S, R240C, F360L, G177D, N184H, R240F, Y113S, V131F, N184K, S69L, Y72H, K96N, N184T, S148N, I150V, A158P, L381M, N396H, P410L, Y372H, I412N, D141G, D418Y, Y372N, E423K, Y244C, V193M, Y372P, N165S, S224I, A281V, E66D, R41H, A232S, V106AWLRKS* (SEQ ID NO: 47), and GLVEKIVKF*420AWLRKS* (SEQ ID NO: 44). In some embodiments, a variant BoNT protease as described herein comprises or consists of a sequence selected from SEQ ID NOs.: 12-31 given in Table 2. In some embodiments, or having at least 70% sequence homology to (e.g., at least 70%, at least 80%, at least 85%, at least 90%, at least 95%, at least 96%, at least 97%, at least 98%, at least 99%, at least 99.5%, at least 99.9%, or more identity to) a sequence selected from SEQ ID NOs.: 12-31. In some embodiments, the lowercase amino acid residues indicate the amino acid substitutions.

In some embodiments, a variant BoNT X protease comprises at least 1, at least 2, at least 3, at least 4, at least 5, at least 6, at least 7, at least 8 mutations provided in Table 1B, Tables 10-12, or FIGS. 55D, 56B, 57C, 57E, and 57F. In some embodiments, a BoNT X variant has at least one mutation at the following positions: E68, V98, E113, Q150, A166, S280, S405, and R435. In some embodiments, a BoNT X variant has at least one mutation selected from the following mutations: E68A, V98G, E113K, Q150L, A166E, S280L, S405L, and R435L. In some embodiments, a variant BoNT protease as described herein comprises or consists of a sequence selected from SEQ ID NOs.: 36-43 as given in Table 2. In some embodiments, or having at least 70% sequence homology to (e.g., at least 70%, at least 80%, at least 85%, at least 90%, at least 95%, at least 96%, at least 97%, at least 98%, at least 99%, at least 99.5%, at least 99.9%, or more identity to) a sequence selected from SEQ ID NOs.: 36-43. In some embodiments, the lowercase amino acid residues indicate the amino acid substitutions.

In some embodiments, a BoNT-X protease has a mutation in at least one of the following positions: N144, A166, T167, and Y314. In some embodiments, a BoNT-X protease has a mutation in at least one of the following positions: A166, T167, R257, Q322, L364, and S413. In some embodiments, the C-terminal region of a BoNT-X protease comprises the amino acid sequence YLNSKN (SEQ ID NO: 48). In some embodiments, a BoNT-X protease has a mutation in at least one of the following positions: A166, T167, R257, and Q322. In some embodiments, a BoNT-X protease has a mutation in at least one of the following positions: A166, T167, R257, Q322, L364, and S413. In some embodiments, a BoNT-X protease has a mutation in at least one of the following positions: N143, N148, A166, T167, Y314, and L364. In some embodiments, a BoNT-X protease has a mutation in at least one of the following positions: A166, T167, Q322, and L364. In some embodiments, the C-terminal region of a BoNT-X protease comprises the amino acid sequence TATQKTNNGDFQHGLARP* (SEQ ID NO: 49). In some embodiments, a BoNT-X protease has a mutation in at least one of the following positions: N143, N148, A166, T167, Y314, and L364. In some embodiments, a BoNT-X protease has a mutation in at least one of the following positions: V98, E113, N143, N148, A166, T167, V345, and L364. In some embodiments, a BoNT-X protease has a mutation in at least one of the following positions: R23, V98, A166, and T167. In some embodiments, a BoNT-X protease has a mutation in at least one of the following positions: D133, N148, A166, T167, and S279. In some embodiments, a BoNT-X protease has a mutation in at least one of the following positions: A166, T167, 1175, L364, and S391. In some embodiments, a BoNT-X protease has a mutation in at least one of the following positions: V98, E100, N143, N148, A166, T167, S279, and L416. In some embodiments, a BoNT-X protease has a mutation at position A166. In some embodiments, a BoNT-X protease has a mutation in at least one of the following positions: N143, A166, R257, L267, L268, Q322, S349, and L364. In some embodiments, a BoNT-X protease has a mutation in at least one of the following positions: N143, and A166. In some embodiments, the C-terminal region of a BoNT-X protease comprises the amino acid sequence AFTATQKSNNGDFQHGLAQP* (SEQ ID NO: 50). In some embodiments, a BoNT-X protease has a mutation in at least one of the following positions: N143, A166, L225, R257, L267, L268, T341, S349, L364, and R425. In some embodiments, a BoNT-X protease has a mutation in at least one of the following positions: A166, T167, and A218. In some embodiments, a BoNT-X protease has a mutation in at least one of the following positions: N148, A166, T167, A218, N241, and K285. In some embodiments, a BoNT-X protease has a mutation in at least one of the following positions: N143, A166, and G169. In some embodiments, a BoNT-X protease has a mutation in at least one of the following positions: N143, A166, R257, L267, L268, S349, and L364.

In some embodiments, a BoNT-X protease has at least one of the following mutations: N144L, A166E, T167I, and Y314S. In some embodiments, a BoNT-X protease has at least one of the following mutations: A166E, T167I, R257C, Q322K, L364I, and S413F. In some embodiments, the C-terminal region of a BoNT-X protease comprises the amino acid sequence YLNSKN (SEQ ID NO: 48). In some embodiments, a BoNT-X protease has at least one of the following mutations: A166E, T167I, R257C, and Q322K. In some embodiments, a BoNT-X protease has at least one of the following mutations: A166E, T167I, R257C, Q322K, L364I, and S413F. In some embodiments, a BoNT-X protease has at least one of the following mutations: N143D, N148T, A166E, T167I, Y314N, and L364I. In some embodiments, a BoNT-X protease has at least one of the following mutations: A166E, T167I, Q322K, and L364V. In some embodiments, the C-terminal region of a BoNT-X protease comprises the amino acid sequence TATQKTNNGDFQHGLARP* (SEQ ID NO: 49). In some embodiments, a BoNT-X protease has at least one of the following mutations: N143D, N148T, A166E, T167I, Y314C, and L364I. In some embodiments, a BoNT-X protease has at least one of the following mutations: V98G, E113K, N143D, N148T, A166E, T167I, V345E, and L364I. In some embodiments, a BoNT-X protease has at least one of the following mutations: R23S, V98G, A166E, T167I. In some embodiments, a BoNT-X protease has at least one of the following mutations: D133N, N148S, A166E, T167I, and S279P. In some embodiments, a BoNT-X protease has at least one of the following mutations: A166E, T167I, I175V, L364I, and S391G. In some embodiments, a BoNT-X protease has at least one of the following mutations: V98G, E100D, N143D, N148T, A166E, T167I, S279P, and L416F. In some embodiments, a BoNT-X protease has at least one of the following mutations: A166E, and YLNSKN (SEQ ID NO: 48). In some embodiments, a BoNT-X protease has at least one of the following mutations: N143D, A166E, R257C, L267I, L268I, Q322K, S349F, and L364I. In some embodiments, a BoNT-X protease has at least one of the following mutations: N143D, and A166E. In some embodiments, the C-terminal region of a BoNT-X protease comprises the amino acid sequence AFTATQKSNNGDFQHGLAQP* (SEQ ID NO.: 50). In some embodiments, a BoNT-X protease has at least one of the following mutations: N143D, A166E, L225W, R257C, L267I, L268I, T341P, S349F, L364I, and R425L. In some embodiments, a BoNT-X protease has at least one of the following mutations: A166E, T167I, and A218V. In some embodiments, a BoNT-X protease has at least one of the following mutations: N148T, A166E, T167A, A218V, N241I, and K285N. In some embodiments, a BoNT-X protease has at least one of the following mutations: N143D, A166E, and G169R. In some embodiments, a BoNT-X protease has at least one of the following mutations: N143D, A166E, R257C, L267I, L268I, S349F, and L364I.

In some embodiments, a BoNT-X protease has a mutation in at least one of the following positions: V98, E113, Q150, A166, and 5280. In some embodiments, a BoNT-X protease has a mutation at position A166. In some embodiments, a BoNT-X protease has a mutation in at least one of the following positions: A166, 5405, and R435. In some embodiments, a BoNT-X protease has a mutation in at least one of the following positions: E68, Q150, and A166. In some embodiments, a BoNT-X protease has a mutation in at least one of the following positions: A166, and R435. In some embodiments, a BoNT-X protease has a mutation in at least one of the following positions: V98, E113, A166, and R435.

In some embodiments, a BoNT-X protease has at least one of the following mutations: V98G, E113K, Q150Q, A166E, and S280L. In some embodiments, a BoNT-X protease has at least one of the following mutations: A166E. In some embodiments, a BoNT-X protease has at least one of the following mutations: A166E, S405L, and R435L. In some embodiments, a BoNT-X protease has at least one of the following mutations: E68A, Q150L, and A166E. In some embodiments, a BoNT-X protease has at least one of the following mutations: A166E, and R435L. In some embodiments, a BoNT-X protease has at least one of the following mutations: V98G, E113K, A166E, and R435L.

In some embodiments, a BoNT-X protease has a mutation in at least one of the following positions: N143, N148, A166, T167, R257, L267, L268, Y314, Q322, S349, L364, and S413.

In some embodiments, a BoNT-X protease has at least one of the following mutations: N143N, N148N, A166E, T167I, R257C, L267L, L268L, Y314Y, Q322K, S349S, L364I, and S413F. In some embodiments, a BoNT-X protease has at least one of the following mutations: N143D, N148T, A166E, T167I, R257R, L267L, L268L, Y314N, Q322Q, S349S, L364I, and S413S. In some embodiments, a BoNT-X protease has at least one of the following mutations: N143D, N148N, A166E, T167T, R257C, L267I, L268I, Y314Y, Q322K, S349F, L364I, and S413S.

In some embodiments, a BoNT-X protease has a mutation in at least one of the following positions: N143, N148, A166, T167, Y314, and L364.

In some embodiments, a BoNT-X protease has at least one of the following mutations: N143D, N148T, A166E, T167I, Y314N, and L364I.

In some embodiments, a BoNT-X protease has a mutation in at least one of the following positions: L3, R26, 165, M71, A128, N143, Q150, N164, A166, Y168, P174, A222, S223, T224, 5240, R257, Y294, K313, Y314, Q322, L339, L364, E366, K410, and C423.

In some embodiments, a BoNT-X protease has at least one of the following mutations: N143D, N164S, Y168C, T224I, S240K, Y294C, Y314H, and C423Y. In some embodiments, a BoNT-X protease has at least one of the following mutations: L31, N143D, N164S, Y168C, T224I, S240K, Y294C, and K410N. In some embodiments, a BoNT-X protease has at least one of the following mutations: I65V, N143D, N164S, Y168C, S223L, T224I, S240K, and Y294C. In some embodiments, a BoNT-X protease has at least one of the following mutations: R26F, N143D, N164S, Y168C, T224I, S240K, Y294C, and Y314H. In some embodiments, a BoNT-X protease has at least one of the following mutations: R26S, N143D, N164S, Y168C, T224I, S240K, Y294C, and Y314H. In some embodiments, a BoNT-X protease has at least one of the following mutations: A128V, N143D, N164S, Y168C, T224I, S240K, Y294C, and Y314H. In some embodiments, a BoNT-X protease has at least one of the following mutations: N143D, N164S, Y168C, T224I, S240K, Y294C, Y314H, and L364F. In some embodiments, a BoNT-X protease has at least one of the following mutations: N143D, N164S, A166E, P174T, A222S, T224I, S240K, and K313R. In some embodiments, a BoNT-X protease has at least one of the following mutations: N143D, N164S, A166E, P174T, A222S, T224I, S240K, and K313R. In some embodiments, a BoNT-X protease has at least one of the following mutations: N143D, N164S, A166E, P174T, A222S, T224I, S240K, K313R, and E366D. In some embodiments, a BoNT-X protease has at least one of the following mutations: M71V, N143D, N164S, A166E, P174T, A222S, T224I, S240K, and K313R. In some embodiments, a BoNT-X protease has at least one of the following mutations: N143D, N164S, A166E, P174T, A222S, T224I, S240K, and K313R. In some embodiments, a BoNT-X protease has at least one of the following mutations: N143D, N164S, A166E, P174T, A222S, T224I, S240K, and K313R. In some embodiments, a BoNT-X protease has at least one of the following mutations: N143D, N164S, A166E, P174T, A222S, T224I, S240K, and K313R. In some embodiments, a BoNT-X protease has at least one of the following mutations: Q150K, N164D, T224I, S240K, K313N, Q322E, and L339F. In some embodiments, a BoNT-X protease has at least one of the following mutations: N143D, N164S, A166E, P174T, A222S, T224I, S240K, and K313R. In some embodiments, a BoNT-X protease has at least one of the following mutations: N164E, T224I, S240K, K313N, Q322E, and L339F. In some embodiments, a BoNT-X protease has at least one of the following mutations: N164D, T224I, S240K, R257C, K313N, Q322E, L339F, and L364F. In some embodiments, a BoNT-X protease has at least one of the following mutations: N164D, T224I, S240K, R257C, K313N, Q322E, L339F, and L364F. In some embodiments, a BoNT-X protease has at least one of the following mutations: N164D, T224I, S240K, R257C, K313N, Q322E, L339F, and L364F.

In some embodiments, a BoNT-X protease has a mutation in at least one of the following positions: N143, Q150, N164, Y168, P174, A222, T224, 5240, K313, Q322, and L339.

In some embodiments, a BoNT-X protease has at least one of the following mutations: N143D, N164S, and P174I. In some embodiments, a BoNT-X protease has at least one of the following mutations: N143D, N164S, Y168C, and P174I. In some embodiments, a BoNT-X protease has at least one of the following mutations: N143D, N164S, P174T, A222S, T224I, S240N, and K313R. In some embodiments, a BoNT-X protease has at least one of the following mutations: N143D, N164S, P174T, A222S, T224I, S240N, and K313R. In some embodiments, a BoNT-X protease has at least one of the following mutations: N143D, N164S, P174T, A222S, T224I, S240N, and K313R. In some embodiments, a BoNT-X protease has at least one of the following mutations: Q150K, N164D, S240N, K313N, Q322E, and L339F. In some embodiments, a BoNT-X protease has at least one of the following mutations: N164D, S240N, K313N, Q322E, and L339F. In some embodiments, a BoNT-X protease has at least one of the following mutations: N164D, S240N, K313N, Q322E, and L339F. In some embodiments, a BoNT-X protease has at least one of the following mutations: N164D, S240N, K313N, Q322E, and L339F.

In some embodiments, a BoNT-E protease has a mutation in at least one of the following positions: C26, Q27, E28, 135, G49, H56, D65, E79, S99, G101, N118, D156, E159, N161, S162, S163, S166, M172, I203, I232, T242, R244, N248, I262, I263, A313, I316, G353, Q354, Y355, Y357, K359, N365, 5367, N390, G403, and L404.

In some embodiments, a BoNT-E protease has at least one of the following mutations: Q27H, S99A, G101S, N118D, E159L, N161Y, S162Q, S163R, M172K, I232T, Q354R, Y357Y, and L404*. In some embodiments, a BoNT-E protease has at least one of the following mutations: C26Y, Q27H, S99A, G101S, N118D, D156N, E159L, N161Y, S162Q, S163R, M172K, I232T, N248K, Q354R, Y355P, and Y357F. In some embodiments, a BoNT-E protease has at least one of the following mutations: C26Y, Q27H, S99A, G101S, N118D, D156N, E159L, N161Y, S162Q, S163R, M172K, I232T, N248K, I262T, Q354W, Y357F, and N390D. In some embodiments, a BoNT-E protease has at least one of the following mutations: Q27H, S99A, G101S, N118D, E159L, N161Y, S162Q, S163R, M172K, I232T, N248K, G353E, Q354R, Y355P, and Y357F. In some embodiments, a BoNT-E protease has at least one of the following mutations: Q27H, S99A, G101S, N118D, E159L, N161Y, S162Q, S163R, M172K, I232T, N248K, Q354W, Y355P, Y357F, and N390D. In some embodiments, a BoNT-E protease has at least one of the following mutations: C26Y, Q27H, D65G, S99A, G101S, N118D, D156N, E159L, N161Y, S162Q, S163R, M172K, I232T, N248K, Q354R, Y355P, Y357F, and L404*. In some embodiments, a BoNT-E protease has at least one of the following mutations: Q27H, S99A, G101S, N118D, D156N, E159L, N161Y, S162Q, S163R, M172K, I232T, N248K, I316T, Q354W, and Y357F. In some embodiments, a BoNT-E protease has at least one of the following mutations: Q27H, S99T, G101S, N118D, D156N, E159L, N161Y, S162Q, S163R, M172K, I232T, T242A, N248K, Q354R, Y355P, and Y357F. In some embodiments, a BoNT-E protease has at least one of the following mutations: Q27H, S99A, G101S, N118D, E159L, N161Y, S162Q, S163R, M172K, I232T, I316T, Q354R, Y357Y, and L404*. In some embodiments, a BoNT-E protease has at least one of the following mutations: C26Y, Q27H, S99A, G101S, N118D, D156N, E159L, N161Y, S162Q, S163R, S166R, M172K, I232T, N248K, I263V, Q354R, Y355P, Y357F, and S367F. In some embodiments, a BoNT-E protease has at least one of the following mutations: C26Y, Q27H, S99A, G101S, N118D, D156N, E159L, N161Y, S162Q, S163R, M172K, I232T, R244V, N248K, Q354R, Y355P, Y357F, and K359R. In some embodiments, a BoNT-E protease has at least one of the following mutations: C26Y, Q27H, E79D, S99A, G101S, N118D, D156N, E159L, N161Y, S162Q, S163R, M172K, I203V, I232T, N248K, Q354R, Y355H, and Y357F. In some embodiments, a BoNT-E protease has at least one of the following mutations: C26Y, Q27H, S99A, G101S, N118D, E159L, N161Y, S162Q, S163R, M172K, I232T, N248K, Q354R, Y355P, and Y357F. In some embodiments, a BoNT-E protease has at least one of the following mutations: C26Y, Q27H, E28K, H56L, S99A, G101S, N118D, D156N, E159L, N161Y, S162Q, S163R, M172K, I232T, N248K, Q354R, Y355P, Y357F, and L404*. In some embodiments, a BoNT-E protease has at least one of the following mutations: Q27H, S99A, G101S, N118D, E159L, N161Y, S162Q, S163R, M172K, I232T, Q354R, and Y357Y. In some embodiments, a BoNT-E protease has at least one of the following mutations: C26Y, Q27H, H56L, S99A, G101S, N118D, D156N, E159L, N161Y, S162Q, S163R, M172K, I232T, N248K, Q354R, Y355P, and Y357F. In some embodiments, a BoNT-E protease has at least one of the following mutations: Q27H, S99A, G101S, N118D, D156N, E159L, N161Y, S162Q, S163R, M172K, I232T, N248K, Q354R, Y355P, Y357F, and L404*. In some embodiments, a BoNT-E protease has at least one of the following mutations: C26Y, Q27H, G49S, S99A, G101S, N118D, D156N, E159L, N161Y, S162Q, S163R, M172K, I232T, N248K, A313V, Q354R, Y355P, Y357F, and G403E. In some embodiments, a BoNT-E protease has at least one of the following mutations: C26Y, Q27H, S99A, G101S, N118D, D156N, E159L, N161Y, S162Q, S163R, M172K, I232T, N248K, Q354R, Y355P, and Y357F. In some embodiments, a BoNT-E protease has at least one of the following mutations: Q27H, H56Y, S99A, G101S, N118D, D156N, E159L, N161Y, S162Q, S163R, M172K, I232T, N248K, Q354R, Y355P, and Y357F. In some embodiments, a BoNT-E protease has at least one of the following mutations: C26Y, Q27H, S99A, G101S, N118D, D156N, E159L, N161Y, S162Q, S163R, M172K, I232T, N248K, Q354R, Y355P, Y357F, and L404*. In some embodiments, a BoNT-E protease has at least one of the following mutations: Q27H, I35V, S99A, G101S, N118D, D156N, E159L, N161Y, S162Q, S163R, M172K, I232T, N248K, Q354W, Y355P, Y357F, N365S, and L404*.

In some embodiments, a BoNT-E protease has a mutation in at least one of the following positions: C26, Q27, S99, G101, N118, D156, E159, N161, 5162, 5163, M172, I232, N248, Q354, Y355, and Y357.

In some embodiments, a BoNT-E protease has at least one of the following mutations: C26Y, Q27H, S99A, G101S, N118D, D156N, E159L, N161Y, S162Q, S163R, M172K, I232T, N248K, Q354R, Y355P, and Y357F.

TABLE 2

| SEQ ID NO | Amino Acid Sequence | Description |
|---|---|---|
| 1 | MPFVNKQFNYKDPVNGVDIAYIKIPNAGQMQPVKAFKI HNKIWVIPERDTFTNPEEGDLNPPPEAKQVPVSYYDSTY LSTDNEKDNYLKGVTKLFERIYSTDLGRMLLTSIVRGIPF WGGSTIDTELKVIDTNCINVIQPDGSYRSEELNLVIIGPSA DIIQFECKSFGHEVLNLTRNGYGSTQYIRFSPDFTFGFEES LEVDTNPLLGAGKFATDPAVTLAHELIHAGHRLYGIAIN PNRVFKVNTNAYYEMSGLEVSFEELRTFGGHDAKFIDSL QENEFRLYYYNKFKDIASTLNKAKSIVGTTASLQYMKN VFKEKYLLSEDTSGKFSVDKLKFDKLYKMLTEIYTEDNF VKFFKVLNRKTYLNFDKAVFKINIVPKVNYTIYDGFNLR NTNLAANFNGQNTEINNMNFTKLKNFTGLFEFYKLL | Botulinum neurotoxin serotype A Light Chain (BoNT A) |
| 2 | MPVTINNFNYNDPIDNNNIIMMEPPFARGTGRYYKAFKI TDRIWIIPERYTFGYKPEDFNKSSGIFNRDVCEYYDPDYL NTNDKKNIFLQTMIKLFNRIKSKPLGEKLLEMIINGIPYLG DRRVPLEEFNTNIASVTVNKLISNPGEVERKKGIFANLIIF GPGPVLNENETIDIGIQNHFASREGFGGIMQMKFCPEYVS VFNNVQENKGASIFNRRGYFSDPALILMHELIHVLHGLY GIKVDDLPIVPNEKKFFMQSTDAIQAEELYTFGGQDPSIIT PSTDKSIYDKVLQNFRGIVDRLNKVLVCISDPNININIYK NKFKDKYKFVEDSEGKYSIDVESFDKLYKSLMFGFTETN IAENYKIKTRASYFSDSLPPVKIKNLLDNEIYTIEEGFNISD KDMEKEYRGQNKAINKQAYEEISKEHLAVYKIQM | Botulinum neurotoxin serotype B Light Chain (BoNT B) |
| 3 | MPITINNFNYSDPVDNKNILYLDTHLNTLANEPEKAFRIT GNIWVIPDRFSRNSNPNLNKPPRVTSPKSGYYDPNYLST DSDKDTFLKEIIKLFKRINSREIGEELIYRLSTDlPFPGNNN TPINTFDFDVDFNSVDVKTRQGNNWVKTGSINPSVIITGP RENIIDPETSTFKLTNNTFAAQEGFGALSIISISPRFMLTYS NATNDVGEGRFSKSEFCMDPILILMHELNHAMHNLYGI AIPNDQTISSVTSNIFYSQYNVKLEYAEIYAFGGPTIDLIP KSARKYFEEKALDYYRSIAKRLNSITTANPSSFNKYIGEY KQKLIRKYRFVVESSGEVTVNRNKFVELYNELTQIFTEF NYAKIYNVQNRKIYLSNVYTPVTANILDDNVYDIQNGFN IPKSNLNVLFMGQNLSRNPALRKVNPENMLYLFTKF | Botulinum neurotoxin serotype C Light Chain (BoNT C) |
| 4 | MTWPVKDFNYSDPVNDNDILYLRIPQNKLITTPVKAFMI TQNIWVIPERFSSDTNPSLSKPPRPTSKYQSYYDPSYLST DEQKDTFLKGIIKLFKRINERDIGKKLINYLVVGSPFMGD SSTPEDTFDFTRHTTNIAVEKFENGSWKVTNIITPSVLIFG PLPNILDYTASLTLQGQQSNPSFEGFGTLSILKVAPEFLLT FSDVTSNQSSAVLGKSIFCMDPVIALMHELTHSLHQLYGI NIPSDKRIRPQVSEGFFSQDGPNVQFEELYTFGGLDVEIIP QIERSQLREKALGHYKDIAKRLNNINKTIPSSWISNIDKY KKIFSEKYNFDKDNTGNFVVNIDKFNSLYSDLTNVMSEV VYSSQYNVKNRTHYFSRHYLPVFANILDDNIYTIRDGFN LTNKGFNIENSGQNIERNPALQKLSSESVVDLFTKV | Botulinum neurotoxin serotype D Light Chain (BoNT D) |
| 5 | MPKINSFNYNDPVNDRTILYIKPGGCQEFYKSFNIMKNI WIIPERNVIGTTPQDFHPPTSLKNGDSSYYDPNYLQSDEE KDRFLKIVTKIFNRINNNLSGGILLEELSKANPYLGNDNT PDNQFHIGDASAVEIKFSNGSQHILLPNVIIMGAEPDLFET NSSNISLRNNYMPSNHGFGSIAIVTFSPEYSFRFNDNSINE FIQDPALTLMHELIHSLHGLYGAKGITTTCIITQQQNPLIT NRKGINIEEFLTFGGNDLNIITVAQYNDIYTNLLNDYRKI ASKLSKVQVSNPQLNPYKDIFQEKYGLDKDASGIYSVNI NKFDDILKKLYSFTEFDLATKFQVKCRETYIGQYKYFKL SNLLNDSIYNISEGYNINNLKVNFRGQNANLNPRIIKPITG RGLVKKIIRF | Botulinum neurotoxin serotype E Light Chain (BoNT E) (wild type, residues 1-411): |
| 6 | MPVVINSFNYNDPVNDDTILYMQIPYEEKSKKYYKAFEI MRNVWIIPERNTIGTDPSDFDPPASLENGSSAYYDPNYLT TDAEKDRYLKTTIKLFKRINSNPAGEVLLQEISYAKPYLG NEHTPINEFHPVTRTTSVNIKSSTNVKSSIILNLLVLGAGP DIFENSSYPVRKLMDSGGVYDPSNDGFGSINIVTFSPEYE YTFNDISGGYNSSTESFIADPAISLAHELIHALHGLYGAR GVTYKETIKVKQAPLMIAEKPIRLEEFLTFGGQDLNIITSA MKEKIYNNLLANYEKIATRLSRVNSAPPEYDINEYKDYF QWKYGLDKNADGSYTVNENKFNEIYKKLYSFTEIDLAN KFKVKCRNTYFIKYGFLKVPNLLDDDIYTVSEGFNIGNL AVNNRGQNIKLNPKIIDSIPDKGLVEKIVKF | Botulinum neurotoxin serotype F Light Chain (BoNT F) |

TABLE 2-continued

| Sequence Listing | | |
| --- | --- | --- |
| SEQ ID NO | Amino Acid Sequence | Description |
| 7 | MPVNIKNFNYNDPINNDDIIMMEPFNDPGPGTYYKAFRII DRIWIVPERFTYGFQPDQFNASTGVFSKDVYEYYDPTYL KTDAEKDKFLKTMIKLFNRINSKPSGQRLLDMIVDAIPY LGNASTPPDKFAANVANVSINKKIIQPGAEDQIKGLMTN LIIFGPGPVLSDNFTDSMIMNGHSPISEGFGARMMIRFCPS CLNVFNNVQENKDTSIFSRRAYFADPALTLMHELIHVLH GLYGIKISNLPITPNTKEFFMQHSDPVQAEELYTFGGHDP SVISPSTDMNIYNKALQNFQDIANRLNIVSSAQGSGIDISL YKQIYKNKYDFVEDPNGKYSVDKDKFDKLYKALMFGF TETNLAGEYGIKTRYSYFSEYLPPIKTEKLLDNTIYTQNE GFNIASKNLKTEFNGQNKAVNKEAYEEISLEHLVIYRIA MCKPVMYKNAPPTPG | Botulinum neurotoxin serotype G Light Chain (BoNT G) |
| 8 | MKLEINKFNYNDPIDGINVITMRPPRHSDKINKGKGPFK AFQVIKNIWIVPERYNFTNNTNDLNIPSEPIMEADAIYNP NYLNTPSEKDEFLQGVIKVLERIKSKPEGEKLLELISSSIP LPLVSNGALTLSDNETIAYQENNNIVSNLQANLVIYGPGP DIANNATYGLYSTPISNGEGTLSEVSFSPFYLKPFDESYG NYRSLVNIVNKFVKREFAPDPASTLMHELVHVTHNLYGI SNRNFYYNFDTGKIETSRQQNSLIFEELLTFGGIDSKAISS LIIKKIIETAKNNYTTLISERLNTVTVENDLLKYIKNKIPV QGRLGNFKLDTAEFEKKLNTILFVLNESNLAQRFSILVRK HYLKERPIDPIYVNILDDNSYSTLEGFNISSQGSNDFQGQ LLESSYFEKIESNALRAFIKICPRNGLLYNAIYRNSKN | Botulinum neurotoxin serotype X Light Chain (BoNT X) |
| 9 | MPVVINSFNYNDPVNDDTILYMQIPYEEKSKKYYKAFEI MRNVWIIPERNTIGTDPSDFDPPASLENGSSAYYDPNYLT TDAEKDRYLKTTIKLFKRINSNPAGEVLLQEISYAKPYLG NEHTPINEFHPVTRTTSVNIKSSTNVKSSIILNLLVLGAGP DIFENSSYPVRKLMDSGGVYDPSNDGFGSINIVTFSPEYE YTFNDISGGYNSSTESFIADPAISLAHELIHALHGLYGAR GVTYKETIKVKQAPLMIAEKPIRLEEFLTFGGQDLNIITSA MKEKIYNNLLANYEKIATRLSRVNSAPPEYDINEYKDYF QWKYGLDKNADGSYTVNENKFNEIYKKLYSFTEIDLAN KFKVKCRNTYFIKYGFLKVPNLLDDDIYTVSEGFNIGNL AVNNRGQNIKLNPKIIDSIPDKGLVEKIVKF* | Wild-Type BoNT F |
| 10 | CKSVIPRKGTKAPPRLCIRVNNRELFFVASESSYNENDIN TPKEIDDTTNLNNNYRNNLDEVILDYNSETIPQISNQTLN TLVQDDSYVPRYDSNGTSEIEEHNVVDLNVFFYLHAQK VPEGETNISLTSSIDTALSEESQVYTFFSSEFINTINKPVHA ALFISWINQVIRDFTTEATQKSTFDKIADISLVVPYVGLA LNIGNEVQKENFKEAFELLGAGILLEFVPELLIPTILVFTIK SFIGSSENKNKIIKAINNSLMERETKWKEIYSWIVSNWLT RINTQFNKRKEQMYQALQNQVDAIKTVIEYKYNNYTSD ERNRLESEYNINNIREELNKKVSLAMENIERFITESSIFYL MKLINEAKVSKLREYDEGVKEYLLDYISEHRSILGNSVQ ELNDLVTSTLNNSIPFELSSYTNDKILILYF | BoNT F HC$_N$, translocation domain |
| 11 | NKLYKKIKDNSILDMRYENNKFIDISGYGSNISINGDVYI YSTNRNQFGIYSSKPSEVNIAQNNDIIYNGRYQNFSISFW VRIPKYFNKVNLNNEYTIIDCIRNNNSGWKISLNYNKIIW TLQDTAGNNQKLVFNYTQMISISDYINKWIFVTITNNRL GNSRIYINGNLIDEKSISNLGDIHVSDNILFKIVGCNDTRY VGIRYFKVFDTELGKTEIETLYSDEPDPSILKDFWGNYLL YNKRYYLLNLLRTDKSITQNSNFLNINQQRGVYQKPNIF SNTRLYTGVEVIIRKNGSTDISNTDNFVRKNDLAYINVV DRDVEYRLYADISIAKPEKIIKLIRTSNSNNSLGQIIVMDSI GNNCTMNFQNNNGGNIGLLGFHSNNLVASSWYYNNIR KNTSSNGCFWSFISKEHGWQEN | BoNT F HC$_C$, Binding domain |
| 12 | MPVVINSFNYNDPVNDDTILYMQIPYEEKSKKYYKAFEI MRNVWIIPERNTIGTDPSDFDPPASLENGSSAYYDPNYLT TDAEKDRYLKTTIKLFKRINSNPAGEVLLQEISYAKPYLG NEHTPINEFHPVTRTTSVNIKSSTNVKSSIILNLLVLGAGP DIFENSSYPVRKLMDSGGVYDPSNDGFGSINIVTFSPEYE YTFNDISGGYNSSTESFIADPAISLAHELIHALHGLYGAR GVTYKETIKVKQAPLMIAEKPIRLEEFLTFGGQDLNIITSA MKEKIYNNLLANYEKIATRLSRVNSAPPEYDINEYKDYF QWKYGLDKNADGSYTVNENKFNEIYKKLYSFTEIDLAN KFKVKCRNTYFIKYGFLKVPNLLDDDIYTVSEGFNIGNL AVNNRGQNIKLNPKIIDSIPDKGLVEKIVKF* | BoNT F Light Chain Variant - F1 |
| 13 | MPVVINSFNYNDPVNDDTILYMQIPYEEKSKKYYKAFEI MHNVWIIPERNTIGTDPSDFDPPASLENGSSAYYDPNYLT | BoNT F Light Chain |

TABLE 2-continued

<div align="center">Sequence Listing</div>

| SEQ ID NO | Amino Acid Sequence | Description |
|---|---|---|
|  | TDAEKDRYLKTTIKLFNRINSNPAGEVLLQEISYAKPYLG NEHTPINEFHPVTRTTSVNIKSSTNVKSSIILNLLVLGAGP DIFENYSYPVRKLMDSGGVYDPSNDGFGSINIVTFSPEYE YTFNDISGGYNSSTESFIADPAISLAHELIHALHGLYGAL GVTYKETIKVKQAPLMIAEKPIRLEEFLTFGGQDLNIITSA MKEKIYNNLLANYEKIATRLSRVNSAPPEYDINEYKDYF QWKYGLDKNADGSYTVNENKFNEIYKKLYSFTEIDLAN KFKVKCRNTYFIKHGFLKVPNLLDDDIYTVSEGFNIGNL AVNNRGQNIKLNPKIIGSIPDKGLVEKIVKF* | Variant - F1.1A |
| 14 | MPVVINSFNYNDPVNDDTILYMQIPYEEKSKKYYKAFEI MHNVWIIPERNTIGTDPSDFDPPASLENGSSAYYDPNYLT TDAEKDRYLKTTIKLFNRINSNPAGEVLLQEISYAKPYLG NEHTPINEFHPVTRTTSVNIKSSTNVKSSIILNLLVLGAGP DIFENYSYPVRKLMDSGGVYDPSNDGFGSINIVTFSPEYE YTFNDISGGYNSSTESFIADPAISLAHELIHALHGLYGAC GVTYKETIKVKQAPLMIAEKPIRLEEFLTFGGQDLNIITSA MKEKIYNNLLANYEKIATRLSRVNSAPPEYDINEYKDYF QWKYGLDKNADGSYTVNENKFNEIYKKLYSFTEIDLAN KFKVKCRNTYFIKHGFLKVPNLLDDDIYTVSEGFNIGNL AVNNRGQNIKLNPKIIGSIPDKGLVEKIVKF* | BoNT F Light Chain Variant - F1.1B |
| 15 | MPVVINSFNYNDPVNDDTILYMQIPYEEKSKKYYKAFEI MRNVWIIPERNTIGTDPSDFDPPASLENGSSAYYDPNYLT TDAEKDRYLKTTIKLFKRINSNPAGEVLLQEISYAKPYLG NEHTPINEFHPVTRTTSVNIKSSTNVKSSIILNLLVLGAGP DIFENYSYPVRKLMDSGGVYDPSHDGFGSINIVTFSPEYE YTFNDISGGYNSSTESFIADPAISLAHELIHALHGLYGAL GVTYKETIKVKQAPLMIAEKPIRLEEFLTFGGQDLNIITSA MKEKIYNNLLANYEKIATRLSRVNSAPPEYDINEYKDYF QWKYGLDKNADGSYTVNENKGNEIYKKLYSFTEIDLAN KLKVKCRNTYFIKHGFLKVPNLLDDDIYTVSEGFNIGNL AVNNRGQNIKLNLKIIGSIPDKGLVEKIVKF* | BoNT F Light Chain Variant - F1.2A |
| 16 | MPVVINSFNYNDPVNDDTILYMQIPYEEKSKKYYKAFEI MRNVWIIPERNTIGTDPSDFDPPASLENGSSAYYDPNYLT TDAEKDRYLKTTIKLFKRINSNPAGEVLLQEISYAKPYLG NEHTPINEFHPVTRTTSVNIKSSTNVKSSIILNLLVLGAGP DIFENYSYPVRKLMDSGGVYDPSKDGFGSINIVTFSPEYE YTFNDISGGYNSSTESFIADPAISLAHELIHALHGLYGAL GVTYKETIKVKQAPLMIAEKPIRLEEFLTFGGQDLNIITSA MKEKIYNNLLANYEKIATRLSRVNSAPPEYDINEYKDYF QWKYGLDKNADGSYTVNENKGNEIYKKLYSFTEIDLAN KLKVKCRNTYFIKHGFLKVPNLLDDDIYTVSEGFNIGNL AVNNRGQNIKLNLKIIGSIPDKGLVEKIVKF* | BoNT F Light Chain Variant - F1.2B |
| 17 | MPVVINSFNYNDPVNDDTILYMQIPYEEKSKKYYKAFEI MRNVWIIPERNTIGTDPSDFDPPASLENGSSAYYDPNYLT TDAEKDRYLKTTIKLFKRINSNPAGEVLLQEISYAKPYLG NEHTPINEFHPVTRTTSVNIKSSTNVKSSIILNLLVLGAGP DIFENYSYPVRKLMDSGGVYDPSKDGFGSINIVTFSPEYE YTFNDISGGYNSSTESFIADPAISLAHELIHALHGLYGAL GVTYKETIKVKQAPLMIAEKPIRLEEFLTFGGQDLNIITSA MKEKIYNNLLANYEKIATRLSRVNSAPPEYDINEYKDYF QWKYGLDKNADGSYTVNENKGNEIYKKLYSFTEIDLAN KLKVKCRNTYFIKHGFLKVPNLLDDDIYTVSEGFNIGHL AVNNRGQNIKLNLKIIDSIPDKAWLRKS* | BoNT F Light Chain Variant - F1.3 |
| 18 | MPVVINSFNYNDPVNDDTILYMQIPYEEKSKKYYKAFEI MRNVWIIPERNTIGTDPSDFDPPASLENGSSAYYDPNYLT TDAEKDRYLKTTIKLFKRINSNPAGEALLQEISYAKPYLG NEHTPINEFHPVTRTTSVNIKSSTNVKSSIILNLLVLGAGP DIFESYIYPVRKLMDSGGVYDPSKDGFGSINIVTFSPEYE YTFNDISGGYNSSTESFIADPAISLAHELIHALHGLYGAL GVTYKETIKVKQAPLMIAEKPIRLEEFLTFGGQDLNIITSA MKEKIYNNLLANYEKIATRLSRVNSAPPEYDINEYKDYF QWKYGLDKNADGSYTVNENKGNEIYKKLYSFTEIDLAN KLKVKCRNTYFIKHGFLKVPNLLDDDIYTVSEGFNIGHL AVNNRGQNIKLNLKIIDSIPDKAWLRKS* | BoNT F Light Chain Variant - F1.4 |
| 19 | MPVVINSFNYNDPVNDDTILYMQIPYEEKSKKYYKAFEI MRNVWIIPERNTIGTDPSDFDPPASLENGSSAYYDPNYLT TDAEKDRYLKTTIKLFKRINSNPAGEALLQEISDAKPYLG NEHTPINEFHPVTRTTSVNIKSSTNVKSSIILNLLVLGAGP DIFENYIYPVRKLMDSGGVYDPSHDGFGSINIVTFSPEYK | BoNT F Light Chain Variant - F1.7A |

TABLE 2-continued

Sequence Listing

| SEQ ID NO | Amino Acid Sequence | Description |
|---|---|---|
| | YTFNDISGGYNSSTESFIADPAISLAHELIHALHGLYGAL GVTCKETIKVKQAPLMIAEKPIRLEEFLTFGGQDLNIITSA MKEKIYNNLLANYEKIATRLSRVNSAPPEYDINEYKDYF QWKYGLDKNADGSYTVNENKGNEIYKKLYSFTEIDLAN KLKVKCRNTYFIKHGFLKVPNLLDDDIYTVSEGFNIGHL AVNNRGQNIKLNLKIIDSIPDKAWLRKS* | |
| 20 | MPVVINSFNYNDPVNDDTILYMQIPYEEKSKKYYKAFEI MRNVWIIPERNTIGTDPSDFDPPASLENGSSAYYDPNYLT TDAEKDRYLKTTIKLFKRINSNPAGEALLQEISDAKPYLG NEHTPINEFHPVTRTTSVNIKSSTNVKSSIILNLLVLGAGP DIFENYIYPVRKLMDSGGVYDPSKDGFGSINIVTFSPEYK YTFNDISGGYNSSTESFIADPAISLAHELIHALHGLYGAL GVTCKETIKVKQAPLMIAEKPIRLEEFLTFGGQDLNIITSA MKEKIYNNLLANYEKIATRLSRVNSAPPEYDINEYKDYF QWKYGLDKNADGSYTVNENKGNEIYKKLYSFTEIDLAN KLKVKCRNTYFIKHGFLKVPNLLDDDIYTVSEGFNIGHL AVNNRGQNIKLNLKIIDSIPDKAWLRKS* | BoNT F Light Chain Variant - F1.7B |
| 21 | MPVVINSFNYNDPVNDDTILYMQIPYEEKSKKYYKAFEI MRNVWIIPERNTIGTDPSDFDPPASLENGSSAYYDPNYLT TDAEKDRYLKTTIKLFKRINSNPAGEALLQEISDAKPYLG NEHTPINEFHPVTRTTSVNIKSSTNVKSSIILNLLVLGAGP DIFENYIYPVRKLMDSGGVYDPSSDGFGSINIVTFSPEYK YTFNDISGGYNSSTESFIADPAISLAHELIHALHGLYGAL GVTCKETIKVKQAPLMIAEKPIRLEEFLTFGGQDLNIITSA MKEKIYNNLLANYEKIATRLSRVNSAPPEYDINEYKDYF QWKYGLDKNADGSYTVNENKGNEIYKKLYSFTEIDLAN KLKVKCRNTYFIKHGFLKVPNLLDDDIYTVSEGFNIGHL AVNNRGQNIKLNLKIIDSIPDKAWLRKS* | BoNT F Light Chain Variant - F1.7C |
| 22 | MPVVINSFNYNDPVNDDTILYMQIPYEEKSKKYYKAFEI MRNVWIIPERNTIGTDPSDFDPPASLENGSSAYYDPNYLT TDAEKDRYLKTTIKLFKRINSNPAGEALLQEISSAKPYLG NEHTPINEFHPVTRTTSVNIKSSTNVKSSIILNLLVLGAGP DIFENYIYPVRKLMDSGGVYDPSHDGFGSINIVTFSPEYK YTFNDISGGYNSSTESFIADPAISLAHELIHALHGLYGAL GVTCKETIKVKQAPLMIAEKPIRLEEFLTFGGQDLNIITSA MKEKIYNNLLANYEKIATRLSRVNSAPPEYDINEYKDYF QWKYGLDKNADGSYTVNENKGNEIYKKLYSFTEIDLAN KLKVKCRNTYFIKHGFLKVPNLLDDDIYTVSEGFNIGHL AVNNRGQNIKLNLKIIDSIPDKAWLRKS* | BoNT F Light Chain Variant - F1.7D |
| 23 | MPVVINSFNYNDPVNDDTILYMQIPYEEKSKKYYKAFEI MRNVWIIPERNTIGTDPSDFDPPASLENGSSAYYDPNYLT TDAEKDRYLKTTIKLFKRINSNPAGEALLQEISSAKPYLG NEHTPINEFHPVTRTTSVNIKSSTNVKSSIILNLLVLGAGP DIFENYIYPVRKLMDSGGVYDPSKDGFGSINIVTFSPEYK YTFNDISGGYNSSTESFIADPAISLAHELIHALHGLYGAL GVTCKETIKVKQAPLMIAEKPIRLEEFLTFGGQDLNIITSA MKEKIYNNLLANYEKIATRLSRVNSAPPEYDINEYKDYF QWKYGLDKNADGSYTVNENKGNEIYKKLYSFTEIDLAN KLKVKCRNTYFIKHGFLKVPNLLDDDIYTVSEGFNIGHL AVNNRGQNIKLNLKIIDSIPDKAWLRKS* | BoNT F Light Chain Variant - F1.7E |
| 24 | MPVVINSFNYNDPVNDDTILYMQIPYEEKSKKYYKAFEI MRNVWIIPERNTIGTDPSDFDPPASLENGSSAYYDPNYLT TDAEKDRYLKTTIKLFKRINSNPAGEALLQEISSAKPYLG NEHTPINEFHPVTRTTSVNIKSSTNVKSSIILNLLVLGAGP DIFENYIYPVRKLMDSGGVYDPSSDGFGSINIVTFSPEYK YTFNDISGGYNSSTESFIADPAISLAHELIHALHGLYGAL GVTCKETIKVKQAPLMIAEKPIRLEEFLTFGGQDLNIITSA MKEKIYNNLLANYEKIATRLSRVNSAPPEYDINEYKDYF QWKYGLDKNADGSYTVNENKGNEIYKKLYSFTEIDLAN KLKVKCRNTYFIKHGFLKVPNLLDDDIYTVSEGFNIGHL AVNNRGQNIKLNLKIIDSIPDKAWLRKS* | BoNT F Light Chain Variant - F1.7F |
| 25 | MPVVINSFNYNDPVNDDTILYMQIPYEEKSKKYYKAFEI MRNVWIIPERNTIGTDPSDFDPPASLDNGSSAYYDPNYL TTDAEKDRYLKTTIKLFKRINSNPAGEALLQEISYAKPYL GNEHTPINEFHPVTRTTSVNIKSSTNVKSSIILNLLVLGAG PDIFENYIYPVRKLMGSGGVYDPSKDGFGSINIVTFSPEY GYTFNDISGGYNSSTISFIADPAISLAHELIHALHGLYGAL GVTYKETIKVKQAPLMIAEKPIRLEEFLTFGGQDLNIITSA MKEKIYNNLLANYEKIATRLSRVNSAPPEYDINEYKDYF | BoNT F Light Chain Variant - F7.1A |

TABLE 2-continued

Sequence Listing

| SEQ ID NO | Amino Acid Sequence | Description |
|---|---|---|
| | QWKYGSDKNADGSYTVNENKGNEIYKKLYSFTEIDLAN KLKVKCRNTYFIKHGFLKVPNLLDDDIYTVSEGFNIGHL AVNNRGQNIKLNLKIIDSIPYKAWLRKS* | |
| 26 | MPVVINSFNYNDPVNDDTILYMQIPYEEKSKKYYKAFEI MRNVWIIPERNTIGTDPSDFDPPASLDNGSSAYYDPNYL TTDAEKDRYLKTTIKLFKRINSNPAGEALLQEISYAKPYL GNEHTPINEFHPVTRTTSVNIKSSTNVKSSIILNLLVLGAG PDIFENYIYPVRKLMGSGGVYDPSKDGFGSINIVTFSPEY GYTFNDISGGYNSSTISFIADPAISLAHELIHALHGLYGAF GVTYKETIKVKQAPLMIAEKPIRLEEFLTFGGQDLNIITSA MKEKIYNNLLANYEKIATRLSRVNSAPPEYDINEYKDYF QWKYGSDKNADGSYTVNENKGNEIYKKLYSFTEIDLAN KLKVKCRNTYFIKHGFLKVPNLLDDDIYTVSEGFNIGHL AVNNRGQNIKLNLKIIDSIPYKAWLRKS* | BoNT F Light Chain Variant - F7.1B |
| 27 | MPVVINSFNYNDPVNDDTILYMQIPYEEKSKKYYKAFEI MRNVWIIPERNTIGTDPSDFDPPASLENGSSAHYDPNYLT TDAEKDRYLKTTIKLFKRISSNPAGEALLQEISYAKPYLG NEHTPINEFHPGTRTTSVNIKTSTNVKSSIILNLLLVLGAGP DIFENYIYPVRKLTDSGGVYDPSTDGFGSINIMTFSPEYG YTFNDISGGYNSSTISFIADPAISLAHELIHALHGLYGALG VTYKETIKVKQAPLMIAEKPIRLEEFLTFGGQDLNIITSA MKEKIYNNLLANYEKIATRLSRVNSAPPEYDINEYKDYF QWKYGLDKNADGSYTVNENKGNEIYKKLYSFTEIDLAN KLKVKCRNTYFIKHGFLKVPNLLDDDIYTVSEGFNIGHL AVNNRGQNIKLNLKIIDSIPDKAWLRKS* | BoNT F Light Chain Variant - F7.2A |
| 28 | MPVVINSFNYNDPVNDDTILYMQIPYEEKSKKYYKAFEI MRNVWIIPERNTIGTDPSDFDPPASLENGSSAHYDPNYLT TDAEKDRYLKTTIKLFKRISSNPAGEALLQEISYAKPYLG NEHTPINEFHPGTRTTSVNIKTSTNVKSSIILNLLLVLGAGP DIFENYIYPVRKLTDSGGVYDPSTDGFGSINIMTFSPEYG YTFNDISGGYNSSTISFIADPAISLAHELIHALHGLYGAFG VTYKETIKVKQAPLMIAEKPIRLEEFLTFGGQDLNIITSA MKEKIYNNLLANYEKIATRLSRVNSAPPEYDINEYKDYF QWKYGLDKNADGSYTVNENKGNEIYKKLYSFTEIDLAN KLKVKCRNTYFIKHGFLKVPNLLDDDIYTVSEGFNIGHL AVNNRGQNIKLNLKIIDSIPDKAWLRKS* | BoNT F Light Chain Variant - F7.2B |
| 29 | MPVVINSFNYNDPVNDDTILYMQIPYEEKSKKYYKAFEI MRNVWIIPERNTIGTDPSDFDPPASLENGSSAHYDPNYLT TDAEKDRYLKTTIKLFKRINSNPAGEALLQEISYAKPYLG NEHTPINEFHPGTRTTSVNIKTSTNVKSSIILNLLLVLGAGP DIFENYIYPVRKLMTSGGVYDPSNDGFGSINIVTFSPEYG YTFNDISGGYNSSTESFIADPAIILAHELIHALHGLYGALG VTYKETIKVKQAPLMIAEKPIRLEEFLTFGGQDLNIITSA MKEKIYNNLLANYEKIATRLSRVNSAPPEYDINEYKDYF QWKYGLDKNADGSYTVNENKFNEIYKKLYGFTEIDLAN KLKVKCRNTYFIKHGFLKVPNLLDDDIYTVSEGFNIGHL AVNNRGQNIKLNLKIIDSIPDKAWLRKS* | BoNT F Light Chain Variant - F.7A[2.6] |
| 30 | MPVVINSFNYNDPVNDDTILYMQIPYEEKSKKYYKAFEI MRNVWIIPERNTIGTDPSDFDPPASLENGLSAHYDPNYLT TDAEKDRYLKTTIKLFKRINSNPAGEALLQEISYAKPYLG NEHTPINEFHPVTRTTSVNIKSSTNVKSNIVLNLLVLGPG PDIFENYIYPVRKLMMSDGVYDPSHDGFGSINIVTFSPEY GYTFNDISGGYNSSTESFIADPAIILAHELIHSLHGLYGAL GVTYKETIKVKQAPLMIAEKPIRLEEFLTFGGQDLNIITSA MKEKIYNNLLANYEKIATRLSRVNSAPPEYDINEYKDYF QWKYGLDKNADGSYTVNENKFNEIYKKLYGFTEIDLAN KLKVKCRNTYFIKNGFLKVPNLMDDDIYTVSEGFNIGHL AVNNRGQNIKLNLKIIDSIPDKAWLRKS* | BoNT F Light Chain Variant - F7[N-1.3] |
| 31 | MPVVINSFNYNDPVNDDTILYMQIPYEEKSNKYYKAFEI MRNVWIIPERNTIGTDPSDFDPPASLENGSSAHYDPNYLT TDAEKDRYLKTTIKLFNRINSNPAGEALLQEISYAKPYLG NEHTPINEFHPFTRTTSVNIKSSTNVKSSIILNLLVLGAGP DIFENYLYPVRKLMMSGGVYDPSNDGFGSINIVTFSPEY GYTFNDISGGYNSSTESFIADPAIILAHELIHALHGLYGAL GVTYKETIKVKQAPLMIAEKPIRLEEFLTFGGQDLNIITSV MKEKIYNNLLANYEKIATRLSHVNSAPPEYDINEYKDYF QWKYGLDKNADGSYTVNENKFNEIYKKLYGFTEVDLA NKLKVKCRNTYFIKPGFLKVPNLLDDDIYTVSEGFNIGH LAVNNRGQNIKLNLKNIDSIPDKAWLRKS* | BoNT F Light Chain Variant - F7[15-2.1] |

53

54

TABLE 2-continued

<u>Sequence Listing</u>

| SEQ ID NO | Amino Acid Sequence | Description |
|---|---|---|
| 32 | MSAPAQPPAEGTEGTAPGGGPPGPPPNMTSNRRLQQTQ AQVEEVVDIIRVNVDKVLERDQKLSELDDRADALQAGA SQFESSAAKLKRKYWWKNCKMMIMLGAICAIIVVVIVR RG | VAMP1 |
| 33 | TSNRRLQQTQAQVEEVVDIIRVNVDKVLERDQKLSELD DRADALQAGASQFESSAAKLKR | VAMP1 - Cleavage Sequence |
| 34 | MAILFAVVARGTTILAKHAWCGGNFLEDPFERSRAFNFL NEIKKRFQTTYGSRAQTALPYAMNSEFSSVLAAQLKHHS ENKGLDKVMETQAQVDELKGIMVRNIDLVAQRGERLEL LIDKTENLVDSSVTFKTTSRNLARAMCMKNLKLTIIIIIVS IVFIYIIVSPLCGGFTWPSCVKK | VAMP7 |
| 35 | KGLDKVMETQAQVDELKGIMVRNIDLVAQRGERLELLI DKTENLVDSSVTFKTTSRNLARGGSGGSGGS | VAMP7 - Cleavage Sequence |
| 36 | MKLEINKFNYNDPIDGINVITMRPPRHSDKINKGKGPFK AFQVIKNIWIVPERYNFTNNTNDLNIPSEPIMEADAIYNP NYLNTPSEKDEFLQGVIKGLERIKSKPEGEKLLKLISSSIP LPLVSNGALTLSDNETIAYQENNNIVSNLQANLVIYGPGP DIANNETYGLYSTPISNGEGTLSEVSFSPFYLKPFDESYG NYRSLVNIVNKFVKREFAPDPASTLMHELVHVTHNLYGI SNRNFYYNFDTGKIETSRQQNSLIFEELLTFGGIDSKAISL LIIKKIIETAKNNYTTLISERLNTVTVENDLLKYIKNKIPV QGRLGNFKLDTAEFEKKLNTILFVLNESNLAQRFSILVRK HYLKERPIDPIYVNILDDNSYSTLEGFNISSQGSNDFQGQ LLESSYFEKIESNALRAFIKICPRNGLLYNAIYRNSKN | BoNT X Light Chain Variant - a |
| 37 | MKLEINKFNYNDPIDGINVITMRPPRHSDKINKGKGPFK AFQVIKNIWIVPERYNFTNNTNDLNIPSEPIMEADAIYNP NYLNTPSEKDEFLQGVIKVLERIKSKPEGEKLLELISSSIP LPLVSNGALTLSDNETIAYQENNNIVSNLQANLVIYGPGP DIANNETYGLYSTPISNGEGTLSEVSFSPFYLKPFDESYG NYRSLVNIVNKFVKREFAPDPASTLMHELVHVTHNLYGI SNRNFYYNFDTGKIETSRQQNSLIFEELLTFGGIDSKAISS LIIKKIIETAKNNYTTLISERLNTVTVENDLLKYIKNKIPV QGRLGNFKLDTAEFEKKLNTILFVLNESNLAQRFSILVRK HYLKERPIDPIYVNILDDNSYSTLEGFNISSQGSNDFQGQ LLESSYFEKIESNALRAFIKICPRNGLLYNAIYRNSKN | BoNT X Light Chain Variant - b |
| 38 | MKLEINKFNYNDPIDGINVITMRPPRHSDKINKGKGPFK AFQVIKNIWIVPERYNFTNNTNDLNIPSEPIMEADAIYNP NYLNTPSEKDEFLQGVIKVLERIKSKPEGEKLLELISSSIP LPLVSNGALTLSDNETIAYQENNNIVSNLQANLVIYGPGP DIANNETYGLYSTPISNGEGTLSEVSFSPFYLKPFDESYG NYRSLVNIVNKFVKREFAPDPASTLMHELVHVTHNLYGI SNRNFYYNFDTGKIETSRQQNSLIFEELLTFGGIDSKAISS LIIKKIIETAKNNYTTLISERLNTVTVENDLLKYIKNKIPV QGRLGNFKLDTAEFEKKLNTILFVLNESNLAQRFSILVRK HYLKERPIDPIYVNILDDNSYSTLEGFNISSQGSNDFQGQ LLELSYFEKIESNALRAFIKICPRNGLLYNAIYLNSKN | BoNT X Light Chain Variant - c |
| 39 | MKLEINKFNYNDPIDGINVITMRPPRHSDKINKGKGPFK AFQVIKNIWIVPERYNFTNNTNDLNIPSAPIMEADAIYNP NYLNTPSEKDEFLQGVIKVLERIKSKPEGEKLLELISSSIP LPLVSNGALTLSDNETIAYQENNNIVSNLLANLVIYGPGP DIANNETYGLYSTPISNGEGTLSEVSFSPFYLKPFDESYG NYRSLVNIVNKFVKREFAPDPASTLMHELVHVTHNLYGI SNRNFYYNFDTGKIETSRQQNSLIFEELLTFGGIDSKAISS LIIKKIIETAKNNYTTLISERLNTVTVENDLLKYIKNKIPV QGRLGNFKLDTAEFEKKLNTILFVLNESNLAQRFSILVRK HYLKERPIDPIYVNILDDNSYSTLEGFNISSQGSNDFQGQ LLESSYFEKIESNALRAFIKICPRNGLLYNAIYRNSKN | BoNT X Light Chain Variant - d |
| 40 | MKLEINKFNYNDPIDGINVITMRPPRHSDKINKGKGPFK AFQVIKNIWIVPERYNFTNNTNDLNIPSEPIMEADAIYNP NYLNTPSEKDEFLQGVIKVLERIKSKPEGEKLLELISSSIP LPLVSNGALTLSDNETIAYQENNNIVSNLQANLVIYGPGP DIANNETYGLYSTPISNGEGTLSEVSFSPFYLKPFDESYG NYRSLVNIVNKFVKREFAPDPASTLMHELVHVTHNLYGI SNRNFYYNFDTGKIETSRQQNSLIFEELLTFGGIDSKAISS | BoNT X Light Chain Variant - e |

TABLE 2-continued

Sequence Listing

| SEQ ID NO | Amino Acid Sequence | Description |
|---|---|---|
| | LIIKKIIETAKNNYTTLISERLNTVTVENDLLKYIKNKIPV QGRLGNFKLDTAEFEKKLNTILFVLNESNLAQRFSILVRK HYLKERPIDPIYVNILDDNSYSTLEGFNISSQGSNDFQGQ LLESSYFEKIESNALRAFIKICPRNGLLYNAIYRNSKN | |
| 41 | MKLEINKFNYNDPIDGINVITMRPPRHSDKINKGKGPFK AFQVIKNIWIVPERYNFTNNTNDLNIPSEPIMEADAIYNP NYLNTPSEKDEFLQGVIKVLERIKSKPEGEKLLELISSSIP LPLVSNGALTLSDNETIAYQENNNIVSNLQANLVIYGPGP DIANNETYGLYSTPISNGEGTLSEVSFSPFYLKPFDESYG NYRSLVNIVNKFVKREFAPDPASTLMHELVHVTHNLYGI SNRNFYYNFDTGKIETSRQQNSLIFEELLTFGGIDSKAISS LIIKKIIETAKNNYTTLISERLNTVTVENDLLKYIKNKIPV QGRLGNFKLDTAEFEKKLNTILFVLNESNLAQRFSILVRK HYLKERPIDPIYVNILDDNSYSTLEGFNISSQGSNDFQGQ LLESSYFEKIESNALRAFIKICPRNGLLYNAIYRNSKN | BoNT X Light Chain Variant - f |
| 42 | MKLEINKFNYNDPIDGINVITMRPPRHSDKINKGKGPFK AFQVIKNIWIVPERYNFTNNTNDLNIPSEPIMEADAIYNP NYLNTPSEKDEFLQGVIKVLERIKSKPEGEKLLELISSSIP LPLVSNGALTLSDNETIAYQENNNIVSNLQANLVIYGPGP DIANNETYGLYSTPISNGEGTLSEVSFSPFYLKPFDESYG NYRSLVNIVNKFVKREFAPDPASTLMHELVHVTHNLYGI SNRNFYYNFDTGKIETSRQQNSLIFEELLTFGGIDSKAISS LIIKKIIETAKNNYTTLISERLNTVTVENDLLKYIKNKIPV QGRLGNFKLDTAEFEKKLNTILFVLNESNLAQRFSILVRK HYLKERPIDPIYVNILDDNSYSTLEGFNISSQGSNDFQGQ LLESSYFEKIESNALRAFIKICPRNGLLYNAIYLNSKN | BoNT X Light Chain Variant - g |
| 43 | MKLEINKFNYNDPIDGINVITMRPPRHSDKINKGKGPFK AFQVIKNIWIVPERYNFTNNTNDLNIPSEPIMEADAIYNP NYLNTPSEKDEFLQGVIKGLERIKSKPEGEKLLKLISSSIP LPLVSNGALTLSDNETIAYQENNNIVSNLQANLVIYGPGP DIANNETYGLYSTPISNGEGTLSEVSFSPFYLKPFDESYG NYRSLVNIVNKFVKREFAPDPASTLMHELVHVTHNLYGI SNRNFYYNFDTGKIETSRQQNSLIFEELLTFGGIDSKAISS LIIKKIIETAKNNYTTLISERLNTVTVENDLLKYIKNKIPV QGRLGNFKLDTAEFEKKLNTILFVLNESNLAQRFSILVRK HYLKERPIDPIYVNILDDNSYSTLEGFNISSQGSNDFQGQ LLESSYFEKIESNALRAFIKICPRNGLLYNAIYLNSKN | BoNT X Light Chain Variant - h |

This disclosure relates, in part, to the discovery that continuous evolution methods (e.g., PACE) are useful for producing BoNT protease variants that have altered peptide cleaving activities (altered peptide cleaving functions). For example, in some embodiments, a BoNT protease variant as described herein cleaves a VAMP7 protein or peptide. In some embodiments, a BoNT protease variant as described by the disclosure cleaves the target sequence SEQ ID NO.: 35.

In some embodiments, a BoNT protease variant cleaves a target peptide (e.g., VAMP7, etc.) with higher activity than a wild-type BoNT protease. A BoNT protease variant that cleaves a target peptide (e.g., VAMP7, etc.) with higher activity can have an increase in catalytic efficiency ranging from about 1.1-fold, about 1.5-fold, 2-fold to about 100-fold, about 5-fold to about 50-fold, or about 10-fold to about 40-fold, relative to the catalytic efficiency of the wild-type BoNT protease from which the BoNT protease variant was derived. In some embodiments, a BoNT protease variant described herein cleaves a target peptide (e.g., VAMP7, Ykt6, etc.) with about 1% to about 100% (e.g., about 1%, 2%, 5%, 10%, 20%, 50%, 80%, 90%, 100%) of the catalytic efficiency with which wild-type BoNT cleaves its native substrate (e.g., VAMP1, etc.). In some embodiments, a BoNT protease variant described herein cleaves a target peptide (e.g., VAMP7, Ykt6, etc.) with about 1% to about 100% (e.g., about 1%, 2%, 5%, 10%, 20%, 50%, 80%, 90%, 100%) of the catalytic efficiency with which wild-type BoNT cleaves a second substrate (e.g., VAMP2, etc.). Catalytic efficiency can be measured or determined using any suitable method known in the art, for example, using methods described in Harris et al. (2009) *Methods* Enzymol. 463; 57-71.

Generally, the evolution of proteases with altered specificity has focused on the destruction of therapeutically relevant extracellular proteins. However BoNTs provide a built-in cytosolic delivery mechanism, and thus are able, in some embodiments, to degrade intracellular targets. For example, in some embodiments, a BoNT protease variant as described herein comprises one or more protein domains that facilitate transport of the protease across a cellular membrane. In some embodiments, the one or more protein domains that facilitate transport across the membrane are selected from a BoNT HC, a BoNT HCC domain, and a BoNT HCN domain. In some embodiments, BoNT protease variants described by the disclosure are capable of crossing the cellular membrane and entering the intracellular environment of a cell, e.g., neuronal cells.

Some aspects of this disclosure provide methods for using a BoNT variant provided herein. In some embodiments, such methods include contacting a protein comprising a protease target cleavage sequence (e.g., VAMP7, for example SEQ ID NO.: 35), for example, ex vivo, in vitro, or in vivo (e.g., in a subject), with the BoNT variant. In some embodiments, the protein to be cleaved by the BonNT variant is a therapeutic target. In some embodiments, the therapeutic target is VAMP7. Generally, VAMP7 is an intracellular, soluble N-ethylmaleimide-sensitive factor attachment protein receptor (SNARE) family protein that mediates the fusion of transport vesicles to their target membrane. Without wishing to be bound by any particular theory, VAMP7 functions as a mediator of MT1-MMP secretion during tumor invasion and granzyme B and perforin secretion, for example, during organ transplantation. Accordingly, in some aspects, the disclosure provides methods of decreasing VAMP7 activity in a cell by contacting the cell with, or introducing into the intracellular environment of the cell, a variant BoNT protease as described herein.

In some embodiments, the cell (or intracellular environment) is characterized by increased or undesired activity of a target protein (e.g., VAMP7, etc.) relative to a normal cell or extracellular environment (e.g., a healthy cell, or extracellular environment, not characterized by increased activity of the target protein). In some embodiments, increased activity of a target protein (e.g., VAMP7, etc.) occurs when, in a cell, the activity of the target protein is about 2-fold, 3-fold, 4-fold, 5-fold, 10-fold, 25-fold, 50-fold, 100-fold, 500-fold, or 1000-fold over activity of the target protein in a normal healthy cell, or extracellular environment. In some embodiments, a cell characterized by increased expression of a target protein (e.g., VAMP7, etc.) is derived from a subject (e.g., a mammalian subject, such as a human or mouse) that has or is suspected of having a disease associated with increased activity of the target protein, for example, cancer in the context of VAMP7 overexpression or increased activity. In some embodiments, the methods provided herein comprise contacting (e.g., cleaving) the target protein (e.g., VAMP7, PTEN, etc., or a protein comprising an amino acid sequence set forth in SEQ ID NOs.: 35 (e.g., VAMP7, etc.)) with a BoNT protease variant described herein in vitro. In some embodiments, the methods provided herein comprise contacting the target protein with the protease variant described herein in vivo. In some embodiments, the methods provided herein comprise contacting the target protein (e.g., VAMP7, etc., or a protein comprising an amino acid sequence set forth in SEQ ID NOs.: 35 (e.g., VAMP7, etc.)) with a BoNT protease variant described herein in an intracellular environment (e.g. in a cell). In some embodiments, the methods provided herein comprise contacting the target protein (e.g., VAMP7, etc., or a protein comprising an amino acid sequence set forth in SEQ ID NOs.: 35 (e.g. VAMP7, etc.)) with a BoNT protease variant in a subject, e.g., by administering the BoNT protease variant to the subject, either locally or systemically. In some such embodiments, the protease variant is administered to the subject in an amount effective to result in a measurable decrease in the level of full-length (or functional) target protein (e.g., VAMP7, etc.) in the subject, or in a measurable increase in the level of a cleavage product generated by the BoNT protease variant upon cleavage of the target protein. In some embodiments, the decrease in the level of full-length (or functional) target protein (e.g., VAMP7, etc.) is at least 10% or more (e.g., at least 10%, at least 30%, at least 40%, at least 50%, at least 60%, at least 70%, at least 80%, at least 85%, at least 90%, at least 95%, at least 96%, at least 97%, at least 98%, at least 99%, or more). Engineering of BoNT Protease Variants using PACE Some aspects of this disclosure provide methods of evolving a BoNT protease. In some embodiments, a method of evolving a protease is provided that comprises (a) contacting a population of host cells with a population of vectors comprising a gene encoding a protease to be evolved. The vectors are typically deficient in at least one gene required for the transfer of the phage vector from one cell to another, e.g., a gene required for the generation of infectious phage particles. In some embodiments of the provided methods, (1) the host cells are amenable to transfer of the vector; (2) the vector allows for expression of the protease in the host cell, can be replicated by the host cell, and the replicated vector can transfer into a second host cell; and (3) the host cell expresses a gene product encoded by the at least one gene for the generation of infectious phage particles (a) in response to the activity of the protease, and the level of gene product expression depends on the activity of the protease. The methods of protease evolution provided herein typically comprise (b) incubating the population of host cells under conditions allowing for mutation of the gene encoding the protease, and the transfer of the vector comprising the gene encoding the protease of interest from host cell to host cell. The host cells are removed from the host cell population at a certain rate, e.g., at a rate that results in an average time a host cell remains in the cell population that is shorter than the average time a host cell requires to divide, but long enough for the completion of a life cycle (uptake, replication, and transfer to another host cell) of the vector. The population of host cells is replenished with fresh host cells that do not harbor the vector. In some embodiments, the rate of replenishment with fresh cells substantially matches the rate of removal of cells from the cell population, resulting in a substantially constant cell number or cell density within the cell population. The methods of protease evolution provided herein typically also comprise (c) isolating a replicated vector from the host cell population of step (b), wherein the replicated vector comprises a mutated version of the gene encoding the protease.

In some embodiments the host cell used in the method of evolving a BoNT F protease further expresses a dominant negative gene product for the at least one gene for the generation of infectious phage particles which expresses an antagonistic effect to infectious phage production in response to the activity of the canonical protease activity of native BoNT F.

Some embodiments provide a continuous evolution system, in which a population of viral vectors, e.g., M13 phage vectors, comprising a gene encoding a protease of interest to be evolved replicates in a flow of host cells, e.g., a flow through a lagoon, wherein the viral vectors are deficient in a gene encoding a protein that is essential for the generation of infectious viral particles, and wherein that gene is in the host cell under the control of a conditional promoter, the activity of which depends on the activity of the protease of interest. In some embodiments, transcription from the conditional promoter may be activated by cleavage of a fusion protein comprising a transcription factor and an inhibitory protein fused to the transcriptional activator via a linker comprising a target site of the protease.

Some embodiments of the protease PACE technology described herein utilize a "selection phage," a modified phage that comprises a gene of interest to be evolved and lacks a full-length gene encoding a protein required for the generation of infectious phage particles. In some such embodiments, the selection phage serves as the vector that replicates and evolves in the flow of host cells. For example, some M13 selection phages provided herein comprise a nucleic acid sequence encoding a protease to be evolved, e.g., under the control of an M13 promoter, and lack all or part of a phage gene encoding a protein required for the generation of infectious phage particles, e.g., gI, gII, gIII, gIV, gV, gVI, gVII, gVIII, gIX, or gX, or any combination thereof. For example, some M13 selection phages provided herein comprise a nucleic acid sequence encoding a protease to be evolved, e.g., under the control of an M13 promoter, and lack all or part of a gene encoding a protein required for the generation of infectious phage particles, e.g., the gIII gene encoding the pIII protein.

One prerequisite for evolving proteases with a desired activity is to provide a selection system that confers a selective advantage to mutated protease variants exhibiting such an activity. The expression systems and fusion proteins comprising transcriptional activators in an inactive form that are activated by protease activity thus constitute an important feature of some embodiments of the protease PACE technology provided herein.

In some embodiments, the transcriptional activator directly drives transcription from a target promoter. For example, in some such embodiments, the transcriptional activator may be an RNA polymerase. Suitable RNA polymerases and promoter sequences targeted by such RNA polymerases are well known to those of skill in the art. Exemplary suitable RNA polymerases include, but are not limited to, T7 polymerases (targeting T7 promoter sequences) and T3 RNA polymerases (targeting T3 promoter sequences). Additional suitable RNA polymerases will be apparent to those of skill in the art based on the instant disclosure, which is not limited in this respect.

In some embodiments, the transcriptional activator does not directly drive transcription, but recruits the transcription machinery of the host cell to a specific target promoter. Suitable transcriptional activators, such as, for example, Gal4 or fusions of the transactivation domain of the VP16 transactivator with DNA-binding domains, will be apparent to those of skill in the art based on the instant disclosure, and the disclosure is not limited in this respect.

In some embodiments, it is advantageous to link protease activity to enhanced phage packaging via a transcriptional activator that is not endogenously expressed in the host cells in order to minimize leakiness of the expression of the gene required for the generation of infectious phage particles through the host cell basal transcription machinery. For example, in some embodiments, it is desirable to drive expression of the gene required for the generation of infectious phage particles from a promoter that is not or is only minimally active in host cells in the absence of an exogenous transcriptional activator, and to provide the exogenous transcriptional activator, such as, for example, T7 RNA polymerase, as part of the expression system linking protease (e.g., BoNT protease variant) activity to phage packaging efficiency. In some embodiments, the at least one gene for the generation of infectious phage particles is expressed in the host cells under the control of a promoter activated by the transcriptional activator, for example, under the control of a T7 promoter if the transcriptional activator is T7 RNA polymerase, and under the control of a T3 promoter if the transcriptional activator is T3 polymerase, and so on.

In some embodiments, the transcriptional activator is fused to an inhibitor that either directly inhibits or otherwise hinders the transcriptional activity of the transcriptional activator, for example, by directly interfering with DNA binding or transcription, by targeting the transcriptional activator for degradation through the host cells protein degradation machinery, or by directing export from the host cell or localization of the transcriptional activator into a compartment of the host cell in which it cannot activate transcription from its target promoter. In some embodiments, the inhibitor is fused to the transcriptional activator's N-terminus. In other embodiments, it is fused to the activator's C-terminus.

In some embodiments, the protease evolution methods provided herein comprise an initial or intermittent phase of diversifying the population of vectors by mutagenesis, in which the cells are incubated under conditions suitable for mutagenesis of the gene encoding the protease in the absence of stringent selection or in the absence of any selection for evolved protease variants that have acquired a desired activity. Such low-stringency selection or no selection periods may be achieved by supporting expression of the gene for the generation of infectious phage particles in the absence of desired protease activity, for example, by providing an inducible expression construct comprising a gene encoding the respective packaging protein under the control of an inducible promoter and incubating under conditions that induce expression of the promoter, e.g., in the presence of the inducing agent. Suitable inducible promoters and inducible expression systems are described herein and in International PCT Application, PCT/US2011/066747, filed Dec. 22, 2011, published as WO 2012/088381 on Jun. 28, 2012; and U.S. Ser. No. 13/922,812, filed Jun. 20, 2013; International PCT Application, PCT/US2015/057012, filed Oct. 22, 2015, published as WO 2016/077052; and, PCT/US2016/027795, filed Apr. 15, 2016, published as WO 2016/168631, the entire contents of each of which are incorporated herein by reference. Additional suitable promoters and inducible gene expression systems will be apparent to those of skill in the art based on the instant disclosure. In some embodiments, the method comprises a phase of stringent selection for a mutated protease version. If an inducible expression system is used to relieve selective pressure, the stringency of selection can be increased by removing the inducing agent from the population of cells in the lagoon, thus turning expression from the inducible promoter off, so that any expression of the gene required for the generation of infectious phage particles must come from the protease activity-dependent expression system.

One aspect of the PACE protease evolution methods provided herein is the mutation of the initially provided vectors encoding a protease of interest. In some embodiments, the host cells within the flow of cells in which the vector replicates are incubated under conditions that increase the natural mutation rate. This may be achieved by contacting the host cells with a mutagen, such as certain types of radiation or to a mutagenic compound, or by expressing genes known to increase the cellular mutation rate in the cells. Additional suitable mutagens will be known to those of skill in the art, and include, without limitation, those described in International PCT Application, PCT/US2011/066747, filed Dec. 22, 2011, published as WO 2012/088381 on Jun. 28, 2012; and U.S. Ser. No. 13/922, 812, filed Jun. 20, 2013; International PCT Application, PCT/US2015/057012, filed Oct. 22, 2015, published as WO 2016/077052; and, PCT/US2016/027795, filed Apr. 15, 2016, published as WO 2016/168631, the entire contents of each of which are incorporated herein by reference and the disclosure is not limited in this respect.

In some embodiments, the host cells comprise the accessory plasmid encoding the at least one gene for the generation of infectious phage particles, e.g., of the M13 phage, encoding the protease to be evolved and a helper phage, and together, the helper phage and the accessory plasmid comprise all genes required for the generation of infectious phage particles. Accordingly, in some such embodiments, variants of the vector that do not encode a protease variant that can untether the inhibitor from the transcriptional activator will not efficiently be packaged, since they cannot effect an increase in expression of the gene required for the generation of infectious phage particles from the accessory plasmid. On the other hand, variants of the vector that encode a protease variant that can efficiently cleave the inhibitor from the transcriptional activator will effect increased transcription of the at least one gene required for the generation of infectious phage particles from the accessory plasmid and thus be efficiently packaged into infectious phage particles.

In some embodiments, the protease PACE methods provided herein further comprises a negative selection for undesired protease activity in addition to the positive selection for a desired protease activity. Such negative selection methods are useful, for example, in order to maintain protease specificity when increasing the cleavage efficiency of a protease directed towards a specific target site. This can avoid, for example, the evolution of proteases that show a generally increased protease activity, including an increased protease activity towards off-target sites, which is generally undesired in the context of therapeutic proteases.

In some embodiments, negative selection is applied during a continuous evolution process as described herein, by penalizing the undesired activities of evolved proteases. This is useful, for example, if the desired evolved protease is an enzyme with high specificity for a target site, for example, a protease with altered, but not broadened, specificity. In some embodiments, negative selection of an undesired activity, e.g., off-target protease activity, is achieved by causing the undesired activity to interfere with pIII production, thus inhibiting the propagation of phage genomes encoding gene products with an undesired activity. In some embodiments, expression of a dominant-negative version of pIII or expression of an antisense RNA complementary to the gIII RBS and/or gIII start codon is linked to the presence of an undesired protease activity. Suitable negative selection strategies and reagents useful for negative selection, such as dominant-negative versions of M13 pIII, are described herein and in International PCT Application, PCT/US2011/066747, filed Dec. 22, 2011, published as WO 2012/088381 on Jun. 28, 2012; and U.S. Ser. No. 13/922,812, filed Jun. 20, 2013; International PCT Application, PCT/US2015/057012, filed Oct. 22, 2015, published as WO 2016/077052; and, PCT/US2016/027795, filed Apr. 15, 2016, published as WO 2016/168631, the entire contents of each of which are incorporated herein by reference.

In some embodiments, counter-selection against activity on non-target substrates is achieved by linking undesired evolved protease activities to the inhibition of phage propagation. In some embodiments, a dual selection strategy is applied during a continuous evolution experiment, in which both positive selection and negative selection constructs are present in the host cells. In some such embodiments, the positive and negative selection constructs are situated on the same plasmid, also referred to as a dual selection accessory plasmid.

One advantage of using a simultaneous dual selection strategy is that the selection stringency can be fine-tuned based on the activity or expression level of the negative selection construct as compared to the positive selection construct. Another advantage of a dual selection strategy is that the selection is not dependent on the presence or the absence of a desired or an undesired activity, but on the ratio of desired and undesired activities, and, thus, the resulting ratio of pIII and pIII-neg that is incorporated into the respective phage particle.

For example, in some embodiments, the host cells comprise an expression construct encoding a dominant-negative form of the at least one gene for the generation of infectious phage particles, e.g., a dominant-negative form of the pIII protein (pIII-neg), under the control of an inducible promoter that is activated by a transcriptional activator other than the transcriptional activator driving the positive selection system. Expression of the dominant-negative form of the gene diminishes or completely negates any selective advantage an evolved phage may exhibit and thus dilutes or eradicates any variants exhibiting undesired activity from the lagoon.

For example, if the positive selection system comprises a T3 promoter driving the expression of the at least one gene for the generation of infectious phage particles, and an evolved variant of T7 RNA polymerase that transcribes selectively from the T3 promoter, fused to a T7-RNA polymerase inhibitor via a linker comprising a protease target site that is cleaved by a desired protease activity, the negative selection system uses an orthogonal RNA polymerase. For example, in some such embodiments, the negative selection system could be based on T7 polymerase activity, e.g., in that it comprises a T7 promoter driving the expression of a dominant-negative form of the at least one gene for the generation of infectious phage particles, and a T7 RNA polymerase fused to a T7-RNA polymerase inhibitor via a linker comprising a protease target site that is cleaved by an undesired protease activity. In some embodiments, the negative selection polymerase is a T7 RNA polymerase gene comprising one or more mutations that render the T7 polymerase able to transcribe from the T3 promoter but not the T7 promoter, for example: N67S, R96L, K98R, H176P, E207K, E222K, T375A, M401I, G675R, N748D, P759L, A798S, A819T, etc. In some embodiments the negative selection polymerase may be fused to a T7-RNA polymerase inhibitor via a linker comprising a protease target site that is cleaved by an undesired protease activity. When used together, such positive-negative PACE selection results in the evolution of proteases that exhibit the desired activity but not the undesired activity. In some embodiments, the undesired function is cleavage of an off-target protease cleavage site. In some embodiments, VAMP7 is selected to be evolved (e.g., cleaved more efficiently), while VAMP1 is negatively selected (e.g., cleaved less efficiently, or not at all). In some embodiments, Ykt6 is selected for (e.g., cleaved more efficiently), while VAMP1 is negatively selected (e.g., cleaved less efficiently, or not at all). In some embodiments, the undesired function is cleavage of the linker sequence of the fusion protein outside of the protease cleavage site.

Some aspects of this invention provide or utilize a dominant negative variant of pIII (pIII-neg). These aspects are based on the recognition that a pIII variant that comprises the two N-terminal domains of pIII and a truncated, termination-incompetent C-terminal domain is not only inactive but is a dominant-negative variant of pIII. A pIII variant comprising the two N-terminal domains of pIII and a truncated, termination-incompetent C-terminal domain was described in Bennett, N. J.; Rakonjac, J., Unlocking of the filamentous bacteriophage virion during infection is mediated by the C domain of pIII. *Journal of Molecular Biology* 2006, 356 (2), 266-73; the entire contents of which are incorporated herein by reference. The dominant negative property of such pIII variants has been described in more detail in PCT Application PCT/US2011/066747, filed Dec. 22, 2011, published as WO 2012/088381 on Jun. 28, 2012, the entire contents of which are incorporated herein by reference.

The pIII-neg variant as provided in some embodiments herein is efficiently incorporated into phage particles, but it does not catalyze the unlocking of the particle for entry during infection, rendering the respective phage noninfectious even if wild type pIII is present in the same phage particle. Accordingly, such pIII-neg variants are useful for devising a negative selection strategy in the context of PACE, for example, by providing an expression construct comprising a nucleic acid sequence encoding a pIII-neg variant under the control of a promoter comprising a recognition motif, the recognition of which is undesired. In other embodiments, pIII-neg is used in a positive selection strategy, for example, by providing an expression construct in which a pIII-neg encoding sequence is controlled by a promoter comprising a nuclease target site or a repressor recognition site, the recognition of either one is desired.

In some embodiments, a protease PACE experiment according to methods provided herein is run for a time sufficient for at least 10, at least 20, at least 30, at least 40, at least 50, at least 100, at least 200, at least 300, at least 400, at least, 500, at least 600, at least 700, at least 800, at least 900, at least 1000, at least 1250, at least 1500, at least 1750, at least 2000, at least 2500, at least 3000, at least 4000, at least 5000, at least 7500, at least 10000, or more consecutive viral life cycles. In certain embodiments, the viral vector is an M13 phage, and the length of a single viral life cycle is about 10-20 minutes.

In some embodiments, the host cells are contacted with the vector and/or incubated in suspension culture. For example, in some embodiments, bacterial cells are incubated in suspension culture in liquid culture media. Suitable culture media for bacterial suspension culture will be apparent to those of skill in the art, and the invention is not limited in this regard. See, for example, *Molecular Cloning: A Laboratory Manual*, 2nd Ed., ed. by Sambrook, Fritsch, and Maniatis (Cold Spring Harbor Laboratory Press: 1989); Elizabeth Kutter and Alexander Sulakvelidze: *Bacteriophages: Biology and Applications*. CRC Press; 1ˢᵗ edition (December 2004), ISBN: 0849313368; Martha R. J. Clokie and Andrew M. Kropinski: *Bacteriophages: Methods and Protocols, Volume 1: Isolation, Characterization, and Interactions (Methods in Molecular Biology)* Humana Press; 1ˢᵗ edition (December, 2008), ISBN: 1588296822; Martha R. J. Clokie and Andrew M. Kropinski: *Bacteriophages: Methods and Protocols, Volume 2: Molecular and Applied Aspects (Methods in Molecular Biology)* Humana Press; 1ˢᵗ edition (December 2008), ISBN: 1603275649; all of which are incorporated herein in their entirety by reference for disclosure of suitable culture media for bacterial host cell culture).

The protease PACE methods provided herein are typically carried out in a lagoon. Suitable lagoons and other laboratory equipment for carrying out protease PACE methods as provided herein have been described in detail elsewhere. See, for example, International PCT Application, PCT/US2011/066747, filed Dec. 22, 2011, published as WO2012/088381 on Jun. 28, 2012, the entire contents of which are incorporated herein by reference. In some embodiments, the lagoon comprises a cell culture vessel comprising an actively replicating population of vectors, for example, phage vectors comprising a gene encoding the protease of interest (e.g., BoNT), and a population of host cells, for example, bacterial host cells. In some embodiments, the lagoon comprises an inflow for the introduction of fresh host cells into the lagoon and an outflow for the removal of host cells from the lagoon. In some embodiments, the inflow is connected to a turbidostat comprising a culture of fresh host cells. In some embodiments, the outflow is connected to a waste vessel or sink. In some embodiments, the lagoon further comprises an inflow for the introduction of a mutagen into the lagoon. In some embodiments that inflow is connected to a vessel holding a solution of the mutagen. In some embodiments, the lagoon comprises an inflow for the introduction of an inducer of gene expression into the lagoon, for example, of an inducer activating an inducible promoter within the host cells that drives expression of a gene promoting mutagenesis (e.g., as part of a mutagenesis plasmid), as described in more detail elsewhere herein. In some embodiments, that inflow is connected to a vessel comprising a solution of the inducer, for example, a solution of arabinose.

In some embodiments, a PACE method as provided herein is performed in a suitable apparatus as described herein. For example, in some embodiments, the apparatus comprises a lagoon that is connected to a turbidostat comprising a host cell as described herein. In some embodiments, the host cell is an *E. coli* host cell. In some embodiments, the host cell comprises an accessory plasmid as described herein, a helper plasmid as described herein, a mutagenesis plasmid as described herein, and/or an expression construct encoding a fusion protein as described herein, or any combination thereof. In some embodiments, the lagoon further comprises a selection phage as described herein, for example, a selection phage encoding a protease of interest. In some embodiments, the lagoon is connected to a vessel comprising an inducer for a mutagenesis plasmid, for example, arabinose. In some embodiments, the host cells are *E. coli* cells comprising the F' plasmid, for example, cells of the genotype F'proA⁺B⁺ Δ(lacIZY) zzf::Tn10(TetR)/endA1 recA1 galE15 galK16 nupG rpsL ΔlacIZYA araD139 Δ(ara,leu) 7697 mcrA Δ(mrr-hsdRMS-mcrBC) proBA::pir116λ⁻.

Some aspects of this invention relate to host cells for continuous evolution processes as described herein. In some embodiments, a host cell is provided that comprises at least one viral gene encoding a protein required for the generation of infectious viral particles under the control of a conditional promoter, and a fusion protein comprising a transcriptional activator targeting the conditional promoter and fused to an inhibitor via a linker comprising a protease cleavage site. For example, some embodiments provide host cells for phage-assisted continuous evolution processes, wherein the host cell comprises an accessory plasmid comprising a gene required for the generation of infectious phage particles, for example, M13 gIII, under the control of a conditional promoter, as described herein. In some embodiments, the host cells comprises an expression construct encoding a fusion protein as described herein, e.g., on the same accessory plasmid or on a separate vector. In some embodiments, the host cell further provides any phage functions that are not contained in the selection phage, e.g., in the form of a helper phage. In some embodiments, the host cell provided further comprises an expression construct comprising a gene encoding a mutagenesis-inducing protein, for example, a mutagenesis plasmid as provided herein.

In some embodiments, modified viral vectors are used in continuous evolution processes as provided herein. In some embodiments, such modified viral vectors lack a gene required for the generation of infectious viral particles. In some such embodiments, a suitable host cell is a cell comprising the gene required for the generation of infectious viral particles, for example, under the control of a constitutive or a conditional promoter (e.g., in the form of an accessory plasmid, as described herein). In some embodiments, the viral vector used lacks a plurality of viral genes. In some such embodiments, a suitable host cell is a cell that comprises a helper construct providing the viral genes required for the generation of infectious viral particles. A cell is not required to actually support the life cycle of a viral vector used in the methods provided herein. For example, a cell comprising a gene required for the generation of infectious viral particles under the control of a conditional promoter may not support the life cycle of a viral vector that does not comprise a gene of interest able to activate the promoter, but it is still a suitable host cell for such a viral vector.

In some embodiments, the host cell is a prokaryotic cell, for example, a bacterial cell. In some embodiments, the host cell is an *E. coli* cell. In some embodiments, the host cell is a eukaryotic cell, for example, a yeast cell, an insect cell, or a mammalian cell. The type of host cell, will, of course, depend on the viral vector employed, and suitable host cell/viral vector combinations will be readily apparent to those of skill in the art.

In some embodiments, the viral vector is a phage and the host cell is a bacterial cell. In some embodiments, the host cell is an *E. coli* cell. Suitable *E. coli* host strains will be apparent to those of skill in the art, and include, but are not limited to, New England Biolabs (NEB) Turbo, Top10F', DH12S, ER2738, ER2267, and XL1-Blue MRF'. These strain names are art recognized and the genotype of these strains has been well characterized. It should be understood that the above strains are exemplary only and that the invention is not limited in this respect.

In some PACE embodiments, for example, in embodiments employing an M13 selection phage, the host cells are *E. coli* cells expressing the Fertility factor, also commonly referred to as the F factor, sex factor, or F-plasmid. The F-factor is a bacterial DNA sequence that allows a bacterium to produce a sex pilus necessary for conjugation and is essential for the infection of *E. coli* cells with certain phage, for example, with M13 phage. For example, in some embodiments, the host cells for M13-PACE are of the genotype F'proA⁺B⁺ Δ(lacIZY) zzf::Tn10(TetR)/endA1 recA1 galE15 galK16 nupG rpsL ΔlacIZYA araD139 Δ(ara, leu)7697 mcrA Δ(mrr-hsdRMS-mcrBC) proBA::pir116λ.

Some of the embodiments, advantages, features, and uses of the technology disclosed herein will be more fully understood from the Examples below. The Examples are intended to illustrate some of the benefits of the present disclosure and to describe particular embodiments, but are not intended to exemplify the full scope of the disclosure and, accordingly, do not limit the scope of the disclosure.

EXAMPLES

Example 1

Among the most notable protein systems capable of cytoplasmic delivery are the Clostridial neurotoxins, which include eight serologically distinct Botulinum neurotoxins (BoNT A-G, and X) and a single Tetanus Syntaxin neurotoxin (TeNT). These modular proteins are expressed as a single 150 kDa single protein, which is proteolyzed into two components, a 100 kDa "heavy chain" (HC) and 50 kDa "light chain" (LC), which remain associated through a single disulfide linkage. The BoNT HC is further subdivided into a HCC binding domain, responsible for binding to cholinergic motor nerve terminals, and HCN translocation domain.

Upon binding and endocytosis by neurons, endosomal acidification drives a structural reorganization of the translocation domain (HCN) which transports the tethered LC zinc metalloprotease (BoNT LC) to the neurotoxins cytoplasm (FIG. 1). The protease is then released after reduction of the disulfide linkage, and proceeds to block neurotransmitter release by proteolytic cleavage of vesicular membrane fusion (SNARE) proteins, thereby causing paralysis (FIG. 1). The catalytic nature of this event, and the long intracellular lifetime of these proteases results in BoNT neurotoxins being among the most potent neurotoxic agents known.

Two BoNT serotypes (BoNT A and BoNT B) are approved for several therapeutic applications, including cervical dystonia, blepharospasm, and spasticity. Therapies based on wild-type BoNTs are notable for their exquisite selectivity for both neuronal cells and for specific SNARE proteins, but these characteristics also limit the broader application of these proteins for modulating cellular chemistry. While notable advances have been made in retargeting BoNT toxins to novel neuronal subtypes or to non-neuronal cells, the preferential SNARE substrates for BoNT LC proteases function primarily in neuronal signaling. Efforts to modify the activity of the BoNT LC protease to overcome this restriction have met with much more limited success, and the inaccessibility of new intracellular targets for BoNT LC proteases remains the primary barrier in extending BoNT-type therapeutic strategies.

Proteolysis represents one of the most common post-translational modifications, and the ability to redirect selective BoNT LC proteases to novel substrates within the cell would constitute a powerful therapeutic tool. Reprogramming proteases to permanently modify disease-associated proteins has been a longstanding goal within the protein engineering community, but the challenges of altering protease activity and selectivity have limited the broad utilization of proteases in medicine. Substantial efforts to reprogram proteases have demonstrated the feasibility of tuning protease activity and selectivity by directed evolution. However, because most reported successes to date have been limited to single-residue specificity changes, commonly with greatly impaired levels of activity, therapeutic applications of proteases have thus far been limited to proteases that perform native functions in vivo. BoNT proteases are not exempt from to this trend. Only limited success in protease engineering successes have been reported, and have thus far been unable to substantially broaden the applications of BoNT therapies.

Figure 2:
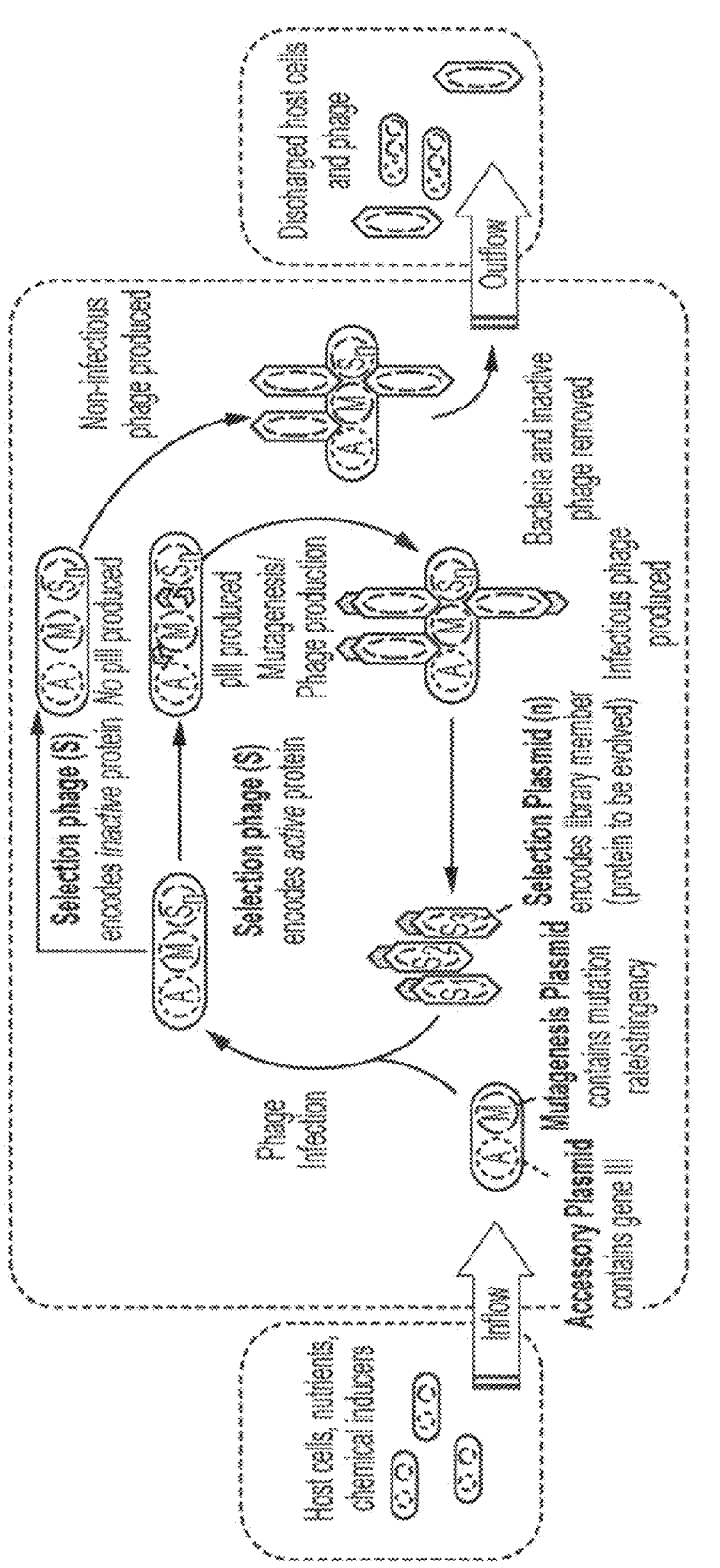
FIG. 2 is a schematic overview of Phage-assisted Continuous Evolution (PACE).
Figure 3:
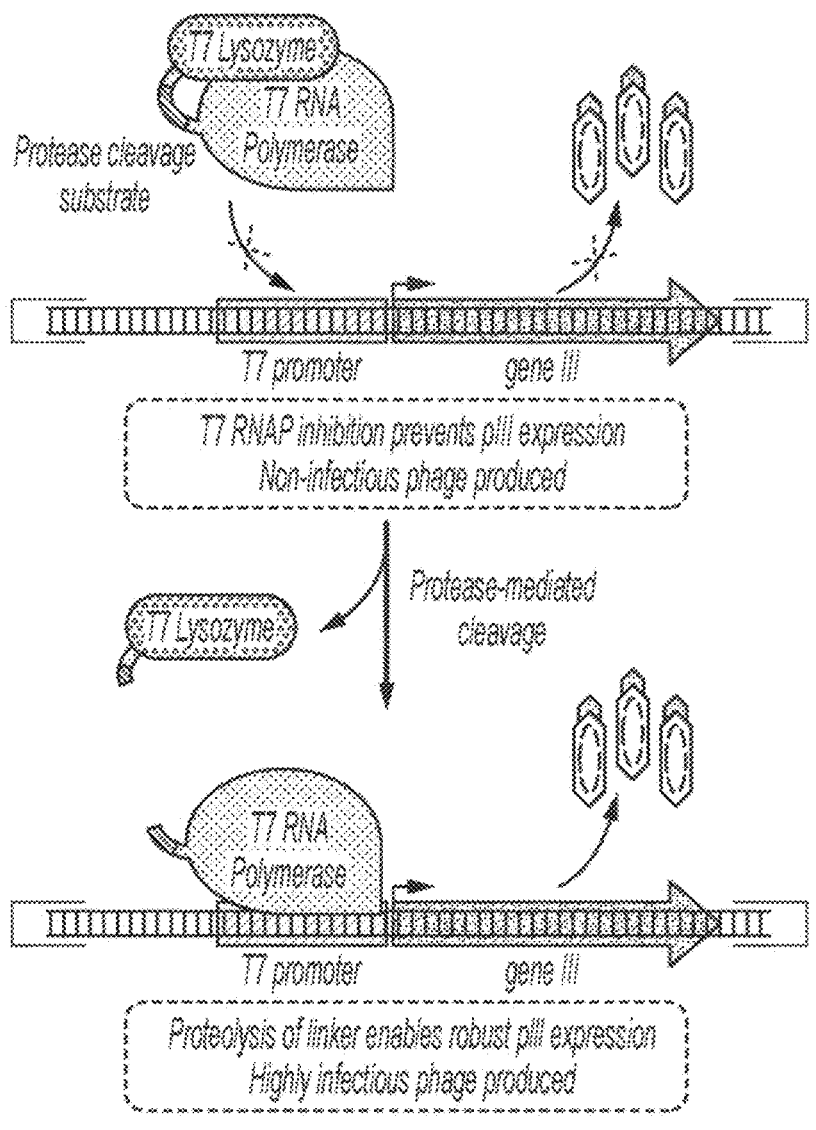
FIG. 3 is a schematic depiction of proteolysis-activated T7 RNA polymerase for PACE selection of proteases.

Phage assisted continuous evolution (PACE) has recently emerged as a powerful strategy for the development of new activity in proteins, including new promoter selectivity in RNA polymerases, new binding selectivity among protein-DNA interactions, new binding activity in protein-protein interactions, and drug resistance among viral proteases. The PACE selection is built around a modified M13 filamentous bacteriophage, which is unable to infect new hosts due to a lack of the essential gene III and its product, the coat protein pIII (FIG. 2). This essential gene has been moved to *E. coli* host cells, and its transcription is placed under the control of a specified activity of interest. In order to select for improved activity, the protein to be evolved is carried by the phage (selection phage) and is expressed upon bacterial host infection. Because pIII is essential for this infection process, only phage carrying active library members will be able to produce infectious progeny, and their infectivity increases in proportion to the activity of the encoded protein. The selection itself takes place in a dynamic lagoon environment undergoing constant dilution with new *E. coli* cells and with constant outflow to removing inactive phage library members, thereby allowing only phage containing the most active protein variants to persist. The ability to perform and control in situ mutagenesis, selection, and replication in PACE offers many advantages over traditional directed evolution approaches. Generally, PACE enables much faster selections with large gene libraries, resulting in a ~100-fold increase in the rate of protein evolution efforts, as hundreds of rounds of evolution can be performed in the course of a one-week PACE experiment with minimal researcher intervention. Improvements in controlling selection stringency and mutagenesis rate allow PACE to cover a vast region of a given protein's adaptive landscape, making it a powerful approach that can surpass rational engineering efforts in accessing novel protein activities. While highly efficient, PACE selection requires linkage of protein activity to transcription of gene-III to drive the selection, for example, a protease-activated T7 RNA polymerase (referred to hereafter as T7-PAP) that is capable of driving the evolution of proteases including BoNT protease and the Hepatitis C viral (HCV) NS3/4Aprotease. In this example platform, gene-III is placed under the control of the T7 promoter, and the cognate T7 polymerase is expressed as a fusion construct with T7 lysozyme with a protease-sensitive linker. Because T7 lysozyme is a natural inhibitor of T7 RNAP, T7pos is unable to transcribe pIII until the linking domain is proteolytically cleaved. (FIG. 3). Upon hydrolysis, the T7 polymerase becomes activated, and is able to transcribe gene-III from the T7 promoter in the accessory plasmid. Importantly, the linker region in T7pos can be varied to accommodate a variety of cleavage sequence, and is sensitive to the intrinsic selectivity of a theco-expressed protease.

Eukaryotic organisms, including humans, rely heavily on lipid membranes to compartmentalize and control biochemical processes. Complementary sets of SNARE proteins control trafficking of vesicular organelles, and are the primary mechanism by which cells catalyze membrane fusion events that lead to secretion, autophagy, and membrane remodeling. Despite the obvious potential for controlling signal networks through control over these processes, this therapeutic strategy remains underexplored, and the only small-molecule secretion inhibitors known have limited clinical viability due to low specificity and high toxicity. BoNT neurotoxins, offer a solution to this limitation, but require expansion of their activity to extend the scope of this therapeutic strategy. BoNT B, BoNT D, and BoNT F LC proteases selectively hydrolyze vesicle associated membrane protein-1 (VAMP1) and VAMP2, thereby blocking neurotransmitter secretion. However, several other VAMP family members such as VAMP7 (TI-VAMP), mediate important cellular events including autophagy, plasma membrane remodeling, and secretion, but are not cleaved by BoNT proteases. VAMP7 is the primary v-SNARE responsible for MT1-MMP secretion during tumor cell invasion, and also mediates granzyme B and perforin secretion during natural killer mediated cell death, a major hurdle in transplantation efforts. Given its close relationship to natural BoNT substrates, VAMP7 represents an ideal first target for simultaneously expanding BoNT LC protease activity for biomacromolecular modulation of intracellular chemistry, and broadening the applications for targeted inhibitors of trafficking and secretion.

In addition to providing an engineered BoNT protease with potential therapeutic relevance, this example establishes a foundation for extending intracellular biological treatments using the BoNT platform.

Evolution of BoNTs Using PACE

Figures 4C, 4D:
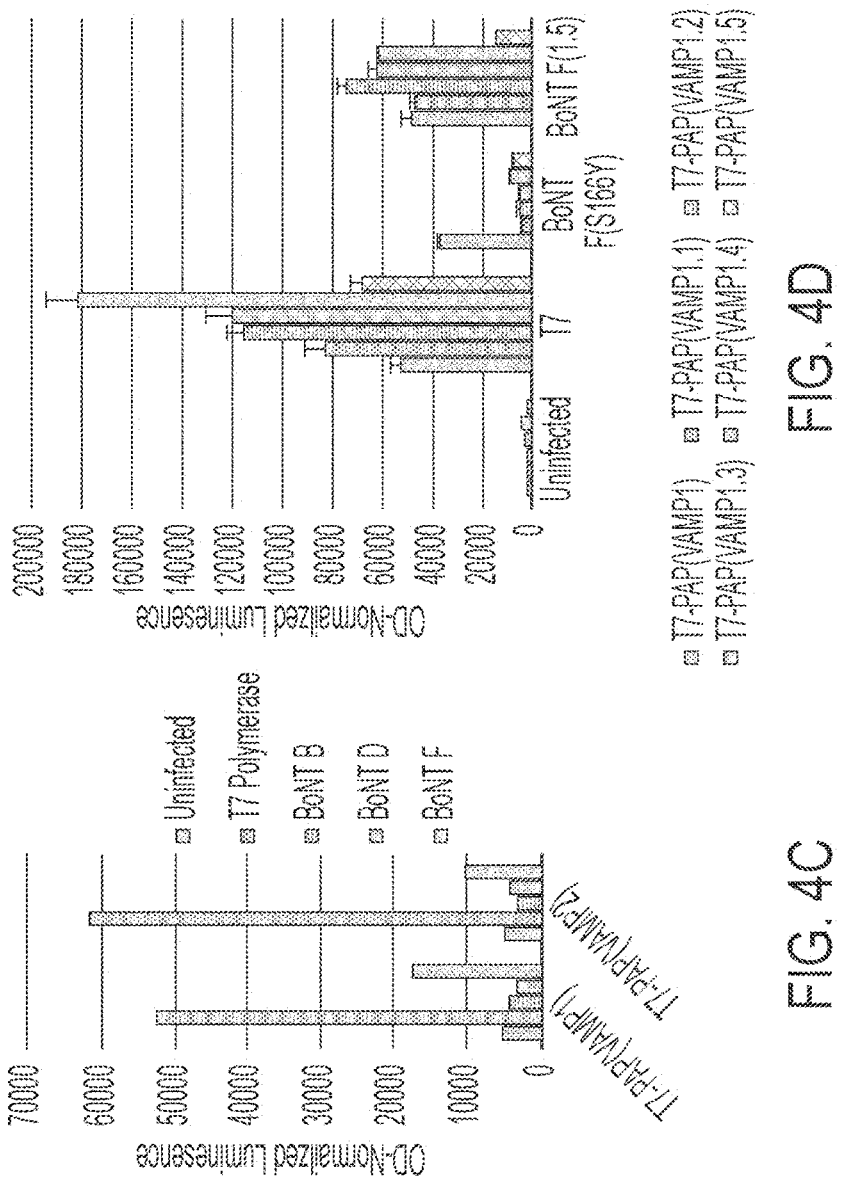

The first-generation T7-PAP construct possessed only a short (seven amino acid) substrate sequence, and was flanked by flexible linkers to allow T7 lysozyme binding in the unhydrolyzed state (FIG. 4B). However, this condensed cleavage sequence differs dramatically from the extended substrate recognition site in BoNT proteases. VAMP-cleaving BoNT proteases require a sequence of approximately 30 amino acids to perform efficient hydrolysis in isolated peptides, and thus it becomes essential to establish whether an elongated substrate sequence can be incorporated into the T7-PAP with retention of protease-dependent transcriptional activity. In order to validate expression and proteolytic activity of recombinantly expressed BoNT LC proteases (hereafter annotated to as BoNT N, where N denotes the neurotoxin serotype), selection phagemids containing each of the three VAMP1-cleaving BoNT serotypes (BoNT LC B, D, and F) were obtained. These proteases were assayed against VAMP1 and VAMP2-linked T7-PAP constructs (T7-PAP(VAMP1)/T7-PAP(VAMP2)) in a coupled luciferase assay (FIG. 4C). The resulting data demonstrate that BoNT F is expressed upon M13 phage infection of *E. coli*, and can drive protease-dependent transcription from the SNARE-derived T7-PAPs. Selection phage were then submitted to a PACE on the T7-PAPVAMP1 substrate, yielding a mutation (S166Y) that dramatically improves cleavage activity on the natural substrate (FIG. 4D, third column). These results demonstrate that PACE selection can be applied to BoNT protease evolution using a SNARE-protein adapted T7-PAP.

Previous characterization of BoNT F protease promiscuity has revealed a collection of residues in VAMP1 that are important for efficient cleavage activity, and a number of these sites coincide with non-conserved amino acids in VAMP7 (FIG. 4A). These residues (as shows in FIG. 4B) were selected as primary targets for assessing initial PACE trajectories for BoNT protease reprogramming. A panel of AP's encoding T7-PAPs containing VAMP1 single-mutant substrates for VAMP7-targeted evolution was produced, and the activity of BoNT F(wt) and the evolved BoNT F(S166Y) on these constructs was measured. Many of these single mutant substrates were efficiently cleaved using the more active BoNT F(VAMP1) evolved protease. The T7-PAP(VAMP71.1) AP, carrying the VAMP1(D58G) mutation, displays lower cleavage efficiency (FIG. 4D) and was targeted for subsequent PACE selection. After a 72h PACE positive selection, phage with dramatically enhanced cleavage activity (FIG. 4D) were selected. The selected variants carried a set of highly-enriched mutations: S166Y, R240L, and Y372H.

Negative Selection and Evolved Proteases that Cleave VAMP7

Figure 5A:
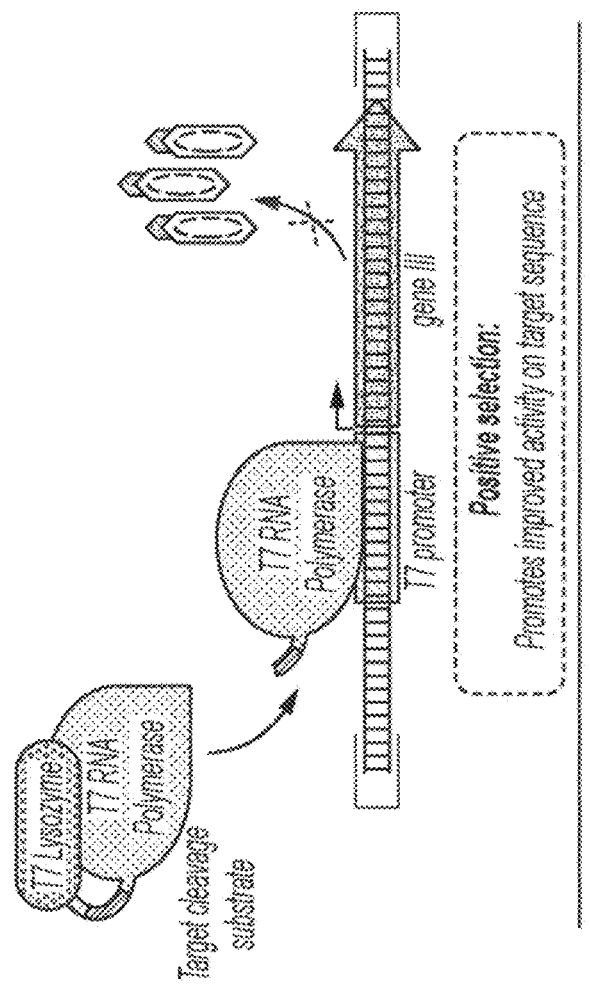
FIG. 5 is a schematic depicting an orthogonal polymerase strategy against non-selective proteases, and examples of negative selection constructs.
Figure 5B:
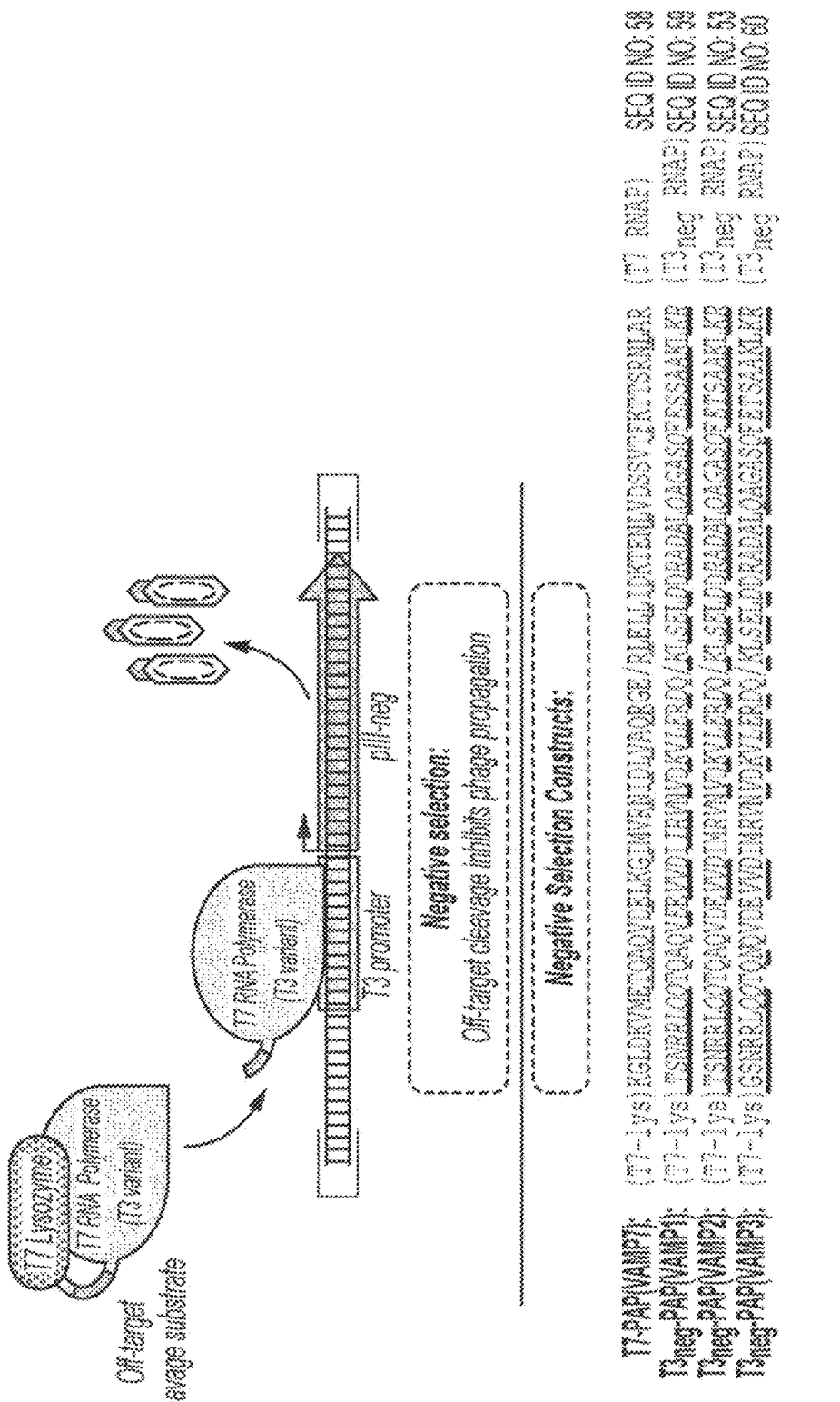

Because positive selection generally results in broadened activity with low specificity, it was important to develop a negative selection strategy to select for BoNT F proteases with high specificity for the desired VAMP7 sequence. Here, a modified T7 polymerase that selectively transcribes from the T3 polymerase target sequence was fused with T7 lysozyme to generate an orthogonal protease-activated polymerase (T3neg-PAP) and was coupled to expression of a dominant negative mutant of gene III, pIII-neg, upon cleavage by non-selective BoNT (e.g., a BoNT having an undesired proteolytic activity). Competitive expression of pIII-neg effectively suppresses phage propagation by generating phage incapable of infecting new hosts, and is initiated upon cleavage of an off-target sequence in the protease-sensitive linker of T3neg (FIG. 5). Because this gene cassette (containing the orthogonal polymerase and pIII-neg) are encoded on a separate plasmid, the concentration of substrate (T3neg)

and the amount of pIII-neg produced per hydrolysis event can be modulated through plasmid copy number, promoter engineering, and ribosome binding sequence optimization of the resulting mRNA transcript. This allows for tunable negative selection stringency, and increases the likelihood that selective BoNT mutants can be enriched. Certain evolutionary trajectories between VAMP1 and VAMP7 cover a large number of non-natural SNARE protein sequences. Therefore, in order to obtain high specificity, negative selection against a only relatively small number of naturally-occurring off-target substrates will be performed. In some embodiments, a VAMP1-linked T3neg-PAP selects against the most likely off-target substrate for the evolved protease. Additional in vitro substrate profiling can be performed using related SNARE proteins such as VAMP2, VAMP3, and VAMP8 to ensure a high degree of specificity for the target VAMP7.

Characterization of Evolved BoNT Proteases

The chemical and biological properties evolved BoNT proteases are investigated. Recombinant expression and isolation of BoNT F LC proteases was performed and is sufficient to obtain material for in vitro cleavage assays. Single-mutant reversions of the evolved BoNT proteases are assayed to interrogate their role in controlling enzymatic activity and specificity. SNARE substrate cleavage is assayed by both gel electrophoresis and LC/MS to determine enzyme kinetics. Stability (both thermal and proteolytic) of the evolved protease is assessed in quantitative assays. The therapeutic potential of BoNT variants to bring about selective membrane fusion blockade by cleaving VAMP7 is investigated by characterizing the ability of the variants to function as targeted secretion inhibitors in human cells, for example using the MT1-MMP secretion model. Briefly, BoNT protease variant is introduced into MDA-MB-231 breast cancer cells via transfection, and extracellular matrix degradation is assayed using a fluorescent gelatin plating medium. Transwell migration assays are also performed; siRNA and anti-VAMP7 antibody data are compared with BoNT activity to determine the relative potency of BoNT protease variant treatment. Surface labeling with anti-MT1-MMP antibodies is also performed as an orthogonal assay for VAMP7 function in this invasion assay.

Example 2

PACE of BoNT Protease Variants

Figure 6A:
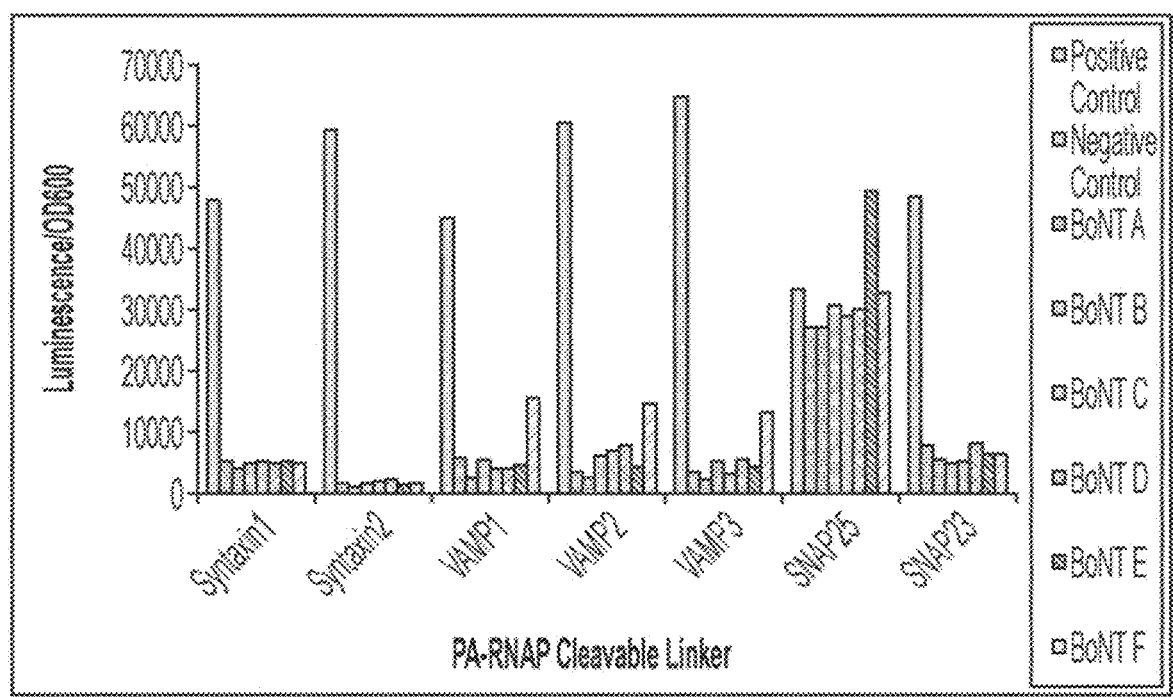
FIGS. 6A-6B show proteolytic activity of BoNT proteases.
Figure 6B:
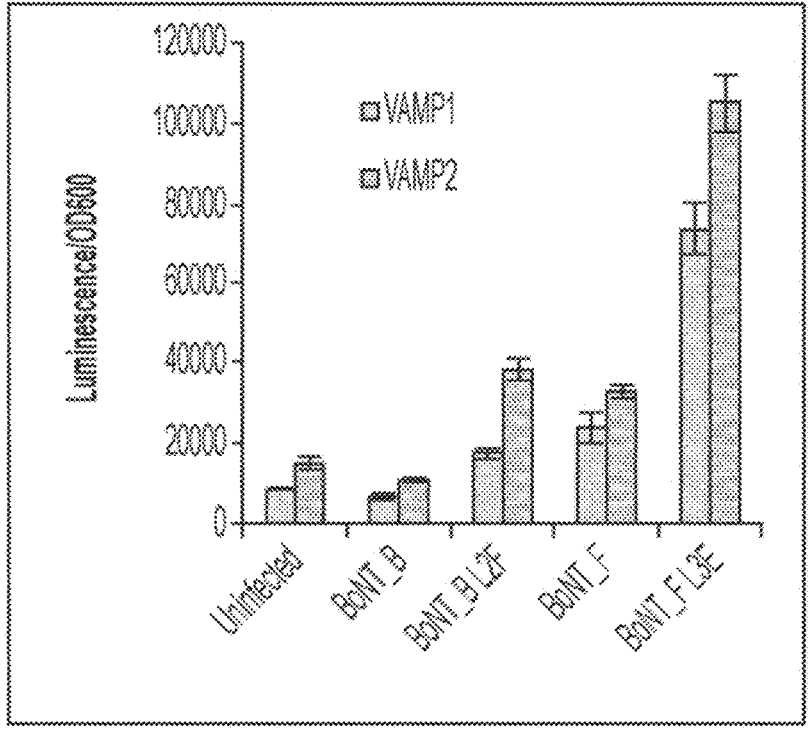

In contrast to previous selections, where protease activity and selectivity is dictated by a short (approximately 7 amino acid) peptide sequence, BoNT LC serotypes recognize an extended sequence of their cognate SNARE protein substrates. Data indicate that that a 60 amino acid fragment of VAMP1, extending from residues 28-87, serves as a suitable linker between T7 RNAP and T7 lysozyme, affording up to 3-fold activation of the polymerase upon proteolytic cleavage (FIG. 6A). Notably, BoNT serotypes B and F perform best on this substrate in accord with their in vivo activity, while other BoNT LC serotypes exhibit PA-RNAP activation exclusively for their cognate substrates (BoNT E on SNAP25). The VAMP1 PA-RNAP has been shown to be sufficient to carry out PACE selection, and has yielded BoNT B and BoNT F variants with increased apparent VAMP1 and VAMP2 cleavage activity (FIG. 6B).

Figure 7:
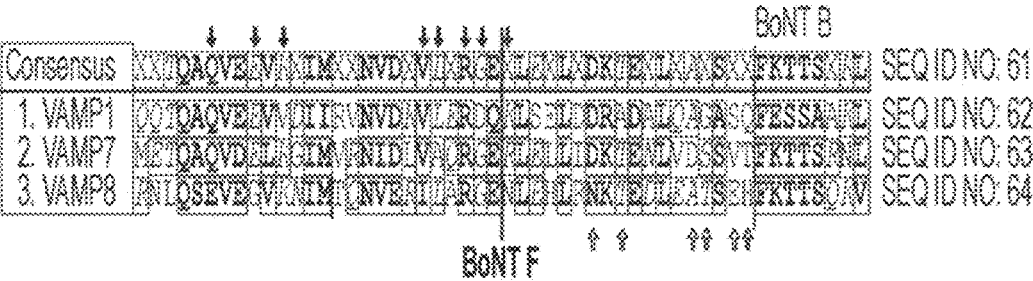
FIG. 7 shows a primary sequence alignment of VAMP1, VAMP7, and VAMP8. The BoNT LC cleavage sites for serotypes B (are marked on the bottom) and F (are marked on the top). Residues marked with an arrow lead to a decrease in cleavage activity by at least 50% on VAMP2 upon removal of the residue side chain.

The efficiency of PACE makes practical a stepping-stone approach in which a protein evolves recognition of a successively altered series of substrates towards a dramatically altered final substrate. Alignment of VAMP1, VAMP7, and VAMP8 shows a high degree of sequence homology, but notable deviation in activity-promoting residues for both the BoNT B and BoNT F serotypes (see FIG. 6B, BoNT B L2F and BoNT F L3E, and FIG. 7). Evolutionary pathways were designed that gradually evolve wild-type protease specificities by successive introduction of each amino acid substitution (or set of substitutions) in the VAMP7/8 target sequences into the VAMP1 PA-RNAP, followed by PACE selection on the resulting AP construct. This strategy allows a stepwise accumulation of LC mutations that result in a gradual shift in protein activity toward the desired VAMP substrates.

Figure 8:
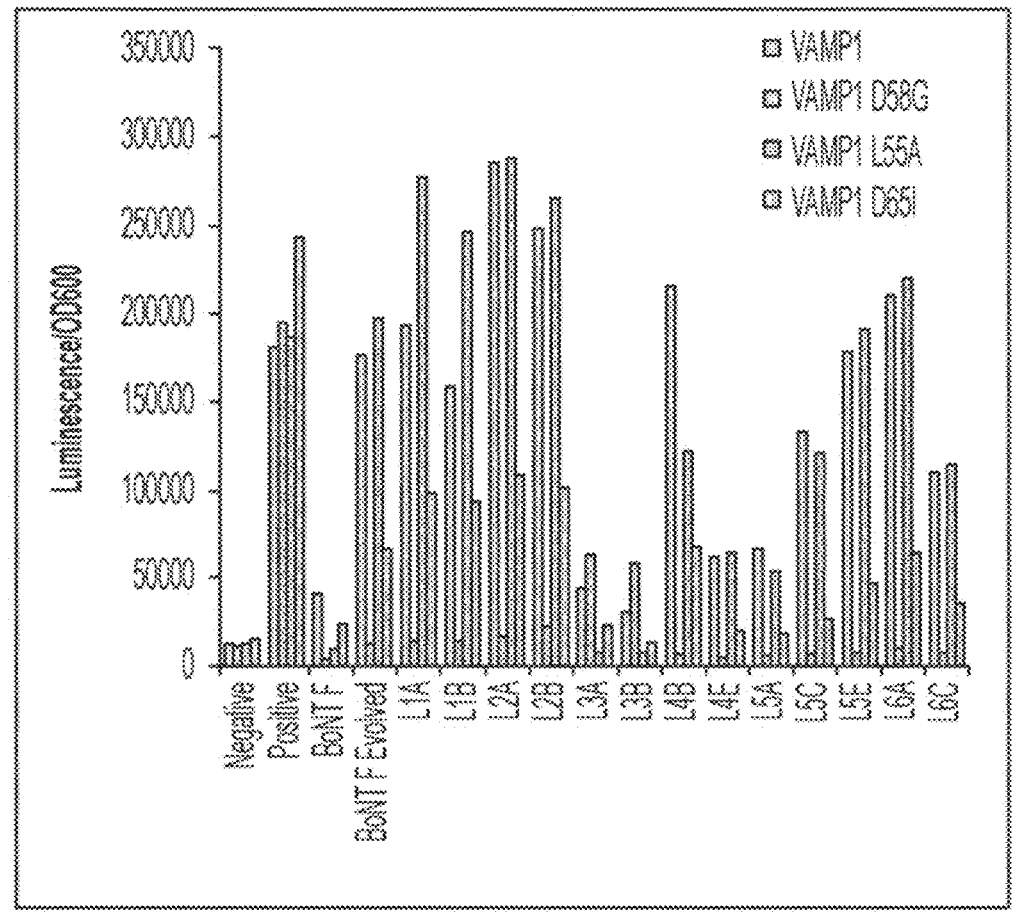
FIG. 8 shows evolved BoNT F variants displaying varied activity on a collection of VAMP1 single residue mutants. L1/L2 were evolved to cleave VAMP1 L55A, L3/4 were evolved to cleave VAMP1 D58G, and L5/L6 were evolved to cleave VAMP1 D65I. Columns 1-4, as read left to right of each grouping of 4 columns: VAMP1, VAMP1 D58G, VAMP1 L55A, and VAMP1 D65I.

As a means for interrogating the baseline promiscuity and potential evolutionary trajectories for BoNT B and F LCs, a panel of single-residue mutants in the VAMP1 PA-RNAP in which the native VAMP1 residue has been converted into the corresponding VAMP7 or VAMP8 residue were assayed. Data indicate that BoNT F LC tolerates many of the individual VAMP7 substitutions, however three of these substitutions (VAMP1 L55A, D58G, and D65I) attenuated the protease-dependent luciferase signal. Particularly difficult substitutions such as these were targeted first, in order to enter challenging selections from wild-type activity levels. Separate PACE selection for cleavage of each these mutant substrates have yielded evolved variants with improved activity against the respective mutant substrate, indicating that the designed PA-RNAP constructs facilitate evolution of BoNT proteases (FIG. 8). Importantly, the ease with which new PA-RNAP constructs can be developed, and the efficiency of PACE selection enable multiple evolutionary pathways to be interrogated in parallel, thereby increasing the probability of success. For example, each of the evolved BoNT F variants in FIG. 8 represents a different evolutionary trajectory that can be carried forward to access new substrates with increased similarity to VAMP7.

Example 3

Evolution of BoNT F by PACE

Figure 9:
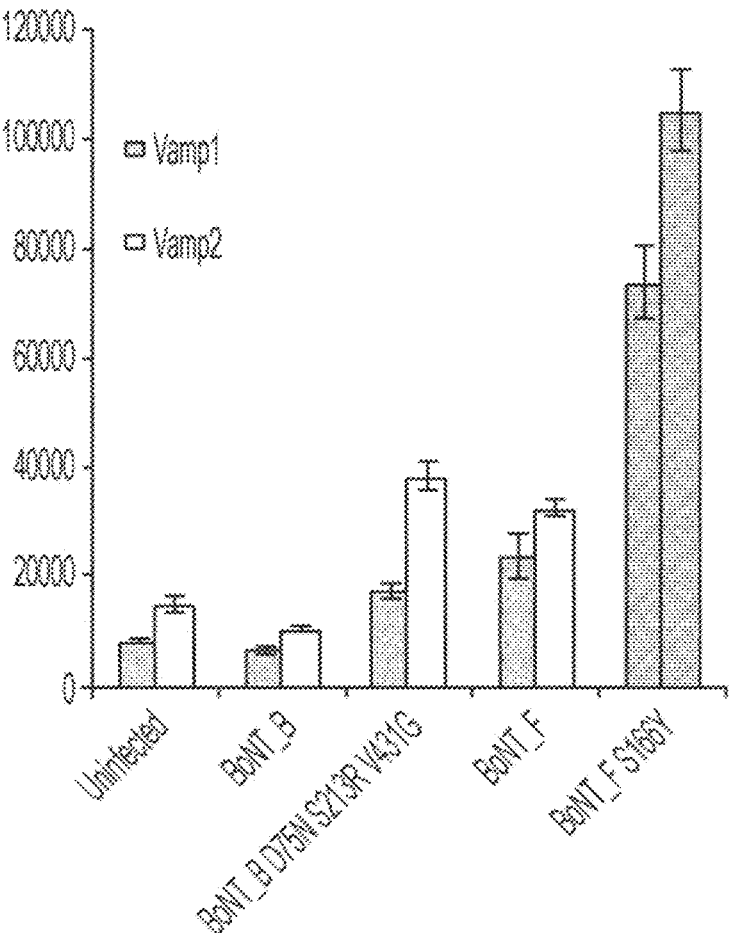
FIG. 9 shows luciferase assay data indicating that BoNT B and BoNT F can be evolved to cleave VAMP1/2. Columns 1-2, as read left to right of each grouping of two columns: VAMP 1 and VAMP2.
Figure 10:
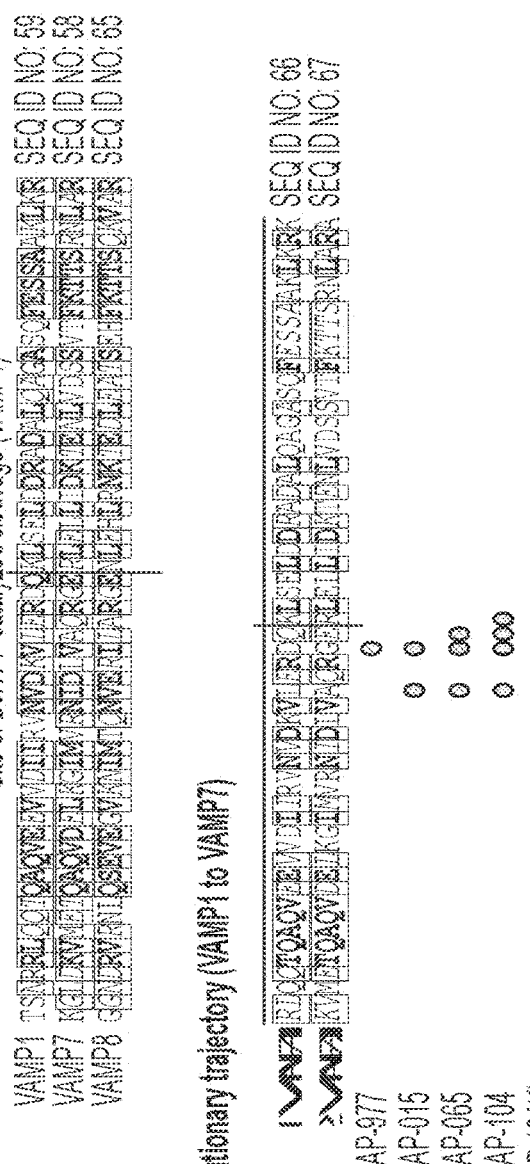
FIG. 10 shows an alignment of the amino acid sequences of VAMP1, VAMP7 and VAMP8 (top) and an example of a VAMP1 to VAMP7 evolutionary trajectory (bottom). AP: accessory plasmid.

First-Pass PACE Evolution was Performed on BoNT Serotypes B, D, and F. Luciferase assay data indicates that BoNT B and BoNT F can be evolved to alter protease activity, for example to increase cleavage of the native VAMP1/2 substrate (FIG. 9). FIG. 10 shows one example of an evolutionary trajectory for VAMP1 to VAMP7 cleaving proteases and examples of accessory plasmids for achieving the same.

Figure 11:
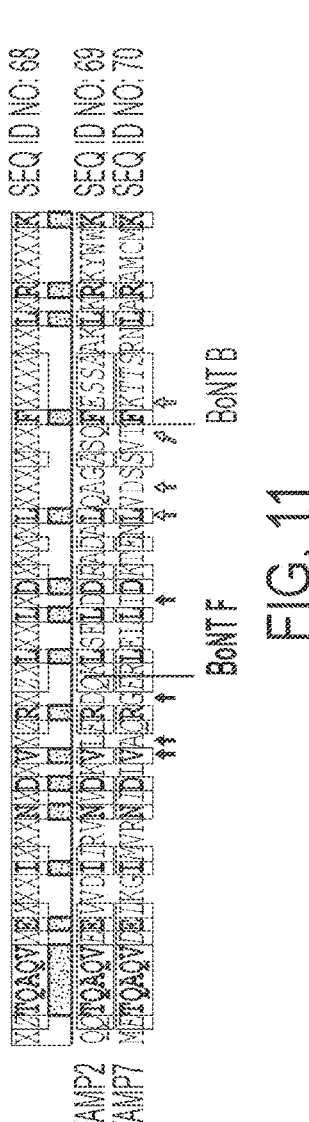
FIG. 11 shows an alignment of BoNT F and BoNT B VAMP2 (a natural substrate) cleavage domains with VAMP7. First four arrows, as read left to right are associated with BoNT F, last four arrows as ready left to right, are associated with BoNT B.
Figure 12:
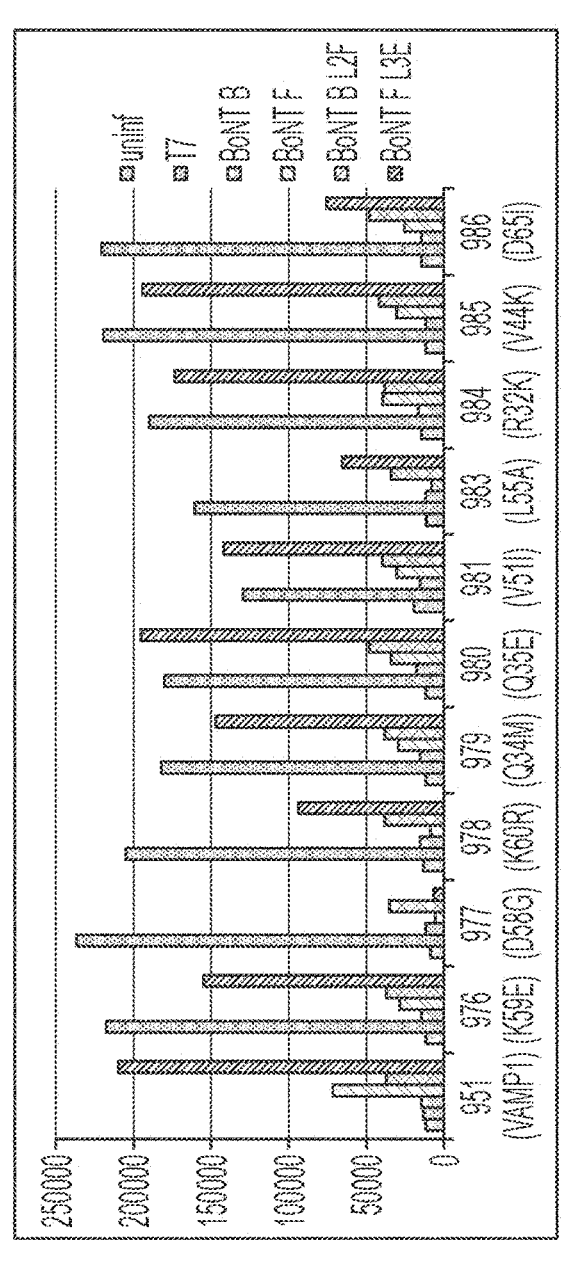
FIG. 12 shows data indicating that evolution of BoNT B and F by PACE (e.g., using AP's 977, 983 and 986 for BoNT F) resulted in BoNT variants with improved activity. Columns 1-6, as read left to right, of each grouping of six columns: Unif (uninfected), T7, BoNT B, BoNT F, BoNT B L2F, and BoNT F L3E.
Figure 13:
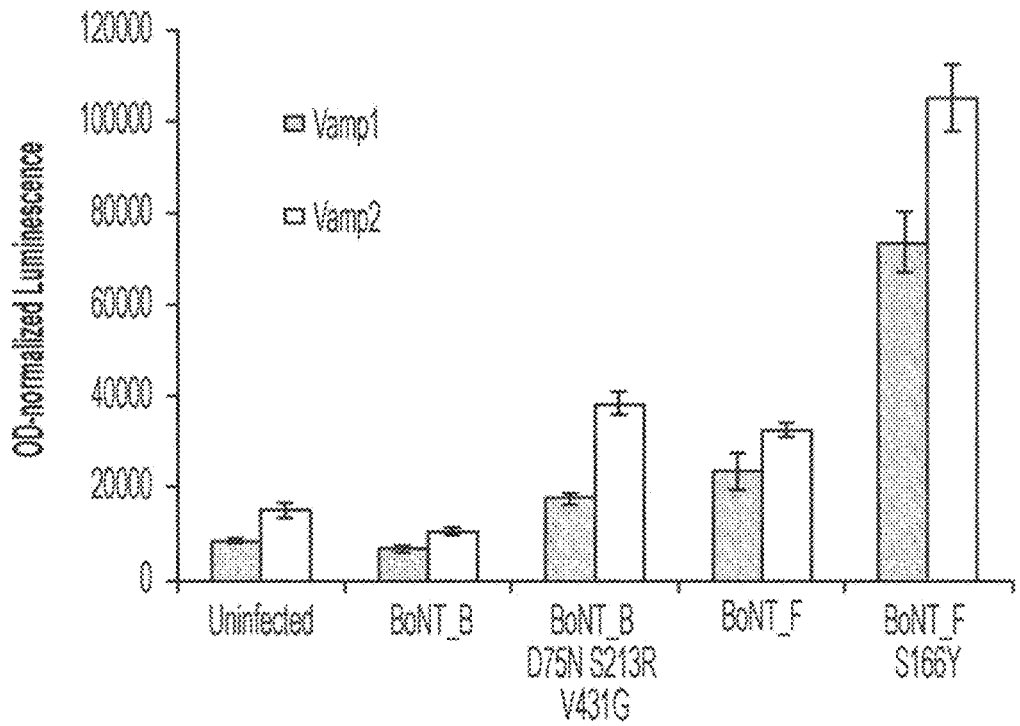
FIG. 13 shows representative data relating to validation of BoNT Light Chain (LC) selection; data indicate that evolution of BoNT F protease on VAMP1 enriches for the S166Y mutation, which confers broadly increased activity. Columns 1-2, as read left to right, of each grouping of two columns: VAMP1 and VAMP 2.

VAMP7 participates in phagocytosis, mitosis, cell migration, membrane repair and growth. FIG. 11 depicts an alignment of BoNT F and BoNT B VAMP2 (a natural substrate) cleavage domains with VAMP7. FIG. 12 provides data indicating that evolution of BoNT B and F by PACE (e.g., using AP's 977, 983 and 986 for BoNT F) resulted in BoNT variants with improved activity. FIG. 13 shows representative data relating to validation of BoNT Light Chain (LC) selection; data indicate that evolution of BoNT F protease on VAMP1 enriches for the S166Y mutation, which confers broadly increased activity. Evolution of BoNT F (S166Y) on AP-977 also enriches strongly for mutations at position 240, which directly contacts the altered substrate residue (D→G).

Figure 14:
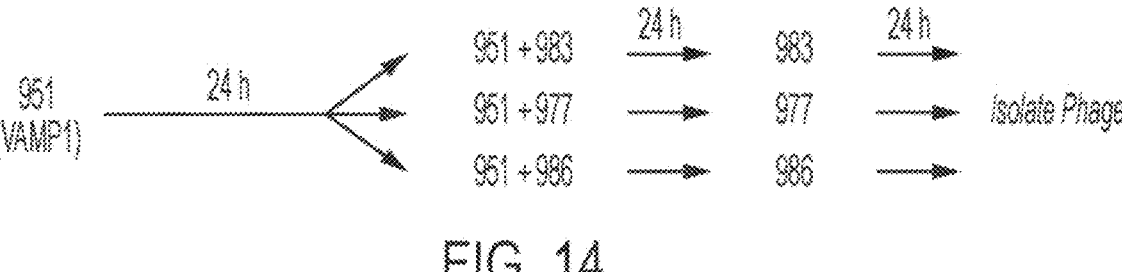
FIG. 14 shows one example of a stepping-stone evolutionary pathway for production of BoNT F variants that cleave VAMP7.
Figure 15:
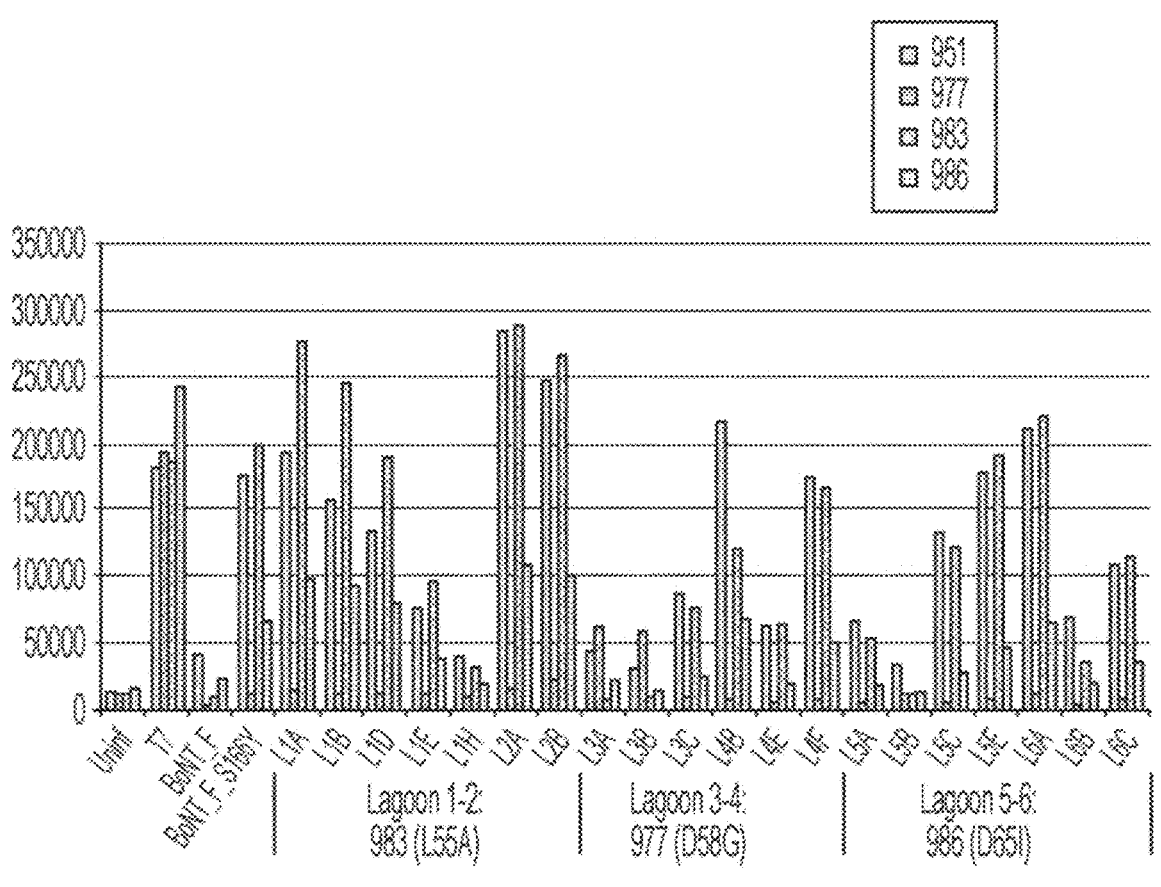
FIG. 15 shows protease activity assays for BoNT F variants from three different experiments (Lagoons 1-6). Each experiment produced clones that cleave VAMP1 substrates containing a different single site mutation (L55A, D58G, or D65I). Columns 1-4, as read left to right, of each grouping of four columns: 951, 977, 983, and 986

FIG. 14 shows one example of a stepping-stone evolutionary pathway for production of BoNT F variants that cleave VAMP7. FIG. 15 shows protease activity assays for BoNT F variants from three different experiments (Lagoons 1-6). Each experiment produced a different single mutant variant (L55A, D58G, D65I). Lagoons 1~4 were carried forward for PACE experiments using a double mutant substrate (AP-015: L55A/D58G) AP.

Figure 16:
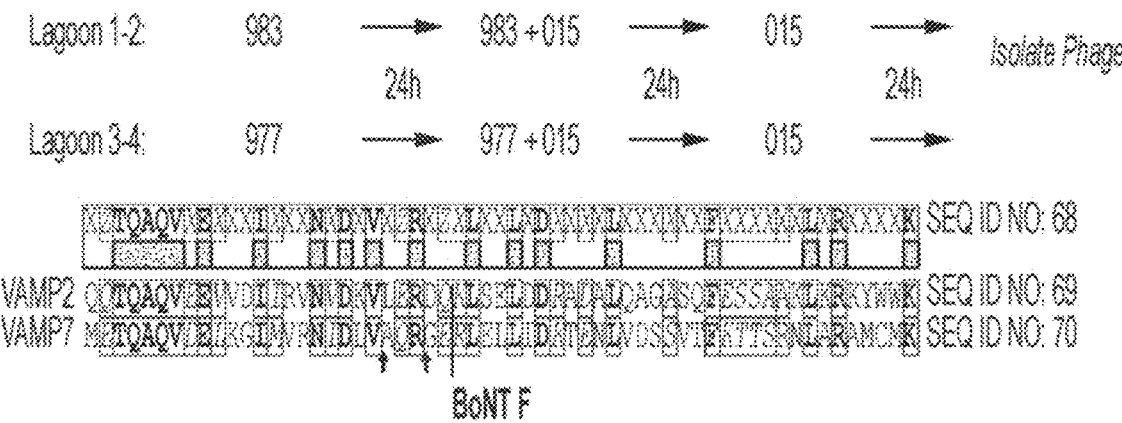
FIG. 16 is a schematic depiction of PACE experiments to evolve BoNT F that cleave double mutant substrates; the amino acid sequence of the double mutant VAMP1 (L55A/ D58G) is also shown.
Figure 17:
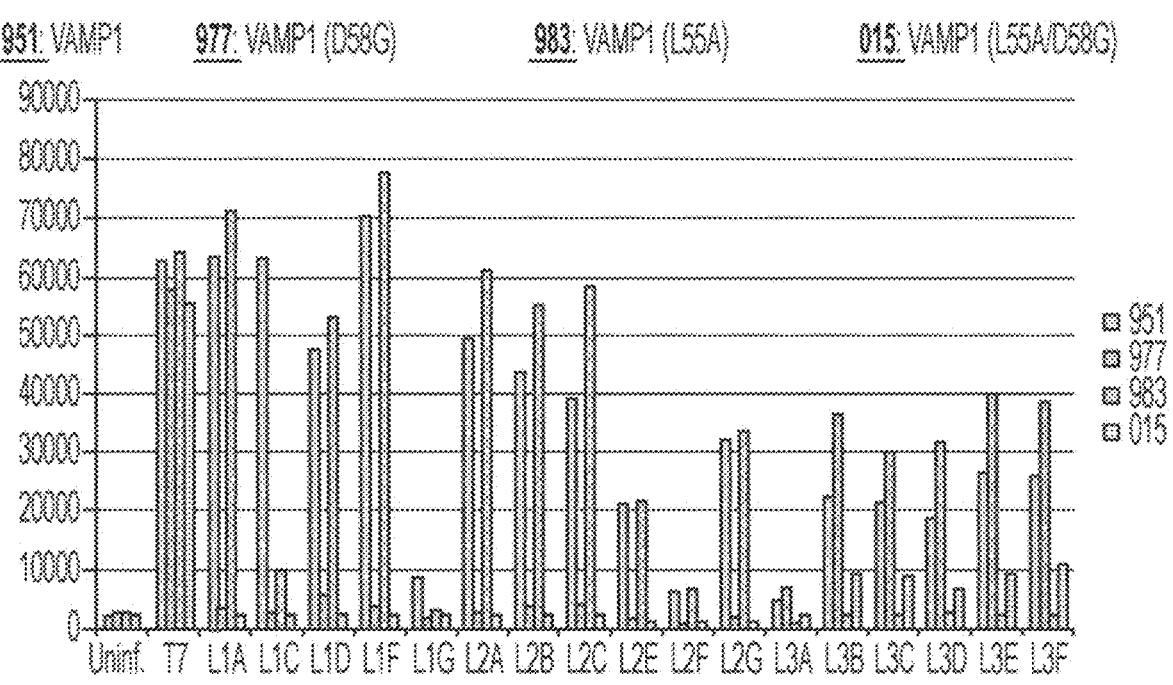
FIG. 17 shows protease-dependent luciferase assay data indicating that certain BoNT F variants produced by PACE can cleave the double mutant VAMP1 substrate (L55A/ D58G). Columns 1-4, as read left to right, of each grouping of four columns: 951, 977, 983, and 015.

FIG. 16 shows a schematic depiction of double mutant PACE experiments to evolve BoNT F; the amino acid sequence of the double mutant VAMP1 (LSSA/D58G) is also shown. Protease-dependent luciferase assay data indicate that BoNT F variants that cleave the double mutant VAMP1 substrate were produced by PACE (FIG. 17).

Figure 18:
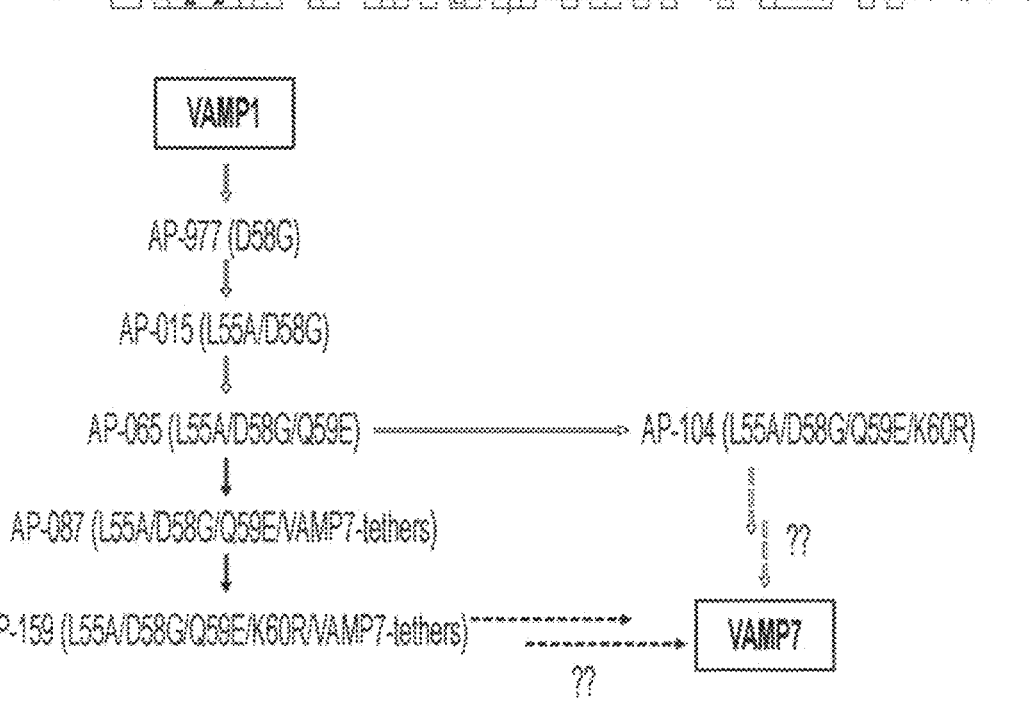
FIG. 18 shows one example of a VAMP1-VAMP7 stepping stone evolutionary trajectory.

FIG. 18 shows one example of an evolutionary "stepping stone" strategy for mutation of BoNT F to cleave VAMP7. FIG. 19 shows representative data for triple mutant (L55A/D58G/Q59E) selection of BoNT F variants. Data indicate that variants L132-L1C and L132-L3A cleave VAMP1 containing three VAMP7 mutations (L55A/D58G/Q59E).

FIG. 20 shows representative data for tetramutant (L55A/D58G/Q59E/K60R) selection of BoNT F variants. It was observed that several selected BoNT F variants (e.g., 216-

Figure 21:
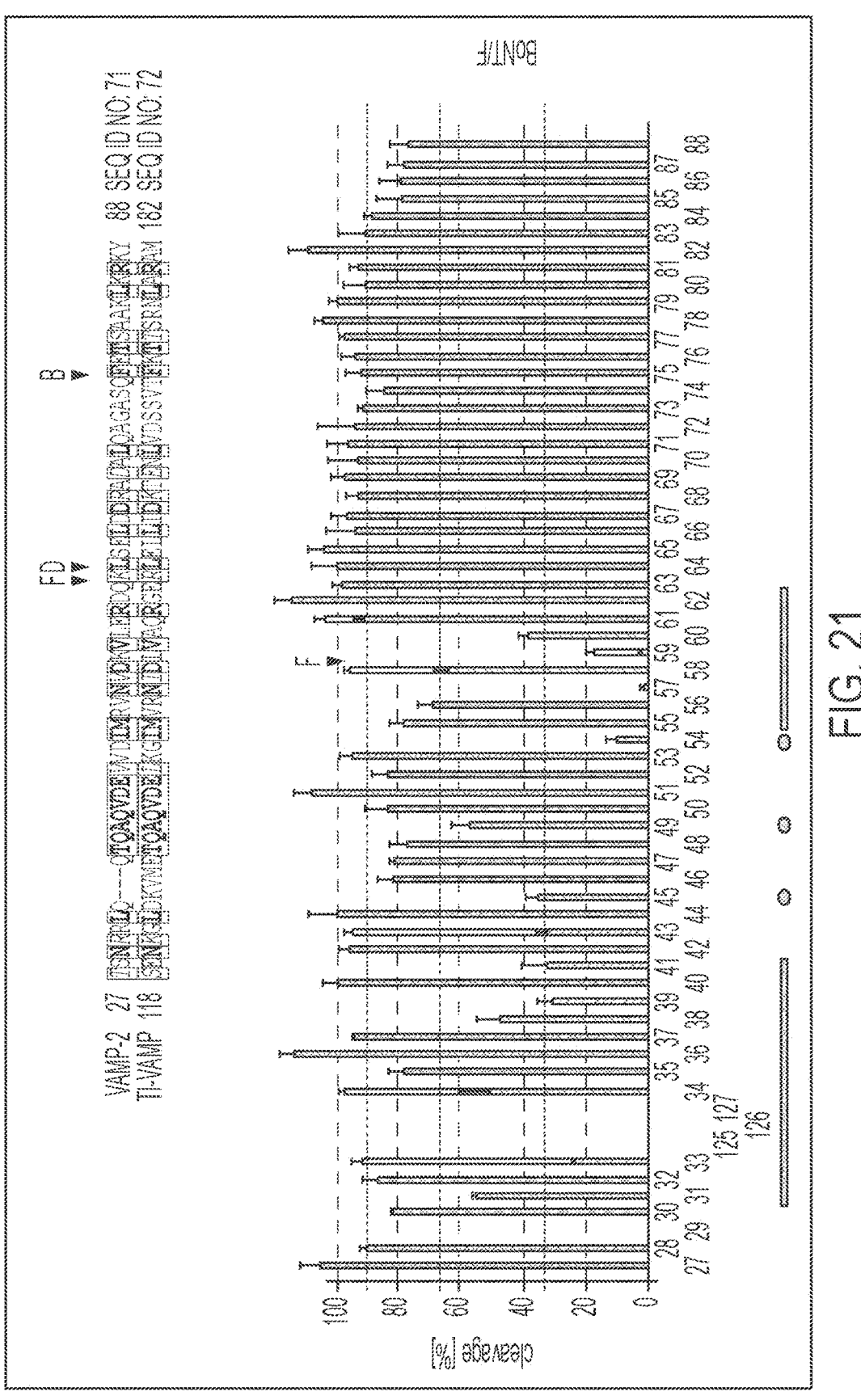
FIG. 21 shows data indicating that the activity of proteases on VAMP1 substrates containing mutations V44K (shown as V43 in the figure) and Q32M (shown as Q33 in the figure) can be readily evolved.

L1C, 216-L1E, 216-L3B, 216-L3G) cleave the VAMP1 containing four VAMP7 mutations (L55A/D58G/Q59E/K60R), indicating that four of the five least permissive mutation sites in VAMP1 have been addressed. FIG. 21 shows that activity of proteases on V44K (shown as V43 in the figure) and Q32M (shown as Q33 in the figure) can be readily evolved. BoNT F proteases tolerant of VAMP7 termini have also been observed.

Figure 22:
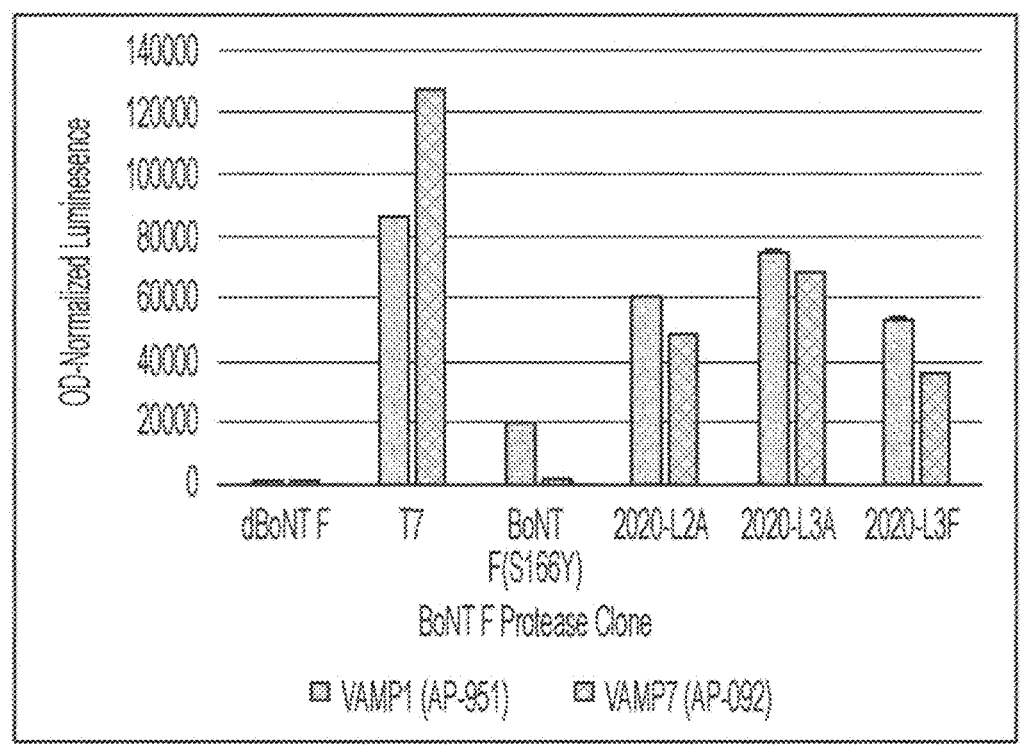
FIG. 22 shows data indicating that iterative selection on progressively more complex VAMP substrates produces several BoNT F variants that cleave VAMP7. Columns 1-2, as read left to right, of each grouping of two columns: VAMP1 (AP-951) and VAMP7 (AP-092).
Figure 23:
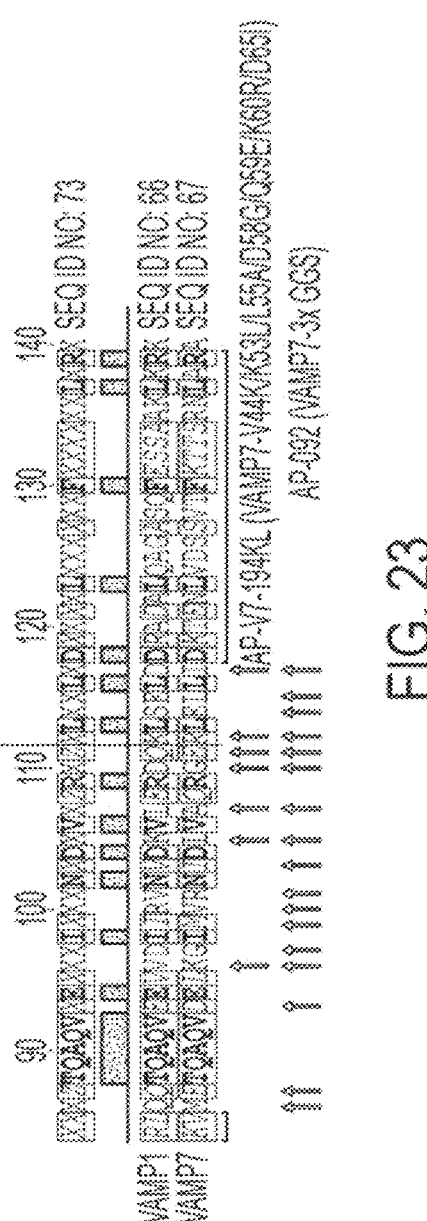
FIG. 23 shows an alignment of VAMP1 and VAMP7 amino acid sequences, along with AP-V7-194KL, which contains seven VAMP7 mutations (V44K/K53L/L55A/ D58G/Q59E/K60R/D65I).

Iterative selection on progressively more complex VAMP substrates afforded several BoNT F variants that cleave VAMP7 (FIG. 22). FIG. 23 shows an alignment of VAMP1 and VAMP7 amino acid sequences, along with AP-V7-194KL, which contains seven VAMP7 mutations (V44K/K53L/L55A/D58G/Q59E/K60R/D65I). Table 3 below shows mutations observed in several BoNT F variants after PACE with AP-V7-194KL for 48 h, followed by AP-V7-194KL+AP-092 for 24 hours, followed by AP-092 for 48 hours.

TABLE 3

| | | | | | | | | | | | |
|---|---|---|---|---|---|---|---|---|---|---|---|
| L1 | a | E66D | | | S166Y | | D175G | N184K | | E200G | |
| | b | E66D | | | S166Y | | D175G | N184K | | E200G | Y210H |
| | c | E66D | | | S166Y | | D175G | N184K | | E200G | |
| | d | E66D | | | S166Y | | D175G | N184K | | E200G | |
| | e | | | | S166Y | | D175G | N184K | | E200G | |
| | f | E66D | | | S166Y | | D175G | N184K | | E200G | |
| | g | E66D | | | S166Y | | D175G | N184K | | E200G | |
| | h | E66D | | | S166Y | | D175G | N184K | | E200G | |
| L2 | a | | | V106A | S166Y | S167I | | | | E200G | |
| | b | | | V106A | S166Y | S167I | | | | E200G | |
| | c | | | V106A | S166Y | S167I | | | | E200G | |
| | d | | N76D | V106A | S166Y | S167I | | | | E200G | |
| | e | | | V106A | S166Y | S167I | | | | E200G | |
| | f | | | V106A | S166Y | S167I | | | | E200G | |
| | g | | | V106A | S166Y | S167I | | | | E200G | |
| | h | | | V106A | S166Y | S167I | | | | E200G | |
| L3 | a | | | | S166Y | | | N184K | | E200G | |
| | b | | | | S166Y | | | N184K | | E200G | |
| | c | | | | S166Y | | | N184K | | E200G | |
| | d | | | | S166Y | | | N184K | Y199H | E200G | |
| | e | | | | S166Y | | | N184K | | E200G | |
| | f | | | | S166Y | | | N184K | | E200G | |
| | g | | | | S166Y | | | N184K | | E200G | |
| | h | | S70F | E164K | S166Y | | | N184K | | E200G | |

| | | | | | | | | | | | |
|---|---|---|---|---|---|---|---|---|---|---|---|
| L1 | a | | | S224I | R240F | | | | R303H | P309T | |
| | b | | | S224I | R240F | | | | | | |
| | c | | | S224I | R240F | | | | | | |
| | d | | E215G | | R240L | | | | | | |
| | e | T214I | | S224I | R240F | | | | | | |
| | f | | | S224I | R240F | | | | | | |
| | g | | | S224I | R240F | | | | | | |
| | h | | E215G | | R240L | Y244C | | | | | |
| L2 | a | | | S224I | R240L | | | | | | S350G |
| | b | | | S224I | R240L | | | | | | S350G |
| | c | | | S224I | R240L | | | | | | S350G |
| | d | | | S224I | R240L | | | | | | S350G |
| | e | | | S224I | R240L | | | | | | S350G |
| | f | | | S224I | R240L | | | | | | S350G |
| | g | | | S224I | R240L | | | | | | S350G |
| | h | | | S224I | R240L | | | | | | S350G |
| L3 | a | | | S224I | R240F | | | | | T335S | |
| | b | | | S224I | R240F | | | N276T | | T335S | |
| | c | | | S224I | R240F | | | | | T335S | |
| | d | | | S224I | R240F | | | | | T335S | |
| | e | | | S224I | R240F | | | | | T335S | |
| | f | | | S224I | R240F | | A258S | N276S | | | |
| | g | | | S224I | R240F | | | | | T335S | |
| | h | | | S224I | R240F | | | | | | |

| | | | | | | |
|---|---|---|---|---|---|---|
| L1 | a | F360L | | Y372H | P410L | 420(AWLRKS*) |
| | b | F360L | | Y372H | P410L | 420(AWLRKS*) |
| | c | F360L | | Y372H | P410L | 420(AWLRKS*) |
| | d | F360L | K371E | Y372H | P410L | 420(AWLRKS*) |
| | e | F360L | | Y372H | P410L | 420(AWLRKS*) |

TABLE 3-continued

| | | | | | | | | | |
|---|---|---|---|---|---|---|---|---|---|
| | f | F360L | | Y372H | | | P410L | | 420(AWLRKS*) | |
| | g | F360L | | Y372H | | | P410L | | 420(AWLRKS*) | |
| | h | F360L | K371E | Y372H | | | P410L | | 420(AWLRKS*) | |
| L2 | a | F360L | | Y372H | | N396H | P410L | | 420(AWLRKS*) | |
| | b | F360L | | Y372H | | N396H | P410L | | 420(AWLRKS*) | |
| | c | F360L | | Y372H | | N396H | P410L | | 420(AWLRKS*) | |
| | d | F360L | | Y372H | | N396H | P410L | | 420(AWLRKS*) | |
| | e | F360L | | Y372H | | N396H | P410L | | 420(AWLRKS*) | |
| | f | F360L | | Y372H | | N396H | P410L | | 420(AWLRKS*) | |
| | g | F360L | | Y372H | | N396H | P410L | | 420(AWLRKS*) | |
| | h | F360L | | Y372H | | N396H | P410L | | 420(AWLRKS*) | |
| L3 | a | F360L | | Y372H | | N396H | P410L | D418Y | | E423K |
| | b | F360L | | Y372H | | N396H | P410L | D418Y | | E423K |
| | c | F360L | | Y372H | | N396H | P410L | D418Y | | E423K |
| | d | F360L | | Y372H | | N396H | P410L | D418Y | | E423K |
| | e | F360L | | Y372H | | N396H | P410L | D418Y | | E423K |
| | f | F360L | | Y372H | L375R | N396H | P410L | | | E423K |
| | g | F360L | | Y372H | | N396H | P410L | D418Y | | E423K |
| | h | F360L | | Y372H | L375R | N396H | P410L | | | E423K |

Several VAMP7-cleaving BoNT F variants were [20] expressed in vitro. FIG. 24 shows protein blot analysis for protein expression of two BoNT F evolved variants (2020 L2A, 2020 L3A).

Figure 26:
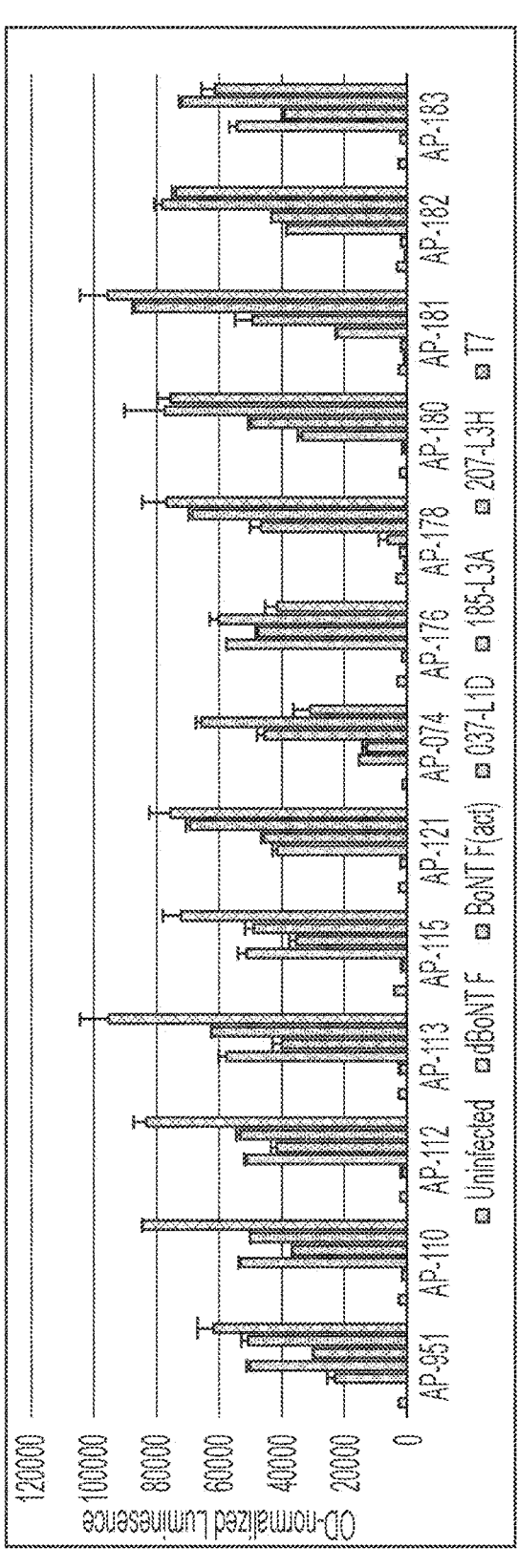
FIG. 26 shows representative data that indicates VAMP7-evolved BoNT F proteases have a broadened activity profile. Columns 1-7, as read left to right, of each grouping of seven columns: Uninfected, dBoNT F, BoNT F(act), 037-L1D, 185-L3A, 207-L3H, and T7.

VAMP7-evolved proteases were then used to screen a VAMP8 double mutant substrate panel. FIG. 25 shows a [25] schematic diagram of an alignment of VAMP1 and VAMP8 amino acid sequences and double mutant accessory plasmids (APs) used in the screen. Data indicates that VAMP7-evolved BoNT F proteases have a broadened activity profile (FIG. 26).

Figure 27:
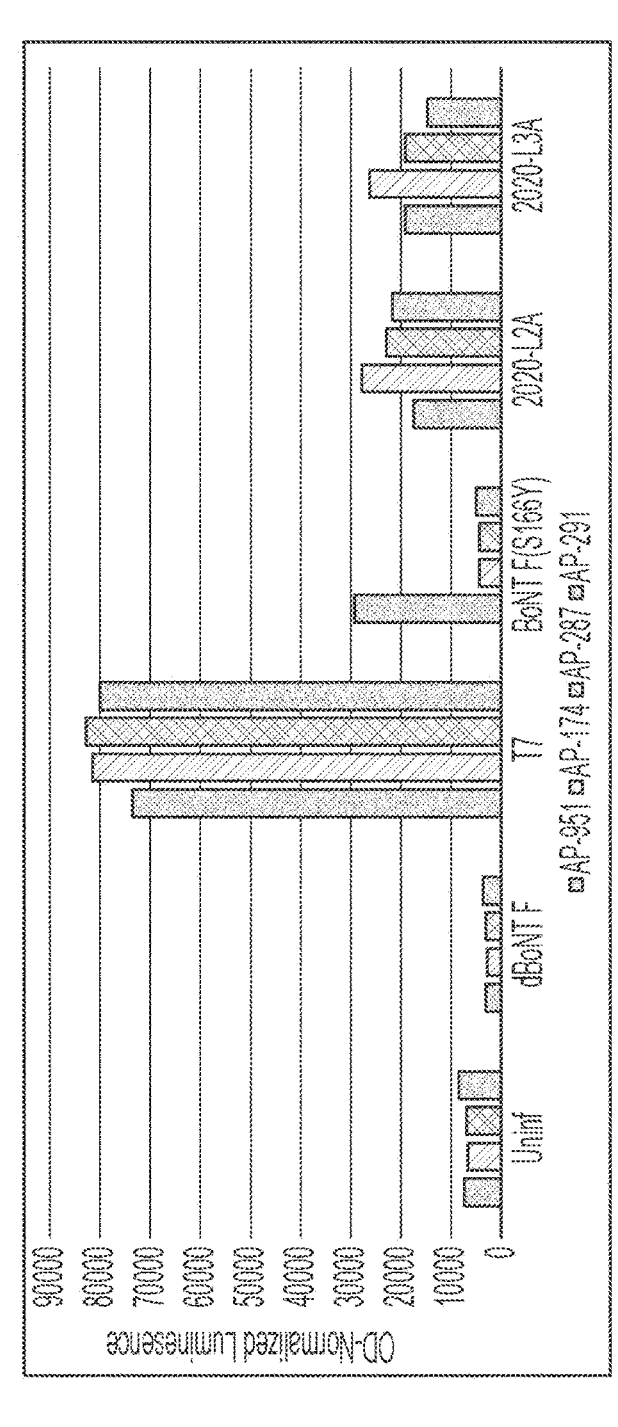
FIG. 27 shows an alignment of VAMP1 and VAMP8 amino acid sequences, along with several APs used to evolve VAMP8-cleaving BoNT F variants. Data indicate that VAMP8 APs have high background, but BoNT F variants that cleave VAMP8 were identified. Columns 1-4, as read left to right, of each grouping of four columns: AP-951, AP-174, AP-287, and AP-291.
Figure 28:
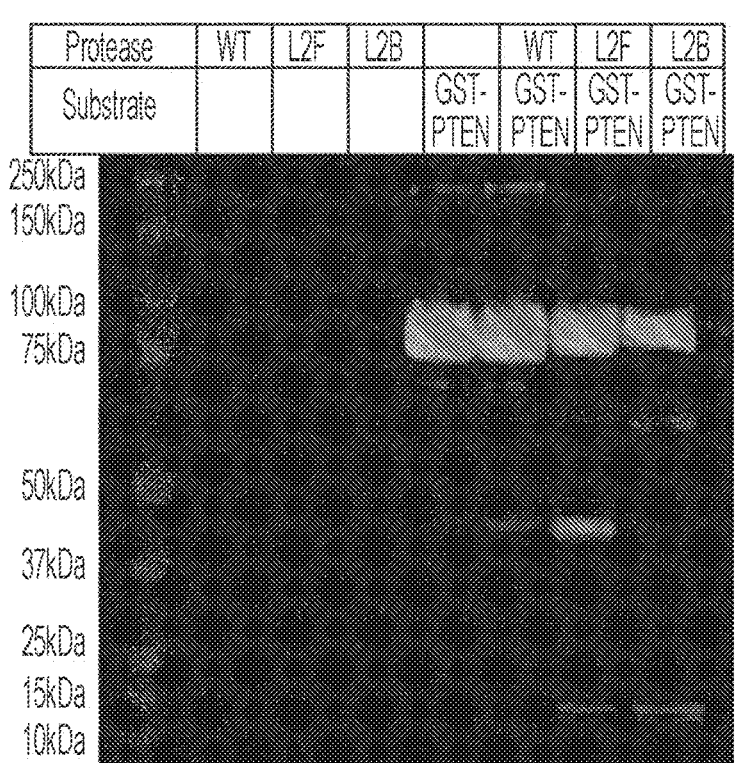
FIG. 28 shows data indicating BoNT E variant L2B after both positive and negative selection PACE cleaves full-length human PTEN protein at a single peptide bond yielding fragments of approximately the expected molecular weight.

FIG. 27 shows an alignment of VAMP1 and VAMP8 [30] amino acid sequences, along with several APs used to evolve VAMP8-cleaving BoNT F variants. Data indicate that VAMP8 APs have high background but BoNT F variants that cleave VAMP8 were identified (FIG. 27).

Example 4

Characterization of Evolved BoNT Proteases

This example describes expression and isolation of [40] evolved BoNT F proteases. An expression construct comprising a nucleic acid encoding PACE-2020 BoNT F protease variant L2A was produced. The expression construct also included an N-terminal maltose binding protein (MBP) tag and a poly-histidine C-terminal tag. Transformed cells were subjected to cell disruptor lysis, following by primary purification using Ni-NTA and secondary purification by amylose column (which binds to the MBP).

Figure 29A:
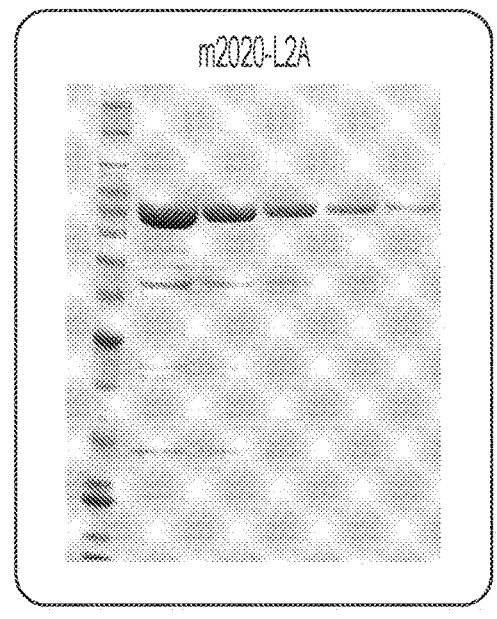
FIGS. 29A-29B show protease expression and isolation of evolved BoNT proteases.
Figure 29B:
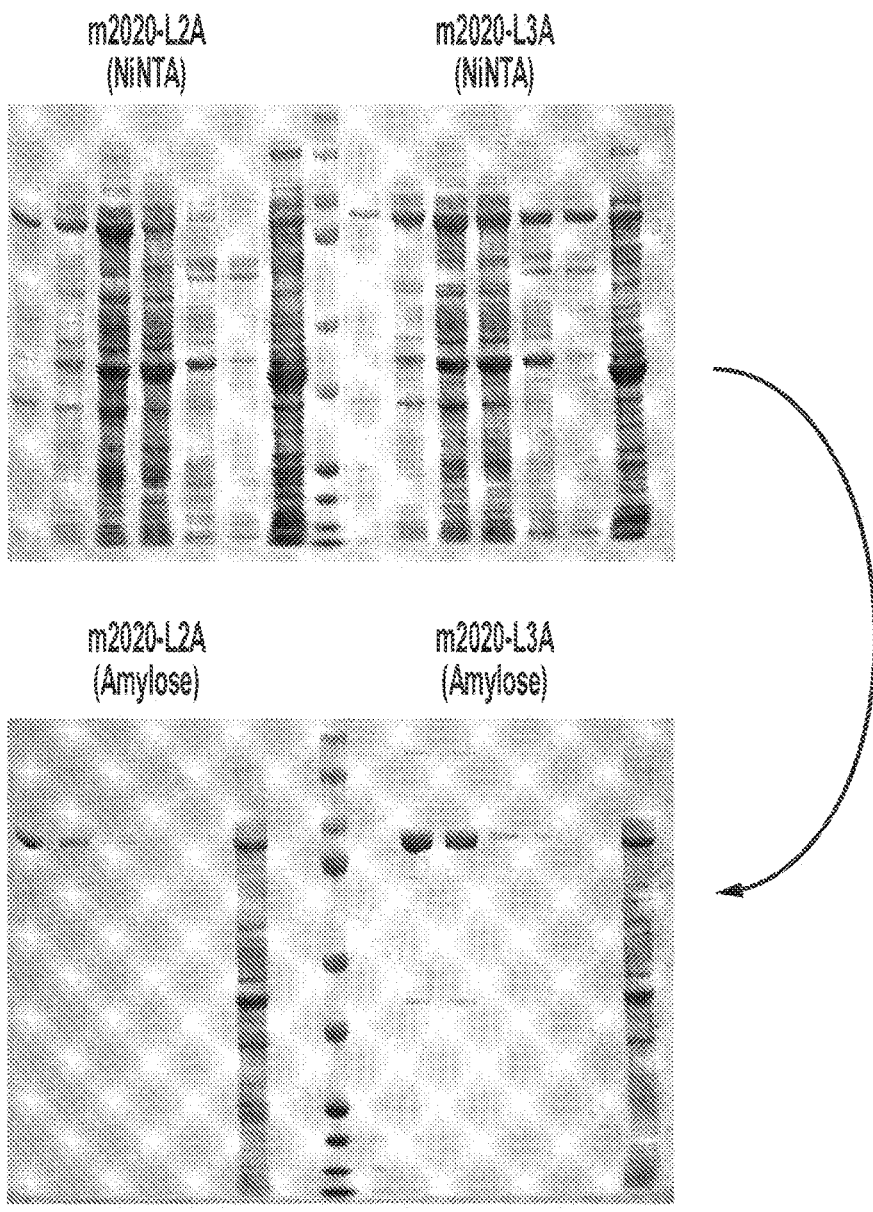

FIGS. 29A-29B show protease expression and isolation of evolved BoNT proteases. FIG. 29A shows a Western blot of evolved BoNT F protease m2020-L2A ("m" indicates a maltose-binding protein tag on the N-terminus of the protein). FIG. 29B shows a Western blot of Ni-NTA (top) purified BoNT F proteases m2020-L2A and m2020-L3A and subsequent Amylose-purification of BoNT F proteases m2020-L2A and m2020-L3A.

Figure 30:
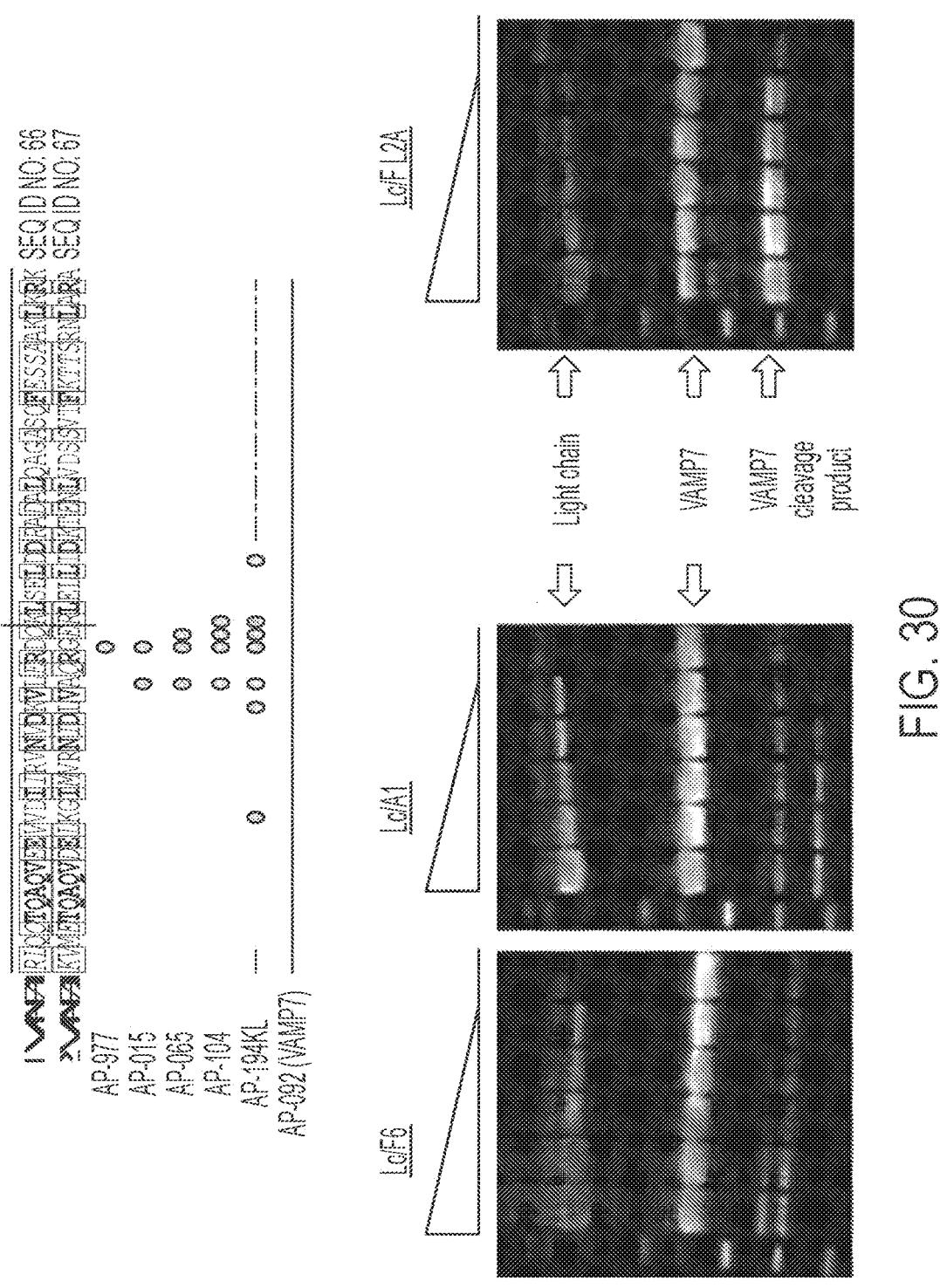
FIG. 30 shows data indicating that BoNT F variant 2020-L2A protease is active in vitro, as measured by a VAMP7 cleavage assay.
Figure 31:
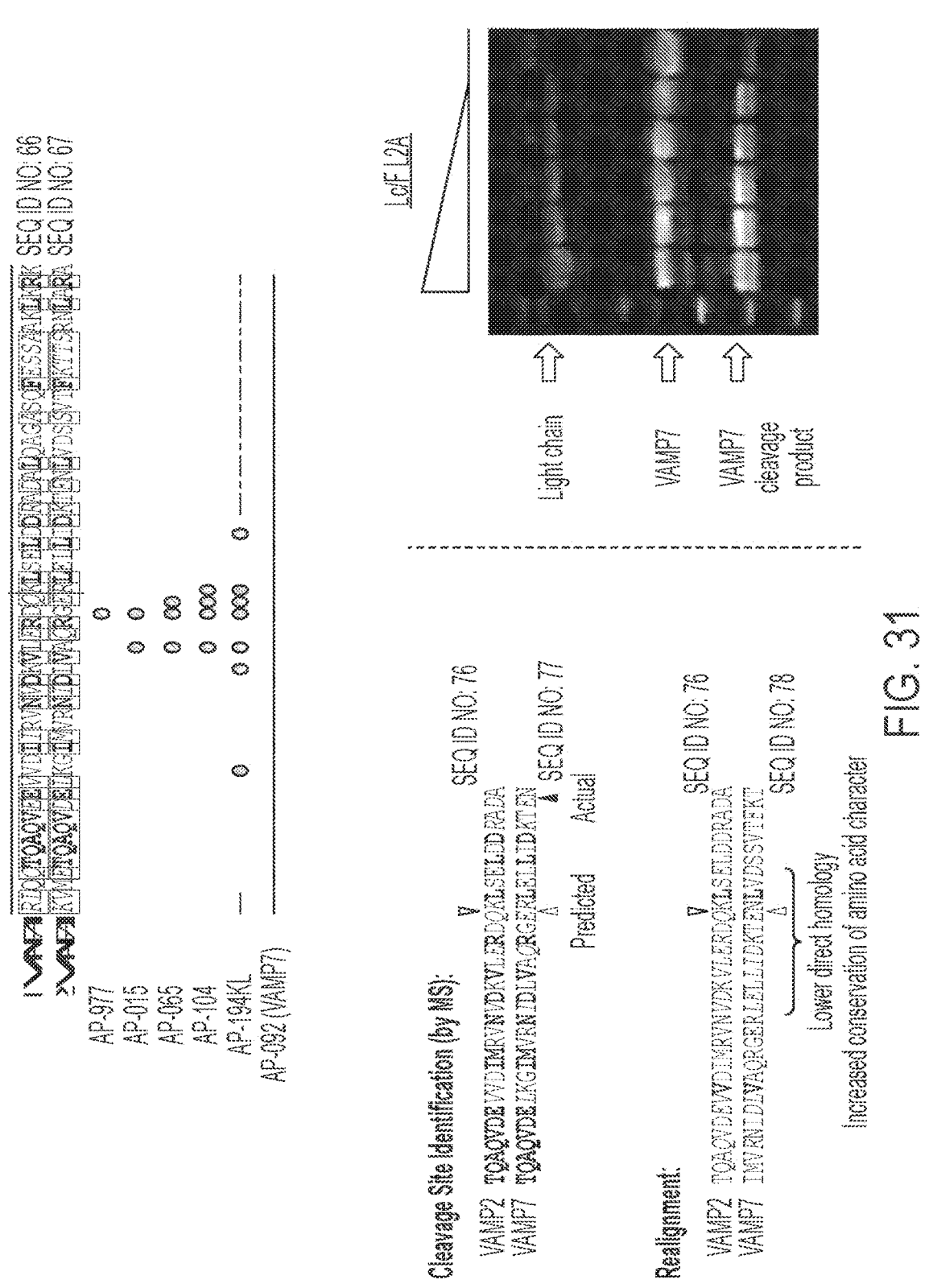
FIG. 31 shows data indicating that the cleavage site of BoNT F variant 2020-L2A protease in VAMP7 has shifted relative to the predicted cleavage site, as measured by mass spectroscopy.

In vitro activity of BoNT F variant 2020-L2A was tested using a VAMP7 cleavage assay. FIG. 30 shows data indicating that BoNT F variant 2020-L2A protease is active in vitro. FIG. 31 shows data indicating that the cleavage site of BoNT F variant 2020-L2A protease in VAMP7 has shifted relative to the predicted cleavage site, as measured by MS.

Figure 32:
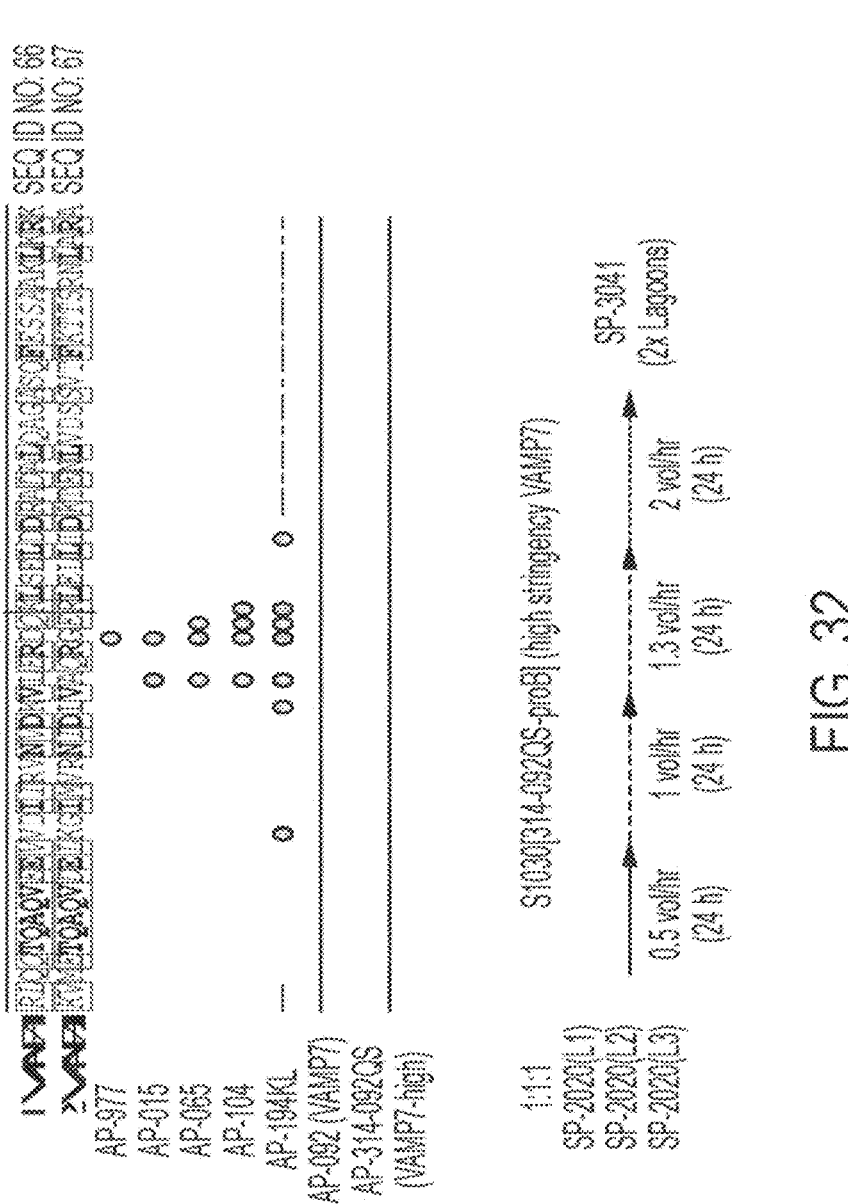
FIG. 32 shows results of a high-stringency PACE experiment to improve VAMP7 cleavage activity of BoNT F protease variants (PACE-3401).

PACE experiments using high stringency positive selection were performed in order to improve activity of evolved BoNT F proteases. FIG. 32 shows the selection strategy used during PACE-3401. Table 4 describes mutations present in clones isolated from PACE-3401.

TABLE 4

| | | | | | | | | | | |
|---|---|---|---|---|---|---|---|---|---|---|
| L1 | a | | | | | V106A | | | | |
| | b | | Y72H | | | V106A | | | S141T | |
| | c | | Y72H | | | V106A | | | S141T | |
| | d | | Y72H | | | V106A | | | S141T | |
| | e | K31N | Y72H | N99S | | V106A | | | | |
| | f | | | | | V106A | | | | |
| | g | | | | | V106A | | | | |
| | h | | | N99S | | V106A | | | | |
| L2 | a | | Y72H | | | V106A | Y113C | V131G | S141T | |
| | b | | | | | V106A | | | | |
| | c | | | | | V106A | | | | |
| | d | K29E | | | | V106A | | | | I150T |
| | e | | | N99S | N101D | V106A | | | | I150T |
| | f | | Y72H | | | V106A | | V131G | S141T | |
| | g | | | | | V106A | | | | |
| | h | | Y72H | | | V106A | | V131G | | |

| | | | | | | | | |
|---|---|---|---|---|---|---|---|---|
| L1 | a | S166Y | S167I | | | | E200G | |
| | b | S166Y | S167I | | N184T | | E200G | Y210H |
| | c | S166Y | S167I | | | | E200G | |
| | d | S166Y | S167I | | N184T | | E200G | |
| | e | S166Y | S167I | G178A | | | E200G | |
| | f | S166Y | S167I | | | V193M | E200G | |
| | g | S166Y | | | N184K | | E200G | |
| | h | S166Y | S167I | | | | E200G | |

TABLE 4-continued

| | | | | | | | | | |
|---|---|---|---|---|---|---|---|---|---|
| L2 | a | | S166Y | S167I | | | | | E200G |
| | b | | S166Y | S167I | | | | V193M | E200G |
| | c | | S166Y | S167I | | | | | E200G |
| | d | | S166Y | S167I | M174T | | | | E200G |
| | e | | S166Y | S167I | | G177A | | | E200G |
| | f | | S166Y | S167I | M174T | | | | E200G |
| | g | V155I | S166Y | S167I | M174T | | | | E200G |
| | h | | S166Y | S167I | | | | V193M | E200G |

| | | | | | | | | | | | |
|---|---|---|---|---|---|---|---|---|---|---|---|
| L1 | a | | | S224I | R240L | | | | | | |
| | b | | | S224I | R240L | | | | | | S350G |
| | c | | | S224I | R240L | | | | | | S350G |
| | d | | E215G | S224I | R240L | | | | | | S350G |
| | e | T214I | | S224I | R240L | | | | | | S350G |
| | f | | | S224I | R240L | | | | | | S350G |
| | g | | | S224V | R240F | | | I297L | | T335S | |
| | h | | E215G | S224I | R240L | F267I | F270V | | | | |
| L2 | a | | | S224I | R240L | | | | | | S350G |
| | b | | | S224I | R240L | | | | | | S350G |
| | c | | | S224I | R240L | | | | | | S350G |
| | d | | | S224I | R240L | | | | R303C | | S350G |
| | e | | | S224I | R240L | | F270V | N293D | | | S350G |
| | f | | | S224I | R240L | | | | | | S350G |
| | g | | | S224I | R240L | | | | | | S350G |
| | h | | | S224I | R240L | | | | | | S350G |

| | | | | | | | | | |
|---|---|---|---|---|---|---|---|---|---|
| L1 | a | F360L | Y372H | N396H | P410L | | | | 420(AWLRKS*) |
| | b | F360L | Y372H | N396H | P410L | | | | 420(AWLRKS*) |
| | c | F360L | Y372H | N396H | P410L | | | | 420(AWLRKS*) |
| | d | F360L | Y372H | N396H | P410L | | | | 420(AWLRKS*) |
| | e | F360L | Y372H | N396H | P410L | | | | 420(AWLRKS*) |
| | f | F360L | Y372H | N396H | P410L | | | | 420(AWLRKS*) |
| | g | F360L | Y372H | N396H | P410L | D418Y | F420S | E423K | |
| | h | F360L | Y372H | N396H | P410L | D418Y | | E423K | |
| L2 | a | F360L | Y372H | N396H | P410L | | | | 20(AWLRKSRSSNNGDFQHGLAQP* |
| | b | F360L | Y372H | N396H | P410L | | | | 420(AWLRKS*) |
| | c | F360L | Y372H | N396H | P410L | | | | 420(AWLRKS*) |
| | d | F360L | Y372H | N396H | P410L | | | | 420(AWLRKS*) |
| | e | F360L | Y372H | N396H | P410L | | | | 420(AWLRKS*) |
| | f | F360L | Y372H | N396H | P410L | | | | 420(AWLRKS*) |
| | g | F360L | Y372H | N396H | P410L | | | | 420(AWLRKS*) |
| | h | F360L | Y372H | N396H | P410L | | | | 420(AWLRKS*) |

Figure 33:
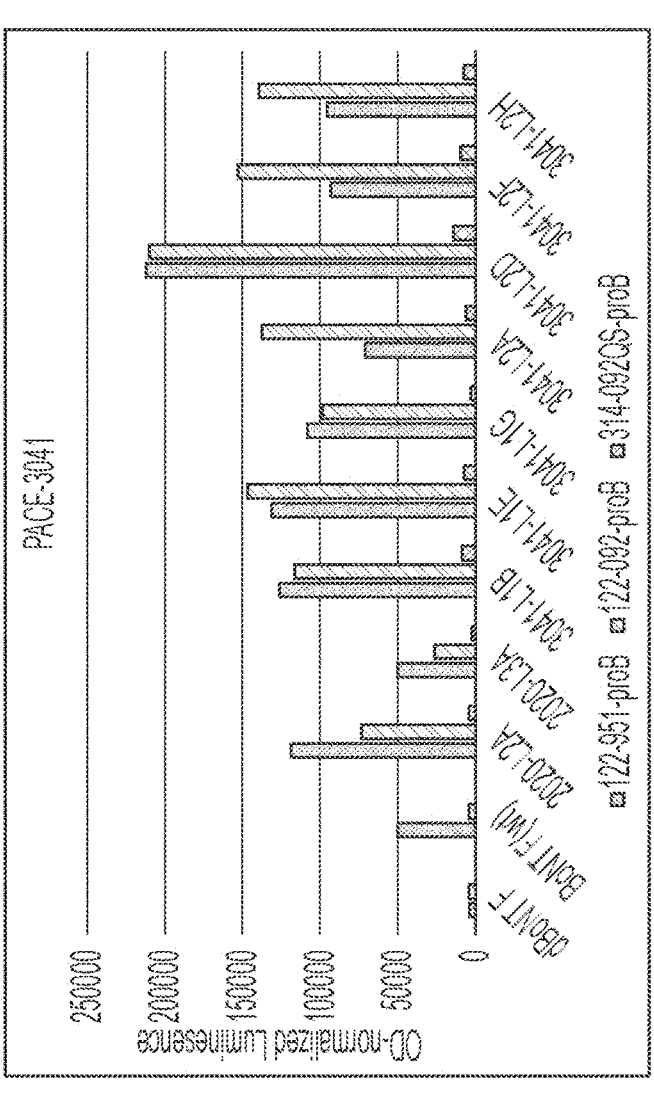
FIG. 33 shows luciferase assay data comparing 2020-L2A and 2020-L3A BoNT F protease-containing phage to PACE-3041 clones. 122-951-proB=low stringency VAMP1; 122-092-proB—low stringency VAMP7; 314-092QS-proB=high stringency VAMP7. Columns 1-3, as read left to right, of each grouping of three columns: 122-951-proB, 122-092-proB, and 314-092QS-proB.

Luciferase assays were performed to investigate the activity of PACE-3041 BoNT F variants. It was observed that PACE-3041 protease variants have improved apparent activity relative to the parental PACE-2020 protease variants from which they were evolved. For example, FIG. 33 shows luciferase assay data comparing 2020-L2A and 2020-L3A BoNT F protease-containing phage to PACE-3041 clones.

Figure 34:
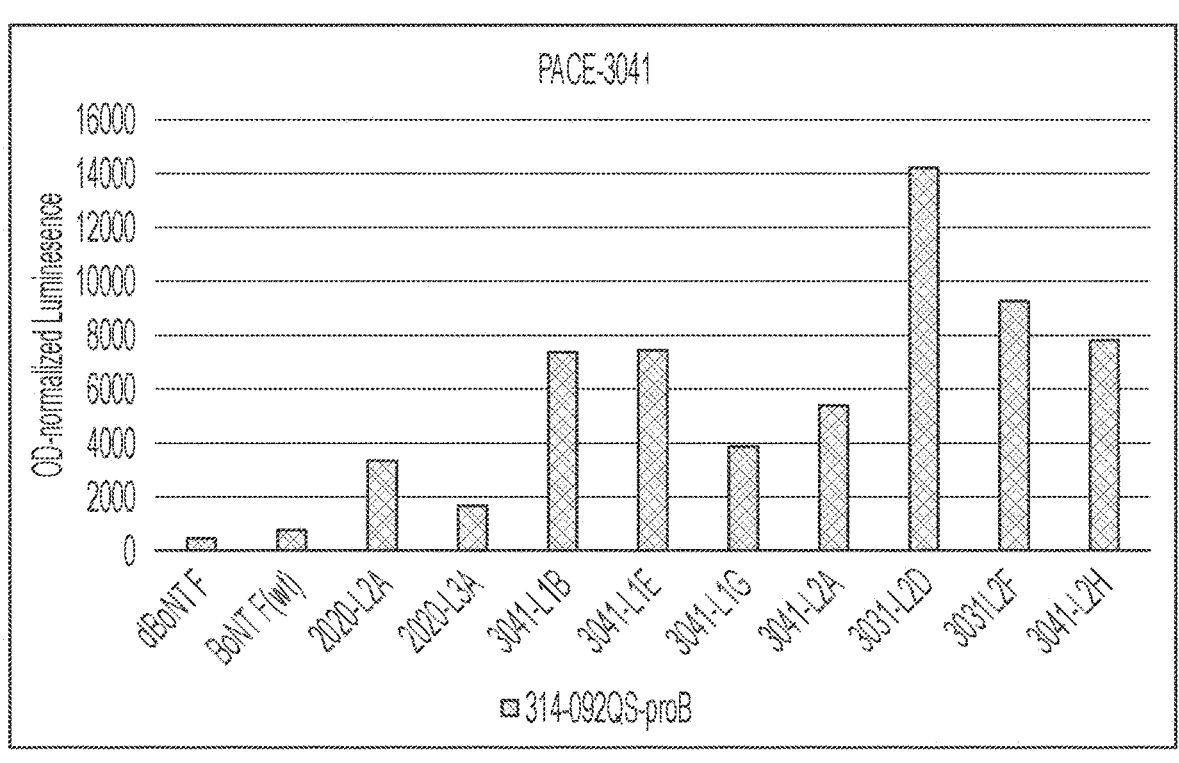
FIG. 34 shows luciferase assay data comparing 2020-L2A and 2020-L3A BoNT F protease-containing phage to PACE-3041 clones isolated from 314-092QS-proB lagoons.

FIG. 34 shows luciferase assay data comparing 2020-L2A and 2020-L3A BoNT F protease-containing phage to PACE-3041 clones isolated from 314-092QS-proB lagoons.

Figure 35:
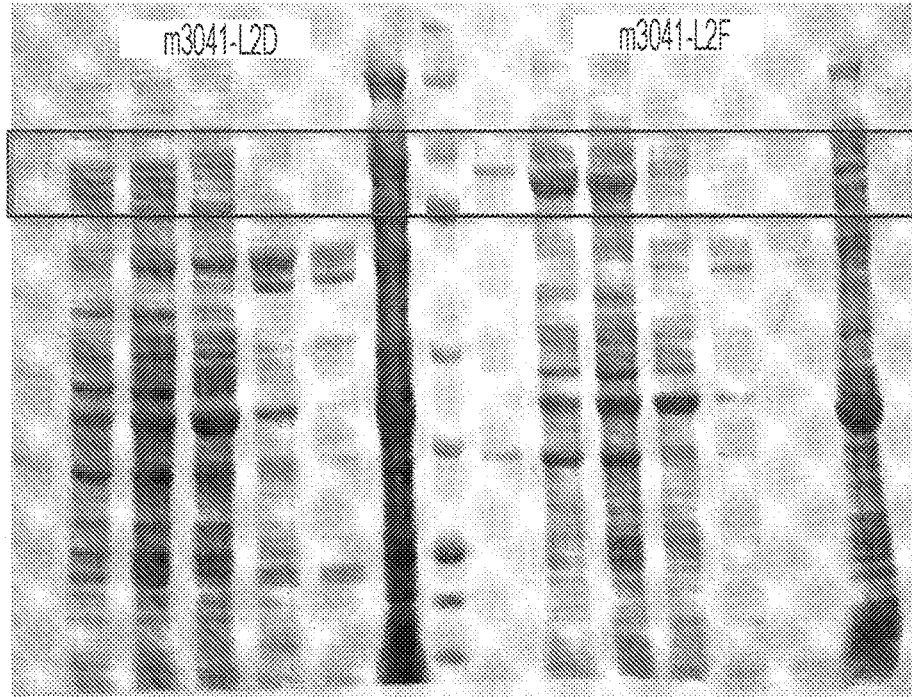
FIG. 35 shows data relating to in vitro characterization of BoNT F protease variants (m3041-L2D and m3041-L2F).
Figure 36:
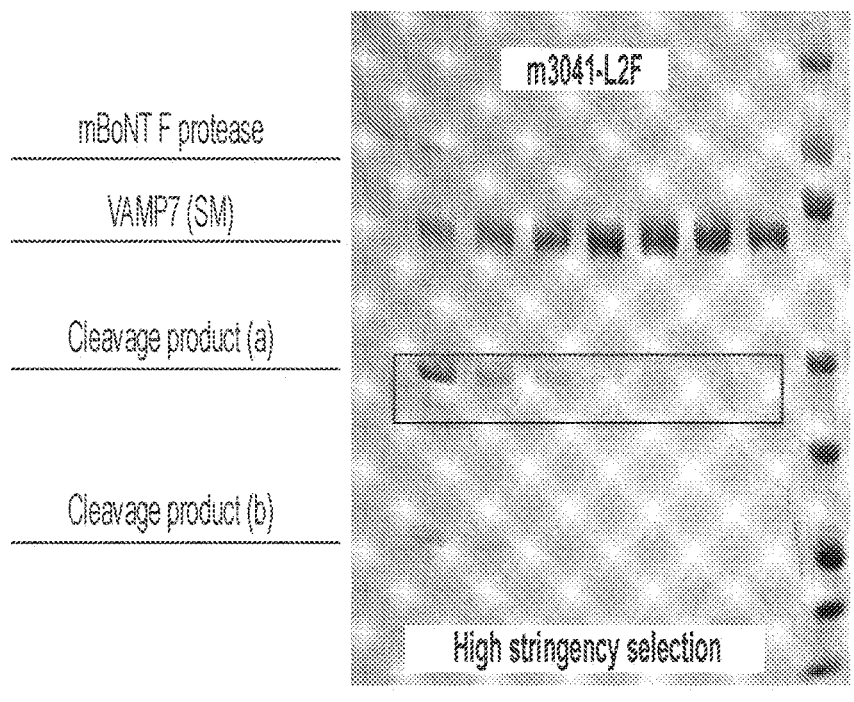
FIG. 36 shows data relating to in vitro validation of BoNT F variants m3041-L2D and m3041-L2F. Clone m3041-L2F was observed to have retained catalytic activity in vitro.

It was observed that BoNT F PACE-3041 variants were difficult to express and isolated; however, two clones, 3041-L2F and 3041-L2D were successfully isolated and recom-binantly expressed. See, FIG. 35. In vitro validation of m3041-L2F was subsequently performed. FIG. 36 shows data indicating that m3041-L2F retained catalytic activity in vitro.

Figure 37:
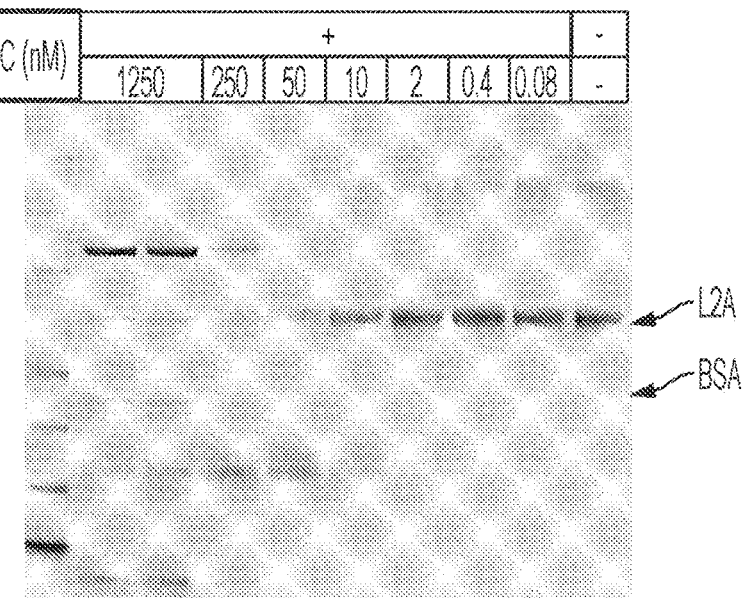
FIG. 37 shows data relating to selectivity of evolved BoNT protease variants. Off-target cleavage was observed for BoNT F 2020-L2A samples.
Figure 38:
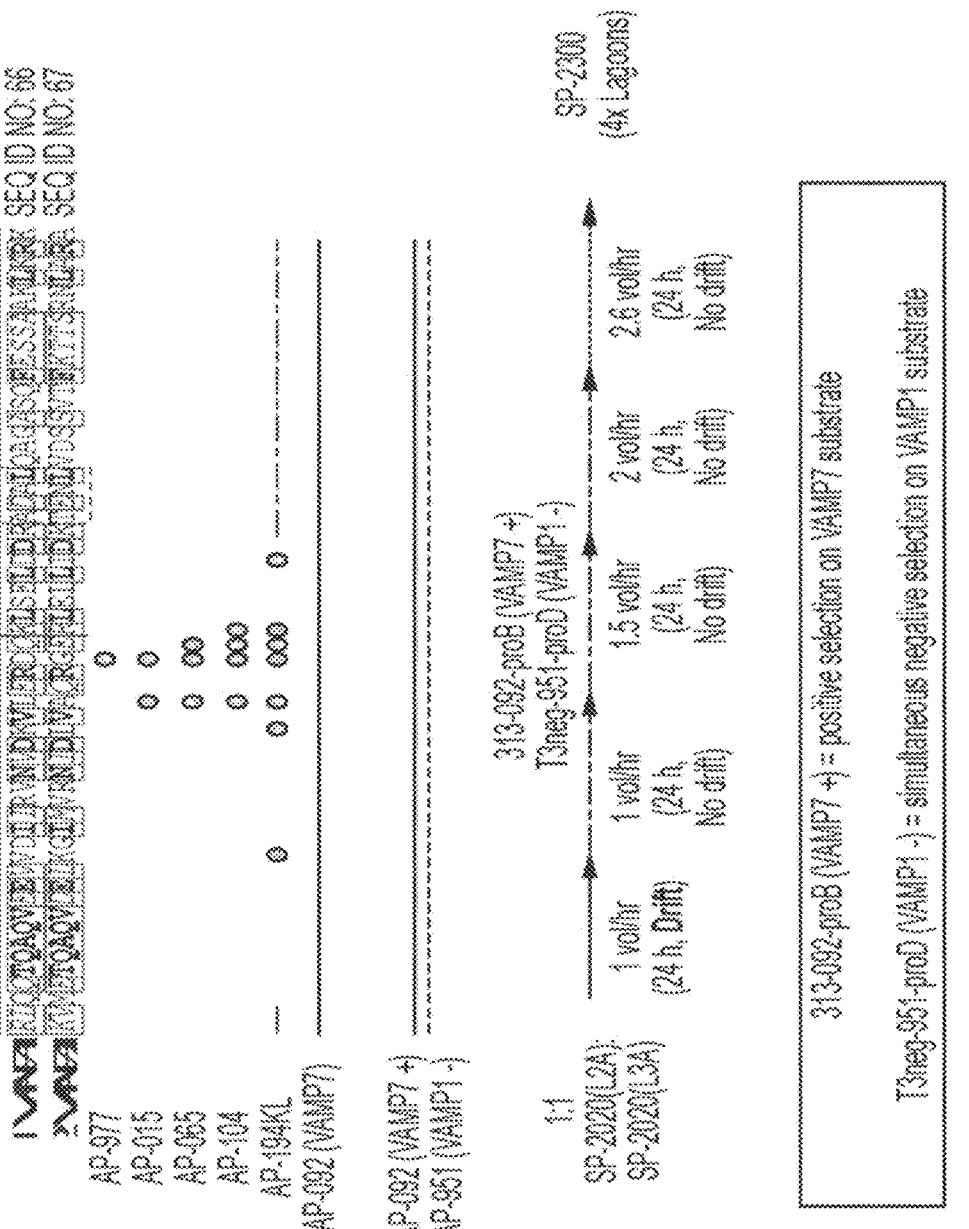
FIG. 38 shows data relating to PACE experiment PACE-2300 (VAMP7 positive selection, VAMP1 negative selection). 313-092-proB (VAMP7+)=positive selection on VAMP7 substrate; T3neg-951-proD (VAMP1–)=simultaneous negative selection on VAMP1 substrate.

Selectivity of BoNT F 2020 protease variants was also tested. See, FIG. 37. Data indicated that off-target cleavage was observed for BoNT F 2020-L2A samples.

In order to improve selectivity of BoNT F protease variants, a dual-selection approach was used. Briefly, positive selection for VAMP7 cleavage was combined with negative selection for VAMP1 cleavage (referred to as PACE-2300). Genotypes of BoNT F protease variants isolated from PACE-2300 are shown in Table 4.

TABLE 5

| | | | | | | | | | | | | |
|---|---|---|---|---|---|---|---|---|---|---|---|---|
| L1 | a | N6S | | | 152V | | | | | | | V106A | |
| | b | N6S | | | | D58Y | E60D | | S70H | | | V106A | |
| | c | N6S | | | | | | A63V | | A63V | | V106A | |
| | d | N6S | | | 152V | | | | | | | V106A | |
| | e | N6S | | | | | | A63V | | A63V | | V106A | |
| | f | N6S | | | | | | A63V | | A63V | | V106A | |
| | g | N6S | | | | | | A63V | | A63V | | V106A | |
| | h | N6S | | | | D58Y | E60D | | S70H | | T90I | V106A | |
| L2 | a | | | | | | | | | | | V106A | |
| | b | | Y10C | R49L | | | | | | | | | |
| | c | | | | | | | | | | | V106A | |
| | d | | | | | | | | | | | V106A | |
| | e | | | | | | | | | | | V106A | T132I |
| | f | | | | | | | | | | | V106A | |
| | g | | | | | | | | | | | V106A | T132I |
| | h | | | | | | | | | | | V106A | T132I |

TABLE 5-continued

| | | | | | |
|---|---|---|---|---|---|
| L3 | a | | | | V106A |
| | b | | | | V106A |
| | c | D16N | | | V106A |
| | d | | G53S | | V106A |
| | e | | | | V106A |
| | f | | | | V106A |
| | g | | | | V106A |
| | h | | | | V106A |
| L4 | a | | | | V106A |
| | b | | | | V106A |
| | c | | | | V106A |
| | d | | | | V106A |
| | e | | | E66K | V106A |
| | f | | | | V106A |
| | g | | | | V106A |
| | h | | | | V106A |

| | | | | | | | | | | | |
|---|---|---|---|---|---|---|---|---|---|---|---|
| L1 | a | | | | S166Y | S167I | E200G | N211S | S224I | | |
| | b | | | | S166Y | S167I | E200G | | S224I | | |
| | c | | | | S166Y | S167I | E200G | | S224I | | |
| | d | | | | S166Y | S167I | E200G | N211S | S224I | | |
| | e | | | | S166Y | S167I | E200G | | S224I | | |
| | f | | | | S166Y | S167I | E200G | | S224I | | |
| | g | | | | S166Y | S167I | E200G | | S224I | | |
| | h | | | | S166Y | S167I | E200G | | S224I | | |
| L2 | a | | | | S166Y | S167I | E200G | | S224I | | |
| | b | | | | S166Y | N184K | E200G | | S224I | A226S | |
| | c | | | | S166Y | S167I | E200G | | S224I | | |
| | d | | | D161G | S166Y | S167I | E200G | | S224I | | |
| | e | | | | S166Y | S167I | E200G | | S224I | | |
| | f | | | | S166Y | S167I | E200G | F217L | S224I | | |
| | g | | | | S166Y | S167I | E200G | | S224I | | A232T |
| | h | | | | S166Y | S167I | E200G | | S224I | | |
| L3 | a | | G159S | | S166Y | S167I | E200G | | S224I | | |
| | b | | | | S166Y | S167I | E200G | | S224I | | |
| | c | T123M | | | S166Y | S167I | E200G | | S224I | | |
| | d | V145I | | | S166Y | S167I | E200G | | S224I | | |
| | e | | | | S166Y | S167I | E200G | | S224I | A226S | |
| | f | | | | S166Y | S167I | E200G | | S224I | | |
| | g | | | | S166Y | S167I | E200G | | S224I | | A232T |
| | h | | | | S166Y | S167I | E200G | Y201H | S224I | | |
| L4 | a | | | | S166Y | S167I | E200G | | S224I | | |
| | b | | | | S166Y | S167I | E200G | | S224I | | |
| | c | | | | S166Y | S167I | E200G | | S224I | | |
| | d | | | | S166Y | S167I | E200G | | S224I | | |
| | e | T123S | | | S166Y | S167I | E200G | | S224I | A226S | |
| | f | | | | S166Y | S167I | E200G | | S224I | | |
| | g | | | | S166Y | S167I | E200G | | S224I | | A232T |
| | h | | | | S166Y | S167I | E200G | Y201H | S224I | | |

| | | | | | | | | | | | |
|---|---|---|---|---|---|---|---|---|---|---|---|
| L1 | a | R240L | | | N314S | | | | | S350G | F360L |
| | b | R240L | | | | | | | N339S | S350G | F360I |
| | c | R240L | | | | | | | | S350G | F360L |
| | d | R240L | | | N314S | | | | | S350G | F360L |
| | e | R240L | | | | | | | | S350G | F360L |
| | f | R240L | | | | | | | | S350G | F360L |
| | g | R240L | | | | | | | | S350G | F360L |
| | h | R240L | | | | | | T335I | N339S | S350G | F360L |
| L2 | a | R240L | | | | | | | | S350G | F360L |
| | b | R240F | | | | | | T335S | | | F360L |
| | c | R240L | | | | | | | | S350G | F360L |
| | d | R240L | | | G325S | | | | | S350G | F360L |
| | e | R240L | | | | | | | | S350G | F360L |
| | f | R240L | I262T | | | | | | | S350G | F360L |
| | g | R240L | | | | | | | | S350G | F360L |
| | h | R240L | | | | | | | | S350G | F360L |
| L3 | a | R240L | | | | | | | | S350G | F360L |
| | b | R240L | | | | | S333F | | | S350G | F360L |
| | c | R240L | | | | | | | | S350G | F360L |
| | d | R240L | | | | | | | | S350G | F360L |
| | e | R240F | | | | | S333F | | | S350G | F360L |
| | f | R240L | | | | | S333F | | | S350G | F360L |
| | g | R240L | | | | | S333F | | | S350G | F360L |
| | h | R240L | | | | | S333F | | | S350G | F360L |
| L4 | a | R240L | | D274M | | D331G | | | | S350G | F360L |
| | b | R240L | L264M | | | | | | | S350G | F360L |
| | c | R240L | L264M | | | | | | | S350G | F360L |
| | d | R240L | L264M | | | | | | | S350G | F360L |
| | e | R240F | | | | | | | | S350G | F360L |
| | f | R240L | L264M | | | | | | | S350G | F360L |

TABLE 5-continued

| | | | | | | | | | | |
|---|---|---|---|---|---|---|---|---|---|---|
| g | | R240L | L264M | | | | | | S350G | F360L |
| h | | R240L | L264M | | | | | | S350G | F360L |
| L1 | a | | | Y372H | | N396H | | P410L | 420(AWLRKS*) | |
| | b | | | Y372H | | N396H | | P410L | 420(AWLRKS*) | |
| | c | | | Y372H | | N396H | | P410L | 420(AWLRKS*) | |
| | d | | | Y372H | | N396H | | P410L | 420(AWLRKS*) | |
| | e | | | Y372H | | N396H | | P410L | 420(AWLRKS*) | |
| | f | | | Y372H | | N396H | | P410L | 420(AWLRKS*) | |
| | g | | | Y372H | | N396H | | P410L | 420(AWLRKS*) | |
| | h | | | Y372H | | N396H | | P410L | 420(AWLRKS*) | |
| L2 | a | T367S | | Y372H | | N396Y | | P410L | 420(AWLRKS*) | |
| | b | | F369F | Y372H | | N396H | | P410L | D418Y | E423K |
| | c | | | Y372H | | N396H | | P410L | 420(DWLRKS*) | |
| | d | | | Y372H | | N396H | | P410L | 420(DWLRKS*) | |
| | e | | | Y372H | V377I | N396H | | P410L | 420(AWLRKS*) | |
| | f | | | Y372H | | N396H | | P410L | 420(AWLRKS*) | |
| | g | | | Y372H | V377I | N396H | | P410L | 420(AWLRKS*) | |
| | h | | | Y372H | V377I | N396H | | P410L | 420(DWLRKS*) | |
| L3 | a | T367S | | Y372H | | N396H | | P410L | 420(AWLRKS*) | |
| | b | | F369F | Y372H | | N396H | N409D | P410L | 420(AWLRKS*) | |
| | c | | | Y372H | | N396H | | P410L | 420(AWLRKS*) | |
| | d | | | Y372H | | N396H | | P410L | 420(AWLRKS*) | |
| | e | | | Y372H | | N396H | N409D | P410L | 420(AWLRKS*) | |
| | f | | | Y372H | | N396H | N409D | P410L | 420(AWLRKS*) | |
| | g | | | Y372H | | N396H | N409D | P410L | 420(AWLRKS*) | |
| | h | | | Y372H | | N396H | N409D | P410L | 420(DWLRKS*) | |
| L4 | a | T367S | | Y372H | | N396H | | P410L | 420(AWLRKS*) | |
| | b | | F369F | Y372H | | N396H | | P410L | 420(AWLRKS*) | |
| | c | | | Y372H | | N396H | | P410L | 420(AWLRKS*) | |
| | d | | | Y372H | | N396H | | P410L | 420(AWLRKS*) | |
| | e | | | Y372H | N379H | N396H | | P410L | 420(AWLRKS*) | |
| | f | | | Y372H | | N396H | | P410L | 420(AWLRKS*) | |
| | g | | | Y372H | | N396H | | P410L | 420(AWLRKS*) | |
| | h | | | Y372H | | N396H | | P410L | 420(DWLRKS*) | |

Figure 39:
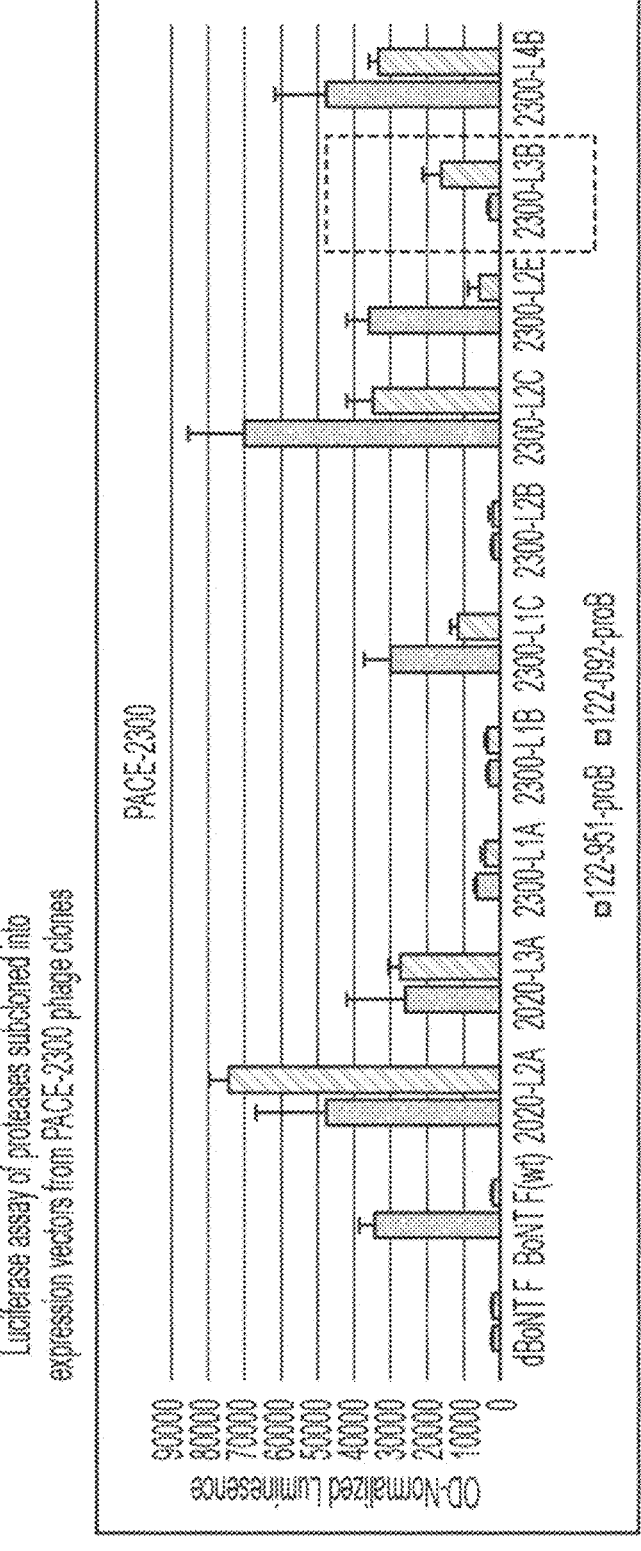
FIG. 39 shows luciferase assay data relating to PACE experiment PACE-2300. One clone possesses apparent selectivity: BoNT F(2300-L3B). Columns 1-2, as read left to right, of each grouping of two columns: 122-95, proB and 122-092-proB.
Figure 40:
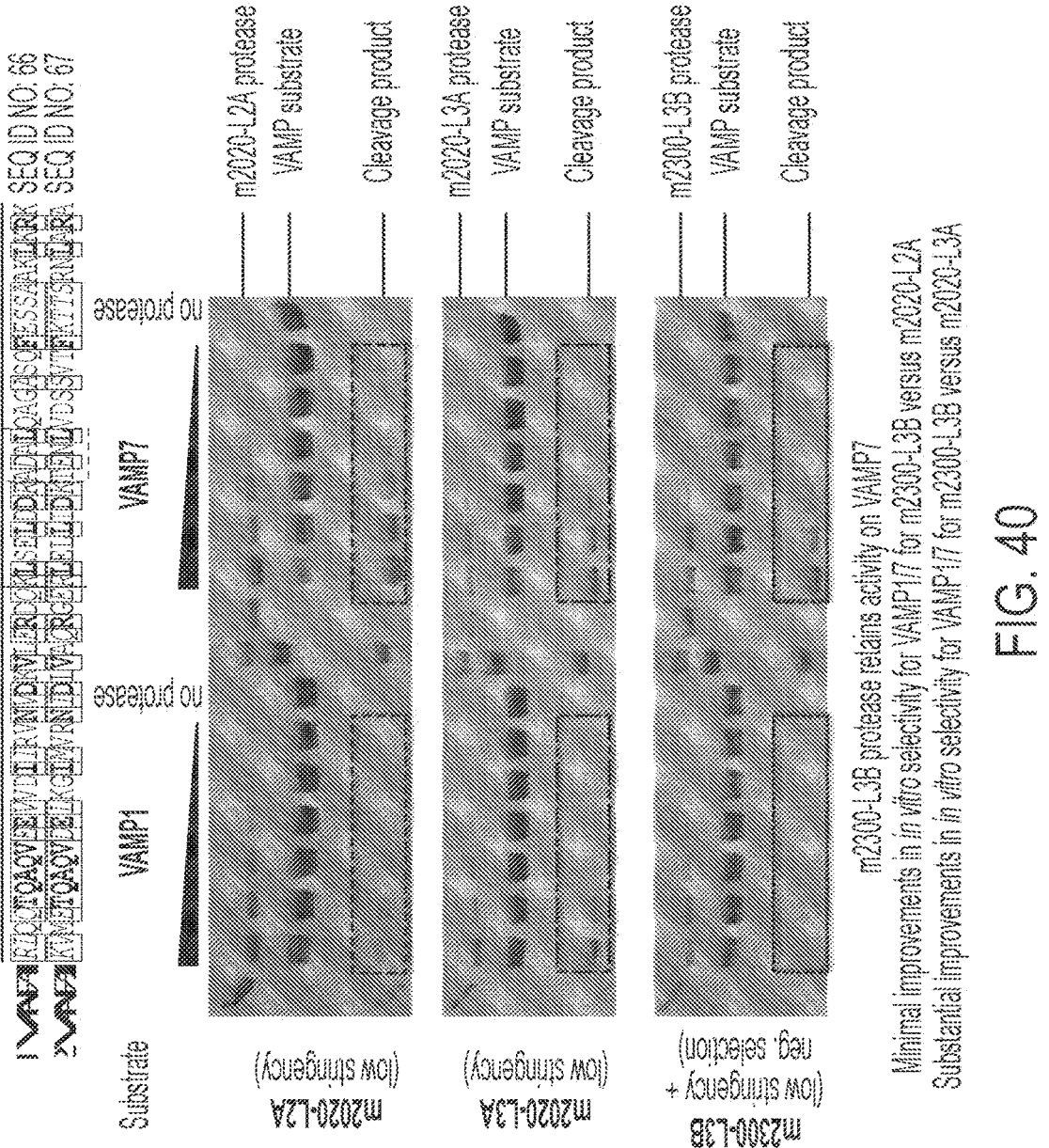
FIG. 40 shows data relating to the in vitro characterization of m2300-L3B. m2300-L3B protease retains activity on VAMP7. Improvements in in vitro selectivity for VAMP1/7 for m2300-L3B versus m2020-L2A were observed. Substantial improvements in in vitro selectivity for VAMP1/7 for m2300-L3B versus m2020-L3A were observed.

A single clone with apparent activity was isolated from PACE-2300, which was cloned and recombinantly expressed. Luciferase assay data indicated that BoNT F 2300-L3B is active in vitro (FIG. 39). Further in vitro characterization experiments were performed. FIG. 40 shows data relating to the in vitro characterization of m2300-L3B. m2300-L3B protease retains activity on VAMP7. Improvements in in vitro selectivity for VAMP1/7 for m2300-L3B versus m2020-L2A were observed. Substantial improvements in in vitro selectivity for VAMP1/7 for m2300-L3B versus m2020-L3A were observed.

Figure 41:
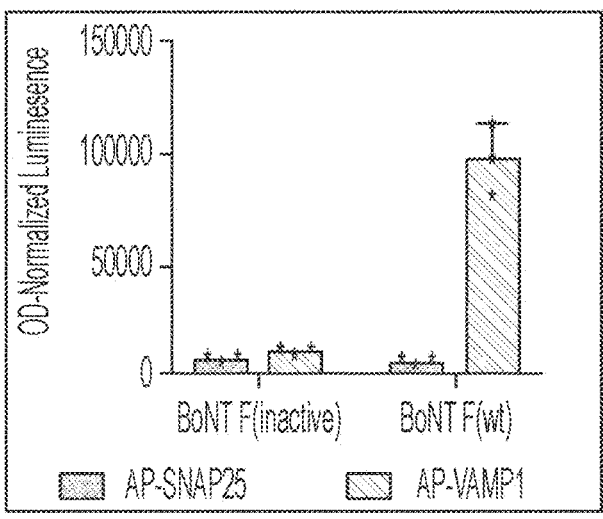
FIG. 41 shows activity dependent expression of the BoNT F LC leads to activation of a T7-PAP encoding residues 29-88 of human VAMP1, while displaying no activation of a SNAP25-linked construct. Columns 1-2, as read left to right, of each grouping of two columns: AP-SNAP25 and AP-VAMP1.
Figure 42:
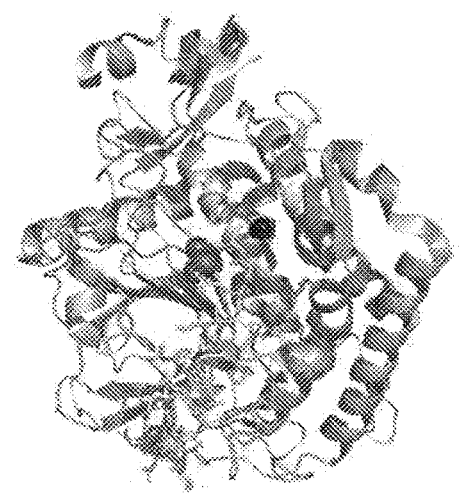
FIG. 42 shows a PACE evolution on BoNT on endogenous substrate VAMP1 yielded a population enriched in a single point mutation, S166Y.
Figure 43:
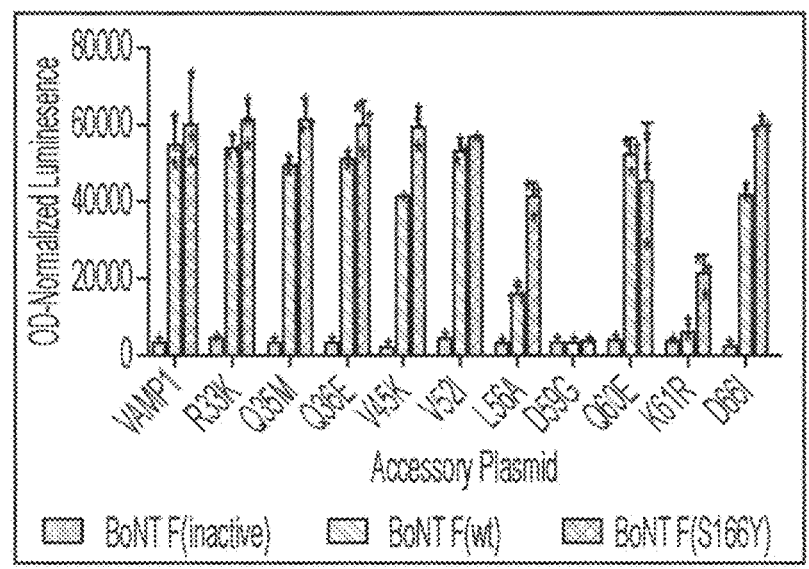
FIG. 43 shows the effect on proteolytic activity of the S166Y mutation of FIG. 42, confers broadly enhanced proteolytic activity on a panel of VAMP1 point mutants. Columns 1-3, as read left to right, of each grouping of three columns: BoNT F(inactive), BoNT F(wt), and BoNT F(S166Y).

Example 5: Evolution of a BoNT Light Chain with Activity on a Non-Canonical SNARE Substrate In contrast to the viral proteases previously used in PACE, BoNT LC proteases require a substantially longer primary cleavage sequence due to required exosite binding prior to hydrolysis. It was therefore verified that BoNT proteases, specifically the light chain of BoNT/F, recapitulate their native activity in the context of host-encoded T7-PAP. Expression of the BoNT/F LC leads to activation of a T7-PAP encoding residues 29-88 of human VAMP1, while displaying no activation of a SNAP25-linked construct (FIG. 41). Additionally, PACE selection of wild-type BoNT/F selection phage on endogenous substrate VAMP1 yielded a population enriched in a single point mutation, S166Y (FIG. 42). This mutation, confers broadly enhanced proteolytic activity on a panel of VAMP1 point mutants relevant to the planned VAMP7 evolutionary trajectory with the exception of the D59G (VAMP1 numbering) mutation known to strongly disrupt BoNT/F activity on VAMP1/2 (FIG. 43). Therefore, this substrate was prioritized as the initial step in the evolutionary trajectory towards VAMP7.

An evolving pool of phage encoding protease F.0 from a host strain harboring a VAMP1-activated polymerase was transitioned to a strain requiring activity on AP-SS.1, which carried the D59G mutation in VAMP1. Phage isolated from this evolution were strongly enriched for three new mutations at residues R240, Y372, and D414. Two of these mutations, R240 and Y372, are localized to the active site, and R240 in particular has been shown to contact the mutated D59 in native VAMP2 binding. Assessment of clones from this population using an *E. coli* based luciferase reporter indicated that indeed, activity on the SS.1 AP had improved substantially. This evolution indicated that the BoNT/F LC possesses at least a basal level of evolvability, and encouraged moving forward towards VAMP7 (FIG. 44).

Figure 48:
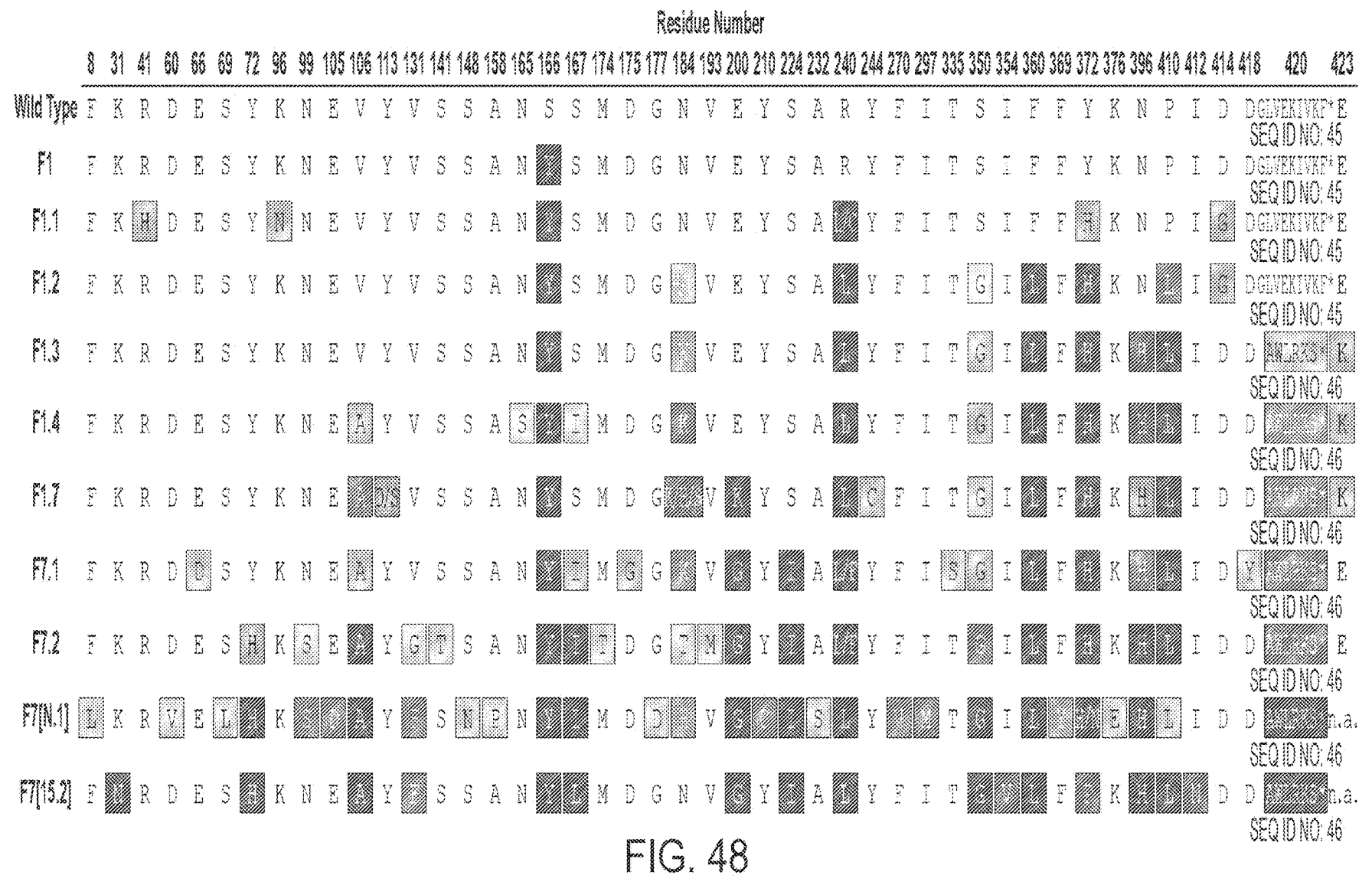
Figure 49:
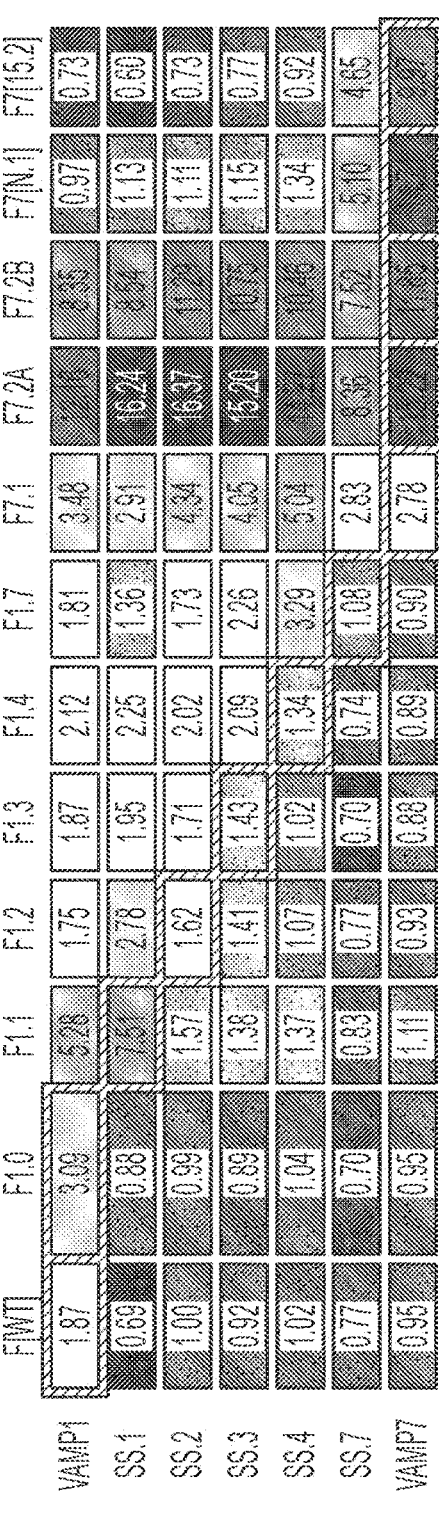
FIG. 49 shows that population level activity of SP isolates across the selection constructs of the evolutionary trajectory.
Figure 50:
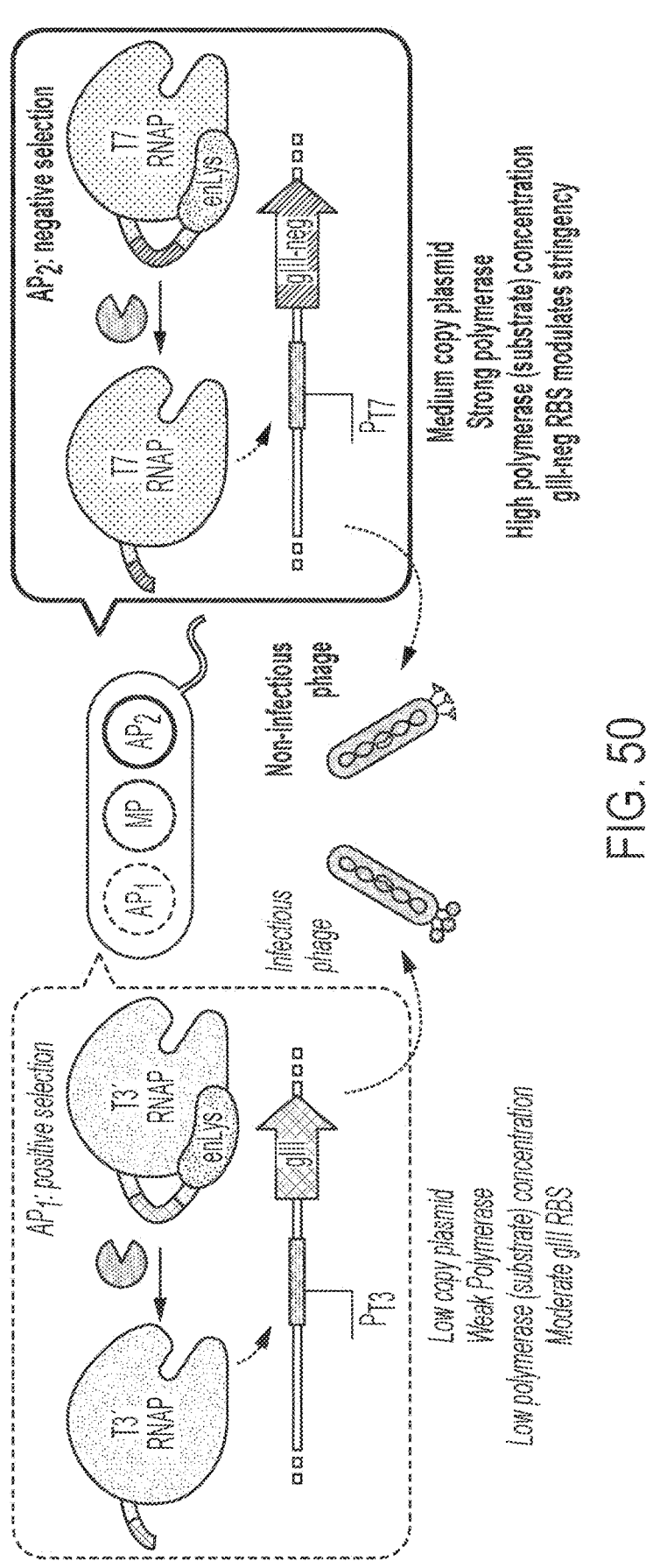
FIG. 50 shows a strategy for simultaneous negative selection in protease PACE.

Having addressed one of the most difficult substrate challenges in the wild-type substrate, and seeking to preserve diversity over an extended evolutionary trajectory, the surviving phage was split into three separate populations for evolution in parallel. Each of these populations was carried through an identical set of iterative PACE selections over several stepping stones to progressively incorporate additional VAMP7 character into the cleavage substrate. The VAMP1 mutations L56A (SS.2), Q60E (SS.3), and K61R (SS.4) were successively prioritized. Alteration of each of these residues individually has been shown to directly influence catalytic function of the BoNT/F protease. Selection on these substrates produced phage populations carrying several new mutations at positions either proximal to the active site or substrate binding groove. These included positions N165, S167, and N184. Additional mutations at V106, 5350, F360, N396, P410, and a C-terminal frameshift that altered the final eight amino acids of the protease were also enriched in non-active site regions of the evolving protein. Having accounted for substrate changes proximal to the site of hydrolysis, and therefore adjacent to the active site, peripheral changes were made to the selection substrate in SS.7 by incorporating three additional mutations (V45K, K54L, and D66I) within the canonical BoNT/F binding sequence (FIG. 44). Additionally, it was sought to finalize the evolutionary trajectory by evolving in as close to the desired sequence context as possible, and therefore replaced VAMP1 residues 29-34 and 69-89 with corresponding VAMP7 sequence at the termini of the selection substrate. Selection on this substrate let to the enrichment of several mutations across all populations, most notably E200K, which occupies the bottom of an active site adjacent pocket, and directly contacts 5224. Following this evolution, selections were directly on the desired VAMP7 cleavage site, to afford the population BoNT F7.1 (FIG. 44). Interestingly, the resulting populations demonstrated further sampling at residue 240, and independently converged on an optimized residue 200, pairing an E200G mutation with an adjacent S224I substitution. Indeed, both the population and individual clones from this selection showed apparent cleavage activity on the desired VAMP7 substrate in luciferase reporter assays, and the most promising candidates were isolated and purified. These proteins are competent proteases in vitro, but have relatively poor catalytic efficiency (see supporting information). To evolve improved activity on the desired VAMP7 cleavage site, the stringency of the positive selection was increased through polymerase and T7 promoter engineering in the AP, and seeded the resulting PACE selections with phage from all F7.1 phage subpopulations in an attempt to filter for the variants with highest relative fitness. This selection resulted in populations F7.2A and F7.2B (FIGS. 48-49), which both enriched for a similar set of mutations. The resulting phage fixed mutations A106V, S167I, R240L, and S350G, which were present in only one of the three input populations. Additionally, new mutations Y72H, N99S, and V131G emerged in these experiments. After analysis of several clones from the F7.2A and F7.2B populations, isolation and in vitro characterization was performed for clone F7A[2.6], confirming robust activity on the VAMP7 primary sequence present in the selection construct. This represents only the second example of a substantial reprogramming of a sequence specific protease, and the first example in the deliverable BoNT LC family of proteases. However, while successful in reprogramming the BoNT/F light chain to cleave a new substrate, activity on the native VAMP1 substrate was continuously observed in the luciferase reporter assays (FIG. 49). Removing this activity thus became the primary focus of subsequent evolution efforts.

Development and Implementation of a Protease-PACE Negative Selection

Because the ultimate goal of reprogrammed therapeutic proteases is to precisely modify target proteins without off-target activity, it was sought to develop a means to perform negative selection in the protease PACE selections. In theory, this would allow residual VAMP1 cleavage activity to be ablated on the natural target of the BoNT/F protease while maintaining activity on VAMP7. Negative selection has been performed in PACE previously using a dominant negative variant of gIII, "gIII-neg", to suppress phage propagation in the presence of undesired activity. This work produced a T7-RNAP polymerase with high selectivity for transcription from the T3 promoter, referred to here as the T3'-RNAP. Recognizing the utility of this entity in the selection scheme, it was converted into an orthogonal protease-activated polymerase (T3'-PAP) for driving simultaneous positive and negative selection in PACE (FIG. 48).

To maintain high stringency in the positive selection, a positive selection circuit was constructed, which expressed the weaker T3'-PAP at low levels, and it was to transcribe gIII from a low-copy number plasmid in response to VAMP7 cleavage. The highly active wild-type T7-PAP was then shifted onto a medium-copy plasmid with high constitutive expression, inducing high levels of gIII-neg transcription upon VAMP1 cleavage. Finally, the ribosome binding site (RBS) in the gIII-neg transcript was used to control dosing of the resulting protein product, and thereby control the relative stringency of the negative selection in four separate strains.

Figure 51:
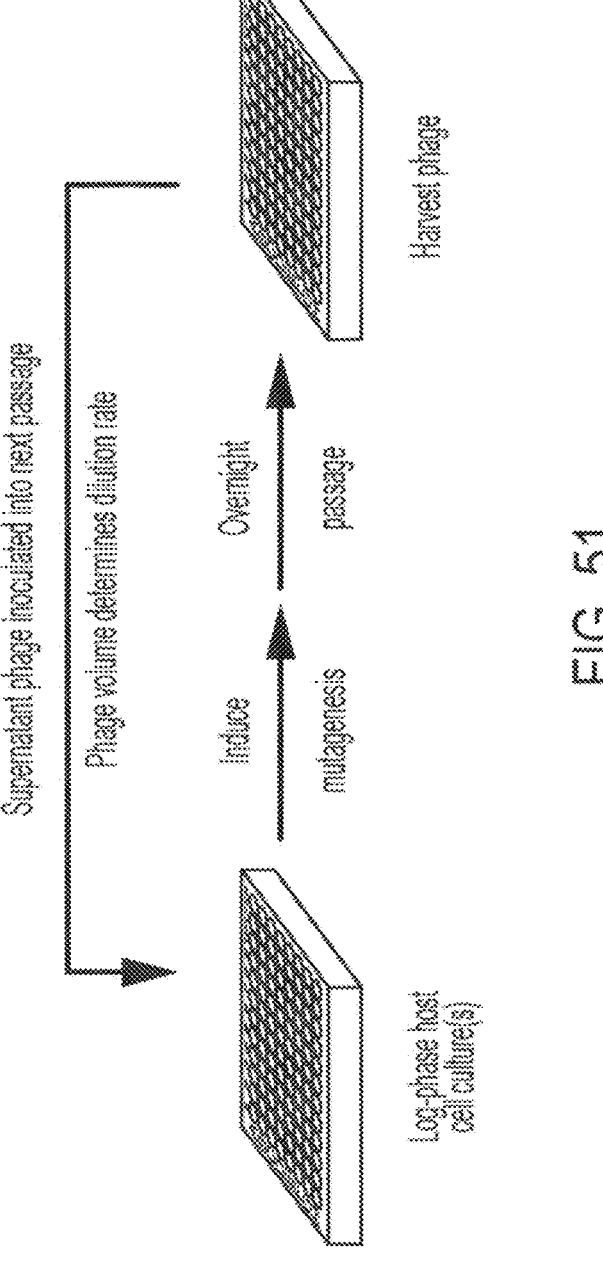
FIG. 51 shows an overview of Phage-Assisted Non-continuous Evolution (PANCE).

While PACE is highly purifying and excels at rapidly filtering unbiased mutants throughout a gene, it struggles to offer a high degree of control over stringency in real-time since much of the selection circuitry is encoded in the host strain. This requires new chemostats to be employed for each selection strain, ultimately placing practical limits on instrumentation and space for PACE selections. The lab has also used an alternate selection method, Phage-Assisted Non-Continuous Evolution (PANCE), which represents a lower stringency (low effective flow-rate) selection while offering more stable monitoring and higher maintenance of evolving phage populations in a high-throughput format (FIG. 51). This represents a considerable advantage for dual-selection applications, where the tuning of relative stringency (positive vs. negative) on a host-cell level is difficult, and it may be necessary to iterate through several stringencies to achieve maximal activity and selectivity. Thus, four separate host strains were investigated covering a range of negative selection stringencies, with identical positive selection stringencies. These parallel selections were run in duplicate, to increase the likelihood of accessing solutions that reside closer to a global maximum in activity and selectivity.

Figures 52A, 52B:
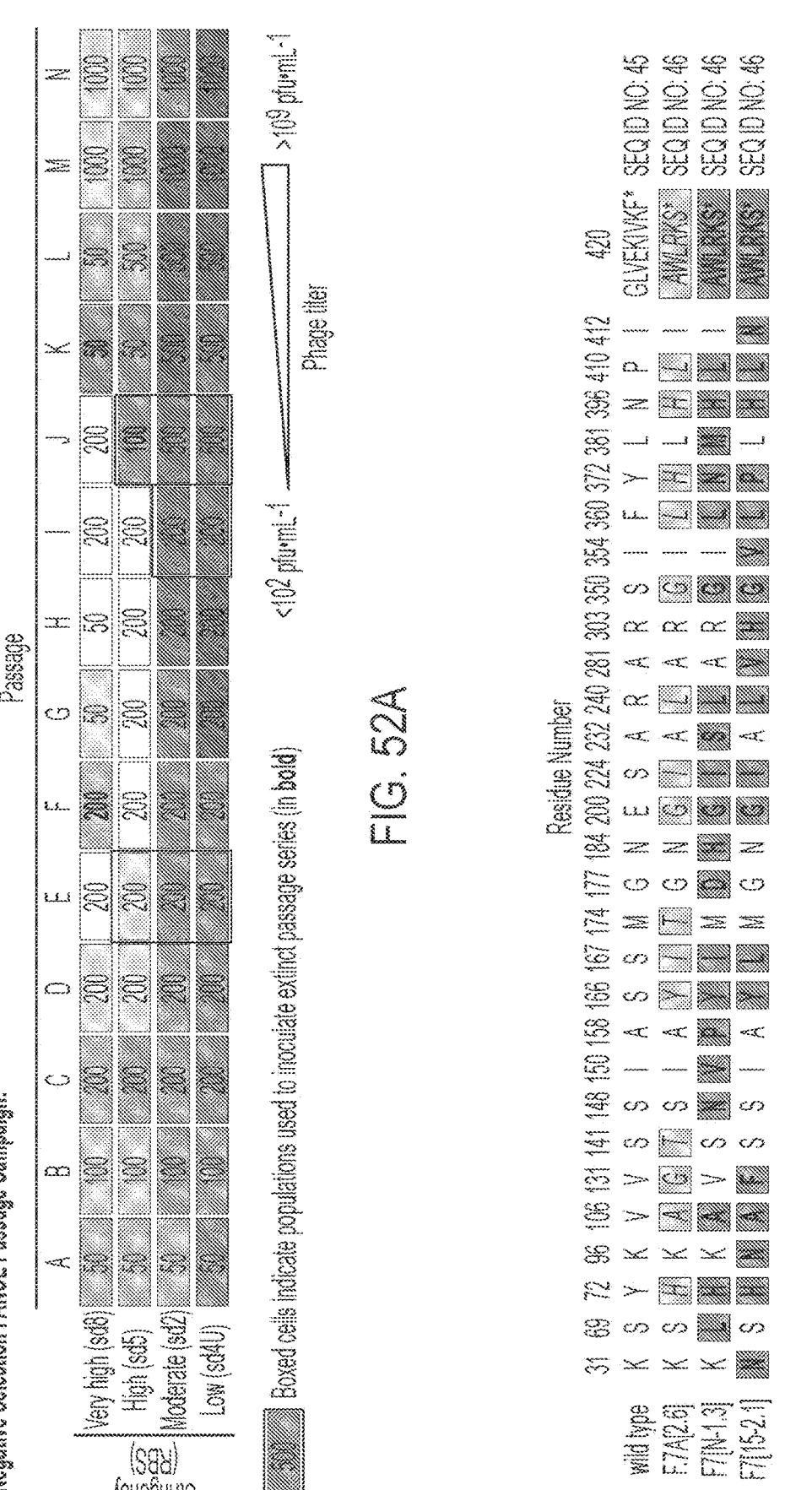
FIGS. 52A-52C show results of the negative selection PANCE Passage Campaign. Higher throughput PANCE approach allows a large number of stringencies to be manually investigated in parallel (FIG. 52A). Boxed cells indication populations used to inoculate extinct passage series. There was a strong apparent increase in selectivity in luciferase assays after negative selection (FIG. 52B). OD-Normalized luminescence is shown in FIG. 52C, columns 1-2, as read left to right, of each grouping of two columns: VAMP1 and VAMP7.
Figure 52C:
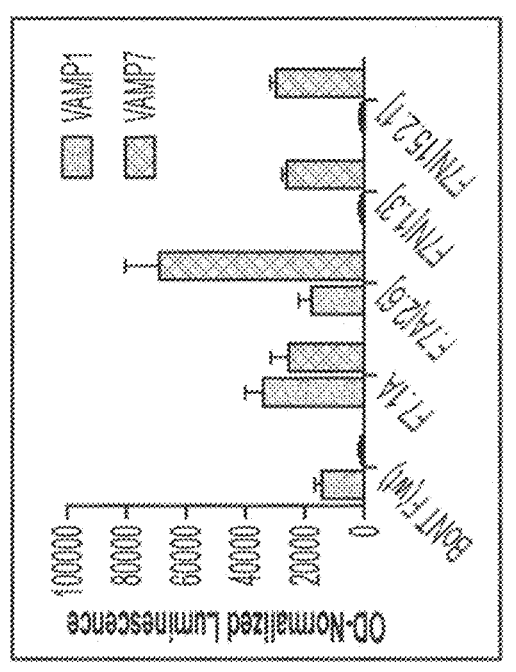

With a selection strategy in hand, a PANCE campaign was performed to evolve improved selectivity into the BoNT F7.2 populations. The initial three rounds of PANCE selection were performed at low dilution rate, which was additionally interspersed with overnight rounds of genetic drift to provide increased diversity within the evolving populations. Subsequently, dilution rate was increased, and drift passages were ceased, forcing phage to persist on selective activity alone. As expected, phage did not initially persist at even low dilution rates in high stringency selection strains, but did maintain relatively high titers under lower stringency conditions. The populations from these low stringency selection conditions were maintained throughout the PANCE campaign, and were subsequently challenged on higher stringency conditions (Passage F, Passage J, Passage K) (FIG. 52A). As the low stringency populations continued to evolve, eventually variants became accessible that were capable of persisting in high stringency selection strains at high dilution rate. The two populations from the parallel PANCE trajectories were assessed in the standard luciferase assay (FIGS. 52B-52C), displaying drastically reduced activity on VAMP1 and similar primary sequences.

Characterization of Evolved VAMP7-Cleaving Proteases

Figure 45A:
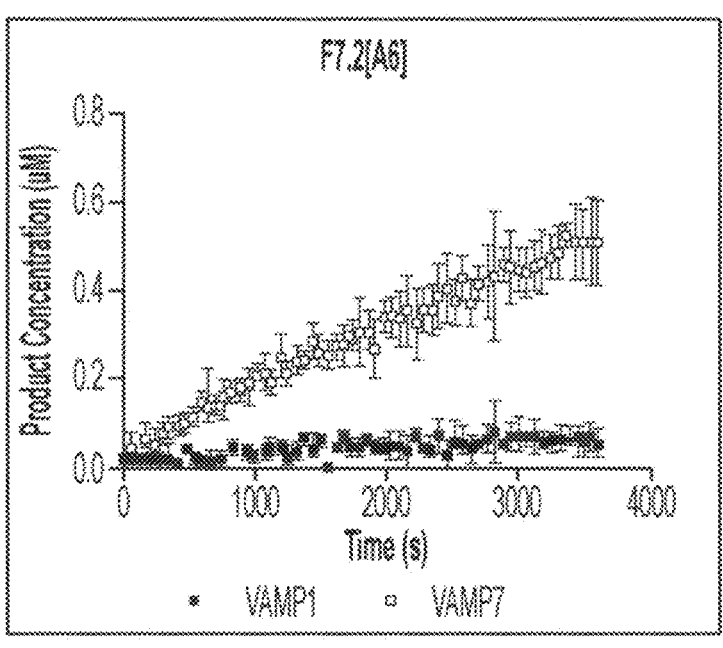
Figure 45B:
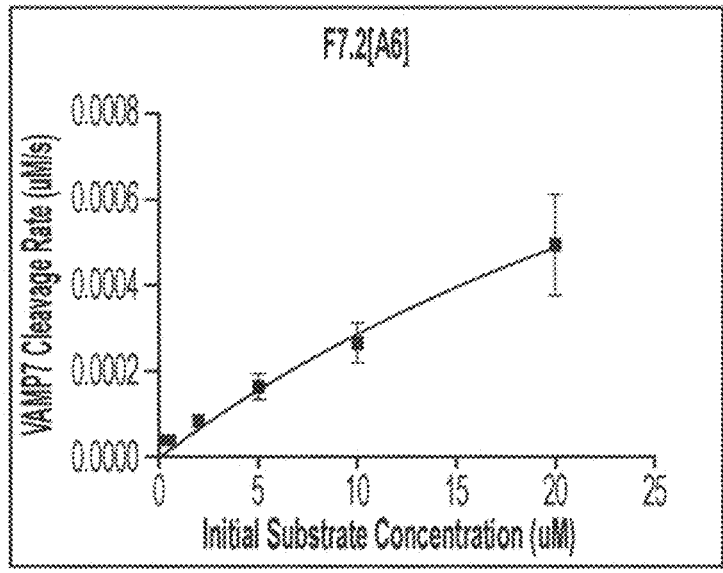
Figure 45C:
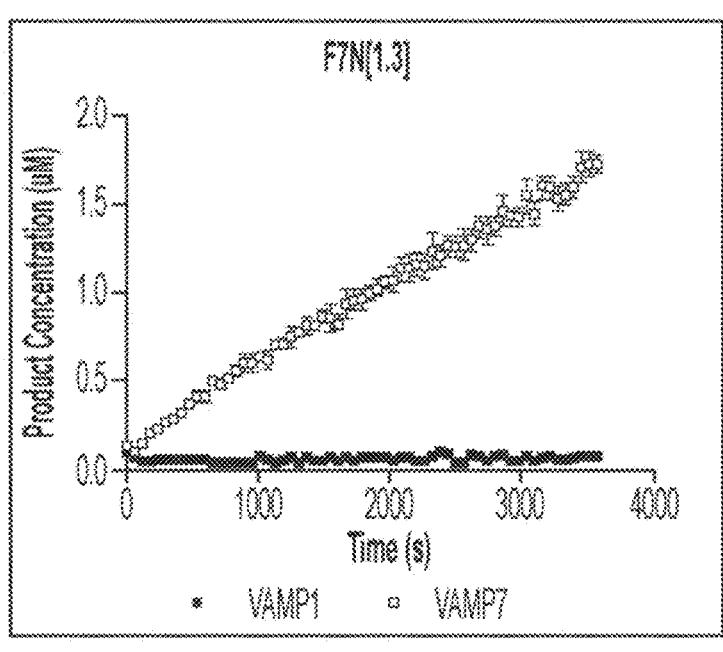
Figure 45D:
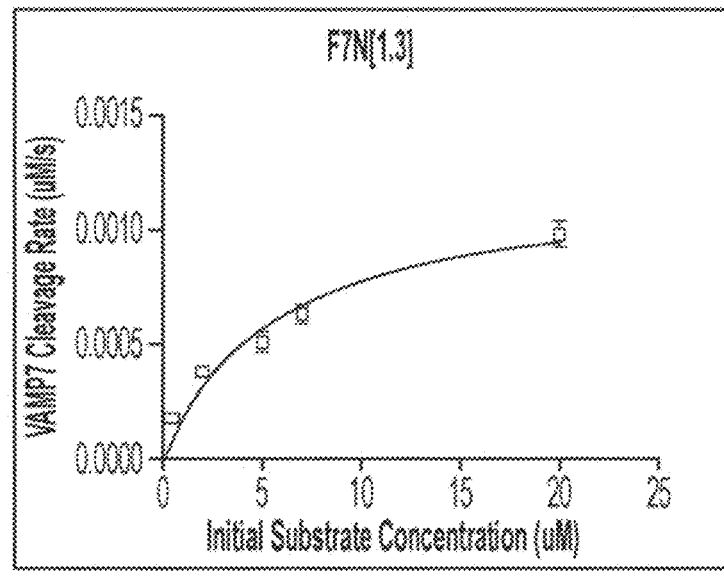
Figure 46:
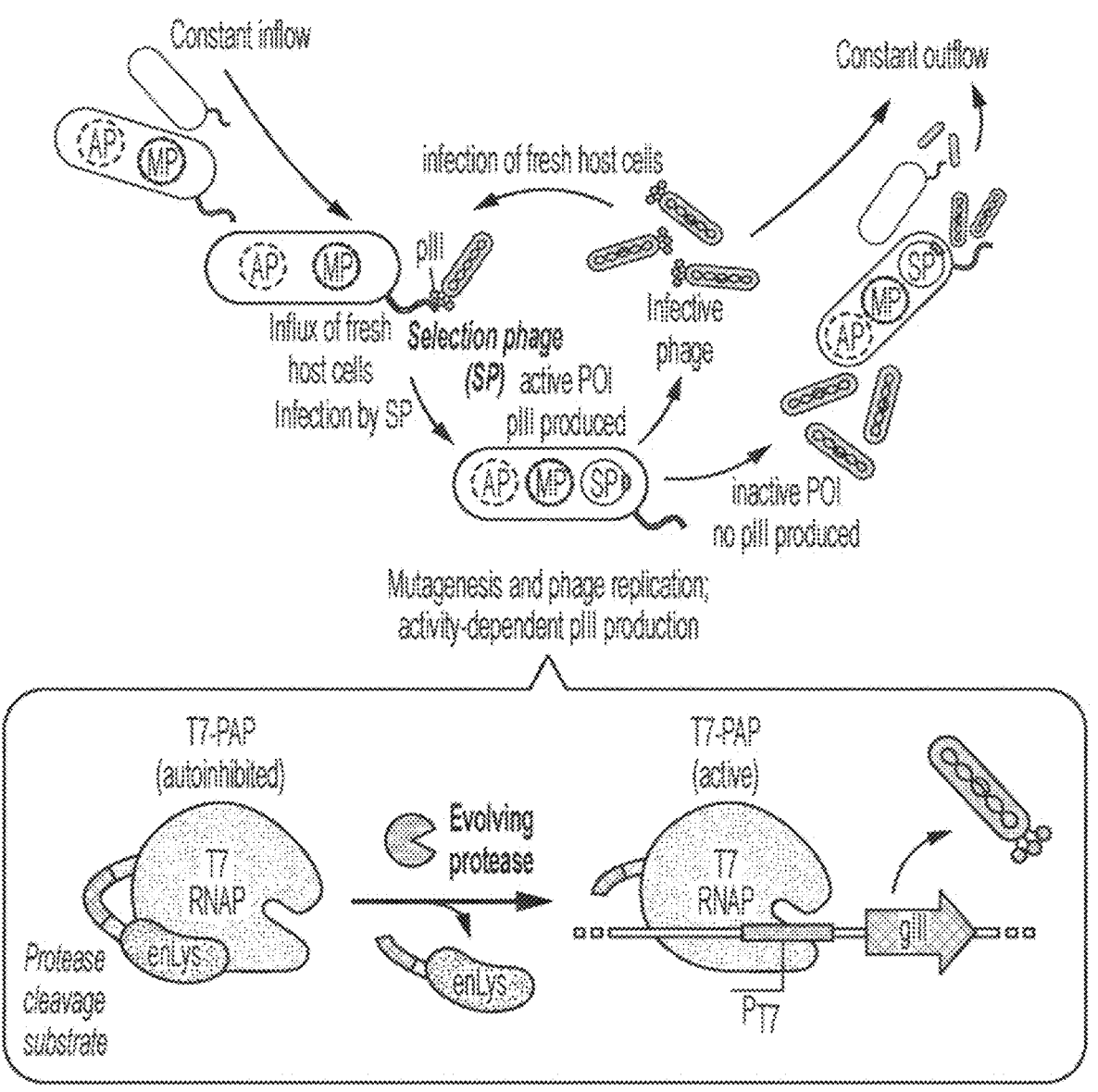
FIG. 46 shows an overview of PACE selection for protease evolution using the T7 protease-activated polymerase (T7-PAP) selection mechanism.
Figure 53A:
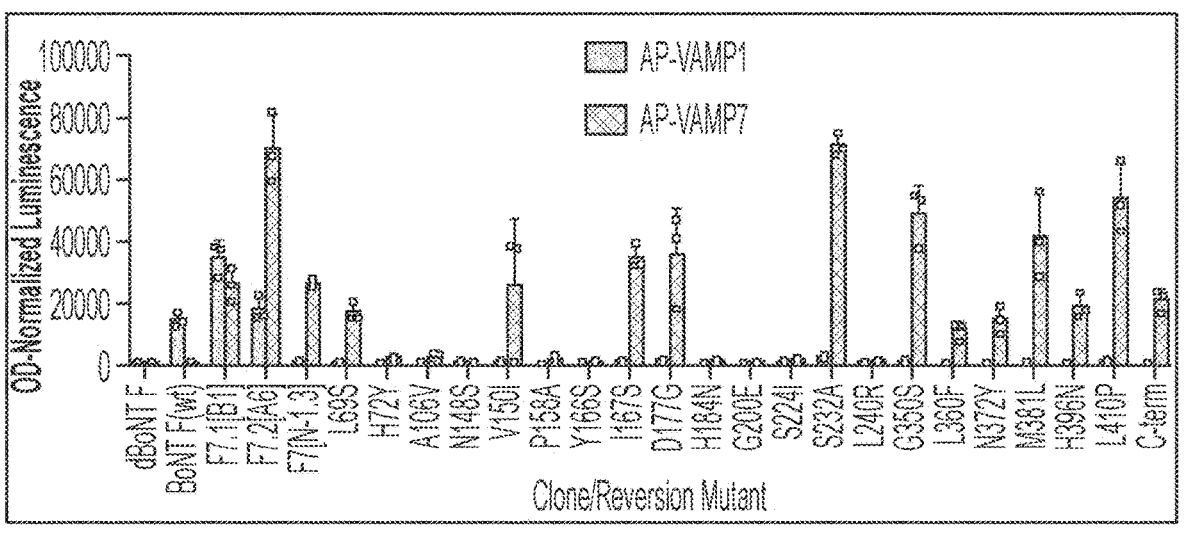
FIG. 53A shows reversion analysis for various reversion mutants. Columns 1-2, as read left to right, of each grouping of two columns: AP-VAMP1 and AP-VAMP7.
Figure 53B:
FIG. 53B shows the structure of the F7N[1.3] Protease.

With variants in hand that gave high apparent selectivity for VAMP7 over VAMP1, it was sought to thoroughly validate and characterize their activity (FIGS. 45A-45F). Based on initial assessment of activity in coupled luciferase assays, several clones were prioritized for in vitro analysis. Variants were further filtered by activity and expressibility considerations, to arrive at a two clones (F7.2[A6] from positive selection and F7N[1.3] from negative selection) for in-depth characterization. In vitro kinetic analysis was performed using an adapted version of the commercial BoTest FRET sensor, and demonstrated that the evolved proteases are indeed active on their target VAMP7 sequence, and have kinetic characteristics in within an order of magnitude of naturally-occurring neurotoxins such as Tetanus neurotoxin (TeNT) (FIGS. 45A-45D). Comparing selected clones both before and after negative selection suggested that selectivity for VAMP7 over VAMP1 is primarily achieved by a decrease in $K_M$ rather than a substrate-dependent modification to catalysis (FIG. 45E). In an effort to gain insight into the role of individual mutations in the evolved proteases, reversion analysis was performed for both VAMP7-selective variants, and their activity was assessed by the cell-based luciferase assay (FIG. 53A). None of the reversion mutants recovered meaningful VAMP1 cleavage activity, demonstrating that the origins of selectivity in the evolved enzymes cannot be attributed to a single mutation. Additionally, several reversions (H72Y, A106V, S148N, P158A, Y166S, H184N, G200E, S224I, and L240R) ablate activity in the luciferase assay, indicating that they are important either for VAMP7-cleavage activity or soluble expression in *E. coli*. Four additional reversions were identified which increased activity in this cell-based assay: S232A, G350S, M381L, and L410P. While none of these mutations impacted VAMP1-VAMP7 selectivity individually, they combine to yield a promiscuous protease (FIG. 53B). This is consistent with the complex nature of substrate recognition by BoNT proteases, which is driven by both discreet binding interactions as well as conformational effects. Based on the potential for non-intuitive epistatic interactions in reversion mutants of F7N[1.3], this clone was pursued directly in downstream studies.

Figures 54A, 54B:
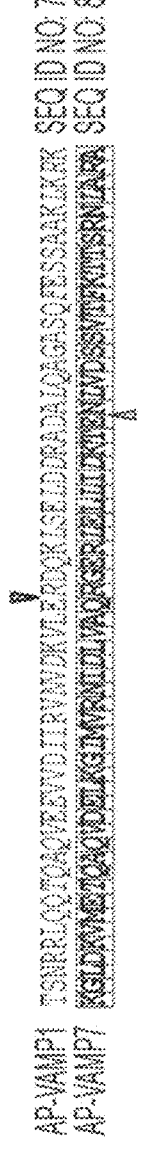
Figure 55A:
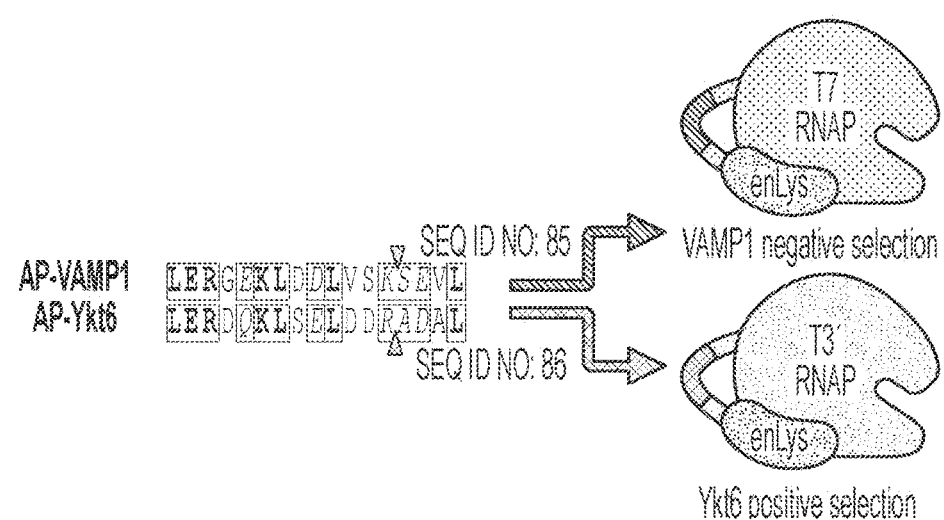
FIGS. 55A-55D show the evolution and selectivity of BoNT X.
Figure 55B:
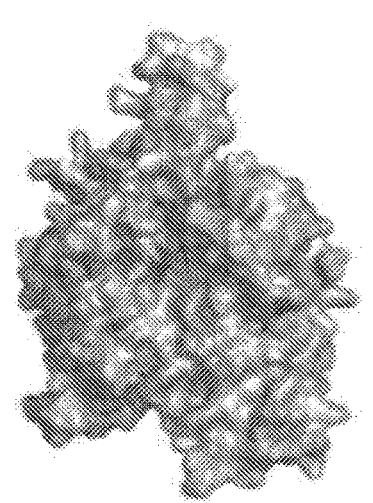
Figure 55C:
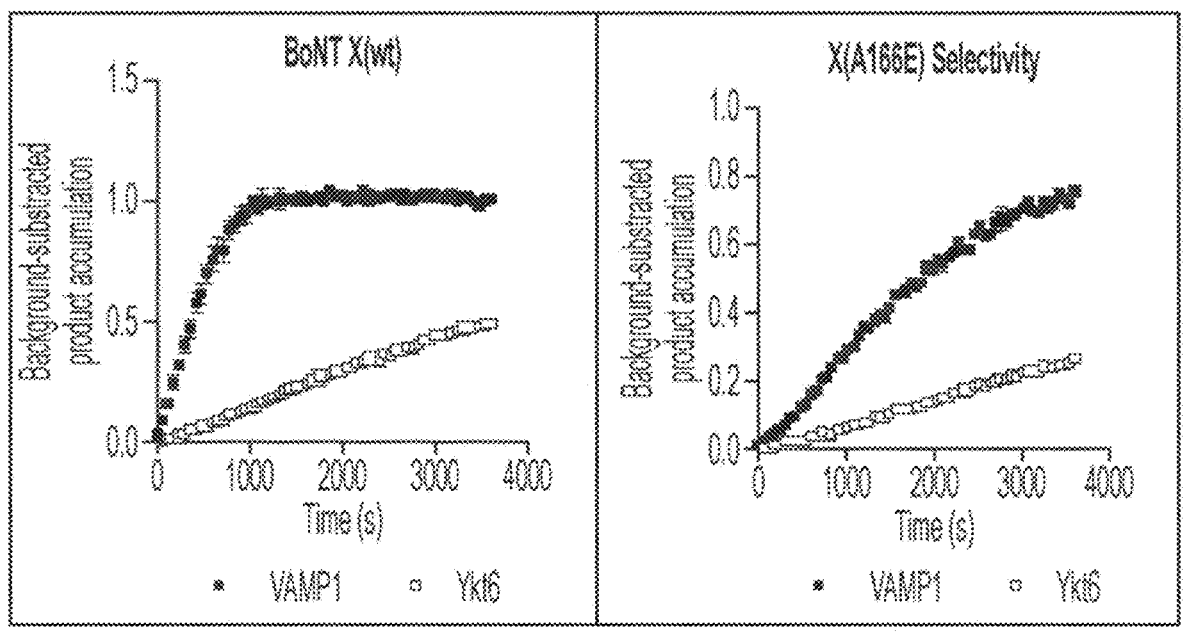
Figure 55D:
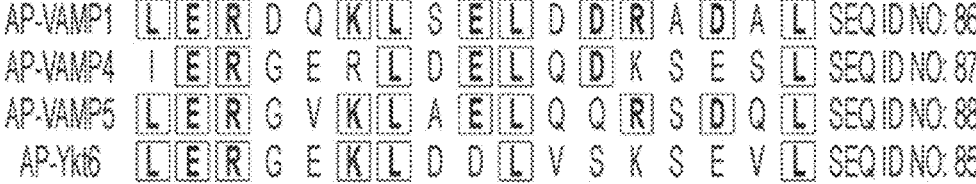

While dual negative selection is capable of refining binary selectivity between two cleavage targets, a more holistic understanding of selectivity in the evolve proteases was sought for targets which did not undergo explicit negative selection. To this end, the activity of protease F7N[1.3] was tested against a number of related VAMP-family SNARE targets. Interestingly, F7N[1.3] proved highly selective for VAMP7 over all other tested sequences (FIGS. 45E-45F). While the origin of this selectivity is not fully understood, it was observed that the evolved protease obtained after positive selection only, did not cleave VAMP7 at the anticipated position (VAMP7-E153), but instead cleaved nine residues C-terminal at E162. Upon evaluation of the primary sequence for this second cleavage site, it was noted that it possessed reduced identity to the native VAMP1 substrate, but did have increased local similarity (FIG. 54). It appears likely that this shift in primary sequence enables the evolution of high selectivity, as this region of VAMP7 contains several residues that diverge in character from other family members, most notably Leu156, Ile158, Thr161, and Asn163. Interestingly, the ability of PACE to accommodate an extended cleavage site into the selection construct facilitates a promiscuous protease to self-select for an optimal sequence during iterative positive selection, and negative selection necessarily refines this activity to achieve high specificity.

Example 6: Intracellular Delivery of Evolved VAMP7-Cleaving Proteases

Botulinum neurotoxins represent a powerful biomacromolecular strategy for manipulating intracellular chemistry, but are their applications are limited by their high specificity for the SNARE proteins responsible for neurotransmitter secretion. The PACE method has been applied for directed evolution to evolve the botulinum neurotoxin serotype F light chain protease to cleave a new substrate, VAMP7, through iterative positive selection over several evolutionary stepping stones. As part of this evolutionary campaign, it was validated that the T7-PAP that drives protease evolution in PACE can accommodate extended cleavage sequences (>60 amino acids). This capability proved useful, as the evolving BoNT F LC proteases shifted their preferred site of hydrolysis during the evolution campaign. Collectively, this advance represents the one of only a few examples of significant specificity reprogramming in proteases, and the first example in the botulinum neurotoxin family.

Seeking to a means to access selective proteases, simultaneous negative selection capabilities were developed and implemented into protease PACE-type selections by employing orthogonal protease-activated polymerases. The practical limitations of stringency modulation in a dual selection system were overcome with PANCE, a higher throughput method of phage-assisted evolution. The increased throughput of PANCE selections allowed for a broader array of selection stringencies to be assessed in tandem, ultimately allowing the gradual maturation of highly selective proteases over many passages. Analysis of the evolved proteases in vitro suggest that the increases in selectivity are due primarily to a decrease in $K_M$, while $k_{cat}$ was minimally perturbed between positive and negative selection. Mutational analysis suggests that origin of selectivity appears to be complex, and is related to multiple mutations throughout the BoNT F/LC enzyme. However, even though negative selection was only carried out against a single substrate (VAMP1), the evolved proteases displayed a strong preference for cleavage of VAMP7 alone over all other VAMP-family SNARE proteins in vitro. This was fortuitous, and cannot always be a guaranteed outcome in protease evolution studies, but it underscores the higher order nature of protease substrate recognition relative to other sequence-specific modes of recognition, such as protein-DNA interactions.

Example 7: BoNT X Evolved with Positive and Negative Selection

Figure 56A:
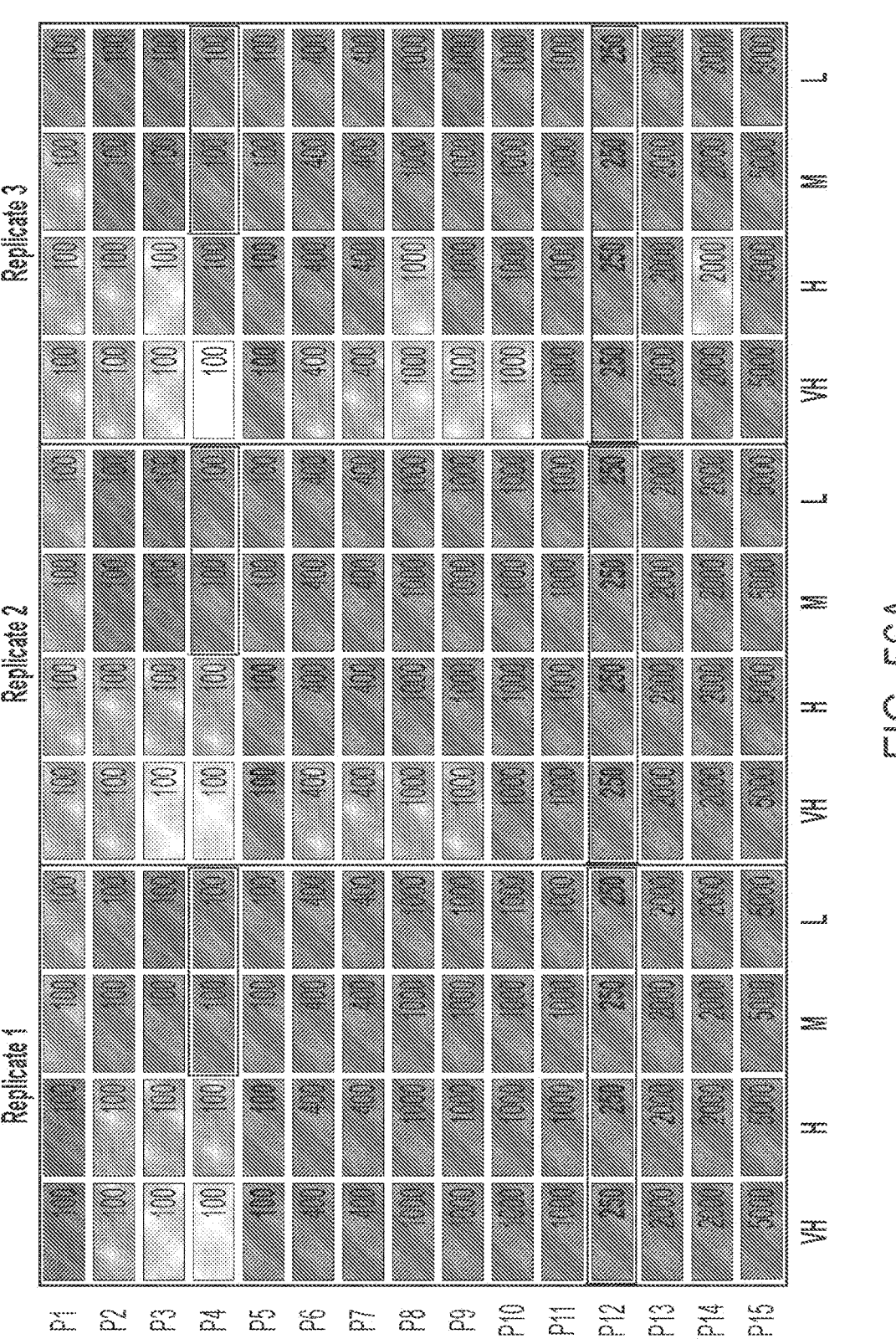
Figure 57A:
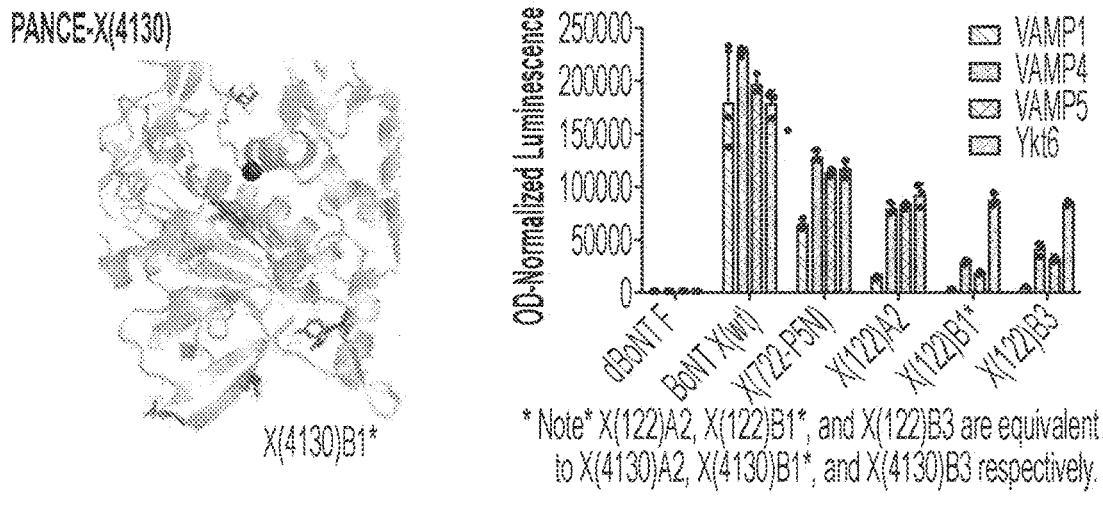
Figure 57B:
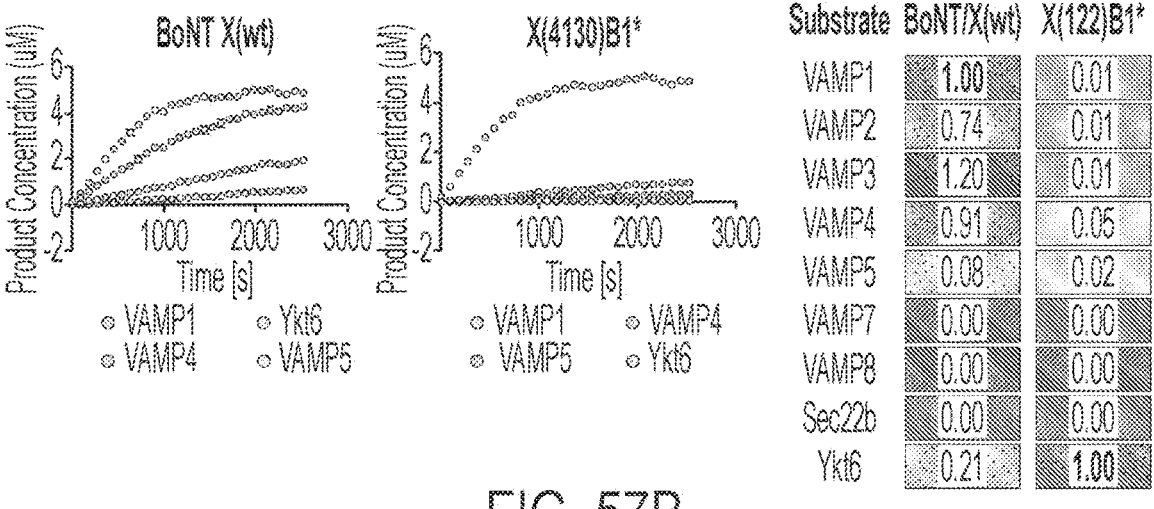
Figure 57E:
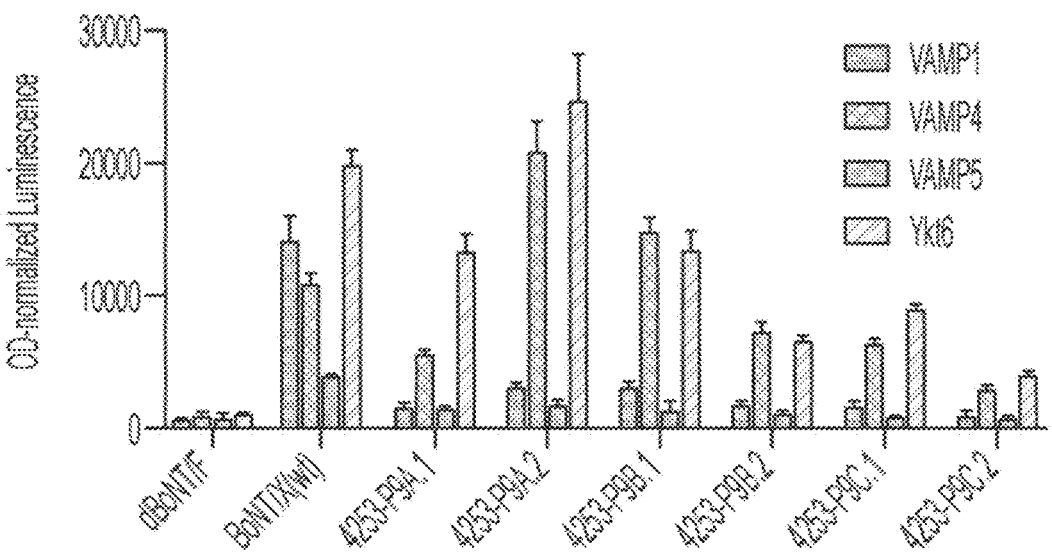
Figure 57G:
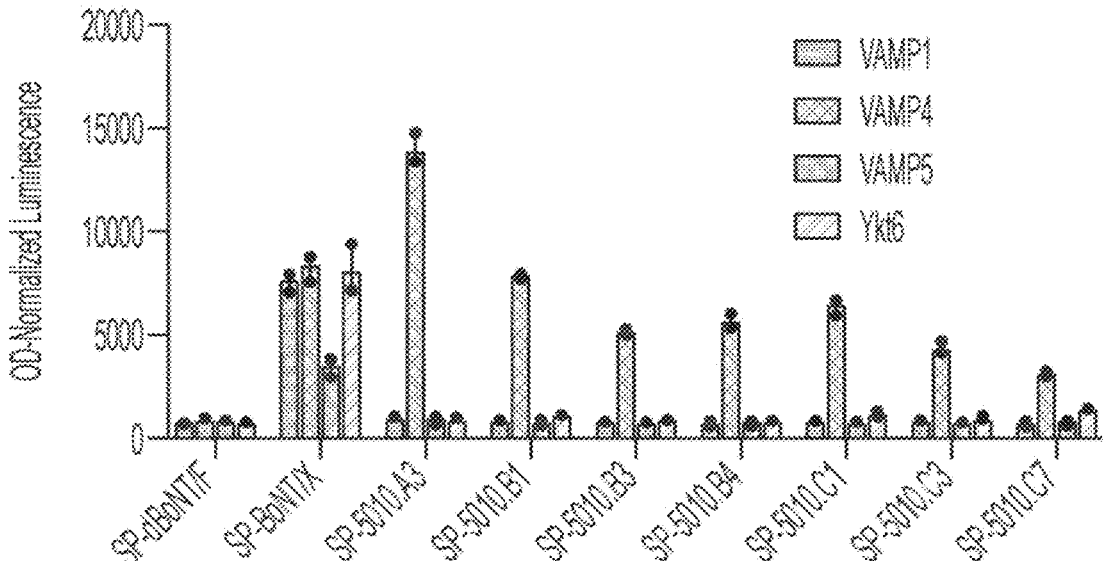
Figure 58A:
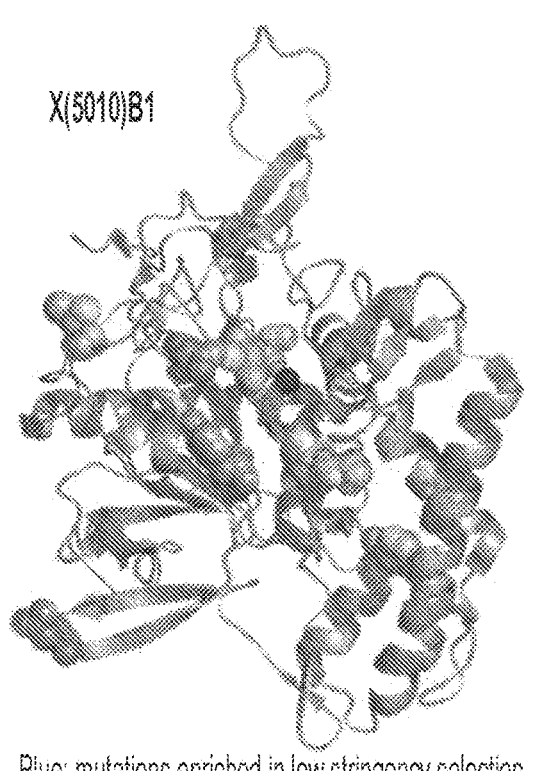

Experiments were carried out to determine phage titers after positive selection of VAMP7-cleaving proteases and negative selection of VAMP1-cleaving proteases over two replicates of 15 passages (FIG. 56A). Evolution mapping was performed to show the mutations in passages (FIG. 56B). The characteristics of the PANCE evolved BoNT-X variant were assessed by evaluating activity on substrates. The results are shown as BoNT serotypes (F and X wt) against various evolved variants, on 4 different substrates, VAMP1, VAMP4, VAMP5, and Ykt6 (FIG. 57A) The product concentration over time for wt BoNT-X on the four different substrates (left panel), and variant X(4130)B1* (middle panel) was determined with luciferase assay data (FIG. 57B). An evolution strategy including positive and negative selection APs was mapped as used in a BoNT-X PANCE evolution (FIG. 57C). Phage titers were determined (FIG. 57D). An evolution of different BoNT-X proteases and activity of variants on four different substrates (FIG. 57E) and evolution of BoNT-X (5010) over passages (FIG. 57F). The activity of BoNT-X (5010) on various substrates was determined. The quantification of activity of each variant on two different substrates was determined (FIG. 58A). Product concentration over time of BoNT-X (5010) on four substrates, BoNT-X(5010)A3 (top panel), BoNT-X(5010)B1 (middle panel), and BoNT-X(5010)C1 (bottom panel) was assessed (FIG. 58B).

Example 8: BoNT E Evolved to Cleave PTEN

Figure 59A:
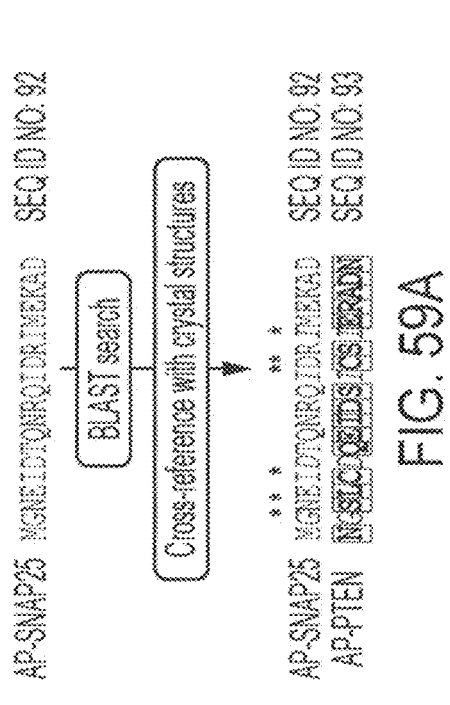
Figure 59B:
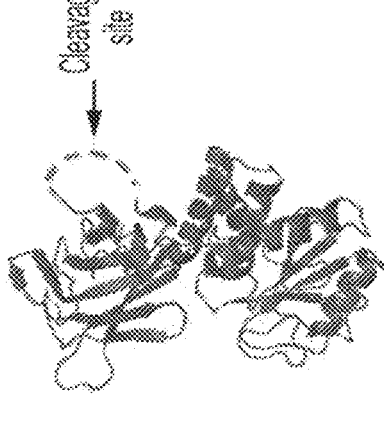
Figure 59E:
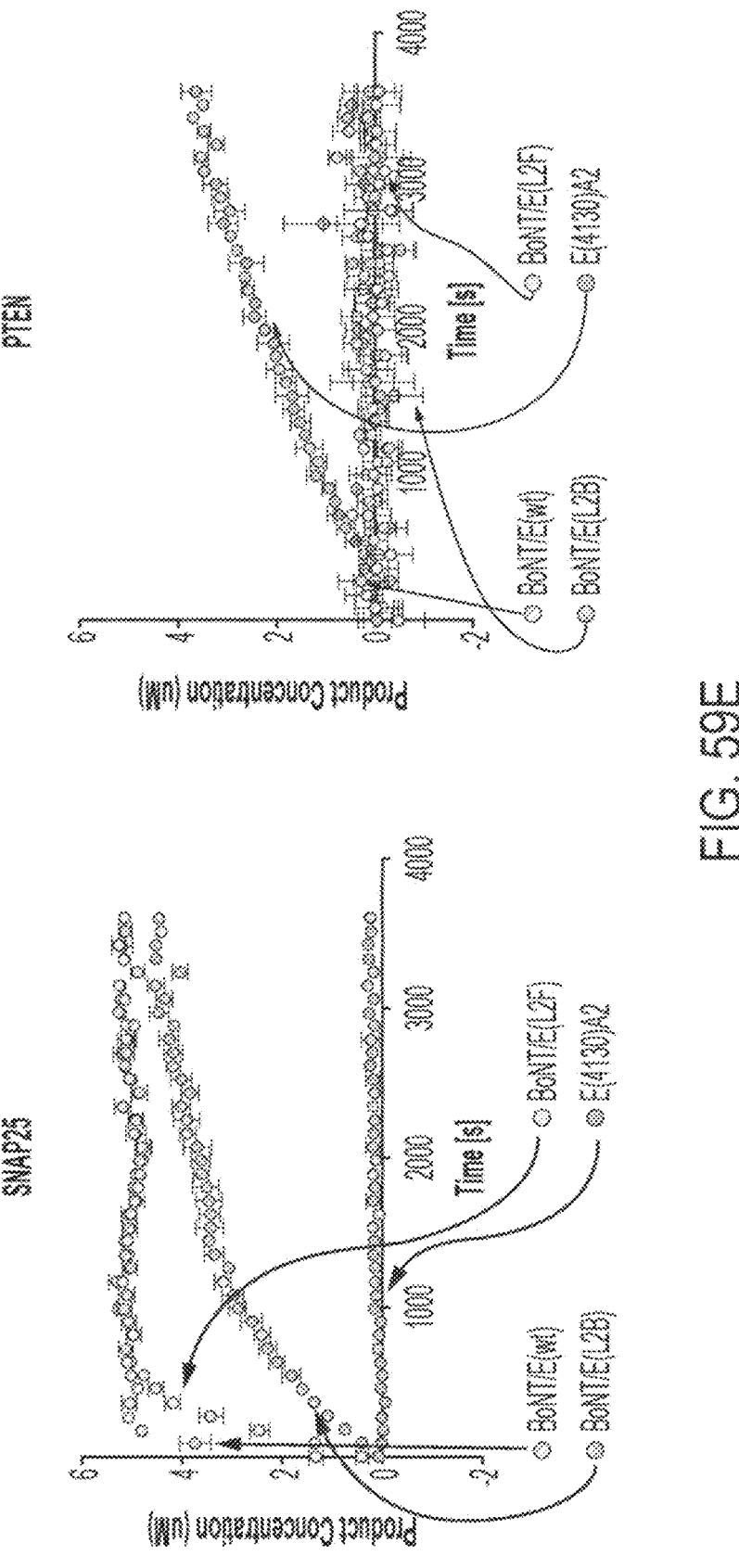
Figure 59F:
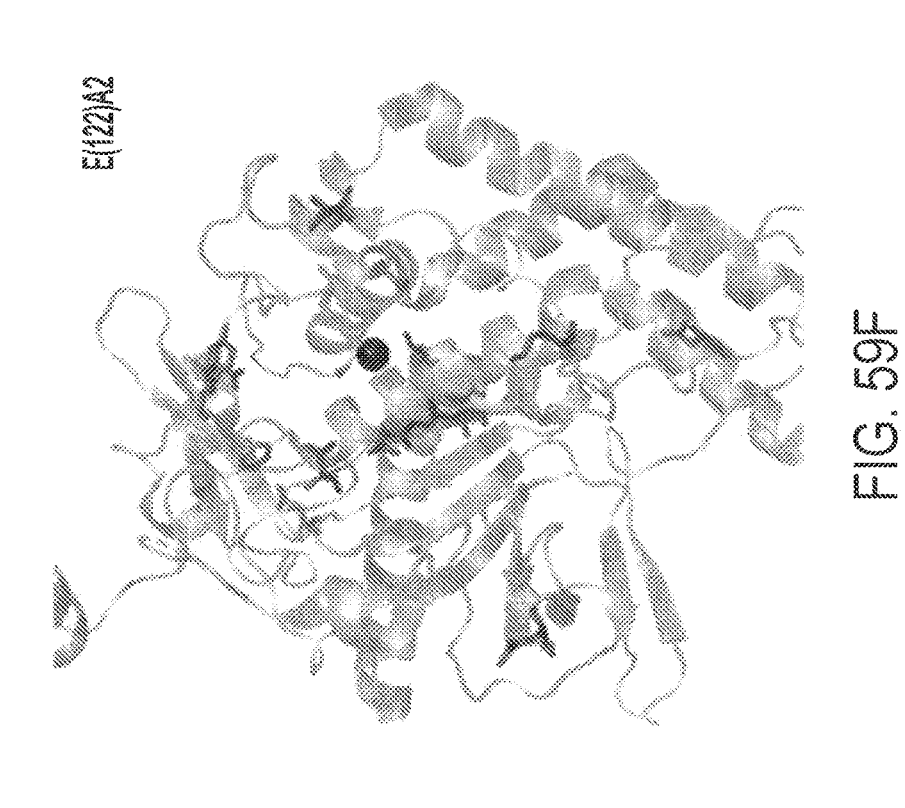
Figure 59G:
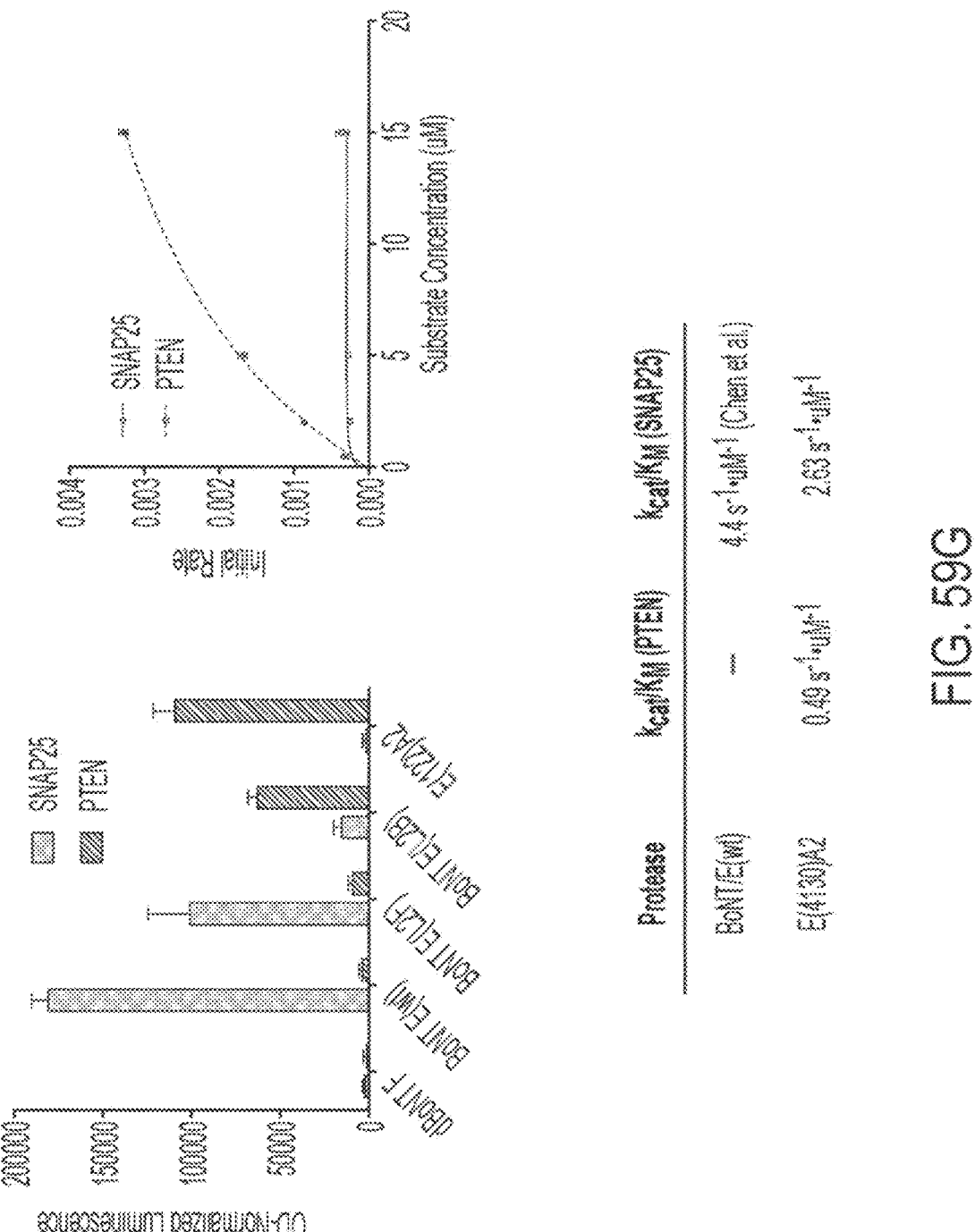

A cross-reference of a BoNT substrate to a PTEN substrate was assessed (FIG. 59A). A PTEN structure and cleavage site were evaluated (FIG. 59B). Two positive selection trajectories from SNAP-25 substrate to PTEN and a negative selection strategy are evaluated (FIG. 59C). Phage populations of substrates throughout the evolution are determined (FIG. 59D). Evolved BoNT-E proteases are evaluated on various substrates, SNAP25 (left panel) and PTEN (right panel) (FIG. 59E). BoNT-E(122)A2 is evolved (FIG. 59F). The activity of an evolved BoNT-E protease on various substrates is evaluated (FIG. 59G).

Figure 60:
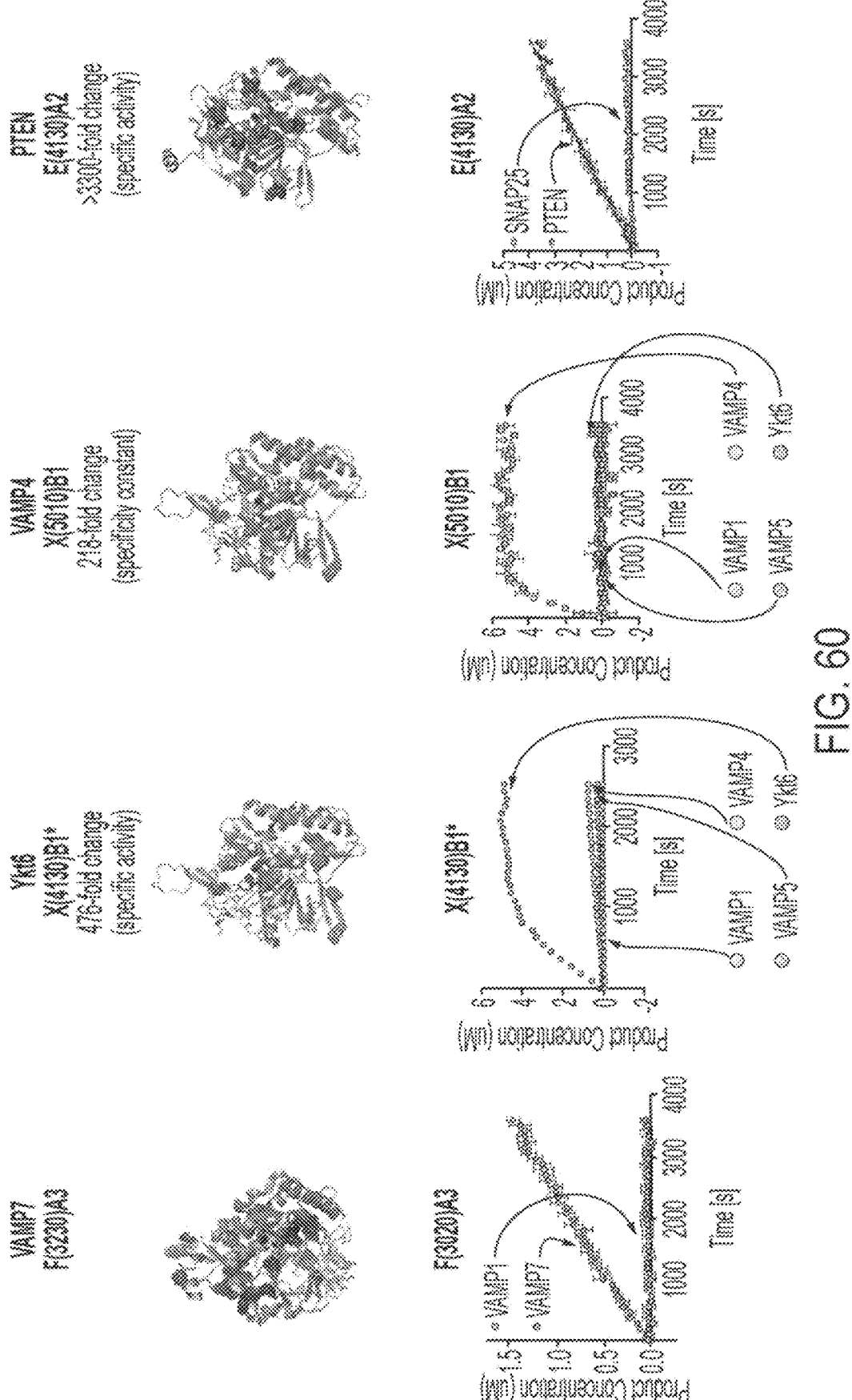
FIG. 60 shows a comparison of different evolved BoNT proteases acting on various substrates.

The evolved BoNT proteases are evaluated (FIG. 60).

TABLE 6

3230 - Passage 8

| Group | # | | | | | |
|---|---|---|---|---|---|---|
| 122 | 43 | b | | K31N | | R49H |
| | 44 | c | | | | |
| | 45 | f | | | | |
| | 46 | g | | K31N | E48D | |
| 720 | 47 | a | | | | |
| | 48 | c | | | | |
| | 49 | d | | | | |
| | 50 | e | | | | |
| | 51 | f | | | | |
| | 52 | g | | | | |
| 721 | 53 | a | | | | |
| | 54 | b | | K31N | | |
| | 55 | c | | | | |
| | 56 | d | | | | |
| | 57 | e | | | | |
| | 58 | f | | | | |
| | 59 | g | | | | |
| | 60 | h | N9T | | E38K | |
| 722 | 61 | a | | K31N | | |
| | 62 | b | | | E38K | |
| | 63 | c | | K31N | | |
| | 64 | e | | K31N | | |
| | 65 | f | | | | |
| | 66 | g | S7R | K31N | | |
| | 67 | h | | | | |

| Group | # | | | | | | |
|---|---|---|---|---|---|---|---|
| 122 | 43 | b | | | Y72H | | |
| | 44 | c | | | | | N99S |
| | 45 | f | | S69L | Y72H | | |
| | 46 | g | | | Y72H | | |
| 720 | 47 | a | | S69L | Y72H | | |
| | 48 | c | | S69L | Y72H | | |
| | 49 | d | D60N | S69L | Y72H | | |
| | 50 | e | | S69L | Y72H | | |
| | 51 | f | | S69L | Y72H | | |
| | 52 | g | | S69L | Y72H | | |
| 721 | 53 | a | | | | | |
| | 54 | b | | | Y72H | | |
| | 55 | c | | | | | N99S |
| | 56 | d | | | | T90I | N99S |
| | 57 | e | | S69L | Y72H | | |
| | 58 | f | | | | | N99S |
| | 59 | g | | S69L | Y72H | | |
| | 60 | h | | | | | |
| 722 | 61 | a | | | Y72H | | |
| | 62 | b | | | | | N99S |
| | 63 | c | | | Y72H | | |
| | 64 | e | | | Y72H | | |
| | 65 | f | | | | | |
| | 66 | g | | | Y72H | | |
| | 67 | h | | | | | |

| Group | # | | | | | |
|---|---|---|---|---|---|---|
| 122 | 43 | b | V106A | | V131F | |
| | 44 | c | V106A | | V131F | I139T |

TABLE 6-continued

3230 - Passage 8

| Group | # | | | | | |
|---|---|---|---|---|---|---|
| | 45 | f | V106A | | | V131F |
| | 46 | g | V106A | | | V131F |
| 720 | 47 | a | V106A | | | |
| | 48 | c | V106A | | | V131F |
| | 49 | d | V106A | | | |
| | 50 | e | V106A | | N126S | |
| | 51 | f | V106A | | | |
| | 52 | g | V106A | | | |
| 721 | 53 | a | V106A | | | |
| | 54 | b | V106A | | | V131F |
| | 55 | c | V106A | | | V131L |
| | 56 | d | V106A | | | V131A |
| | 57 | e | V106A | | | V131F |
| | 58 | f | V106A | | | V131F |
| | 59 | g | V106A | | | V131F |
| | 60 | h | V106A | | | |
| 722 | 61 | a | V106A | | | V131F |
| | 62 | b | V106A | | | V131F |
| | 63 | c | V106A | | | V131F |
| | 64 | e | V106A | | | V131F |
| | 65 | f | | | | |
| | 66 | g | V106A | | | V131F |
| | 67 | h | V106A | Q109K | | |

| Group | # | | | | | | |
|---|---|---|---|---|---|---|---|
| 122 | 43 | b | | | | | |
| | 44 | c | | | | | P160T |
| | 45 | f | | | | A158P | |
| | 46 | g | | | | | |
| 720 | 47 | a | S148N | | | A158P | |
| | 48 | c | S148N | | | A158P | |
| | 49 | d | S148N | | | A158P | |
| | 50 | e | S148N | | | A158P | |
| | 51 | f | S148N | | | A158P | |
| | 52 | g | S148N | | | A158P | |
| 721 | 53 | a | S148N | | V155I | | |
| | 54 | b | | | | | |
| | 55 | c | | | | | |
| | 56 | d | | | | | |
| | 57 | e | | | | | |
| | 58 | f | | | | A158P | |
| | 59 | g | | | | A158P | |
| | 60 | h | | I149F | V155I | | |
| 722 | 61 | a | | | | | |
| | 62 | b | | | | | |
| | 63 | c | | | | | |
| | 64 | e | | | | A158S | |
| | 65 | f | | | | | |
| | 66 | g | | | | | |
| | 67 | h | S148N | | V155I | | |

| Group | # | | | | | | |
|---|---|---|---|---|---|---|---|
| 122 | 43 | b | S166Y | S167I | | | |
| | 44 | c | S166Y | S167I | | | |
| | 45 | f | S166Y | S167I | | | |
| | 46 | g | S166Y | S167I | | | G177C |
| 720 | 47 | a | S166Y | S167L | | | |
| | 48 | c | S166Y | S167L | M147V | | |
| | 49 | d | S166Y | S167L | M147V | | |
| | 50 | e | S166Y | S167L | | | |
| | 51 | f | S166Y | S167L | M147V | | |
| | 52 | g | S166Y | S167L | M147V | | |
| 721 | 53 | a | S166Y | S167I | M174T | | |
| | 54 | b | S166Y | S167I | | | |
| | 55 | c | S166Y | S167I | | | |
| | 56 | d | S166Y | S167I | | | |
| | 57 | e | S166Y | S167I | | | |
| | 58 | f | S166Y | S167I | | | |
| | 59 | g | S166Y | S167I | | | |
| | 60 | h | S166Y | S167I | M174T | | |
| 722 | 61 | a | S166Y | S167I | | | G178S |
| | 62 | b | S166Y | S167I | | | |
| | 63 | c | S166Y | S167I | | | |
| | 64 | e | S166Y | S167I | | | |
| | 65 | f | | | | | |
| | 66 | g | S166Y | S167I | | | |
| | 67 | h | S166Y | S167I | M174T | S176T | |

| Group | # | | | | |
|---|---|---|---|---|---|
| 122 | 43 | b | E200G | | S224I |
| | 44 | c | E200G | | S224I |

TABLE 6-continued

| | | | 3230 - Passage 8 | | |
|---|---|---|---|---|---|
| | 45 | f | E200G | | S224I |
| | 46 | g | E200G | | S224I |
| 720 | 47 | a | E200G | | S224I |
| | 48 | c | E200G | | S224I |
| | 49 | d | E200G | | S224I |
| | 50 | e | E200G | | S224I |
| | 51 | f | E200G | | S224I |
| | 52 | g | E200G | | S224I |
| 721 | 53 | a | E200G | | S224I |
| | 54 | b | E200G | | S224I |
| | 55 | c | E200G | | S224I |
| | 56 | d | E200G | | S224I |
| | 57 | e | E200G | | S224I |
| | 58 | f | E200G | | S224I |
| | 59 | g | E200G | | S224I |
| | 60 | h | E200G | | S224I |
| 722 | 61 | a | E200G | | S224I |
| | 62 | b | E200G | N204D | S224I |
| | 63 | c | E200G | | S224I |
| | 64 | e | E200G | | S224I |
| | 65 | f | | | |
| | 66 | g | E200G | | S224I |
| | 67 | h | E200G | A219S | S224I |

| | | | | | | |
|---|---|---|---|---|---|---|
| 122 | 43 | b | | | R240L | |
| | 44 | c | | | R240L | |
| | 45 | f | | A239T | R240L | |
| | 46 | g | | | R240L | |
| 720 | 47 | a | | A232S | R240L | |
| | 48 | c | | A232S | R240L | |
| | 49 | d | | A232S | R240L | |
| | 50 | e | | A232S | R240L | |
| | 51 | f | | A232S | R240L | |
| | 52 | g | | A232S | R240L | |
| 721 | 53 | a | | | R240L | |
| | 54 | b | | | R240L | |
| | 55 | c | | | R240L | |
| | 56 | d | | | R240L | |
| | 57 | e | S226V | A232T | R240L | Q252K |
| | 58 | f | | | R240L | |
| | 59 | g | | | R240L | |
| | 60 | h | | | R240L | |
| 722 | 61 | a | | | R240L | |
| | 62 | b | | | R240L | |
| | 63 | c | | | R240L | |
| | 64 | e | | | R240L | |
| | 65 | f | | | R240L | |
| | 66 | g | | | R240L | |
| | 67 | h | | | R240L | |

| | | | | | |
|---|---|---|---|---|---|
| 122 | 43 | b | | S350G | |
| | 44 | c | | S350G | |
| | 45 | f | | S350G | |
| | 46 | g | | | |
| 720 | 47 | a | | S350G | |
| | 48 | c | | S350G | |
| | 49 | d | | S350G | |
| | 50 | e | | S350G | |
| | 51 | f | | S350G | |
| | 52 | g | | S350G | |
| 721 | 53 | a | | S350G | |
| | 54 | b | | S350G | |
| | 55 | c | | S350G | |
| | 56 | d | | S350G | |
| | 57 | e | | S350G | |
| | 58 | f | | S350G | |
| | 59 | g | | S350G | |
| | 60 | h | | S350G | |
| 722 | 61 | a | | S350G | I354V |
| | 62 | b | | | |
| | 63 | c | E310G | S350G | I354V |
| | 64 | e | | S350G | I354V |
| | 65 | f | | S350G | I354V |
| | 66 | g | | S350G | I354V |
| | 67 | h | | S350G | |

| | | | | |
|---|---|---|---|---|
| 122 | 43 | b | F360L | Y372N |
| | 44 | c | F360L | Y372H |

TABLE 6-continued

| | | | 3230 - Passage 8 | | | |
|---|---|---|---|---|---|---|
| | 45 | f | F360L | Y372N | | |
| | 46 | g | | | | |
| 720 | 47 | a | F360L | Y372N | | |
| | 48 | c | F360L | Y372N | | |
| | 49 | d | F360L | Y372N | | |
| | 50 | e | F360L | Y372N | | |
| | 51 | f | F360L | Y372N | | |
| | 52 | g | F360L | Y372N | | |
| 721 | 53 | a | F360L | Y372H | | |
| | 54 | b | F360L | Y372N | | |
| | 55 | c | F360L | Y372H | G373S | D382A |
| | 56 | d | F360L | Y372N | | |
| | 57 | e | F360L | Y372N | | |
| | 58 | f | F360L | Y372H | | |
| | 59 | g | F360L | Y372N | | |
| | 60 | h | F360L | Y372H | | |
| 722 | 61 | a | F360L | Y372H | K376E | |
| | 62 | b | | | | |
| | 63 | c | F360L | Y372P | | |
| | 64 | e | F360L | Y372P | | |
| | 65 | f | F360L | Y372H | K376E | |
| | 66 | g | F360L | Y372P | | |
| | 67 | h | | Y372H | | |

| | | | | | | |
|---|---|---|---|---|---|---|
| 122 | 43 | b | N396H | | P410L | |
| | 44 | c | N396H | | | |
| | 45 | f | N396H | | P410Q | |
| | 46 | g | | | | |
| 720 | 47 | a | N396H | | | |
| | 48 | c | N396H | | | |
| | 49 | d | N396H | | | |
| | 50 | e | N396H | | | |
| | 51 | f | N396H | | | |
| | 52 | g | N396H | | | |
| 721 | 53 | a | N396H | R402C | P410L | |
| | 54 | b | N396H | | P410L | |
| | 55 | c | N396H | | P410L | |
| | 56 | d | N396H | | P410L | |
| | 57 | e | N396H | | P410Q | |
| | 58 | f | N396H | | | |
| | 59 | g | N396H | | P410Q | |
| | 60 | h | N396H | | P410L | I413T |
| 722 | 61 | a | N396H | | P410L | |
| | 62 | b | | | | |
| | 63 | c | N396H | | P410L | I412N |
| | 64 | e | N396H | | P410L | I412N |
| | 65 | f | N396H | | P410L | I412N |
| | 66 | g | N396H | | P410L | I412N |
| | 67 | h | N396H | | P410L | |

| | | | | |
|---|---|---|---|---|
| 122 | 43 | b | D414G | G420AWLRKS |
| | 44 | c | | G420AWLRKS |
| | 45 | f | | G420AWLRKS |
| | 46 | g | | |
| 720 | 47 | a | | G420AWLRKS |
| | 48 | c | | G420AWLRKS |
| | 49 | d | | G420AWLRKS |
| | 50 | e | | G420AWLRKS |
| | 51 | f | | G420AWLRKS |
| | 52 | g | | G420AWLRKS |
| 721 | 53 | a | | G420AWLRKS* |
| | 54 | b | D414G | G420AWLRKS* |
| | 55 | c | | G420AWLRKS* |
| | 56 | d | D414PSQTRPG* | |
| | 57 | e | | G420AWLRKS* |
| | 58 | f | | G420AWLRNREVILIMEIFNMG* |
| | 59 | g | | G420AWLRKS* |
| | 60 | h | | G420AWLRKS* |
| 722 | 61 | a | | G420AWLRKS* |
| | 62 | b | | |
| | 63 | c | | G420AWLRKS* |
| | 64 | e | | G420AWLRKS* |
| | 65 | f | | G420AWLRKS* |
| | 66 | g | | G420AWLRKS* |
| | 67 | h | | G420AWLRKS* |

89

90

TABLE 7

3230 - Passage G

| 122 | 68 | b |  |  |
|---|---|---|---|---|
|  | 69 | e |  |  |
|  | 70 | f |  |  |
|  | 78 | g |  |  |
|  | 79 | h |  |  |
| 721 | 80 | a |  |  |
|  | 81 | b |  | D16N |
|  | 82 | c |  |  |
|  | 83 | d |  |  |
|  | 84 | e | S7N |  |
|  | 85 | g |  |  |
|  | 86 | h |  |  |
| 722 | 87 | a |  |  |
|  | 88 | b |  |  |
|  | 89 | c |  |  |
|  | 90 | d |  |  |
|  | 91 | e |  |  |
|  | 92 | f |  |  |
|  | 93 | g |  |  |
|  | 94 | h |  |  |

| 122 | 68 | b |  | S69L | Y72H |  |  |  |
|---|---|---|---|---|---|---|---|---|
|  | 69 | e |  | S69L | Y72H |  |  |  |
|  | 70 | f |  | S69L | Y72H |  |  |  |
|  | 78 | g |  | S69L | Y72H |  |  |  |
|  | 79 | h |  |  |  |  |  |  |
| 721 | 80 | a |  |  |  |  |  | N99S |
|  | 81 | b | E66K | S69L | Y72H |  |  |  |
|  | 82 | c |  |  |  |  |  | N99S |
|  | 83 | d |  | S69L | Y72H |  |  |  |
|  | 84 | e |  | S69L | Y72H |  |  |  |
|  | 85 | g |  | S69L | Y72H |  |  |  |
|  | 86 | h |  |  | Y72H |  |  | N99S |
| 722 | 87 | a |  |  | Y72H | T90A |  | N99S |
|  | 88 | b |  |  | Y72H |  |  | N99S |
|  | 89 | c |  |  |  |  |  |  |
|  | 90 | d |  |  |  |  | I92V |  |
|  | 91 | e |  | S69L | Y72H |  |  |  |
|  | 92 | f |  | S69L | Y72H |  |  |  |
|  | 93 | g |  | S69L | Y72H |  |  |  |
|  | 94 | h |  | S69L | Y72H |  |  |  |

| 122 | 68 | b | V106A |  |  |  |
|---|---|---|---|---|---|---|
|  | 69 | e | V106A |  |  |  |
|  | 70 | f | V106A |  |  |  |
|  | 78 | g | V106A |  |  |  |
|  | 79 | h |  |  |  |  |
| 721 | 80 | a | V106A | A114S | V131G |  |
|  | 81 | b | V106A |  |  |  |
|  | 82 | c | V106A | A114S | V131G |  |
|  | 83 | d | V106A |  |  |  |
|  | 84 | e | V106A |  |  |  |
|  | 85 | g | V106A |  |  |  |
|  | 86 | h | V106A |  |  |  |
| 722 | 87 | a | V106A |  |  |  |
|  | 88 | b | V106A |  |  | T134S |
|  | 89 | c | V106A |  |  |  |
|  | 90 | d | V106A |  | V131F |  |
|  | 91 | e | V106A |  |  |  |
|  | 92 | f | V106A |  |  |  |
|  | 93 | g | V106A |  |  |  |
|  | 94 | h | V106A |  |  |  |

TABLE 7-continued

3230 - Passage G

| 122 | 68 | b |  | S148N |  | A158P |
|---|---|---|---|---|---|---|
|  | 69 | e |  | S148N |  | A158P |
|  | 70 | f |  | S148N |  | A158P |
|  | 78 | g |  | S148N |  | A158P |
|  | 79 | h |  |  |  |  |
| 721 | 80 | a |  | S148N |  | A158P |
|  | 81 | b |  | S148N |  | A158P |
|  | 82 | c |  |  |  |  |
|  | 83 | d | K146E | S148N |  | A158P |
|  | 84 | e |  | S148N |  | A158P |
|  | 85 | g |  | S148N |  | A158P |
|  | 86 | h |  |  |  |  |
| 722 | 87 | a |  |  |  |  |
|  | 88 | b |  |  |  |  |
|  | 89 | c |  | S148I |  |  |
|  | 90 | d |  |  | V155I |  |
|  | 91 | e | K140R | S148N | V155I | A158P |
|  | 92 | f |  |  |  | A158P |
|  | 93 | g |  | S148N |  | A158P |
|  | 94 | h |  | S148N |  | A158P |

| 122 | 68 | b | S166Y | S167I |  |  |  |
|---|---|---|---|---|---|---|---|
|  | 69 | e | S166Y | S167I |  |  |  |
|  | 70 | f | S166Y | S167I |  |  |  |
|  | 78 | g | S166Y | S167I |  |  |  |
|  | 79 | h |  |  |  |  |  |
| 721 | 80 | a | S166Y | S167I |  | S176N |  |
|  | 81 | b | S166Y | S167I |  |  |  |
|  | 82 | c | S166Y | S167I |  |  |  |
|  | 83 | d | S166Y | S167I |  |  |  |
|  | 84 | e | S166Y | S167I |  |  | D181E |
|  | 85 | g | S166Y | S167I |  |  |  |
|  | 86 | h | S166Y | S167I |  |  |  |
| 722 | 87 | a | S166Y | S167I |  |  |  |
|  | 88 | b | S166Y | S167I |  |  |  |
|  | 89 | c | S166Y | S167I |  |  |  |
|  | 90 | d | S166Y | S167I | M174T |  | D181A |
|  | 91 | e | S166Y | S167I | M174T |  |  |
|  | 92 | f | S166Y | S167I |  |  |  |
|  | 93 | g | S166Y | S167I |  |  |  |
|  | 94 | h | S166Y | S167I |  |  |  |

| 122 | 68 | b |  | E200G |  |  | S224I |
|---|---|---|---|---|---|---|---|
|  | 69 | e |  |  |  |  |  |
|  | 70 | f |  | E200G |  |  | S224I |
|  | 78 | g |  | E200G |  |  | S224I |
|  | 79 | h |  |  |  |  |  |
| 721 | 80 | a |  | E200G |  |  | S224I |
|  | 81 | b |  | E200G |  |  | S224I |
|  | 82 | c |  | E200G |  |  | S224I |
|  | 83 | d |  | E200G |  |  | S224I |
|  | 84 | e |  | E200G |  |  | S224I |
|  | 85 | g | N184H | E200G |  |  | S224I |
|  | 86 | h |  | E200G | Y210C |  | S224I |
| 722 | 87 | a |  | E200G | Y210C |  | S224I |
|  | 88 | b |  | E200G | Y210C |  | S224I |
|  | 89 | c | N184H | E200G |  |  | S224I |
|  | 90 | d |  | E200G |  |  | S224I |
|  | 91 | e | N184H | E200G |  |  | S224I |
|  | 92 | f |  | E200G |  | A219S | S224I |
|  | 93 | g |  | E200G |  |  | S224I |
|  | 94 | h | N184H | E200G |  |  | S224I |

| 122 | 68 | b | A232S | R240L |  |  |
|---|---|---|---|---|---|---|
|  | 69 | e |  |  |  |  |
|  | 70 | f | A232S | R240L |  |  |
|  | 78 | g | A232S | R240L |  |  |
|  | 79 | h |  | R240L |  |  |
| 721 | 80 | a | A232S | R240L |  |  |
|  | 81 | b | A232S | R240L |  |  |
|  | 82 | c |  | R240L |  |  |
|  | 83 | d | A232S | R240L |  |  |
|  | 84 | e | A232S | R240L |  |  |
|  | 85 | g | A232S | R240L |  |  |
|  | 86 | h |  | R240L |  | Q252H |
| 722 | 87 | a |  | R240L | T247A |  |
|  | 88 | b |  | R240L |  |  |
|  | 89 | c |  | R240L |  |  |
|  | 90 | d |  | R240L |  |  |
|  | 91 | e | A232S | R240L |  |  |
|  | 92 | f |  | R240L |  |  |
|  | 93 | g | A232S | R240L |  |  |
|  | 94 | h | A232S | R240L |  |  |

| 122 | 68 | b |  |  | R303L | S350G |  |
|---|---|---|---|---|---|---|---|
|  | 69 | e |  |  |  |  |  |
|  | 70 | f |  |  |  | S350G | I354N |
|  | 78 | g | I277F | A281V | R303H | S350G |  |
|  | 79 | h |  |  |  | S350G |  |
| 721 | 80 | a |  |  |  | S350G |  |
|  | 81 | b |  |  |  | S350G |  |
|  | 82 | c |  |  |  | S350G |  |
|  | 83 | d |  |  |  | S350G |  |

TABLE 7-continued

3230 - Passage G

|  |  |  |  |  |  |  |
|---|---|---|---|---|---|---|
|  | 84 | e |  |  |  | S350G |
|  | 85 | g |  |  |  | S350G |
|  | 86 | h |  |  |  | S350G |
| 722 | 87 | a |  |  |  | S350G |
|  | 88 | b |  |  | D318G | S350G |
|  | 89 | c |  |  |  | S350G |
|  | 90 | d |  |  |  | S350G |
|  | 91 | e |  |  |  | S350G |
|  | 92 | f |  |  |  | S350G |
|  | 93 | g |  |  |  | S350G |
|  | 94 | h |  |  |  | S350G |

|  |  |  |  |  |  |  |
|---|---|---|---|---|---|---|
| 122 | 68 | b | F360L | Y372N |  |  |
|  | 69 | e |  |  |  |  |
|  | 70 | f | F360L | Y372N |  |  |
|  | 78 | g | F360L | Y372N |  |  |
|  | 79 | h | F360L |  |  |  |
| 721 | 80 | a | F360L | Y372N |  |  |
|  | 81 | b | F360L | Y372N |  |  |
|  | 82 | c | F360L | Y372H |  |  |
|  | 83 | d | F360L | Y372N |  |  |
|  | 84 | e | F360L | Y372N |  |  |
|  | 85 | g | F360L | Y372N |  |  |
|  | 86 | h | F360L | Y372N |  |  |
| 722 | 87 | a | F360L | Y372H |  |  |
|  | 88 | b | F360L | Y372H |  |  |
|  | 89 | c | F360L | Y372H |  |  |
|  | 90 | d | F360L | Y372H |  |  |
|  | 91 | e | F360L | Y372N |  |  |
|  | 92 | f | F360L | Y372H | V377I | P378S |
|  | 93 | g | F360L | Y372H |  |  |
|  | 94 | h | F360L | Y372N |  |  |

|  |  |  |  |  |  |  |
|---|---|---|---|---|---|---|
| 122 | 68 | b | N396H |  | P410L | I413T |
|  | 69 | e |  |  |  |  |
|  | 70 | f | N396H |  | P410L |  |
|  | 78 | g | N396H |  | P410L |  |
|  | 79 | h | N396H | N405S |  |  |

TABLE 7-continued

3230 - Passage G

|  |  |  |  |  |  |
|---|---|---|---|---|---|
| 721 | 80 | a | N396H |  | P410L |
|  | 81 | b | N396H |  | P410L |
|  | 82 | c | N396H |  |  |
|  | 83 | d | N396H |  | P410L |
|  | 84 | e | N396H |  | P410L |
|  | 85 | g | N396H |  | P410L |
|  | 86 | h | N396H |  |  |
| 722 | 87 | a | N396H |  |  |
|  | 88 | b | N396H |  |  |
|  | 89 | c | N396H |  | P410L |
|  | 90 | d | N396H | K407E | P410L |
|  | 91 | e | N396H |  | P410L |
|  | 92 | f | N396H |  | P410L |
|  | 93 | g | N396H |  | P410L |
|  | 94 | h | N396H |  | P410L |

|  |  |  |  |  |  |
|---|---|---|---|---|---|
| 122 | 68 | b |  |  | G420AWLRKS* |
|  | 69 | e |  |  |  |
|  | 70 | f |  | I416S | G420AWLRKL* |
|  | 78 | g |  |  | G420AWLRKS* |
|  | 79 | h |  |  | G420AWLRKS* |
| 721 | 80 | a |  |  | G420AWLRKS* |
|  | 81 | b |  |  | G420AWLRKS* |
|  | 82 | c |  |  | G420AWLRKS* |
|  | 83 | d |  |  | G420AWLRKS* |
|  | 84 | e |  |  | G420AWLRKS* |
|  | 85 | g |  |  | G420AWLRKS* |
|  | 86 | h |  |  | G420AWLKTIVKF* |
| 722 | 87 | a |  |  | G420AWLRKS* |
|  | 88 | b |  |  | G420AWLRKS* |
|  | 89 | c |  | I416N | G420AWLRKS* |
|  | 90 | d |  |  | G420AWLRKS* |
|  | 91 | e |  |  | G420AWLRKS* |
|  | 92 | f | D214V |  | G420AWLRKS* |
|  | 93 | g |  |  | G420AWLRKS* |
|  | 94 | h |  |  | G420AWLRKS* |

TABLE 8

3230 - Passage 15

|  |  |  |  |  |  |
|---|---|---|---|---|---|
| 720 | 95 | a |  | K31N |  |
|  | 96 | b |  | K31N |  |
|  | 97 | c |  | K31N | P56S |
|  | 98 | d |  | K31N |  |
|  | 99 | e |  | K31N |  |
|  | 100 | f |  | K31N |  |
|  | 101 | g |  | K31N |  |
|  | 102 | h |  | K31N |  |
| 721 | 103 | a |  |  |  |
|  | 104 | b |  |  |  |
|  | 105 | c |  |  |  |
|  | 106 | d |  | K31N |  |
|  | 107 | e |  |  |  |
|  | 108 | f |  |  |  |
|  | 109 | g |  |  |  |
|  | 110 | h |  |  |  |
| 722 | 111 | a |  | K31N | S57N |
|  | 112 | b |  | K31N |  |
|  | 113 | c |  | K31N |  |
|  | 114 | d |  | K31N |  |
|  | 115 | e |  |  |  |
|  | 116 | f |  | K31N |  |
|  | 117 | g |  | K31N |  |
|  | 118 | h |  | K31N |  |

|  |  |  |  |  |  |
|---|---|---|---|---|---|
| 720 | 95 | a |  | Y72H | K96N |
|  | 96 | b |  | Y72H |  |
|  | 97 | c |  | Y72H |  |
|  | 98 | d | A71V | Y72H |  |
|  | 99 | e |  | Y72H |  |
|  | 100 | f |  | Y72H |  |
|  | 101 | g |  | Y72H |  |
|  | 102 | h |  | Y72H |  |

TABLE 8-continued

| | | | | | | | |
|---|---|---|---|---|---|---|---|
| 3230 - Passage 15 | | | | | | | |
| 721 | 103 | a | D60V | S69L | Y72H | | |
| | 104 | b | D60V | S69L | Y72H | K96N | |
| | 105 | c | D60V | S69L | Y72H | | |
| | 106 | d | | | Y72H | N76T | R97C |
| | 107 | e | | S69L | Y72H | | |
| | 108 | f | D60V | S69L | Y72H | | |
| | 109 | g | D60V | S69L | Y72H | | |
| | 110 | h | | S69L | Y72H | | |
| 722 | 111 | a | | | Y72H | | |
| | 112 | b | | | Y72H | | |
| | 113 | c | | | Y72H | | |
| | 114 | d | | | Y72H | | |
| | 115 | e | | | | | |
| | 116 | f | | | Y72H | | |
| | 117 | g | | | Y72H | | |
| | 118 | h | | | Y72H | | |

| | | | | | |
|---|---|---|---|---|---|
| 720 | 95 | a | V106A | | V131F |
| | 96 | b | V106A | | V131F |
| | 97 | c | V106A | | V131F |
| | 98 | d | V106A | | V131F |
| | 99 | e | V106A | | V131F |
| | 100 | f | V106A | | V131F |
| | 101 | g | V106A | | V131F |
| | 102 | h | V106A | | V131F |
| 721 | 103 | a | V106A | | V131F |
| | 104 | b | V106A | | V131G |
| | 105 | c | V106A | | V131G |
| | 106 | d | V106A | | V131F |
| | 107 | e | V106A | | V131F |
| | 108 | f | V106A | | V131G |
| | 109 | g | V106A | | V131G |
| | 110 | h | V106A | | V131F |
| 722 | 111 | a | V106A | | V131F |
| | 112 | b | V106A | | V131F |
| | 113 | c | V106A | | V131F |
| | 114 | d | V106A | | V131F |
| | 115 | e | V106A | K109K | |
| | 116 | f | V106A | | V131F |
| | 117 | g | V106A | | V131F |
| | 118 | h | V106A | | V131F |

| | | | | | | | |
|---|---|---|---|---|---|---|---|
| 720 | 95 | a | | | | S166Y | S167L |
| | 96 | b | | | | S166Y | S167L |
| | 97 | c | | | | S166Y | S167L |
| | 98 | d | | | | S166Y | S167L |
| | 99 | e | | | | S166Y | S167L |
| | 100 | f | | | | S166Y | S167L |
| | 101 | g | | | | S166Y | S167L |
| | 102 | h | S147T | | | S166Y | S167L |
| 721 | 103 | a | | | A158P | S166Y | S167I |
| | 104 | b | | I150T | A158P | S166Y | S167I |
| | 105 | c | | I150T | A158P | S166Y | S167I |
| | 106 | d | | I150T | | S166Y | S167L |
| | 107 | e | | | A158P | S166Y | S167I |
| | 108 | f | | I150T | A158P | S166Y | S167I |
| | 109 | g | | I150T | A158S | S166Y | S167I |
| | 110 | h | | | A158P | S166Y | S167I |
| 722 | 111 | a | S147P | | | S166Y | S167I |
| | 112 | b | | | | S166Y | S167L |
| | 113 | c | | | | S166Y | S167L |
| | 114 | d | | | | S166Y | S167I |
| | 115 | e | S148N | V155I | | S166Y | S167I |
| | 116 | f | | | | S166Y | S167I |
| | 117 | g | | | | S166Y | S167I |
| | 118 | h | | | | S166Y | S167I |

| | | | | |
|---|---|---|---|---|
| 720 | 95 | a | | E200G |
| | 96 | b | | E200G |
| | 97 | c | | E200G |
| | 98 | d | | E200G |
| | 99 | e | | E200G |
| | 100 | f | | E200G |
| | 101 | g | | E200G |
| | 102 | h | | E200G |
| 721 | 103 | a | M174T | E200G |
| | 104 | b | | E200G |
| | 105 | c | | E200G |

TABLE 8-continued

| | | | 3230 - Passage 15 | | | | | |
|---|---|---|---|---|---|---|---|---|
| | | 106 | d | | | M174T | | E200G |
| | | 107 | e | | | | | E200G |
| | | 108 | f | | | | | E200G |
| | | 109 | g | | | | | E200G |
| | | 110 | h | | | | | E200G |
| 722 | | 111 | a | | | | | E200G |
| | | 112 | b | | | | | E200G |
| | | 113 | c | | | | | E200G |
| | | 114 | d | | | | | |
| | | 115 | e | | | M174T | | E200G |
| | | 116 | f | | | | | |
| | | 117 | g | | | | | E200G |
| | | 118 | h | | | | | E200G |
| 720 | 95 | | a | | | | S224I | |
| | 96 | | b | | | | S224I | |
| | 97 | | c | | | | S224I | |
| | 98 | | d | | | | S224I | |
| | 99 | | e | | | | S224I | |
| | 100 | | f | | | | S224I | |
| | 101 | | g | | | | S224I | |
| | 102 | | h | | | | S224I | |
| 721 | 103 | | a | | | | S224I | |
| | 104 | | b | | | | S224I | |
| | 105 | | c | | | | S224I | |
| | 106 | | d | | | | S224I | |
| | 107 | | e | | | | S224I | |
| | 108 | | f | | | | S224I | |
| | 109 | | g | | | | S224I | |
| | 110 | | h | | | | S224I | |
| 722 | 111 | | a | | | | S224I | |
| | 112 | | b | | | | S224I | |
| | 113 | | c | | | | S224I | |
| | 114 | | d | | | | S224I | |
| | 115 | | e | T214A | A219S | | S224I | |
| | 116 | | f | | | | S224I | | A232T |
| | 117 | | g | | | | S224I | |
| | 118 | | h | | | | S224I | A226V |
| 720 | 95 | a | R240L | | | | | |
| | 96 | b | R240L | | | | | |
| | 97 | c | R240L | | L255M | | | |
| | 98 | d | R240L | | | | | |
| | 99 | e | R240L | | | I257T | | |
| | 100 | f | R240L | | | | | L264M |
| | 101 | g | R240L | | | | A258E | |
| | 102 | h | R240L | | | | | |
| 721 | 103 | a | R240L | | | | | |
| | 104 | b | R240L | | A253T | | | |
| | 105 | c | R240L | | | | | |
| | 106 | d | R240L | | | | | |
| | 107 | e | R240L | E246D | | | | |
| | 108 | f | R240L | | | | | |
| | 109 | g | R240L | | | | | |
| | 110 | h | R240L | | | | | |
| 722 | 111 | a | R240L | | | | | |
| | 112 | b | R240L | | | | | |
| | 113 | c | R240L | | | | | |
| | 114 | d | R240L | | | | | |
| | 115 | e | R240L | | | | | |
| | 116 | f | R240L | | | | | |
| | 117 | g | R240L | | | | | |
| | 118 | h | R240L | | | | | |
| 720 | 95 | a | | | A281V | | | R303H |
| | 96 | b | | F270L | | | | |
| | 97 | c | | | | | | |
| | 98 | d | | | | | | |
| | 99 | e | | | | | | |
| | 100 | f | | | | | | |
| | 101 | g | | | | | | |
| | 102 | h | | | | | | |
| 721 | 103 | a | | | | | | |
| | 104 | b | | | | | | |
| | 105 | c | | F270L | | | | |
| | 106 | d | | | | | | |
| | 107 | e | | | | | | |
| | 108 | f | | F270L | | | | |

TABLE 8-continued

| | | | 3230 - Passage 15 | | |
|---|---|---|---|---|---|
| | 109 | g | F270L | | |
| | 110 | h | | | |
| 722 | 111 | a | | | |
| | 112 | b | | | |
| | 113 | c | | I286V | |
| | 114 | d | | | |
| | 115 | e | F270V | | |
| | 116 | f | | | |
| | 117 | g | | | |
| | 118 | h | | | |

| | | | | | | |
|---|---|---|---|---|---|---|
| 720 | 95 | a | | | S350G | I354V |
| | 96 | b | | | S350G | |
| | 97 | c | | | S350G | I354V |
| | 98 | d | | | S350G | I354V |
| | 99 | e | | | S350G | I354V |
| | 100 | f | | | S350G | I354V |
| | 101 | g | | S333P | S350G | I354V |
| | 102 | h | S306A | | S350G | I354V |
| 721 | 103 | a | | | S350G | |
| | 104 | b | | | S350G | |
| | 105 | c | | | S350G | |
| | 106 | d | | | S350G | |
| | 107 | e | | Y345H | S350G | |
| | 108 | f | | | S350G | |
| | 109 | g | | | S350G | |
| | 110 | h | | | S350G | |
| 722 | 111 | a | | | S350G | I354V |
| | 112 | b | | | S350G | I354V |
| | 113 | c | | | S350G | I354V |
| | 114 | d | | | S350G | I354V |
| | 115 | e | | | S350G | |
| | 116 | f | | | S350G | I354V |
| | 117 | g | | | S350G | I354V |
| | 118 | h | | | S350G | I354V |

| | | | | | | |
|---|---|---|---|---|---|---|
| 720 | 95 | a | F360L | | | Y372P |
| | 96 | b | F360L | | | Y372N |
| | 97 | c | F360L | | | Y372P |
| | 98 | d | F360L | | | Y372P |
| | 99 | e | F360L | | | Y372P |
| | 100 | f | F360L | | | Y372P |
| | 101 | g | F360L | | | Y372P |
| | 102 | h | F360L | | | Y372P |
| 721 | 103 | a | F360L | | | Y372N |
| | 104 | b | F360L | | | Y372N |
| | 105 | c | F360L | | | |
| | 106 | d | F360L | | | Y372N |
| | 107 | e | F360L | | | Y372N |
| | 108 | f | F360L | | | Y372N |
| | 109 | g | F360L | V362I | | Y372N |
| | 110 | h | F360L | | | Y372N |
| 722 | 111 | a | F360L | | | Y372P |
| | 112 | b | F360L | | | Y372P |
| | 113 | c | F360L | | | Y372P |
| | 114 | d | F360L | | | Y372P |
| | 115 | e | F360L | | N366S | Y372H |
| | 116 | f | F360L | | | Y372P |
| | 117 | g | F360L | | | Y372P |
| | 118 | h | F360L | | | Y372P |

| | | | | | | |
|---|---|---|---|---|---|---|
| 720 | 95 | a | N396H | | P410L | I412N |
| | 96 | b | N396H | | P410L | |
| | 97 | c | N396H | | P410L | I412N |
| | 98 | d | N396H | | P410L | I412N |
| | 99 | e | N396H | | P410L | I412N |
| | 100 | f | N396H | | P410L | I412N |
| | 101 | g | N396H | | P410L | I412N |
| | 102 | h | N396H | | P410L | I412N |
| 721 | 103 | a | N396H | | P410Q | |
| | 104 | b | N396H | | P410L | |
| | 105 | c | N396H | | P410L | |
| | 106 | d | N396H | K407N | P410L | |
| | 107 | e | N396H | R402S | P410Q | |
| | 108 | f | N396H | | P410L | |
| | 109 | g | N396H | | P410L | |
| | 110 | h | N396H | | P410Q | |

US 12,655,182 B2

99     100

TABLE 8-continued

3230 - Passage 15

| 722 | 111 | a | I385V | N396H | | | P410L | I412N |
|---|---|---|---|---|---|---|---|---|
| | 112 | b | | N396H | | | P410L | I412N |
| | 113 | c | | N396H | | | P410L | I412[TLTPSQTRPG*] |
| | 114 | d | | N396H | | | P410L | I412N |
| | 115 | e | | N396H | | | P410L | |
| | 116 | f | | N396H | | | P410L | I412N |
| | 117 | g | | N396H | | | P410L | I412N |
| | 118 | h | | N396H | | | P410L | I412N |
| 720 | 95 | a | | | | | | G420AWLRKS |
| | 96 | b | D414G | | | | | G420AWLRKS |
| | 97 | c | | | | | | G420AWLRKS |
| | 98 | d | | | | | | G420AWLRKS |
| | 99 | e | | | | | | G420AWLRKS |
| | 100 | f | | | | | | G420AWLRKS |
| | 101 | g | | | | | | G420AWLRKS |
| | 102 | h | | | | | | G420AWLRKS |
| 721 | 103 | a | | | | | | G420AWLRKS* |
| | 104 | b | | I416T | | | | G420AWLRKS* |
| | 105 | c | | | | | | G420AWLRKS* |
| | 106 | d | | | | | | G420AWLRKS* |
| | 107 | e | D414G | | | | | G420AWLRKS* |
| | 108 | f | | I416T | | | | G420AWLRKS* |
| | 109 | g | | I416T | | | | G420AWLRKS* |
| | 110 | h | | | | | K419M | G420AWLRKS* |
| 722 | 111 | a | | | | | | G420VWLRKS* |
| | 112 | b | | | | D418G | | |
| | 113 | c | | | | | | G420AWLRKS* |
| | 114 | d | | | | | | |
| | 115 | e | | | | | | G420AWLRKS* |
| | 116 | f | | | | | | G420AWLRKS* |
| | 117 | g | | | | | | G420AWLRKS* |
| | 118 | h | | | | | | G420AWLRKS* |

TABLE 9

3230 - Passage N

| 122 | 119 | a | | | |
|---|---|---|---|---|---|
| | 120 | b | | | |
| | 121 | c | | | |
| | 122 | d | | | |
| | 123 | e | F8L | | |
| | 124 | f | | I45V | |
| | 125 | g | | | |
| | 126 | h | F8L | | |
| 720 | 127 | a | | | |
| | 128 | b | | | |
| | 129 | c | | | |
| | 130 | d | F8L | | |
| | 131 | e | F8L | | |
| | 132 | f | F8L | | |
| | 133 | g | | | |
| | 134 | h | | | |
| 721 | 135 | a | | | |
| | 136 | b | | | |
| | 137 | c | | | |
| | 138 | d | | | |
| | 139 | e | | T51M | |
| | 140 | f | | | |
| | 141 | g | | | |
| | 142 | h | | | |
| 722 | 143 | a | | | |
| | 144 | b | | | |
| | 145 | c | | | |
| | 146 | d | | | |
| | 147 | e | V4A | | |
| | 148 | f | | | |
| | 149 | g | | | |
| | 150 | h | | | |
| 122 | 119 | a | D60V | | Y72H | | N99S |
| | 120 | b | D60V | | Y72H | | N99S |
| | 121 | c | | S69L | Y72H | | |
| | 122 | d | | | Y72H | | N99S |

TABLE 9-continued

| | | | | | | |
|---|---|---|---|---|---|---|
| 3230 - Passage N | | | | | | |
| | 123 | e | | | Y72H | N99S |
| | 124 | f | | | Y72H | N99S |
| | 125 | g | | S69L | Y72H | |
| | 126 | h | | | Y72H | N99S |
| 720 | 127 | a | | S69L | Y72H | |
| | 128 | b | | S69L | Y72H | |
| | 129 | c | | S69L | Y72H | |
| | 130 | d | | | Y72H | N99S |
| | 131 | e | | | Y72H | N99S |
| | 132 | f | | | Y72H | N99S |
| | 133 | g | | | Y72H | N99S |
| | 134 | h | | S69L | Y72H | |
| 721 | 135 | a | | S69L | Y72H | |
| | 136 | b | | S69L | Y72H | |
| | 137 | c | | S69L | Y72H | |
| | 138 | d | | S69L | Y72H | |
| | 139 | e | | S69L | Y72H | |
| | 140 | f | | | Y72H | N99S |
| | 141 | g | | S69L | Y72H | |
| | 142 | h | | | | |
| 722 | 143 | a | | | Y72H | N99S |
| | 144 | b | | S69L | Y72H | |
| | 145 | c | S69L | Y72H | | |
| | 146 | d | | S69L | Y72H | |
| | 147 | e | | | Y72H | N99S |
| | 148 | f | | S69L | Y72H | |
| | 149 | g | | | Y72H | N99S |
| | 150 | h | | | | |

| | | | | | | | | |
|---|---|---|---|---|---|---|---|---|
| 122 | 119 | a | E105D | V106A | | V131F | | |
| | 120 | b | E105D | V106A | | V131F | | |
| | 121 | c | | V106A | | | | |
| | 122 | d | E105D | V106A | | V131F | | |
| | 123 | e | E105D | V106A | | V131F | | |
| | 124 | f | E105D | V106A | | V131F | | |
| | 125 | g | | V106A | | | T134A | |
| | 126 | h | E105D | V106A | | V131F | | |
| 720 | 127 | a | | V106A | | | | |
| | 128 | b | | V106A | | | | |
| | 129 | c | | V106A | | | | |
| | 130 | d | E105D | V106A | | V131F | | |
| | 131 | e | E105D | V106A | | V131F | | |
| | 132 | f | E105D | V106A | | V131F | | |
| | 133 | g | E105D | V106A | | V131F | | |
| | 134 | h | | V106A | | | | |
| 721 | 135 | a | | V106A | | | | |
| | 136 | b | | V106A | | | | |
| | 137 | c | | V106A | | V131F | | |
| | 138 | d | | V106A | | | | V137I |
| | 139 | e | | V106A | | | | |
| | 140 | f | | V106A | | | | |
| | 141 | g | | V106A | | | | |
| | 142 | h | | | | | | |
| 722 | 143 | a | E105D | V106A | | V131F | | |
| | 144 | b | | V106A | | V131F | | |
| | 145 | c | | V106A | Y113C | | | |
| | 146 | d | | V106A | Y113C | | | |
| | 147 | e | E105D | V106A | | V131F | | |
| | 148 | f | | V106A | Y113C | | | |
| | 149 | g | E105D | V106A | | V131F | | |
| | 150 | h | | | | | | |

| | | | | | | | |
|---|---|---|---|---|---|---|---|
| 122 | 119 | a | | | | S166Y | S167I |
| | 120 | b | | | | S166Y | S167I |
| | 121 | c | S148N | I150V | A158P | S166Y | S167I |
| | 122 | d | | | | S166Y | S167I |
| | 123 | e | | | | S166Y | S167I |
| | 124 | f | | | | S166Y | S167I |
| | 125 | g | S148N | | A158P | S166Y | S167I |
| | 126 | h | | | | S166Y | S167I |
| 720 | 127 | a | S148N | | A158P | S166Y | S167I |
| | 128 | b | S148N | | A158P | S166Y | S167I |
| | 129 | c | S148N | | A158P | S166Y | S167I |
| | 130 | d | | | | S166Y | S167I |
| | 131 | e | | | | S166Y | S167I |
| | 132 | f | | | | S166Y | S167I |
| | 133 | g | | | | S166Y | S167I |
| | 134 | h | S148N | | A158P | S166Y | S167L |

TABLE 9-continued

| | | | 3230 - Passage N | | | | | |
|---|---|---|---|---|---|---|---|---|
| 721 | 135 | a | S148N | | | A158P | S166Y | S167I |
| | 136 | b | | | | A158P | S166Y | S167I |
| | 137 | c | S148N | | | A158P | S166Y | S167L |
| | 138 | d | S148N | | | A158P | S166Y | S167I |
| | 139 | e | S148N | | | A158P | S166Y | S167I |
| | 140 | f | | | | | S166Y | S167L |
| | 141 | g | S148N | | | A158P | S166Y | S167I |
| | 142 | h | | | | A158P | S166Y | S167I |
| 722 | 143 | a | | | | | S166Y | S167I |
| | 144 | b | S148N | | | A158P | S166Y | S167I |
| | 145 | c | S148N | | | A158P | S166Y | S167I |
| | 146 | d | S148N | | | A158P | S166Y | S167I |
| | 147 | e | | | | | S166Y | S167I |
| | 148 | f | S148N | | | A158P | S166Y | S167I |
| | 149 | g | | | | | S166Y | S167I |
| | 150 | h | | | | | S166Y | S167I |

| | | | | | | | | |
|---|---|---|---|---|---|---|---|---|
| 122 | 119 | a | | | | | E200G | |
| | 120 | b | | | | | E200G | |
| | 121 | c | | G177D | | N184H | E200G | |
| | 122 | d | | | | | E200G | |
| | 123 | e | | | | | E200G | |
| | 124 | f | | | | | E200G | |
| | 125 | g | | G177D | | N184H | E200G | |
| | 126 | h | | | | | E200G | |
| 720 | 127 | a | | | | | E200G | |
| | 128 | b | | | | | E200G | |
| | 129 | c | | | | N184H | E200G | |
| | 130 | d | | | | | E200G | |
| | 131 | e | | | | | E200G | |
| | 132 | f | | | | | E200G | |
| | 133 | g | | | | Y199N | E200G | |
| | 134 | h | | | | N184H | E200G | |
| 721 | 135 | a | M147V | | | N184H | E200G | |
| | 136 | b | M147V | | | N184H | E200G | |
| | 137 | c | | | | | E200G | |
| | 138 | d | M147V | | | N184H | E200G | |
| | 139 | e | | | | N184H | E200G | |
| | 140 | f | | | | | E200G | N204S |
| | 141 | g | | G177D | | N184H | E200G | |
| | 142 | h | M174T | | | N184H | E200G | |
| 722 | 143 | a | | | | | E200G | |
| | 144 | b | | | | | E200G | |
| | 145 | c | | | S183N | N184H | E200G | |
| | 146 | d | | | | N184H | E200G | |
| | 147 | e | | | | | E200G | |
| | 148 | f | | | | N184H | E200G | |
| | 149 | g | | | | | E200G | |
| | 150 | h | | | | | E200G | |

| | | | | | | |
|---|---|---|---|---|---|---|
| 122 | 119 | a | Y210C | S224I | | |
| | 120 | b | Y210C | S224I | | |
| | 121 | c | | S224I | A232S | |
| | 122 | d | Y210C | S224I | | |
| | 123 | e | Y210C | S224I | | |
| | 124 | f | Y210C | S224I | | |
| | 125 | g | | S224I | A232S | |
| | 126 | h | Y210C | S224I | | |
| 720 | 127 | a | | S224I | A232S | |
| | 128 | b | | S224I | A232S | |
| | 129 | c | | S224I | A232S | L233F |
| | 130 | d | Y210C | S224I | | |
| | 131 | e | Y210C | S224I | | |
| | 132 | f | Y210C | S224I | | |
| | 133 | g | Y210C | S224I | | |
| | 134 | h | | S224I | A232S | |
| 721 | 135 | a | | S224I | A232S | |
| | 136 | b | | S224I | A232S | |
| | 137 | c | | S224I | A232S | |
| | 138 | d | | S224I | A232S | |
| | 139 | e | | S224I | A232S | |
| | 140 | f | Y210C | S224I | | |
| | 141 | g | | S224I | A232S | |
| | 142 | h | | S224I | A232S | |
| 722 | 143 | a | Y210C | S224I | | |
| | 144 | b | | S224I | A232S | |
| | 145 | c | | S224I | A232S | |
| | 146 | d | | S224I | A232S | |

TABLE 9-continued

| | | | | 3230 - Passage N | | |
|---|---|---|---|---|---|---|
| | 147 | e | Y210C | S224I | | |
| | 148 | f | | S224I | A232S | |
| | 149 | g | Y210C | S224I | | |
| | 150 | h | Y210C | S224I | | |
| 122 | 119 | a | R240L | | | |
| | 120 | b | R240L | | | |
| | 121 | c | R240L | | | |
| | 122 | d | R240L | | | E265V |
| | 123 | e | R240L | | | |
| | 124 | f | R240L | | | |
| | 125 | g | R240L | | | |
| | 126 | h | R240L | | | |
| 720 | 127 | a | R240L | | | |
| | 128 | b | R240L | | | |
| | 129 | c | R240L | | | |
| | 130 | d | R240L | | | |
| | 131 | e | R240L | | | |
| | 132 | f | R240L | | | |
| | 133 | g | R240L | | | |
| | 134 | h | R240L | | | |
| 721 | 135 | a | R240L | | | |
| | 136 | b | R240L | | | |
| | 137 | c | R240L | | | |
| | 138 | d | R240L | A253T | | |
| | 139 | e | R240L | | | |
| | 140 | f | R240L | | | |
| | 141 | g | R240L | | | |
| | 142 | h | R240L | | | |
| 722 | 143 | a | R240L | | | |
| | 144 | b | R240L | | | |
| | 145 | c | R240L | | | |
| | 146 | d | R240L | | | |
| | 147 | e | R240L | | | |
| | 148 | f | R240L | | | |
| | 149 | g | R240L | | | |
| | 150 | h | R240L | | | |
| 122 | 119 | a | F270V | | I292T | I297M |
| | 120 | b | F270V | | I292T | I297M |
| | 121 | c | | | | |
| | 122 | d | F270V | | | I297M |
| | 123 | e | F270V | | | I297M |
| | 124 | f | F270V | | | I297M |
| | 125 | g | | | | |
| | 126 | h | F270V | | | I297M |
| 720 | 127 | a | F270V | | | |
| | 128 | b | F270V | | | |
| | 129 | c | F270V | | | |
| | 130 | d | F270V | | | I297M |
| | 131 | e | F270V | | | I297M |
| | 132 | f | F270V | | | I297M |
| | 133 | g | F270V | I277V | | I297M |
| | 134 | h | | | | |
| 721 | 135 | a | | | | |
| | 136 | b | | | | |
| | 137 | c | | | | |
| | 138 | d | | | | |
| | 139 | e | | | | |
| | 140 | f | F270V | | | |
| | 141 | g | | | | |
| | 142 | h | | | | |
| 722 | 143 | a | F270V | | | I297M |
| | 144 | b | | | | |
| | 145 | c | | | | |
| | 146 | d | | | | |
| | 147 | e | F270V | | | I297M |
| | 148 | f | | | | |
| | 149 | g | F270V | | | I297M |
| | 150 | h | F270V | | | I297M |
| 122 | 119 | a | | | | S350G |
| | 120 | b | | | | S350G |
| | 121 | c | | N305S | | S350G |
| | 122 | d | | | | S350G |
| | 123 | e | | | | S350G |
| | 124 | f | | | | S350G |

TABLE 9-continued

| | | | | | | |
|---|---|---|---|---|---|---|
| 3230 - Passage N | | | | | | |
| | 125 | g | | | | S350G |
| | 126 | h | | | | S350G |
| 720 | 127 | a | | | | S350G |
| | 128 | b | | | | S350G |
| | 129 | c | | | | S350G |
| | 130 | d | | | | S350G |
| | 131 | e | | | | S350G |
| | 132 | f | | | | S350G |
| | 133 | g | | | | S350G |
| | 134 | h | | | | S350G |
| 721 | 135 | a | | | | S350G |
| | 136 | b | | | | S350G |
| | 137 | c | | | | S350G |
| | 138 | d | | | | S350G |
| | 139 | e | | | | S350G |
| | 140 | f | | | | S350G |
| | 141 | g | | | | S350G |
| | 142 | h | | | | S350G |
| 722 | 143 | a | | G325D | | S350G |
| | 144 | b | | | | S350G |
| | 145 | c | | | | S350G |
| | 146 | d | | | | S350G |
| | 147 | e | | | | S350G |
| | 148 | f | | | | S350G |
| | 149 | g | | | | S350G |
| | 150 | h | | | | S350G |
| 122 | 119 | a | | F360L | F369Y | Y372H | |
| | 120 | b | | F360L | F369Y | Y372H | |
| | 121 | c | | F360L | | Y372N | |
| | 122 | d | | F360L | | Y372H | |
| | 123 | e | | F360L | F369Y | Y372H | K376E |
| | 124 | f | | F360L | | Y372N | |
| | 125 | g | | F360L | | Y372N | |
| | 126 | h | | F360L | F369Y | Y372H | K376E |
| 720 | 127 | a | | F360L | | Y372N | |
| | 128 | b | | | | Y372N | |
| | 129 | c | | | | Y372N | |
| | 130 | d | | | F369Y | Y372H | K376E |
| | 131 | e | | | F369Y | Y372H | K376E |
| | 132 | f | | F360L | F369Y | Y372H | K376E |
| | 133 | g | | F360L | | Y372P | |
| | 134 | h | N358S | F360L | | Y372N | |
| 721 | 135 | a | | F360L | | Y372N | |
| | 136 | b | | F360L | | Y372N | |
| | 137 | c | | F360L | | Y372N | |
| | 138 | d | | F360L | | Y372N | |
| | 139 | e | | F360L | | Y372N | |
| | 140 | f | | F360L | | Y372H | |
| | 141 | g | | F360L | | Y372N | |
| | 142 | h | | F360L | | Y372N | |
| 722 | 143 | a | | F360L | | Y372H | |
| | 144 | b | | F360L | | Y372N | |
| | 145 | c | | F360L | | Y372N | |
| | 146 | d | | F360L | | Y372N | |
| | 147 | e | | F360L | | Y372H | |
| | 148 | f | | F360L | | Y372N | |
| | 149 | g | | F360L | | Y372H | |
| | 150 | h | | F360L | | Y372H | |
| 122 | 119 | a | | N396H | |
| | 120 | b | | N396H | |
| | 121 | c | L181M | N396H | P410L |
| | 122 | d | | N396H | |
| | 123 | e | | N396H | |
| | 124 | f | | N396H | |
| | 125 | g | | N396H | P410L |
| | 126 | h | | N396H | |
| 720 | 127 | a | | N396H | P410L |
| | 128 | b | | N396R | P410L |
| | 129 | c | | N396H | P410L |
| | 130 | d | | N396H | |
| | 131 | e | | N396H | |
| | 132 | f | | N396H | |
| | 133 | g | | N396H | |
| | 134 | h | | N396H | P410L |
| 721 | 135 | a | | N396H | P410L |
| | 136 | b | | N396H | P410L |

TABLE 9-continued

| | | | | | 3230 - Passage N | |
|---|---|---|---|---|---|---|
| | | 137 | c | | N396H | P410L |
| | | 138 | d | | N396H | P410L |
| | | 139 | e | | N396R | P410L |
| | | 140 | f | | N396H | |
| | | 141 | g | | N396H | P410L |
| | | 142 | h | | N396H | P410L |
| | 722 | 143 | a | | N396H | |
| | | 144 | b | | N396R | P410L |
| | | 145 | c | | N396H | P410L |
| | | 146 | d | | N396H | P410L |
| | | 147 | e | | N396H | |
| | | 148 | f | | N396H | P410L |
| | | 149 | g | | N396H | |
| | | 150 | h | | N396H | |
| 122 | | 119 | a | G420AWERKS | | |
| | | 120 | b | G420AWERKS | | |
| | | 121 | c | G420AWERKS | | |
| | | 122 | d | G420AWERKS | | |
| | | 123 | e | G420AWERKS | | |
| | | 124 | f | G420AWERKS] | | |
| | | 125 | g | G420AWLRKS | | |
| | | 126 | h | G420AWLRKS | | |
| | 720 | 127 | a | G420AWLRKS* | | |
| | | 128 | b | G420AWLRKS* | | |
| | | 129 | c | G420AWLRKS* | | |
| | | 130 | d | G420AWLRKS* | | |
| | | 131 | e | G420AWLRKS* | | |
| | | 132 | f | G420AWLRKS* | | |
| | | 133 | g | G420AWLRKS* | | |
| | | 134 | h | G420AWLRKS* | | |
| | 721 | 135 | a | G420AWLRKS* | | |
| | | 136 | b | G420AWLRKS* | | |
| | | 137 | c | G420ACLRKS* | | |
| | | 138 | d | G420AWLRKS* | | |
| | | 139 | e | G420AWLRKS* | | |
| | | 140 | f | G420AWLRKS* | | |
| | | 141 | g | G420AWLRKS* | | |
| | | 142 | h | G420AWLRKS* | | |
| | 722 | 143 | a | G420AWLRKS* | | |
| | | 144 | b | G420DWLRKS* | | |
| | | 145 | c | G420AWLRKS* | | |
| | | 146 | d | G420AWLRKS* | | |
| | | 147 | e | G420AWLRKS* | | |
| | | 148 | f | G420AWLRKS* | | |
| | | 149 | g | G420AWLRKS* | | |
| | | 150 | h | G420AWLRKS* | | |

TABLE 10

| | | | | | | X(4130)-Mutations, passage 15 | | | | |
|---|---|---|---|---|---|---|---|---|---|---|
| A.2 | | | | | | N144L | | A166E | T167I | |
| A.3 | | | | | | | | A166E | T167I | |
| A.4 | | | | | | | | A166E | T167I | |
| A.6 | | | | | | | | A166E | T167I | |
| B.1 | | | | | N143D | | N148T | A166E | T167I | |
| B.2 | | | | | | | | A166E | T167I | |
| B.3 | | | | | N143D | | N148T | A166E | T167I | |
| B.4 | | V98G | | E113K | N143D | | N148T | A166E | T167I | |
| B.5 | R23S | V98G | | | | | | A166E | T167I | |
| B.6 | | | | D133N | | | N148S | A166E | T167I | |
| B.7 | | | | | | | | A166E | T167I | I175V |
| B.8 | | V98G | E100D | | N143D | | N148T | A166E | T167I | |
| C.1 | | | | | | | | A166E | | |
| C.2 | | | | | N143D | | | A166E | | |
| C.3 | | | | | N143D | | | A166E | | |
| C.4 | | | | | N143D | | | A166E | | |
| C.5 | | | | | | | | A166E | T167I | |
| C.6 | | | | | | | N148T | A166E | T167A | |
| C.7 | | | | | N143D | | | A166E | | G169R |
| C.8 | | | | | N143D | | | A166E | | |

TABLE 10-continued

DVC(P5)-Mutations (prior to X(4130) PANCE selection)

| | | | | | | | | |
|---|---|---|---|---|---|---|---|---|
| A.1 | | V98G | E113K | Q150Q | A166E | S280L | | |
| A.2 | | | | | A166E | | | |
| A.3 | | | | | A166E | | S405L | R435L |
| A.4 | E68A | | | Q150L | A166E | | | |
| A.5 | | | | | A166E | | | |
| A.6 | | | | | A166E | | | |
| A.7 | | | | | A166E | | | R435L |
| A.8 | | V98G | E113K | | A166E | | | R435L |

X(4130)-Mutations, passage 15

| | | | | | | | | | | |
|---|---|---|---|---|---|---|---|---|---|---|
| A.2 | | | | | | | | | Y314S | |
| A.3 | | | | R257C | | | | | | Q322K |
| A.4 | | | | R257C | | | | | | Q322K |
| A.6 | | | | R257C | | | | | | Q322K |
| B.1 | | | | | | | | | Y314N | |
| B.2 | | | | | | | | | | Q322K |
| B.3 | | | | | | | | | Y314C | |
| B.4 | | | | | | | | | | |
| B.5 | | | | | | | | | | |
| B.6 | | | | | | | S279P | | | |
| B.7 | | | | | | | | | | |
| B.8 | | | | | | | S279P | | | |
| C.1 | | | | | | | | | | |
| C.2 | | | | R257C | L267I | L268I | | | | Q322K |
| C.3 | | | | | | | | | | |
| C.4 | | L225W | | R257C | L267I | L268I | | | | |
| C.5 | A218V | | | | | | | | | |
| C.6 | A218V | | N241I | | | | | K285N | | |
| C.7 | | | | | | | | | | |
| C.8 | | | | R257C | L267I | L268I | | | | |

DVC(P5)-Mutations (prior to X(4130) PANCE selection)

| |
|---|
| A.1 |
| A.2 |
| A.3 |
| A.4 |
| A.5 |
| A.6 |
| A.7 |
| A.8 |

| | C-terminus (Y434 onwards) |
|---|---|

X(4130)-Mutations, passage 15

| | | | | | | | | | C-terminus (Y434 onwards) |
|---|---|---|---|---|---|---|---|---|---|
| A.2 | | | | | | | | | |
| A.3 | | | | L364I | | S413F | | | YLNSKN |
| A.4 | | | | | | | | | |
| A.6 | | | | L364I | | S413F | | | |
| B.1 | | | | L364I | | | | | |
| B.2 | | | | L364V | | | | | TATQKTNN GDFQHGL ARP* |
| B.3 | | | | L364I | | | | | YLNSKN |
| B.4 | | V345E | | L364I | | | | | |
| B.5 | | | | | | | | | |
| B.6 | | | | | | | | | |
| B.7 | | | | L364I | S391G | | | | YLNSKN |
| B.8 | | | | | | | L416F | | |
| C.1 | | | | | | | | | YLNSKN |
| C.2 | | | S349F | L364I | | | | | |
| C.3 | | | | | | | | | AFTATQKS NNGDFQH GLAQP* |
| C.4 | T341P | | S349F | L364I | | | | R425L | |
| C.5 | | | | | | | | | AFTATQKS NNGDFQH GLAQP* |
| C.6 | | | | | | | | | |
| C.7 | | | | | | | | | |
| C.8 | | | S349F | L364I | | | | | |

DVC(P5)-Mutations (prior to X(4130) PANCE selection)

| |
|---|
| A.1 |
| A.2 |

TABLE 10-continued

| |
| --- |
| A.3 |
| A.4 |
| A.5 |
| A.6 |
| A.7 |
| A.8 |

TABLE 11

| | Residue Number | | | | | | | | | | | | |
| --- | --- | --- | --- | --- | --- | --- | --- | --- | --- | --- | --- | --- | --- |
| | 143 | 148 | 166 | 167 | 257 | 267 | 268 | 314 | 322 | 349 | 364 | 413 | 434 |
| Wild Type | N | N | A | T | R | L | L | Y | Q | S | L | S | YRNSKN* |
| A3 | | N | E | I | C | L | L | Y | K | S | I | F | YRNSKN* |
| B1 | D | T | E | I | R | L | L | N | Q | S | I | S | TATQKTNNGDFQHGLARP* |
| C2 | D | N | E | T | C | I | I | Y | K | F | I | S | AFTATQKSNNGDFQHGLAQP* |

| | Residue Number | | | | | |
| --- | --- | --- | --- | --- | --- | --- |
| | 143 | 148 | 166 | 167 | 314 | 364 |
| Wild Type | N | N | A | T | Y | L |
| B1* | D | T | E | I | N | I |

TABLE 12

X(5010) mutations

| | | | | | | | | | | | | | |
| --- | --- | --- | --- | --- | --- | --- | --- | --- | --- | --- | --- | --- | --- |
| A.1 | | | | | | N143D | | N164S | | Y168C | | | |
| A.2 | L3I | | | | | N143D | | N164S | | Y168C | | | |
| A.3 | | | I65V | | | N143D | | N164S | | Y168C | | | S223L |
| A.4 | | R26FS | | | | N143D | | N164S | | Y168C | | | |
| A.5 | | | | | A128V | N143D | | N164S | | Y168C | | | |
| A.7 | | | | | | N143D | | N164S | | Y168C | | | |
| B.1 | | | | | | N143D | | N164S | A166E | | P174T | A222S | |
| B.2 | | | | | | N143D | | N164S | A166E | | P174T | A222S | |
| B.3 | | | | | | N143D | | N164S | A166E | | P174T | A222S | |
| B.4 | | | | M71V | | N143D | | N164S | A166E | | P174T | A222S | |
| B.5 | | | | | | N143D | | N164S | A166E | | P174T | A222S | |
| B.6 | | | | | | N143D | | N164S | A166E | | P174T | A222S | |
| B.7 | | | | | | N143D | | N164S | A166E | | P174T | A222S | |
| C.1 | | | | | | | Q150K | N164D | | | | | |
| C.2 | | | | | | N143D | | N164S | A166E | | P174T | A222S | |
| C.3 | | | | | | | | N164E | | | | | |
| C.6 | | | | | | | | N164D | | | | | |
| C.7 | | | | | | | | N164D | | | | | |
| C.8 | | | | | | | | N164D | | | | | |

X(4253) mutations

| | | | | | | | | | | | |
| --- | --- | --- | --- | --- | --- | --- | --- | --- | --- | --- | --- |
| A.1 | N143D | | N164S | | P174I | | | | | | |
| A.2 | N143D | | N164S | Y168C | P174I | | | | | | |
| B.1 | N143D | | N164S | | P174T | A222S | T224I | S240N | K313R | | |
| B.2 | N143D | | N164S | | P174T | A222S | T224I | S240N | K313R | | |
| B.3 | N143D | | N164S | | P174T | A222S | T224I | S240N | K313R | | |
| C.1 | | Q150K | N164D | | | | | S240N | K313N | Q322E | L339F |
| C.2 | | | N164D | | | | | S240N | K313N | Q322E | L339F |
| C.3 | | | N164D | | | | | S240N | K313N | Q322E | L339F |
| C.4 | | | N164D | | | | | S240N | K313N | Q322E | L339F |

X(5010) mutations

| | | | | | | | | | |
| --- | --- | --- | --- | --- | --- | --- | --- | --- | --- |
| A.1 | T224I | S240K | Y294C | | Y314H | | | | C423Y |
| A.2 | T224I | S240K | Y294C | | | | | K410N | |
| A.3 | T224I | S240K | Y294C | | | | | | |
| A.4 | T224I | S240K | Y294C | | Y314H | | | | |
| A.5 | T224I | S240K | Y294C | | Y314H | | | | |
| A.7 | T224I | S240K | Y294C | | Y314H | L364F | | | |
| B.1 | T224I | S240K | | K313R | | | | | |
| B.2 | T224I | S240K | | K313R | | | | | |
| B.3 | T224I | S240K | | K313R | | | E366D | | |

TABLE 12-continued

| | | | | | | | |
|------|-------|------|-------|-------|-------|-------|-------|
| B.4 | T224I | S240K | | K313R | | | |
| B.5 | T224I | S240K | | K313R | | | |
| B.6 | T224I | S240K | | K313R | | | |
| B.7 | T224I | S240K | | K313R | | | |
| C.1 | T224I | S240K | | K313N | Q322E | L339F | |
| C.2 | T224I | S240K | | K313R | | | |
| C.3 | T224I | S240K | | K313N | Q322E | L339F | |
| C.6 | T224I | S240K | R257C | K313N | Q322E | L339F | L364F |
| C.7 | T224I | S240K | R257C | K313N | Q322E | L339F | L364F |
| C.8 | T224I | S240K | R257C | K313N | Q322E | L339F | L364F |
| | T224 | S240 | | | | | |

X(4253) mutations

A.1
A.2
B.1
B.2
B.3
C.1
C.2
C.3
C.4

TABLE 13

| | | | | | | | | | |
|------|-------|------|-------|------|------|------|------|-------|-------|
| A.1 | | Q27H | | | | | | S99A | G101S |
| A.2 | C26Y | Q27H | | | | | | S99A | G101S |
| A.3 | C26Y | Q27H | | | | | | S99A | G101S |
| A.4 | | Q27H | | | | | | S99A | G101S |
| A.5 | | Q27H | | | | | | S99A | G101S |
| A.6 | C26Y | Q27H | | | | D65G | | S99A | G101S |
| A.7 | | Q27H | | | | | | S99A | G101S |
| A.8 | | Q27H | | | | | | S99T | G101S |
| B.1 | | Q27H | | | | | | S99A | G101S |
| B.2 | C26Y | Q27H | | | | | | S99A | G101S |
| B.3 | C26Y | Q27H | | | | | | S99A | G101S |
| B.4 | C26Y | Q27H | | | | | E79D | S99A | G101S |
| B.5 | C26Y | Q27H | | | | | | S99A | G101S |
| B.6 | C26Y | Q27H | E28K | | | H56L | | S99A | G101S |
| B.7 | | Q27H | | | | | | S99A | G101S |
| B.8 | C26Y | Q27H | | | | H56L | | S99A | G101S |
| C.1 | | Q27H | | | | | | S99A | G101S |
| C.2 | C26Y | Q27H | | | G49S | | | S99A | G101S |
| C.3 | C26Y | Q27H | | | | | | S99A | G101S |
| C.4 | | Q27H | | | | H56Y | | S99A | G101S |
| C.5 | C26Y | Q27H | | | | | | S99A | G101S |
| C.5 | | Q27H | | I35V | | | | S99A | G101S |

| | | | | | | | | |
|------|-------|-------|-------|-------|------|-------|-------|-------|
| A.1 | I232T | | | | | | | Q354R |
| A.2 | I232T | | | N248K | | | | Q354R |
| A.3 | I232T | | | N248K | I262T | | | Q354W |
| A.4 | I232T | | | N248K | | | G353E | Q354R |
| A.5 | I232T | | | N248K | | | | Q354W |
| A.6 | I232T | | | N248K | | | | Q354R |
| A.7 | I232T | | | N248K | | I316T | | Q354W |
| A.8 | I232T | T242A | | N248K | | | | Q354R |
| B.1 | I232T | | | | | I316T | | Q354R |
| B.2 | I232T | | | N248K | I263V | | | Q354R |
| B.3 | I232T | | R244V | N248K | | | | Q354R |
| B.4 | I232T | | | N248K | | | | Q354R |
| B.5 | I232T | | | N248K | | | | Q354R |
| B.6 | I232T | | | N248K | | | | Q354R |
| B.7 | I232T | | | | | | | Q354R |
| B.8 | I232T | | | N248K | | | | Q354R |
| C.1 | I232T | | | N248K | | | | Q354R |
| C.2 | I232T | | | N248K | A313V | | | Q354R |
| C.3 | I232T | | | N248K | | | | Q354R |
| C.4 | I232T | | | N248K | | | | Q354R |
| C.5 | I232T | | | N248K | | | | Q354R |
| C.5 | I232T | | | N248K | | | | Q354W |

| | | | | | | | | |
|------|-------|-------|-------|-------|-------|-------|-------|
| A.1 | N118D | | E159L | N161Y | S162Q | S163R | M172K |
| A.2 | N118D | D156N | E159L | N161Y | S162Q | S163R | M172K |
| A.3 | N118D | D156N | E159L | N161Y | S162Q | S163R | M172K |
| A.4 | N118D | | E159L | N161Y | S162Q | S163R | M172K |
| A.5 | N118D | | E159L | N161Y | S162Q | S163R | M172K |
| A.6 | N118D | D156N | E159L | N161Y | S162Q | S163R | M172K |
| A.7 | N118D | D156N | E159L | N161Y | S162Q | S163R | M172K |

TABLE 13-continued

| | 118 | 156 | 159 | 161 | 162 | 163 | 166 | 172 | 203 |
|---|---|---|---|---|---|---|---|---|---|
| A.8 | N118D | D156N | E159L | N161Y | S162Q | S163R | | M172K | |
| B.1 | N118D | | E159L | N161Y | S162Q | S163R | | M172K | |
| B.2 | N118D | D156N | E159L | N161Y | S162Q | S163R | S166R | M172K | |
| B.3 | N118D | D156N | E159L | N161Y | S162Q | S163R | | M172K | |
| B.4 | N118D | D156N | E159L | N161Y | S162Q | S163R | | M172K | I203V |
| B.5 | N118D | D156N | E159L | N161Y | S162Q | S163R | | M172K | |
| B.6 | N118D | D156N | E159L | N161Y | S162Q | S163R | | M172K | |
| B.7 | N118D | | E159L | N161Y | S162Q | S163R | | M172K | |
| B.8 | N118D | D156N | E159L | N161Y | S162Q | S163R | | M172K | |
| C.1 | N118D | D156N | E159L | N161Y | S162Q | S163R | | M172K | |
| C.2 | N118D | D156N | E159L | N161Y | S162Q | S163R | | M172K | |
| C.3 | N118D | D156N | E159L | N161Y | S162Q | S163R | | M172K | |
| C.4 | N118D | D156N | E159L | N161Y | S162Q | S163R | | M172K | |
| C.5 | N118D | D156N | E159L | N161Y | S162Q | S163R | | M172K | |
| C.5 | N118D | D156N | E159L | N161Y | S162Q | S163R | | M172K | |

| | 355 | 357 | 359 | 365 | 367 | 390 | 403 | 404 |
|---|---|---|---|---|---|---|---|---|
| A.1 | | Y357Y | | | | | | L404* |
| A.2 | Y355P | Y357F | | | | | | |
| A.3 | | Y357F | | | | N390D | | |
| A.4 | Y355P | Y357F | | | | | | |
| A.5 | Y355P | Y357F | | | | N390D | | |
| A.6 | Y355P | Y357F | | | | | | L404* |
| A.7 | | Y357F | | | | | | |
| A.8 | Y355P | Y357F | | | | | | |
| B.1 | | Y357Y | | | | | | L404* |
| B.2 | Y355P | Y357F | | | S367F | | | |
| B.3 | Y355P | Y357F | K359R | | | | | |
| B.4 | Y355H | Y357F | | | | | | |
| B.5 | Y355P | Y357F | | | | | | |
| B.6 | Y355P | Y357F | | | | | | L404* |
| B.7 | | Y357Y | | | | | | |
| B.8 | Y355P | Y357F | | | | | | |
| C.1 | Y355P | Y357F | | | | | | L404* |
| C.2 | Y355P | Y357F | | | | | G403E | |
| C.3 | Y355P | Y357F | | | | | | |
| C.4 | Y355P | Y357F | | | | | | |
| C.5 | Y355P | Y357F | | | | | | L404* |
| C.5 | Y355P | Y357F | | N365S | | | | L404* |

TABLE 14

| | Residue Number | | | | | | | | | | | | | | | |
|---|---|---|---|---|---|---|---|---|---|---|---|---|---|---|---|---|
| | 26 | 27 | 99 | 101 | 118 | 156 | 159 | 161 | 162 | 163 | 172 | 232 | 248 | 354 | 355 | 357 |
| wild type | C | Q | S | G | N | D | E | N | S | S | M | I | N | Q | Y | Y |
| A.2 | | Y | H | A | S | D | N | L | Y | Q | R | K | T | K | R | P | F |

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

What is claimed is:

1. A protein comprising an amino acid sequence that is at least 90% identical to SEQ ID NO.: 6, wherein the protein comprises at least three amino acid mutations selected from the group consisting of R303H, T335S, S350G, I354V, S166Y, S167I, M174T, D175G, E200K, K31N, V106A, Y113D, E200G, R240L, V131G, S141T, N99S, R240C, F360L, G177D, N184H, R240F, Y113S, V131F, N184K, S69L, Y72H, K96N, N184T, S148N, I150V, A158P, L381M, N396H, P410L, Y372H, I412N, D414G, D418Y, Y372N, E423K, Y244C, V193M, Y372P, N165S, S224I, A281V, E66D, R41H, A232S, and V106A.

2. The protein of claim 1, wherein the protein comprises at least four amino acid mutations selected from the group consisting of R303H, T335S, S350G, I354V, S166Y, S167I, M174T, D175G, E200K, K31N, V106A, Y113D, E200G, R240L, V131G, S141T, N99S, R240C, F360L, G177D, N184H, R240F, Y113S, V131F, N184K, S69L, Y72H, K96N, N184T, S148N, I150V, A158P, L381M, N396H, P410L, Y372H, I412N, D414G, D418Y, Y372N, E423K, Y244C, V193M, Y372P, N165S, S224I, A281V, E66D, R41H, A232S, and V106A.

3. The protein of claim 1, wherein the protein comprises the amino acid sequence as set forth in any one of SEQ ID NOs.: 13-31.

4. The protein of claim 1, wherein the protein further comprises a neurotoxin HCC domain.

5. The protein of claim 4, wherein the HCC domain comprises SEQ ID NO.: 11.

6. The protein of claim 1, wherein the protein comprises at least three amino acid mutations selected from the group consisting of S69L, Y72H, V106A, S148N, I150V, A158P, S166Y, S167I, G177D, N184H, E200G, S224I, A232S, R240L, S350G, F360L, Y372N, L381M, N396H, and P410L.

7. A pharmaceutical composition comprising the protein of claim 1 and a pharmaceutically acceptable excipient.

8. The protein of claim 1, wherein the protein further comprises a neurotoxin translocation domain (HCN).

9. The protein of claim 8, wherein the HCN domain comprises SEQ ID NO.: 10.

10. The protein of claim 1, wherein the protein comprises the amino acid mutation S166Y.

11. The protein of claim 1, wherein the protein comprises at least three amino acid mutations selected from the group consisting of R41H, K96N, S166Y, R240L, R240C, Y372H, and D414G.

12. The protein of claim 1, wherein the protein comprises at least three amino acid mutations selected from the group consisting of S166Y, N184H, N184K, R240L, S350G, F360L, Y372H, P410L, and D414G.

13. The protein of claim 1, wherein the protein comprises at least three amino acid mutations selected from the group consisting of S166Y, N184K, R240L, S350G, F360L, Y372H, N396H, P410L, and E423K.

14. The protein of claim 1, wherein the protein comprises at least three amino acid mutations selected from the group consisting of V106A, N165S, S166Y, S167I, N184K, R240L, S350G, F360L, Y372H, N396H, P410L, and E423K.

15. The protein of claim 1, wherein the protein comprises at least three amino acid mutations selected from the group consisting of V106A, Y113D, Y113S, S166Y, S167I, N184H, N184K, N184S, E200K, R240L, Y244C, S350G, F360L, Y372H, N396H, P410L, and E423K.

16. The protein of claim 1, wherein the protein comprises at least three amino acid mutations selected from the group consisting of E66D, V106A, S166Y, S167I, D175G, N184K, E200G, S224I, R240L, R240F, T335S, S350G, F360L, Y372H, N396H, P410L, and D418Y.

17. The protein of claim 1, wherein the protein comprises at least three amino acid mutations selected from the group consisting of Y72H, N99S, V106A, V131G, S141T, S166Y, S167I, M174T, N184T, V193M, E200G, S224I, R240L, R240F, S350G, F360L, Y372H, N396H, and P410L.

18. The protein of claim 1, wherein the protein comprises at least three amino acid mutations selected from the group consisting of Y72H, V106A, V131G, S141T, S166Y, S167I, M174T, E200G, S224I, R240L, S350G, F360L, Y372H, N396H, and P410L.

19. A host cell comprising the protein of claim 1.

20. The host cell of claim 19, wherein the host cell is a bacterial cell, yeast cell, or mammalian cell.

* * * * *

SEQUENCE LISTING

```
<160> NUMBER OF SEQ ID NOS: 98

<210> SEQ ID NO 1
<211> LENGTH: 429
<212> TYPE: PRT
<213> ORGANISM: Artificial Sequence
<220> FEATURE:
<223> OTHER INFORMATION: Synthetic

<400> SEQUENCE: 1

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220
```

-continued

```
Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
                260                 265                 270

Phe Ile Asp Ser Leu Gln Glu Asn Glu Phe Arg Leu Tyr Tyr Tyr Asn
                275                 280                 285

Lys Phe Lys Asp Ile Ala Ser Thr Leu Asn Lys Ala Lys Ser Ile Val
        290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
                340                 345                 350

Asn Phe Val Lys Phe Phe Lys Val Leu Asn Arg Lys Thr Tyr Leu Asn
                355                 360                 365

Phe Asp Lys Ala Val Phe Lys Ile Asn Ile Val Pro Lys Val Asn Tyr
        370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu
                420                 425
```

```
<210> SEQ ID NO 2
<211> LENGTH: 436
<212> TYPE: PRT
<213> ORGANISM: Artificial Sequence
<220> FEATURE:
<223> OTHER INFORMATION: Synthetic

<400> SEQUENCE: 2
```

```
Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
                20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
        50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
                100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
        130                 135                 140

Pro Gly Glu Val Glu Arg Lys Lys Gly Ile Phe Ala Asn Leu Ile Ile
145                 150                 155                 160
```

```
Phe Gly Pro Gly Pro Val Leu Asn Glu Asn Glu Thr Ile Asp Ile Gly
            165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
            195                 200                 205

Asn Lys Gly Ala Ser Ile Phe Asn Arg Arg Gly Tyr Phe Ser Asp Pro
            210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
            245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
            275                 280                 285

Tyr Asp Lys Val Leu Gln Asn Phe Arg Gly Ile Val Asp Arg Leu Asn
            290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
            325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
            355                 360                 365

Thr Arg Ala Ser Tyr Phe Ser Asp Ser Leu Pro Pro Val Lys Ile Lys
            370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
            405                 410                 415

Asn Lys Gln Ala Tyr Glu Glu Ile Ser Lys Glu His Leu Ala Val Tyr
            420                 425                 430

Lys Ile Gln Met
            435

<210> SEQ ID NO 3
<211> LENGTH: 436
<212> TYPE: PRT
<213> ORGANISM: Artificial Sequence
<220> FEATURE:
<223> OTHER INFORMATION: Synthetic

<400> SEQUENCE: 3

Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
            20                  25                  30

Pro Glu Lys Ala Phe Arg Ile Thr Gly Asn Ile Trp Val Ile Pro Asp
            35                  40                  45

Arg Phe Ser Arg Asn Ser Asn Pro Asn Leu Asn Lys Pro Pro Arg Val
            50                  55                  60

Thr Ser Pro Lys Ser Gly Tyr Tyr Asp Pro Asn Tyr Leu Ser Thr Asp
65                  70                  75                  80
```

-continued

```
Ser Asp Lys Asp Thr Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
            115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
            195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
            275                 280                 285

Phe Glu Glu Lys Ala Leu Asp Tyr Tyr Arg Ser Ile Ala Lys Arg Leu
    290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
            340                 345                 350

Glu Leu Thr Gln Ile Phe Thr Glu Phe Asn Tyr Ala Lys Ile Tyr Asn
            355                 360                 365

Val Gln Asn Arg Lys Ile Tyr Leu Ser Asn Val Tyr Thr Pro Val Thr
    370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
            420                 425                 430

Phe Thr Lys Phe
            435
```

<210> SEQ ID NO 4
<211> LENGTH: 436
<212> TYPE: PRT
<213> ORGANISM: Artificial Sequence
<220> FEATURE:
<223> OTHER INFORMATION: Synthetic

<400> SEQUENCE: 4

-continued

```
Met Thr Trp Pro Val Lys Asp Phe Asn Tyr Ser Asp Pro Val Asn Asp
1               5                   10                  15

Asn Asp Ile Leu Tyr Leu Arg Ile Pro Gln Asn Lys Leu Ile Thr Thr
            20                  25                  30

Pro Val Lys Ala Phe Met Ile Thr Gln Asn Ile Trp Val Ile Pro Glu
            35                  40                  45

Arg Phe Ser Ser Asp Thr Asn Pro Ser Leu Ser Lys Pro Pro Arg Pro
        50                  55                  60

Thr Ser Lys Tyr Gln Ser Tyr Tyr Asp Pro Ser Tyr Leu Ser Thr Asp
65              70                  75                  80

Glu Gln Lys Asp Thr Phe Leu Lys Gly Ile Ile Lys Leu Phe Lys Arg
                85                  90                  95

Ile Asn Glu Arg Asp Ile Gly Lys Lys Leu Ile Asn Tyr Leu Val Val
            100                 105                 110

Gly Ser Pro Phe Met Gly Asp Ser Ser Thr Pro Glu Asp Thr Phe Asp
        115                 120                 125

Phe Thr Arg His Thr Thr Asn Ile Ala Val Glu Lys Phe Glu Asn Gly
    130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                165                 170                 175

Gln Gln Ser Asn Pro Ser Phe Glu Gly Phe Gly Thr Leu Ser Ile Leu
            180                 185                 190

Lys Val Ala Pro Glu Phe Leu Leu Thr Phe Ser Asp Val Thr Ser Asn
            195                 200                 205

Gln Ser Ser Ala Val Leu Gly Lys Ser Ile Phe Cys Met Asp Pro Val
    210                 215                 220

Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
                245                 250                 255

Phe Phe Ser Gln Asp Gly Pro Asn Val Gln Phe Glu Glu Leu Tyr Thr
            260                 265                 270

Phe Gly Gly Leu Asp Val Glu Ile Ile Pro Gln Ile Glu Arg Ser Gln
        275                 280                 285

Leu Arg Glu Lys Ala Leu Gly His Tyr Lys Asp Ile Ala Lys Arg Leu
    290                 295                 300

Asn Asn Ile Asn Lys Thr Ile Pro Ser Ser Trp Ile Ser Asn Ile Asp
305                 310                 315                 320

Lys Tyr Lys Lys Ile Phe Ser Glu Lys Tyr Asn Phe Asp Lys Asp Asn
                325                 330                 335

Thr Gly Asn Phe Val Val Asn Ile Asp Lys Phe Asn Ser Leu Tyr Ser
            340                 345                 350

Asp Leu Thr Asn Val Met Ser Glu Val Val Tyr Ser Ser Gln Tyr Asn
        355                 360                 365

Val Lys Asn Arg Thr His Tyr Phe Ser Arg His Tyr Leu Pro Val Phe
    370                 375                 380

Ala Asn Ile Leu Asp Asp Asn Ile Tyr Thr Ile Arg Asp Gly Phe Asn
385                 390                 395                 400

Leu Thr Asn Lys Gly Phe Asn Ile Glu Asn Ser Gly Gln Asn Ile Glu
                405                 410                 415
```

```
Arg Asn Pro Ala Leu Gln Lys Leu Ser Ser Glu Ser Val Val Asp Leu
            420                 425                 430

Phe Thr Lys Val
        435

<210> SEQ ID NO 5
<211> LENGTH: 411
<212> TYPE: PRT
<213> ORGANISM: Artificial Sequence
<220> FEATURE:
<223> OTHER INFORMATION: Synthetic

<400> SEQUENCE: 5

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
            85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln His Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
            165                 170                 175

Gly Phe Gly Ser Ile Ala Ile Val Thr Phe Ser Pro Glu Tyr Ser Phe
            180                 185                 190

Arg Phe Asn Asp Asn Ser Ile Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Thr Cys Ile Ile Thr Gln Gln Gln Asn Pro Leu
225                 230                 235                 240

Ile Thr Asn Arg Lys Gly Ile Asn Ile Glu Glu Phe Leu Thr Phe Gly
            245                 250                 255

Gly Asn Asp Leu Asn Ile Ile Thr Val Ala Gln Tyr Asn Asp Ile Tyr
            260                 265                 270

Thr Asn Leu Leu Asn Asp Tyr Arg Lys Ile Ala Ser Lys Leu Ser Lys
        275                 280                 285

Val Gln Val Ser Asn Pro Gln Leu Asn Pro Tyr Lys Asp Ile Phe Gln
    290                 295                 300

Glu Lys Tyr Gly Leu Asp Lys Asp Ala Ser Gly Ile Tyr Ser Val Asn
305                 310                 315                 320

Ile Asn Lys Phe Asp Asp Ile Leu Lys Lys Leu Tyr Ser Phe Thr Glu
            325                 330                 335
```

-continued

```
Phe Asp Leu Ala Thr Lys Phe Gln Val Lys Cys Arg Glu Thr Tyr Ile
        340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
    370                 375                 380

Arg Gly Gln Asn Ala Asn Leu Asn Pro Arg Ile Ile Lys Pro Ile Thr
385                 390                 395                 400

Gly Arg Gly Leu Val Lys Lys Ile Ile Arg Phe
                405                 410

<210> SEQ ID NO 6
<211> LENGTH: 428
<212> TYPE: PRT
<213> ORGANISM: Artificial Sequence
<220> FEATURE:
<223> OTHER INFORMATION: Synthetic

<400> SEQUENCE: 6

Met Pro Val Val Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
            20                  25                  30

Tyr Tyr Lys Ala Phe Glu Ile Met Arg Asn Val Trp Ile Ile Pro Glu
        35                  40                  45

Arg Asn Thr Ile Gly Thr Asp Pro Ser Asp Phe Asp Pro Pro Ala Ser
    50                  55                  60

Leu Glu Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Glu Val Leu Leu Gln Glu Ile Ser
            100                 105                 110

Tyr Ala Lys Pro Tyr Leu Gly Asn Glu His Thr Pro Ile Asn Glu Phe
        115                 120                 125

His Pro Val Thr Arg Thr Thr Ser Val Asn Ile Lys Ser Ser Thr Asn
        130                 135                 140

Val Lys Ser Ser Ile Ile Leu Asn Leu Leu Val Leu Gly Ala Gly Pro
145                 150                 155                 160

Asp Ile Phe Glu Asn Ser Ser Tyr Pro Val Arg Lys Leu Met Asp Ser
                165                 170                 175

Gly Gly Val Tyr Asp Pro Ser Asn Asp Gly Phe Gly Ser Ile Asn Ile
            180                 185                 190

Val Thr Phe Ser Pro Glu Tyr Glu Tyr Thr Phe Asn Asp Ile Ser Gly
            195                 200                 205

Gly Tyr Asn Ser Ser Thr Glu Ser Phe Ile Ala Asp Pro Ala Ile Ser
        210                 215                 220

Leu Ala His Glu Leu Ile His Ala Leu His Gly Leu Tyr Gly Ala Arg
225                 230                 235                 240

Gly Val Thr Tyr Lys Glu Thr Ile Lys Val Lys Gln Ala Pro Leu Met
                245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285
```

```
Asn Leu Leu Ala Asn Tyr Glu Lys Ile Ala Thr Arg Leu Ser Arg Val
    290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
            325                 330                 335

Asn Glu Asn Lys Phe Asn Glu Ile Tyr Lys Lys Leu Tyr Ser Phe Thr
            340                 345                 350

Glu Ile Asp Leu Ala Asn Lys Phe Lys Val Lys Cys Arg Asn Thr Tyr
            355                 360                 365

Phe Ile Lys Tyr Gly Phe Leu Lys Val Pro Asn Leu Leu Asp Asp Asp
    370                 375                 380

Ile Tyr Thr Val Ser Glu Gly Phe Asn Ile Gly Asn Leu Ala Val Asn
385                 390                 395                 400

Asn Arg Gly Gln Asn Ile Lys Leu Asn Pro Lys Ile Ile Asp Ser Ile
            405                 410                 415

Pro Asp Lys Gly Leu Val Glu Lys Ile Val Lys Phe
            420                 425
```

```
<210> SEQ ID NO 7
<211> LENGTH: 449
<212> TYPE: PRT
<213> ORGANISM: Artificial Sequence
<220> FEATURE:
<223> OTHER INFORMATION: Synthetic

<400> SEQUENCE: 7

Met Pro Val Asn Ile Lys Asn Phe Asn Tyr Asn Asp Pro Ile Asn Asn
1               5                   10                  15

Asp Asp Ile Ile Met Met Glu Pro Phe Asn Asp Pro Gly Pro Gly Thr
            20                  25                  30

Tyr Tyr Lys Ala Phe Arg Ile Ile Asp Arg Ile Trp Ile Val Pro Glu
            35                  40                  45

Arg Phe Thr Tyr Gly Phe Gln Pro Asp Gln Phe Asn Ala Ser Thr Gly
    50                  55                  60

Val Phe Ser Lys Asp Val Tyr Glu Tyr Tyr Asp Pro Thr Tyr Leu Lys
65                  70                  75                  80

Thr Asp Ala Glu Lys Asp Lys Phe Leu Lys Thr Met Ile Lys Leu Phe
            85                  90                  95

Asn Arg Ile Asn Ser Lys Pro Ser Gly Gln Arg Leu Leu Asp Met Ile
            100                 105                 110

Val Asp Ala Ile Pro Tyr Leu Gly Asn Ala Ser Thr Pro Pro Asp Lys
            115                 120                 125

Phe Ala Ala Asn Val Ala Asn Val Ser Ile Asn Lys Lys Ile Ile Gln
    130                 135                 140

Pro Gly Ala Glu Asp Gln Ile Lys Gly Leu Met Thr Asn Leu Ile Ile
145                 150                 155                 160

Phe Gly Pro Gly Pro Val Leu Ser Asp Asn Phe Thr Asp Ser Met Ile
            165                 170                 175

Met Asn Gly His Ser Pro Ile Ser Glu Gly Phe Gly Ala Arg Met Met
            180                 185                 190

Ile Arg Phe Cys Pro Ser Cys Leu Asn Val Phe Asn Asn Val Gln Glu
            195                 200                 205

Asn Lys Asp Thr Ser Ile Phe Ser Arg Arg Ala Tyr Phe Ala Asp Pro
    210                 215                 220
```

-continued

```
Ala Leu Thr Leu Met His Glu Leu Ile His Val Leu His Gly Leu Tyr
225                 230                 235                 240

Gly Ile Lys Ile Ser Asn Leu Pro Ile Thr Pro Asn Thr Lys Glu Phe
                245                 250                 255

Phe Met Gln His Ser Asp Pro Val Gln Ala Glu Glu Leu Tyr Thr Phe
                260                 265                 270

Gly Gly His Asp Pro Ser Val Ile Ser Pro Ser Thr Asp Met Asn Ile
                275                 280                 285

Tyr Asn Lys Ala Leu Gln Asn Phe Gln Asp Ile Ala Asn Arg Leu Asn
        290                 295                 300

Ile Val Ser Ser Ala Gln Gly Ser Gly Ile Asp Ile Ser Leu Tyr Lys
305                 310                 315                 320

Gln Ile Tyr Lys Asn Lys Tyr Asp Phe Val Glu Asp Pro Asn Gly Lys
                325                 330                 335

Tyr Ser Val Asp Lys Asp Lys Phe Asp Lys Leu Tyr Lys Ala Leu Met
                340                 345                 350

Phe Gly Phe Thr Glu Thr Asn Leu Ala Gly Glu Tyr Gly Ile Lys Thr
                355                 360                 365

Arg Tyr Ser Tyr Phe Ser Glu Tyr Leu Pro Pro Ile Lys Thr Glu Lys
        370                 375                 380

Leu Leu Asp Asn Thr Ile Tyr Thr Gln Asn Glu Gly Phe Asn Ile Ala
385                 390                 395                 400

Ser Lys Asn Leu Lys Thr Glu Phe Asn Gly Gln Asn Lys Ala Val Asn
                405                 410                 415

Lys Glu Ala Tyr Glu Glu Ile Ser Leu Glu His Leu Val Ile Tyr Arg
                420                 425                 430

Ile Ala Met Cys Lys Pro Val Met Tyr Lys Asn Ala Pro Pro Thr Pro
            435                 440                 445

Gly
```

```
<210> SEQ ID NO 8
<211> LENGTH: 439
<212> TYPE: PRT
<213> ORGANISM: Artificial Sequence
<220> FEATURE:
<223> OTHER INFORMATION: Synthetic

<400> SEQUENCE: 8

Met Lys Leu Glu Ile Asn Lys Phe Asn Tyr Asn Asp Pro Ile Asp Gly
1                   5                   10                  15

Ile Asn Val Ile Thr Met Arg Pro Pro Arg His Ser Asp Lys Ile Asn
                20                  25                  30

Lys Gly Lys Gly Pro Phe Lys Ala Phe Gln Val Ile Lys Asn Ile Trp
            35                  40                  45

Ile Val Pro Glu Arg Tyr Asn Phe Thr Asn Asn Thr Asn Asp Leu Asn
        50                  55                  60

Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
                85                  90                  95

Lys Val Leu Glu Arg Ile Lys Ser Lys Pro Glu Gly Glu Lys Leu Leu
                100                 105                 110

Glu Leu Ile Ser Ser Ser Ile Pro Leu Pro Leu Val Ser Asn Gly Ala
            115                 120                 125

Leu Thr Leu Ser Asp Asn Glu Thr Ile Ala Tyr Gln Glu Asn Asn Asn
```

-continued

```
            130                 135                 140

Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
                165                 170                 175

Asn Gly Glu Gly Thr Leu Ser Glu Val Ser Phe Ser Pro Phe Tyr Leu
                180                 185                 190

Lys Pro Phe Asp Glu Ser Tyr Gly Asn Tyr Arg Ser Leu Val Asn Ile
                195                 200                 205

Val Asn Lys Phe Val Lys Arg Glu Phe Ala Pro Asp Pro Ala Ser Thr
                210                 215                 220

Leu Met His Glu Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
                245                 250                 255

Arg Gln Gln Asn Ser Leu Ile Phe Glu Glu Leu Leu Thr Phe Gly Gly
                260                 265                 270

Ile Asp Ser Lys Ala Ile Ser Ser Leu Ile Ile Lys Lys Ile Ile Glu
                275                 280                 285

Thr Ala Lys Asn Asn Tyr Thr Thr Leu Ile Ser Glu Arg Leu Asn Thr
                290                 295                 300

Val Thr Val Glu Asn Asp Leu Leu Lys Tyr Ile Lys Asn Lys Ile Pro
305                 310                 315                 320

Val Gln Gly Arg Leu Gly Asn Phe Lys Leu Asp Thr Ala Glu Phe Glu
                325                 330                 335

Lys Lys Leu Asn Thr Ile Leu Phe Val Leu Asn Glu Ser Asn Leu Ala
                340                 345                 350

Gln Arg Phe Ser Ile Leu Val Arg Lys His Tyr Leu Lys Glu Arg Pro
                355                 360                 365

Ile Asp Pro Ile Tyr Val Asn Ile Leu Asp Asp Asn Ser Tyr Ser Thr
                370                 375                 380

Leu Glu Gly Phe Asn Ile Ser Ser Gln Gly Ser Asn Asp Phe Gln Gly
385                 390                 395                 400

Gln Leu Leu Glu Ser Ser Tyr Phe Glu Lys Ile Glu Ser Asn Ala Leu
                405                 410                 415

Arg Ala Phe Ile Lys Ile Cys Pro Arg Asn Gly Leu Leu Tyr Asn Ala
                420                 425                 430

Ile Tyr Arg Asn Ser Lys Asn
        435

<210> SEQ ID NO 9
<211> LENGTH: 428
<212> TYPE: PRT
<213> ORGANISM: Artificial Sequence
<220> FEATURE:
<223> OTHER INFORMATION: Synthetic

<400> SEQUENCE: 9

Met Pro Val Val Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
                20                  25                  30

Tyr Tyr Lys Ala Phe Glu Ile Met Arg Asn Val Trp Ile Ile Pro Glu
        35                  40                  45

Arg Asn Thr Ile Gly Thr Asp Pro Ser Asp Phe Asp Pro Pro Ala Ser
```

```
                    50                  55                  60

Leu Glu Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Glu Val Leu Leu Gln Glu Ile Ser
            100                 105                 110

Tyr Ala Lys Pro Tyr Leu Gly Asn Glu His Thr Pro Ile Asn Glu Phe
        115                 120                 125

His Pro Val Thr Arg Thr Thr Ser Val Asn Ile Lys Ser Ser Thr Asn
        130                 135                 140

Val Lys Ser Ser Ile Ile Leu Asn Leu Leu Val Leu Gly Ala Gly Pro
145                 150                 155                 160

Asp Ile Phe Glu Asn Ser Ser Tyr Pro Val Arg Lys Leu Met Asp Ser
            165                 170                 175

Gly Gly Val Tyr Asp Pro Ser Asn Asp Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly Tyr Asn Ser Ser Thr Glu Ser Phe Ile Ala Asp Pro Ala Ile Ser
    210                 215                 220

Leu Ala His Glu Leu Ile His Ala Leu His Gly Leu Tyr Gly Ala Arg
225                 230                 235                 240

Gly Val Thr Tyr Lys Glu Thr Ile Lys Val Lys Gln Ala Pro Leu Met
            245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285

Asn Leu Leu Ala Asn Tyr Glu Lys Ile Ala Thr Arg Leu Ser Arg Val
    290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
            325                 330                 335

Asn Glu Asn Lys Phe Asn Glu Ile Tyr Lys Lys Leu Tyr Ser Phe Thr
            340                 345                 350

Glu Ile Asp Leu Ala Asn Lys Phe Lys Val Lys Cys Arg Asn Thr Tyr
        355                 360                 365

Phe Ile Lys Tyr Gly Phe Leu Lys Val Pro Asn Leu Leu Asp Asp Asp
    370                 375                 380

Ile Tyr Thr Val Ser Glu Gly Phe Asn Ile Gly Asn Leu Ala Val Asn
385                 390                 395                 400

Asn Arg Gly Gln Asn Ile Lys Leu Asn Pro Lys Ile Ile Asp Ser Ile
            405                 410                 415

Pro Asp Lys Gly Leu Val Glu Lys Ile Val Lys Phe
            420                 425
```

<210> SEQ ID NO 10
<211> LENGTH: 431
<212> TYPE: PRT
<213> ORGANISM: Artificial Sequence
<220> FEATURE:
<223> OTHER INFORMATION: Synthetic -continued

<400> SEQUENCE: 10

```
Cys Lys Ser Val Ile Pro Arg Lys Gly Thr Lys Ala Pro Pro Arg Leu
1               5                   10                  15

Cys Ile Arg Val Asn Asn Arg Glu Leu Phe Phe Val Ala Ser Glu Ser
            20                  25                  30

Ser Tyr Asn Glu Asn Asp Ile Asn Thr Pro Lys Glu Ile Asp Asp Thr
            35                  40                  45

Thr Asn Leu Asn Asn Asn Tyr Arg Asn Asn Leu Asp Glu Val Ile Leu
    50                  55                  60

Asp Tyr Asn Ser Glu Thr Ile Pro Gln Ile Ser Asn Gln Thr Leu Asn
65                  70                  75                  80

Thr Leu Val Gln Asp Asp Ser Tyr Val Pro Arg Tyr Asp Ser Asn Gly
            85                  90                  95

Thr Ser Glu Ile Glu Glu His Asn Val Val Asp Leu Asn Val Phe Phe
            100                 105                 110

Tyr Leu His Ala Gln Lys Val Pro Glu Gly Glu Thr Asn Ile Ser Leu
            115                 120                 125

Thr Ser Ser Ile Asp Thr Ala Leu Ser Glu Glu Ser Gln Val Tyr Thr
    130                 135                 140

Phe Phe Ser Ser Glu Phe Ile Asn Thr Ile Asn Lys Pro Val His Ala
145                 150                 155                 160

Ala Leu Phe Ile Ser Trp Ile Asn Gln Val Ile Arg Asp Phe Thr Thr
            165                 170                 175

Glu Ala Thr Gln Lys Ser Thr Phe Asp Lys Ile Ala Asp Ile Ser Leu
            180                 185                 190

Val Val Pro Tyr Val Gly Leu Ala Leu Asn Ile Gly Asn Glu Val Gln
            195                 200                 205

Lys Glu Asn Phe Lys Glu Ala Phe Glu Leu Leu Gly Ala Gly Ile Leu
    210                 215                 220

Leu Glu Phe Val Pro Glu Leu Leu Ile Pro Thr Ile Leu Val Phe Thr
225                 230                 235                 240

Ile Lys Ser Phe Ile Gly Ser Ser Glu Asn Lys Asn Lys Ile Ile Lys
            245                 250                 255

Ala Ile Asn Asn Ser Leu Met Glu Arg Glu Thr Lys Trp Lys Glu Ile
            260                 265                 270

Tyr Ser Trp Ile Val Ser Asn Trp Leu Thr Arg Ile Asn Thr Gln Phe
            275                 280                 285

Asn Lys Arg Lys Glu Gln Met Tyr Gln Ala Leu Gln Asn Gln Val Asp
    290                 295                 300

Ala Ile Lys Thr Val Ile Glu Tyr Lys Tyr Asn Asn Tyr Thr Ser Asp
305                 310                 315                 320

Glu Arg Asn Arg Leu Glu Ser Glu Tyr Asn Ile Asn Asn Ile Arg Glu
            325                 330                 335

Glu Leu Asn Lys Lys Val Ser Leu Ala Met Glu Asn Ile Glu Arg Phe
            340                 345                 350

Ile Thr Glu Ser Ser Ile Phe Tyr Leu Met Lys Leu Ile Asn Glu Ala
            355                 360                 365

Lys Val Ser Lys Leu Arg Glu Tyr Asp Glu Gly Val Lys Glu Tyr Leu
    370                 375                 380

Leu Asp Tyr Ile Ser Glu His Arg Ser Ile Leu Gly Asn Ser Val Gln
385                 390                 395                 400

Glu Leu Asn Asp Leu Val Thr Ser Thr Leu Asn Asn Ser Ile Pro Phe
            405                 410                 415
```

```
Glu Leu Ser Ser Tyr Thr Asn Asp Lys Ile Leu Ile Leu Tyr Phe
        420                 425                 430

<210> SEQ ID NO 11
<211> LENGTH: 419
<212> TYPE: PRT
<213> ORGANISM: Artificial Sequence
<220> FEATURE:
<223> OTHER INFORMATION: Synthetic

<400> SEQUENCE: 11

Asn Lys Leu Tyr Lys Lys Ile Lys Asp Asn Ser Ile Leu Asp Met Arg
1               5                   10                  15

Tyr Glu Asn Asn Lys Phe Ile Asp Ile Ser Gly Tyr Gly Ser Asn Ile
            20                  25                  30

Ser Ile Asn Gly Asp Val Tyr Ile Tyr Ser Thr Asn Arg Asn Gln Phe
        35                  40                  45

Gly Ile Tyr Ser Ser Lys Pro Ser Glu Val Asn Ile Ala Gln Asn Asn
    50                  55                  60

Asp Ile Ile Tyr Asn Gly Arg Tyr Gln Asn Phe Ser Ile Ser Phe Trp
65                  70                  75                  80

Val Arg Ile Pro Lys Tyr Phe Asn Lys Val Asn Leu Asn Asn Glu Tyr
                85                  90                  95

Thr Ile Ile Asp Cys Ile Arg Asn Asn Asn Ser Gly Trp Lys Ile Ser
            100                 105                 110

Leu Asn Tyr Asn Lys Ile Ile Trp Thr Leu Gln Asp Thr Ala Gly Asn
        115                 120                 125

Asn Gln Lys Leu Val Phe Asn Tyr Thr Gln Met Ile Ser Ile Ser Asp
        130                 135                 140

Tyr Ile Asn Lys Trp Ile Phe Val Thr Ile Thr Asn Asn Arg Leu Gly
145                 150                 155                 160

Asn Ser Arg Ile Tyr Ile Asn Gly Asn Leu Ile Asp Glu Lys Ser Ile
                165                 170                 175

Ser Asn Leu Gly Asp Ile His Val Ser Asp Asn Ile Leu Phe Lys Ile
            180                 185                 190

Val Gly Cys Asn Asp Thr Arg Tyr Val Gly Ile Arg Tyr Phe Lys Val
        195                 200                 205

Phe Asp Thr Glu Leu Gly Lys Thr Glu Ile Glu Thr Leu Tyr Ser Asp
    210                 215                 220

Glu Pro Asp Pro Ser Ile Leu Lys Asp Phe Trp Gly Asn Tyr Leu Leu
225                 230                 235                 240

Tyr Asn Lys Arg Tyr Tyr Leu Leu Asn Leu Leu Arg Thr Asp Lys Ser
                245                 250                 255

Ile Thr Gln Asn Ser Asn Phe Leu Asn Ile Asn Gln Gln Arg Gly Val
            260                 265                 270

Tyr Gln Lys Pro Asn Ile Phe Ser Asn Thr Arg Leu Tyr Thr Gly Val
        275                 280                 285

Glu Val Ile Ile Arg Lys Asn Gly Ser Thr Asp Ile Ser Asn Thr Asp
    290                 295                 300

Asn Phe Val Arg Lys Asn Asp Leu Ala Tyr Ile Asn Val Val Asp Arg
305                 310                 315                 320

Asp Val Glu Tyr Arg Leu Tyr Ala Asp Ile Ser Ile Ala Lys Pro Glu
                325                 330                 335

Lys Ile Ile Lys Leu Ile Arg Thr Ser Asn Ser Asn Asn Ser Leu Gly
        340                 345                 350
```

-continued

```
Gln Ile Ile Val Met Asp Ser Ile Gly Asn Asn Cys Thr Met Asn Phe
        355                 360                 365

Gln Asn Asn Asn Gly Gly Asn Ile Gly Leu Leu Gly Phe His Ser Asn
    370                 375                 380

Asn Leu Val Ala Ser Ser Trp Tyr Tyr Asn Asn Ile Arg Lys Asn Thr
385                 390                 395                 400

Ser Ser Asn Gly Cys Phe Trp Ser Phe Ile Ser Lys Glu His Gly Trp
                405                 410                 415

Gln Glu Asn

<210> SEQ ID NO 12
<211> LENGTH: 428
<212> TYPE: PRT
<213> ORGANISM: Artificial Sequence
<220> FEATURE:
<223> OTHER INFORMATION: Synthetic

<400> SEQUENCE: 12

Met Pro Val Val Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
            20                  25                  30

Tyr Tyr Lys Ala Phe Glu Ile Met Arg Asn Val Trp Ile Ile Pro Glu
        35                  40                  45

Arg Asn Thr Ile Gly Thr Asp Pro Ser Asp Phe Asp Pro Pro Ala Ser
    50                  55                  60

Leu Glu Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Glu Val Leu Leu Gln Glu Ile Ser
            100                 105                 110

Tyr Ala Lys Pro Tyr Leu Gly Asn Glu His Thr Pro Ile Asn Glu Phe
        115                 120                 125

His Pro Val Thr Arg Thr Thr Ser Val Asn Ile Lys Ser Ser Thr Asn
    130                 135                 140

Val Lys Ser Ser Ile Ile Leu Asn Leu Leu Val Leu Gly Ala Gly Pro
145                 150                 155                 160

Asp Ile Phe Glu Asn Ser Ser Tyr Pro Val Arg Lys Leu Met Asp Ser
                165                 170                 175

Gly Gly Val Tyr Asp Pro Ser Asn Asp Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly Tyr Asn Ser Ser Thr Glu Ser Phe Ile Ala Asp Pro Ala Ile Ser
    210                 215                 220

Leu Ala His Glu Leu Ile His Ala Leu His Gly Leu Tyr Gly Ala Arg
225                 230                 235                 240

Gly Val Thr Tyr Lys Glu Thr Ile Lys Val Lys Gln Ala Pro Leu Met
                245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285
```

-continued

```
Asn Leu Leu Ala Asn Tyr Glu Lys Ile Ala Thr Arg Leu Ser Arg Val
    290             295             300

Asn Ser Ala Pro Pro Glu Tyr Asp Ile Asn Glu Tyr Lys Asp Tyr Phe
305             310             315             320

Gln Trp Lys Tyr Gly Leu Asp Lys Asn Ala Asp Gly Ser Tyr Thr Val
            325             330             335

Asn Glu Asn Lys Phe Asn Glu Ile Tyr Lys Lys Leu Tyr Ser Phe Thr
            340             345             350

Glu Ile Asp Leu Ala Asn Lys Phe Lys Val Lys Cys Arg Asn Thr Tyr
            355             360             365

Phe Ile Lys Tyr Gly Phe Leu Lys Val Pro Asn Leu Leu Asp Asp Asp
    370             375             380

Ile Tyr Thr Val Ser Glu Gly Phe Asn Ile Gly Asn Leu Ala Val Asn
385             390             395             400

Asn Arg Gly Gln Asn Ile Lys Leu Asn Pro Lys Ile Ile Asp Ser Ile
            405             410             415

Pro Asp Lys Gly Leu Val Glu Lys Ile Val Lys Phe
            420             425
```

```
<210> SEQ ID NO 13
<211> LENGTH: 428
<212> TYPE: PRT
<213> ORGANISM: Artificial Sequence
<220> FEATURE:
<223> OTHER INFORMATION: Synthetic

<400> SEQUENCE: 13
```

```
Met Pro Val Val Ile Asn Ser Phe Asn Tyr Asn Asp Pro Val Asn Asp
1               5               10              15

Asp Thr Ile Leu Tyr Met Gln Ile Pro Tyr Glu Glu Lys Ser Lys Lys
            20              25              30

Tyr Tyr Lys Ala Phe Glu Ile Met His Asn Val Trp Ile Ile Pro Glu
            35              40              45

Arg Asn Thr Ile Gly Thr Asp Pro Ser Asp Phe Asp Pro Pro Ala Ser
    50              55              60

Leu Glu Asn Gly Ser Ser Ala Tyr Tyr Asp Pro Asn Tyr Leu Thr Thr
65              70              75              80

Asp Ala Glu Lys Asp Arg Tyr Leu Lys Thr Thr Ile Lys Leu Phe Asn
            85              90              95

Arg Ile Asn Ser Asn Pro Ala Gly Glu Val Leu Leu Gln Glu Ile Ser
            100             105             110

Tyr Ala Lys Pro Tyr Leu Gly Asn Glu His Thr Pro Ile Asn Glu Phe
            115             120             125

His Pro Val Thr Arg Thr Thr Ser Val Asn Ile Lys Ser Ser Thr Asn
    130             135             140

Val Lys Ser Ser Ile Ile Leu Asn Leu Leu Val Leu Gly Ala Gly Pro
145             150             155             160

Asp Ile Phe Glu Asn Tyr Ser Tyr Pro Val Arg Lys Leu Met Asp Ser
            165             170             175

Gly Gly Val Tyr Asp Pro Ser Asn Asp Gly Phe Gly Ser Ile Asn Ile
            180             185             190

Val Thr Phe Ser Pro Glu Tyr Glu Tyr Thr Phe Asn Asp Ile Ser Gly
            195             200             205

Gly Tyr Asn Ser Ser Thr Glu Ser Phe Ile Ala Asp Pro Ala Ile Ser
    210             215             220
```

-continued

```
Leu Ala His Glu Leu Ile His Ala Leu His Gly Leu Tyr Gly Ala Leu
225                 230                 235                 240

Gly Val Thr Tyr Lys Glu Thr Ile Lys Val Lys Gln Ala Pro Leu Met
                245                 250                 255

Ile Ala Glu Lys Pro Ile Arg Leu Glu Glu Phe Leu Thr Phe Gly Gly
                260                 265                 270

Gln Asp Leu Asn Ile Ile Thr Ser Ala Met Lys Glu Lys Ile Tyr Asn
                275                 280                 285

Asn Leu Leu Ala Asn Tyr Glu Lys Ile Ala Thr Arg Leu Ser Arg Val
                290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
                340                 345                 350

Glu Ile Asp Leu Ala Asn Lys Phe Lys Val Lys Cys Arg Asn Thr Tyr
                355                 360                 365

Phe Ile Lys His Gly Phe Leu Lys Val Pro Asn Leu Leu Asp Asp Asp
                370                 375                 380

Ile Tyr Thr Val Ser Glu Gly Phe Asn Ile Gly Asn Leu Ala Val Asn
385                 390                 395                 400

Asn Arg Gly Gln Asn Ile Lys Leu Asn Pro Lys Ile Ile Gly Ser Ile
                405                 410                 415

Pro Asp Lys Gly Leu Val Glu Lys Ile Val Lys Phe
                420                 425

<210> SEQ ID NO 14
<211> LENGTH: 428
<212> TYPE: PRT
<213> ORGANISM: Artificial Sequence
<220> FEATURE:
<223> OTHER INFORMATION: Synthetic

<400> SEQUENCE: 14

Met Pro Val Val Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
                20                  25                  30

Tyr Tyr Lys Ala Phe Glu Ile Met His Asn Val Trp Ile Ile Pro Glu
                35                  40                  45

Arg Asn Thr Ile Gly Thr Asp Pro Ser Asp Phe Asp Pro Pro Ala Ser
        50                  55                  60

Leu Glu Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Asn
                85                  90                  95

Arg Ile Asn Ser Asn Pro Ala Gly Glu Val Leu Leu Gln Glu Ile Ser
                100                 105                 110

Tyr Ala Lys Pro Tyr Leu Gly Asn Glu His Thr Pro Ile Asn Glu Phe
                115                 120                 125

His Pro Val Thr Arg Thr Thr Ser Val Asn Ile Lys Ser Ser Thr Asn
        130                 135                 140

Val Lys Ser Ser Ile Ile Leu Asn Leu Leu Val Leu Gly Ala Gly Pro
145                 150                 155                 160
```

-continued

```
Asp Ile Phe Glu Asn Tyr Ser Tyr Pro Val Arg Lys Leu Met Asp Ser
            165                 170                 175

Gly Gly Val Tyr Asp Pro Ser Asn Asp Gly Phe Gly Ser Ile Asn Ile
            180                 185                 190

Val Thr Phe Ser Pro Glu Tyr Glu Tyr Thr Phe Asn Asp Ile Ser Gly
            195                 200                 205

Gly Tyr Asn Ser Ser Thr Glu Ser Phe Ile Ala Asp Pro Ala Ile Ser
        210                 215                 220

Leu Ala His Glu Leu Ile His Ala Leu His Gly Leu Tyr Gly Ala Cys
225                 230                 235                 240

Gly Val Thr Tyr Lys Glu Thr Ile Lys Val Lys Gln Ala Pro Leu Met
            245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285

Asn Leu Leu Ala Asn Tyr Glu Lys Ile Ala Thr Arg Leu Ser Arg Val
        290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
            325                 330                 335

Asn Glu Asn Lys Phe Asn Glu Ile Tyr Lys Lys Leu Tyr Ser Phe Thr
            340                 345                 350

Glu Ile Asp Leu Ala Asn Lys Phe Lys Val Lys Cys Arg Asn Thr Tyr
            355                 360                 365

Phe Ile Lys His Gly Phe Leu Lys Val Pro Asn Leu Leu Asp Asp Asp
        370                 375                 380

Ile Tyr Thr Val Ser Glu Gly Phe Asn Ile Gly Asn Leu Ala Val Asn
385                 390                 395                 400

Asn Arg Gly Gln Asn Ile Lys Leu Asn Pro Lys Ile Ile Gly Ser Ile
            405                 410                 415

Pro Asp Lys Gly Leu Val Glu Lys Ile Val Lys Phe
            420                 425
```

```
<210> SEQ ID NO 15
<211> LENGTH: 428
<212> TYPE: PRT
<213> ORGANISM: Artificial Sequence
<220> FEATURE:
<223> OTHER INFORMATION: Synthetic

<400> SEQUENCE: 15
```

```
Met Pro Val Val Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
            20                  25                  30

Tyr Tyr Lys Ala Phe Glu Ile Met Arg Asn Val Trp Ile Ile Pro Glu
            35                  40                  45

Arg Asn Thr Ile Gly Thr Asp Pro Ser Asp Phe Asp Pro Pro Ala Ser
        50                  55                  60

Leu Glu Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
            85                  90                  95
```

```
Arg Ile Asn Ser Asn Pro Ala Gly Glu Val Leu Leu Gln Glu Ile Ser
            100                 105                 110

Tyr Ala Lys Pro Tyr Leu Gly Asn Glu His Thr Pro Ile Asn Glu Phe
            115                 120                 125

His Pro Val Thr Arg Thr Thr Ser Val Asn Ile Lys Ser Ser Thr Asn
    130                 135                 140

Val Lys Ser Ser Ile Ile Leu Asn Leu Leu Val Leu Gly Ala Gly Pro
145                 150                 155                 160

Asp Ile Phe Glu Asn Tyr Ser Tyr Pro Val Arg Lys Leu Met Asp Ser
                165                 170                 175

Gly Gly Val Tyr Asp Pro Ser His Asp Gly Phe Gly Ser Ile Asn Ile
            180                 185                 190

Val Thr Phe Ser Pro Glu Tyr Glu Tyr Thr Phe Asn Asp Ile Ser Gly
            195                 200                 205

Gly Tyr Asn Ser Ser Thr Glu Ser Phe Ile Ala Asp Pro Ala Ile Ser
    210                 215                 220

Leu Ala His Glu Leu Ile His Ala Leu His Gly Leu Tyr Gly Ala Leu
225                 230                 235                 240

Gly Val Thr Tyr Lys Glu Thr Ile Lys Val Lys Gln Ala Pro Leu Met
                245                 250                 255

Ile Ala Glu Lys Pro Ile Arg Leu Glu Glu Phe Leu Thr Phe Gly Gly
                260                 265                 270

Gln Asp Leu Asn Ile Ile Thr Ser Ala Met Lys Glu Lys Ile Tyr Asn
            275                 280                 285

Asn Leu Leu Ala Asn Tyr Glu Lys Ile Ala Thr Arg Leu Ser Arg Val
    290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
            325                 330                 335

Asn Glu Asn Lys Gly Asn Glu Ile Tyr Lys Lys Leu Tyr Ser Phe Thr
            340                 345                 350

Glu Ile Asp Leu Ala Asn Lys Leu Lys Val Lys Cys Arg Asn Thr Tyr
            355                 360                 365

Phe Ile Lys His Gly Phe Leu Lys Val Pro Asn Leu Leu Asp Asp Asp
    370                 375                 380

Ile Tyr Thr Val Ser Glu Gly Phe Asn Ile Gly Asn Leu Ala Val Asn
385                 390                 395                 400

Asn Arg Gly Gln Asn Ile Lys Leu Asn Leu Lys Ile Ile Gly Ser Ile
            405                 410                 415

Pro Asp Lys Gly Leu Val Glu Lys Ile Val Lys Phe
            420                 425
```

<210> SEQ ID NO 16
<211> LENGTH: 428
<212> TYPE: PRT
<213> ORGANISM: Artificial Sequence
<220> FEATURE:
<223> OTHER INFORMATION: Synthetic

<400> SEQUENCE: 16

```
Met Pro Val Val Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
            20                  25                  30
```

-continued

```
Tyr Tyr Lys Ala Phe Glu Ile Met Arg Asn Val Trp Ile Ile Pro Glu
        35              40              45

Arg Asn Thr Ile Gly Thr Asp Pro Ser Asp Phe Asp Pro Pro Ala Ser
        50              55              60

Leu Glu Asn Gly Ser Ser Ala Tyr Tyr Asp Pro Asn Tyr Leu Thr Thr
65              70              75              80

Asp Ala Glu Lys Asp Arg Tyr Leu Lys Thr Thr Ile Lys Leu Phe Lys
                85              90              95

Arg Ile Asn Ser Asn Pro Ala Gly Glu Val Leu Leu Gln Glu Ile Ser
            100             105             110

Tyr Ala Lys Pro Tyr Leu Gly Asn Glu His Thr Pro Ile Asn Glu Phe
            115             120             125

His Pro Val Thr Arg Thr Thr Ser Val Asn Ile Lys Ser Ser Thr Asn
    130             135             140

Val Lys Ser Ser Ile Ile Leu Asn Leu Leu Val Leu Gly Ala Gly Pro
145             150             155             160

Asp Ile Phe Glu Asn Tyr Ser Tyr Pro Val Arg Lys Leu Met Asp Ser
                165             170             175

Gly Gly Val Tyr Asp Pro Ser Lys Asp Gly Phe Gly Ser Ile Asn Ile
            180             185             190

Val Thr Phe Ser Pro Glu Tyr Glu Tyr Thr Phe Asn Asp Ile Ser Gly
            195             200             205

Gly Tyr Asn Ser Ser Thr Glu Ser Phe Ile Ala Asp Pro Ala Ile Ser
    210             215             220

Leu Ala His Glu Leu Ile His Ala Leu His Gly Leu Tyr Gly Ala Leu
225             230             235             240

Gly Val Thr Tyr Lys Glu Thr Ile Lys Val Lys Gln Ala Pro Leu Met
            245             250             255

Ile Ala Glu Lys Pro Ile Arg Leu Glu Glu Phe Leu Thr Phe Gly Gly
            260             265             270

Gln Asp Leu Asn Ile Ile Thr Ser Ala Met Lys Glu Lys Ile Tyr Asn
        275             280             285

Asn Leu Leu Ala Asn Tyr Glu Lys Ile Ala Thr Arg Leu Ser Arg Val
    290             295             300

Asn Ser Ala Pro Pro Glu Tyr Asp Ile Asn Glu Tyr Lys Asp Tyr Phe
305             310             315             320

Gln Trp Lys Tyr Gly Leu Asp Lys Asn Ala Asp Gly Ser Tyr Thr Val
            325             330             335

Asn Glu Asn Lys Gly Asn Glu Ile Tyr Lys Lys Leu Tyr Ser Phe Thr
            340             345             350

Glu Ile Asp Leu Ala Asn Lys Leu Lys Val Lys Cys Arg Asn Thr Tyr
            355             360             365

Phe Ile Lys His Gly Phe Leu Lys Val Pro Asn Leu Leu Asp Asp Asp
    370             375             380

Ile Tyr Thr Val Ser Glu Gly Phe Asn Ile Gly Asn Leu Ala Val Asn
385             390             395             400

Asn Arg Gly Gln Asn Ile Lys Leu Asn Leu Lys Ile Ile Gly Ser Ile
            405             410             415

Pro Asp Lys Gly Leu Val Glu Lys Ile Val Lys Phe
            420             425
```

<210> SEQ ID NO 17
<211> LENGTH: 425
<212> TYPE: PRT

-continued

```
<213> ORGANISM: Artificial Sequence
<220> FEATURE:
<223> OTHER INFORMATION: Synthetic

<400> SEQUENCE: 17

Met Pro Val Val Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
                20                  25                  30

Tyr Tyr Lys Ala Phe Glu Ile Met Arg Asn Val Trp Ile Ile Pro Glu
            35                  40                  45

Arg Asn Thr Ile Gly Thr Asp Pro Ser Asp Phe Asp Pro Pro Ala Ser
        50                  55                  60

Leu Glu Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Glu Val Leu Leu Gln Glu Ile Ser
            100                 105                 110

Tyr Ala Lys Pro Tyr Leu Gly Asn Glu His Thr Pro Ile Asn Glu Phe
        115                 120                 125

His Pro Val Thr Arg Thr Thr Ser Val Asn Ile Lys Ser Ser Thr Asn
    130                 135                 140

Val Lys Ser Ser Ile Ile Leu Asn Leu Leu Val Leu Gly Ala Gly Pro
145                 150                 155                 160

Asp Ile Phe Glu Asn Tyr Ser Tyr Pro Val Arg Lys Leu Met Asp Ser
                165                 170                 175

Gly Gly Val Tyr Asp Pro Ser Lys Asp Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly Tyr Asn Ser Ser Thr Glu Ser Phe Ile Ala Asp Pro Ala Ile Ser
    210                 215                 220

Leu Ala His Glu Leu Ile His Ala Leu His Gly Leu Tyr Gly Ala Leu
225                 230                 235                 240

Gly Val Thr Tyr Lys Glu Thr Ile Lys Val Lys Gln Ala Pro Leu Met
                245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285

Asn Leu Leu Ala Asn Tyr Glu Lys Ile Ala Thr Arg Leu Ser Arg Val
    290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
            325                 330                 335

Asn Glu Asn Lys Gly Asn Glu Ile Tyr Lys Lys Leu Tyr Ser Phe Thr
        340                 345                 350

Glu Ile Asp Leu Ala Asn Lys Leu Lys Val Lys Cys Arg Asn Thr Tyr
        355                 360                 365

Phe Ile Lys His Gly Phe Leu Lys Val Pro Asn Leu Leu Asp Asp Asp
    370                 375                 380

Ile Tyr Thr Val Ser Glu Gly Phe Asn Ile Gly His Leu Ala Val Asn
```

```
385              390              395              400

Asn Arg Gly Gln Asn Ile Lys Leu Asn Leu Lys Ile Ile Asp Ser Ile
            405              410              415

Pro Asp Lys Ala Trp Leu Arg Lys Ser
            420              425

<210> SEQ ID NO 18
<211> LENGTH: 425
<212> TYPE: PRT
<213> ORGANISM: Artificial Sequence
<220> FEATURE:
<223> OTHER INFORMATION: Synthetic

<400> SEQUENCE: 18

Met Pro Val Val Ile Asn Ser Phe Asn Tyr Asn Asp Pro Val Asn Asp
1               5              10              15

Asp Thr Ile Leu Tyr Met Gln Ile Pro Tyr Glu Glu Lys Ser Lys Lys
            20              25              30

Tyr Tyr Lys Ala Phe Glu Ile Met Arg Asn Val Trp Ile Ile Pro Glu
        35              40              45

Arg Asn Thr Ile Gly Thr Asp Pro Ser Asp Phe Asp Pro Pro Ala Ser
    50              55              60

Leu Glu Asn Gly Ser Ser Ala Tyr Tyr Asp Pro Asn Tyr Leu Thr Thr
65              70              75              80

Asp Ala Glu Lys Asp Arg Tyr Leu Lys Thr Thr Ile Lys Leu Phe Lys
            85              90              95

Arg Ile Asn Ser Asn Pro Ala Gly Glu Ala Leu Leu Gln Glu Ile Ser
            100              105              110

Tyr Ala Lys Pro Tyr Leu Gly Asn Glu His Thr Pro Ile Asn Glu Phe
        115              120              125

His Pro Val Thr Arg Thr Thr Ser Val Asn Ile Lys Ser Ser Thr Asn
    130              135              140

Val Lys Ser Ser Ile Ile Leu Asn Leu Leu Val Leu Gly Ala Gly Pro
145              150              155              160

Asp Ile Phe Glu Ser Tyr Ile Tyr Pro Val Arg Lys Leu Met Asp Ser
            165              170              175

Gly Gly Val Tyr Asp Pro Ser Lys Asp Gly Phe Gly Ser Ile Asn Ile
            180              185              190

Val Thr Phe Ser Pro Glu Tyr Glu Tyr Thr Phe Asn Asp Ile Ser Gly
        195              200              205

Gly Tyr Asn Ser Ser Thr Glu Ser Phe Ile Ala Asp Pro Ala Ile Ser
    210              215              220

Leu Ala His Glu Leu Ile His Ala Leu His Gly Leu Tyr Gly Ala Leu
225              230              235              240

Gly Val Thr Tyr Lys Glu Thr Ile Lys Val Lys Gln Ala Pro Leu Met
            245              250              255

Ile Ala Glu Lys Pro Ile Arg Leu Glu Glu Phe Leu Thr Phe Gly Gly
            260              265              270

Gln Asp Leu Asn Ile Ile Thr Ser Ala Met Lys Glu Lys Ile Tyr Asn
        275              280              285

Asn Leu Leu Ala Asn Tyr Glu Lys Ile Ala Thr Arg Leu Ser Arg Val
    290              295              300

Asn Ser Ala Pro Pro Glu Tyr Asp Ile Asn Glu Tyr Lys Asp Tyr Phe
305              310              315              320

Gln Trp Lys Tyr Gly Leu Asp Lys Asn Ala Asp Gly Ser Tyr Thr Val
```

-continued

```
                  325             330             335
Asn Glu Asn Lys Gly Asn Glu Ile Tyr Lys Lys Leu Tyr Ser Phe Thr
              340             345             350

Glu Ile Asp Leu Ala Asn Lys Leu Lys Val Lys Cys Arg Asn Thr Tyr
          355             360             365

Phe Ile Lys His Gly Phe Leu Lys Val Pro Asn Leu Leu Asp Asp Asp
      370             375             380

Ile Tyr Thr Val Ser Glu Gly Phe Asn Ile Gly His Leu Ala Val Asn
385             390             395             400

Asn Arg Gly Gln Asn Ile Lys Leu Asn Leu Lys Ile Ile Asp Ser Ile
              405             410             415

Pro Asp Lys Ala Trp Leu Arg Lys Ser
              420             425

<210> SEQ ID NO 19
<211> LENGTH: 425
<212> TYPE: PRT
<213> ORGANISM: Artificial Sequence
<220> FEATURE:
<223> OTHER INFORMATION: Synthetic

<400> SEQUENCE: 19

Met Pro Val Val Ile Asn Ser Phe Asn Tyr Asn Asp Pro Val Asn Asp
1               5              10              15

Asp Thr Ile Leu Tyr Met Gln Ile Pro Tyr Glu Glu Lys Ser Lys Lys
              20              25              30

Tyr Tyr Lys Ala Phe Glu Ile Met Arg Asn Val Trp Ile Ile Pro Glu
          35              40              45

Arg Asn Thr Ile Gly Thr Asp Pro Ser Asp Phe Asp Pro Pro Ala Ser
      50              55              60

Leu Glu Asn Gly Ser Ser Ala Tyr Tyr Asp Pro Asn Tyr Leu Thr Thr
65              70              75              80

Asp Ala Glu Lys Asp Arg Tyr Leu Lys Thr Thr Ile Lys Leu Phe Lys
              85              90              95

Arg Ile Asn Ser Asn Pro Ala Gly Glu Ala Leu Leu Gln Glu Ile Ser
              100             105             110

Asp Ala Lys Pro Tyr Leu Gly Asn Glu His Thr Pro Ile Asn Glu Phe
          115             120             125

His Pro Val Thr Arg Thr Thr Ser Val Asn Ile Lys Ser Ser Thr Asn
      130             135             140

Val Lys Ser Ser Ile Ile Leu Asn Leu Leu Val Leu Gly Ala Gly Pro
145             150             155             160

Asp Ile Phe Glu Asn Tyr Ile Tyr Pro Val Arg Lys Leu Met Asp Ser
              165             170             175

Gly Gly Val Tyr Asp Pro Ser His Asp Gly Phe Gly Ser Ile Asn Ile
              180             185             190

Val Thr Phe Ser Pro Glu Tyr Lys Tyr Thr Phe Asn Asp Ile Ser Gly
          195             200             205

Gly Tyr Asn Ser Ser Thr Glu Ser Phe Ile Ala Asp Pro Ala Ile Ser
      210             215             220

Leu Ala His Glu Leu Ile His Ala Leu His Gly Leu Tyr Gly Ala Leu
225             230             235             240

Gly Val Thr Cys Lys Glu Thr Ile Lys Val Lys Gln Ala Pro Leu Met
              245             250             255

Ile Ala Glu Lys Pro Ile Arg Leu Glu Glu Phe Leu Thr Phe Gly Gly
```

-continued

```
              260                265                270
Gln Asp Leu Asn Ile Ile Thr Ser Ala Met Lys Glu Lys Ile Tyr Asn
          275                280                285

Asn Leu Leu Ala Asn Tyr Glu Lys Ile Ala Thr Arg Leu Ser Arg Val
      290                295                300

Asn Ser Ala Pro Pro Glu Tyr Asp Ile Asn Glu Tyr Lys Asp Tyr Phe
305                310                315                320

Gln Trp Lys Tyr Gly Leu Asp Lys Asn Ala Asp Gly Ser Tyr Thr Val
              325                330                335

Asn Glu Asn Lys Gly Asn Glu Ile Tyr Lys Lys Leu Tyr Ser Phe Thr
              340                345                350

Glu Ile Asp Leu Ala Asn Lys Leu Lys Val Lys Cys Arg Asn Thr Tyr
          355                360                365

Phe Ile Lys His Gly Phe Leu Lys Val Pro Asn Leu Leu Asp Asp Asp
          370                375                380

Ile Tyr Thr Val Ser Glu Gly Phe Asn Ile Gly His Leu Ala Val Asn
385                390                395                400

Asn Arg Gly Gln Asn Ile Lys Leu Asn Leu Lys Ile Ile Asp Ser Ile
              405                410                415

Pro Asp Lys Ala Trp Leu Arg Lys Ser
          420                425

<210> SEQ ID NO 20
<211> LENGTH: 425
<212> TYPE: PRT
<213> ORGANISM: Artificial Sequence
<220> FEATURE:
<223> OTHER INFORMATION: Synthetic

<400> SEQUENCE: 20

Met Pro Val Val Ile Asn Ser Phe Asn Tyr Asn Asp Pro Val Asn Asp
1                5                10                15

Asp Thr Ile Leu Tyr Met Gln Ile Pro Tyr Glu Glu Lys Ser Lys Lys
          20                25                30

Tyr Tyr Lys Ala Phe Glu Ile Met Arg Asn Val Trp Ile Ile Pro Glu
          35                40                45

Arg Asn Thr Ile Gly Thr Asp Pro Ser Asp Phe Asp Pro Pro Ala Ser
      50                55                60

Leu Glu Asn Gly Ser Ser Ala Tyr Tyr Asp Pro Asn Tyr Leu Thr Thr
65                70                75                80

Asp Ala Glu Lys Asp Arg Tyr Leu Lys Thr Thr Ile Lys Leu Phe Lys
              85                90                95

Arg Ile Asn Ser Asn Pro Ala Gly Glu Ala Leu Leu Gln Glu Ile Ser
          100                105                110

Asp Ala Lys Pro Tyr Leu Gly Asn Glu His Thr Pro Ile Asn Glu Phe
          115                120                125

His Pro Val Thr Arg Thr Thr Ser Val Asn Ile Lys Ser Ser Thr Asn
      130                135                140

Val Lys Ser Ser Ile Ile Leu Asn Leu Leu Val Leu Gly Ala Gly Pro
145                150                155                160

Asp Ile Phe Glu Asn Tyr Ile Tyr Pro Val Arg Lys Leu Met Asp Ser
              165                170                175

Gly Gly Val Tyr Asp Pro Ser Lys Asp Gly Phe Gly Ser Ile Asn Ile
              180                185                190

Val Thr Phe Ser Pro Glu Tyr Lys Tyr Thr Phe Asn Asp Ile Ser Gly
```

-continued

```
              195                 200                 205

Gly Tyr Asn Ser Ser Thr Glu Ser Phe Ile Ala Asp Pro Ala Ile Ser
    210                 215                 220

Leu Ala His Glu Leu Ile His Ala Leu His Gly Leu Tyr Gly Ala Leu
225                 230                 235                 240

Gly Val Thr Cys Lys Glu Thr Ile Lys Val Lys Gln Ala Pro Leu Met
                245                 250                 255

Ile Ala Glu Lys Pro Ile Arg Leu Glu Glu Phe Leu Thr Phe Gly Gly
                260                 265                 270

Gln Asp Leu Asn Ile Ile Thr Ser Ala Met Lys Glu Lys Ile Tyr Asn
                275                 280                 285

Asn Leu Leu Ala Asn Tyr Glu Lys Ile Ala Thr Arg Leu Ser Arg Val
    290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Gly Asn Glu Ile Tyr Lys Lys Leu Tyr Ser Phe Thr
                340                 345                 350

Glu Ile Asp Leu Ala Asn Lys Leu Lys Val Lys Cys Arg Asn Thr Tyr
                355                 360                 365

Phe Ile Lys His Gly Phe Leu Lys Val Pro Asn Leu Leu Asp Asp Asp
    370                 375                 380

Ile Tyr Thr Val Ser Glu Gly Phe Asn Ile Gly His Leu Ala Val Asn
385                 390                 395                 400

Asn Arg Gly Gln Asn Ile Lys Leu Asn Leu Lys Ile Ile Asp Ser Ile
                405                 410                 415

Pro Asp Lys Ala Trp Leu Arg Lys Ser
                420                 425
```

<210> SEQ ID NO 21
<211> LENGTH: 425
<212> TYPE: PRT
<213> ORGANISM: Artificial Sequence
<220> FEATURE:
<223> OTHER INFORMATION: Synthetic

<400> SEQUENCE: 21

```
Met Pro Val Val Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
                20                  25                  30

Tyr Tyr Lys Ala Phe Glu Ile Met Arg Asn Val Trp Ile Ile Pro Glu
            35                  40                  45

Arg Asn Thr Ile Gly Thr Asp Pro Ser Asp Phe Asp Pro Pro Ala Ser
    50                  55                  60

Leu Glu Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Glu Ala Leu Leu Gln Glu Ile Ser
                100                 105                 110

Asp Ala Lys Pro Tyr Leu Gly Asn Glu His Thr Pro Ile Asn Glu Phe
            115                 120                 125

His Pro Val Thr Arg Thr Thr Ser Val Asn Ile Lys Ser Ser Thr Asn
```

-continued

```
                130              135                140

Val Lys Ser Ser Ile Ile Leu Asn Leu Leu Val Leu Gly Ala Gly Pro
145                 150                155                160

Asp Ile Phe Glu Asn Tyr Ile Tyr Pro Val Arg Lys Leu Met Asp Ser
                165              170                175

Gly Gly Val Tyr Asp Pro Ser Ser Asp Gly Phe Gly Ser Ile Asn Ile
            180              185                190

Val Thr Phe Ser Pro Glu Tyr Lys Tyr Thr Phe Asn Asp Ile Ser Gly
        195              200                205

Gly Tyr Asn Ser Ser Thr Glu Ser Phe Ile Ala Asp Pro Ala Ile Ser
    210              215                220

Leu Ala His Glu Leu Ile His Ala Leu His Gly Leu Tyr Gly Ala Leu
225                 230                235                240

Gly Val Thr Cys Lys Glu Thr Ile Lys Val Lys Gln Ala Pro Leu Met
                245              250                255

Ile Ala Glu Lys Pro Ile Arg Leu Glu Glu Phe Leu Thr Phe Gly Gly
            260              265                270

Gln Asp Leu Asn Ile Ile Thr Ser Ala Met Lys Glu Lys Ile Tyr Asn
            275              280                285

Asn Leu Leu Ala Asn Tyr Glu Lys Ile Ala Thr Arg Leu Ser Arg Val
    290              295                300

Asn Ser Ala Pro Pro Glu Tyr Asp Ile Asn Glu Tyr Lys Asp Tyr Phe
305                 310                315                320

Gln Trp Lys Tyr Gly Leu Asp Lys Asn Ala Asp Gly Ser Tyr Thr Val
            325              330                335

Asn Glu Asn Lys Gly Asn Glu Ile Tyr Lys Lys Leu Tyr Ser Phe Thr
            340              345                350

Glu Ile Asp Leu Ala Asn Lys Leu Lys Val Lys Cys Arg Asn Thr Tyr
            355              360                365

Phe Ile Lys His Gly Phe Leu Lys Val Pro Asn Leu Leu Asp Asp Asp
    370              375                380

Ile Tyr Thr Val Ser Glu Gly Phe Asn Ile Gly His Leu Ala Val Asn
385                 390                395                400

Asn Arg Gly Gln Asn Ile Lys Leu Asn Leu Lys Ile Ile Asp Ser Ile
            405              410                415

Pro Asp Lys Ala Trp Leu Arg Lys Ser
            420              425

<210> SEQ ID NO 22
<211> LENGTH: 425
<212> TYPE: PRT
<213> ORGANISM: Artificial Sequence
<220> FEATURE:
<223> OTHER INFORMATION: Synthetic

<400> SEQUENCE: 22

Met Pro Val Val Ile Asn Ser Phe Asn Tyr Asn Asp Pro Val Asn Asp
1               5                10                15

Asp Thr Ile Leu Tyr Met Gln Ile Pro Tyr Glu Glu Lys Ser Lys Lys
            20              25                30

Tyr Tyr Lys Ala Phe Glu Ile Met Arg Asn Val Trp Ile Ile Pro Glu
        35              40                45

Arg Asn Thr Ile Gly Thr Asp Pro Ser Asp Phe Asp Pro Pro Ala Ser
    50              55                60

Leu Glu Asn Gly Ser Ser Ala Tyr Tyr Asp Pro Asn Tyr Leu Thr Thr
```

```
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Glu Ala Leu Leu Gln Glu Ile Ser
            100                 105                 110

Ser Ala Lys Pro Tyr Leu Gly Asn Glu His Thr Pro Ile Asn Glu Phe
            115                 120                 125

His Pro Val Thr Arg Thr Thr Ser Val Asn Ile Lys Ser Ser Thr Asn
        130                 135                 140

Val Lys Ser Ser Ile Ile Leu Asn Leu Leu Val Leu Gly Ala Gly Pro
145                 150                 155                 160

Asp Ile Phe Glu Asn Tyr Ile Tyr Pro Val Arg Lys Leu Met Asp Ser
                165                 170                 175

Gly Gly Val Tyr Asp Pro Ser His Asp Gly Phe Gly Ser Ile Asn Ile
            180                 185                 190

Val Thr Phe Ser Pro Glu Tyr Lys Tyr Thr Phe Asn Asp Ile Ser Gly
            195                 200                 205

Gly Tyr Asn Ser Ser Thr Glu Ser Phe Ile Ala Asp Pro Ala Ile Ser
        210                 215                 220

Leu Ala His Glu Leu Ile His Ala Leu His Gly Leu Tyr Gly Ala Leu
225                 230                 235                 240

Gly Val Thr Cys Lys Glu Thr Ile Lys Val Lys Gln Ala Pro Leu Met
                245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
            275                 280                 285

Asn Leu Leu Ala Asn Tyr Glu Lys Ile Ala Thr Arg Leu Ser Arg Val
        290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Gly Asn Glu Ile Tyr Lys Lys Leu Tyr Ser Phe Thr
            340                 345                 350

Glu Ile Asp Leu Ala Asn Lys Leu Lys Val Lys Cys Arg Asn Thr Tyr
            355                 360                 365

Phe Ile Lys His Gly Phe Leu Lys Val Pro Asn Leu Leu Asp Asp Asp
        370                 375                 380

Ile Tyr Thr Val Ser Glu Gly Phe Asn Ile Gly His Leu Ala Val Asn
385                 390                 395                 400

Asn Arg Gly Gln Asn Ile Lys Leu Asn Leu Lys Ile Ile Asp Ser Ile
                405                 410                 415

Pro Asp Lys Ala Trp Leu Arg Lys Ser
            420                 425
```

<210> SEQ ID NO 23
<211> LENGTH: 425
<212> TYPE: PRT
<213> ORGANISM: Artificial Sequence
<220> FEATURE:
<223> OTHER INFORMATION: Synthetic

<400> SEQUENCE: 23

```
Met Pro Val Val Ile Asn Ser Phe Asn Tyr Asn Asp Pro Val Asn Asp
```

```
1               5               10              15

Asp Thr Ile Leu Tyr Met Gln Ile Pro Tyr Glu Glu Lys Ser Lys Lys
            20              25              30

Tyr Tyr Lys Ala Phe Glu Ile Met Arg Asn Val Trp Ile Ile Pro Glu
            35              40              45

Arg Asn Thr Ile Gly Thr Asp Pro Ser Asp Phe Asp Pro Pro Ala Ser
    50              55              60

Leu Glu Asn Gly Ser Ser Ala Tyr Tyr Asp Pro Asn Tyr Leu Thr Thr
65              70              75              80

Asp Ala Glu Lys Asp Arg Tyr Leu Lys Thr Thr Ile Lys Leu Phe Lys
                85              90              95

Arg Ile Asn Ser Asn Pro Ala Gly Glu Ala Leu Leu Gln Glu Ile Ser
            100             105             110

Ser Ala Lys Pro Tyr Leu Gly Asn Glu His Thr Pro Ile Asn Glu Phe
            115             120             125

His Pro Val Thr Arg Thr Thr Ser Val Asn Ile Lys Ser Ser Thr Asn
    130             135             140

Val Lys Ser Ser Ile Ile Leu Asn Leu Leu Val Leu Gly Ala Gly Pro
145             150             155             160

Asp Ile Phe Glu Asn Tyr Ile Tyr Pro Val Arg Lys Leu Met Asp Ser
                165             170             175

Gly Gly Val Tyr Asp Pro Ser Lys Asp Gly Phe Gly Ser Ile Asn Ile
            180             185             190

Val Thr Phe Ser Pro Glu Tyr Lys Tyr Thr Phe Asn Asp Ile Ser Gly
            195             200             205

Gly Tyr Asn Ser Ser Thr Glu Ser Phe Ile Ala Asp Pro Ala Ile Ser
    210             215             220

Leu Ala His Glu Leu Ile His Ala Leu His Gly Leu Tyr Gly Ala Leu
225             230             235             240

Gly Val Thr Cys Lys Glu Thr Ile Lys Val Lys Gln Ala Pro Leu Met
                245             250             255

Ile Ala Glu Lys Pro Ile Arg Leu Glu Glu Phe Leu Thr Phe Gly Gly
            260             265             270

Gln Asp Leu Asn Ile Ile Thr Ser Ala Met Lys Glu Lys Ile Tyr Asn
            275             280             285

Asn Leu Leu Ala Asn Tyr Glu Lys Ile Ala Thr Arg Leu Ser Arg Val
    290             295             300

Asn Ser Ala Pro Pro Glu Tyr Asp Ile Asn Glu Tyr Lys Asp Tyr Phe
305             310             315             320

Gln Trp Lys Tyr Gly Leu Asp Lys Asn Ala Asp Gly Ser Tyr Thr Val
            325             330             335

Asn Glu Asn Lys Gly Asn Glu Ile Tyr Lys Lys Leu Tyr Ser Phe Thr
            340             345             350

Glu Ile Asp Leu Ala Asn Lys Leu Lys Val Lys Cys Arg Asn Thr Tyr
            355             360             365

Phe Ile Lys His Gly Phe Leu Lys Val Pro Asn Leu Leu Asp Asp Asp
    370             375             380

Ile Tyr Thr Val Ser Glu Gly Phe Asn Ile Gly His Leu Ala Val Asn
385             390             395             400

Asn Arg Gly Gln Asn Ile Lys Leu Asn Leu Lys Ile Ile Asp Ser Ile
            405             410             415

Pro Asp Lys Ala Trp Leu Arg Lys Ser
            420             425
```

```
<210> SEQ ID NO 24
<211> LENGTH: 425
<212> TYPE: PRT
<213> ORGANISM: Artificial Sequence
<220> FEATURE:
<223> OTHER INFORMATION: Synthetic

<400> SEQUENCE: 24

Met Pro Val Val Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
                20                  25                  30

Tyr Tyr Lys Ala Phe Glu Ile Met Arg Asn Val Trp Ile Ile Pro Glu
            35                  40                  45

Arg Asn Thr Ile Gly Thr Asp Pro Ser Asp Phe Asp Pro Pro Ala Ser
        50                  55                  60

Leu Glu Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Glu Ala Leu Leu Gln Glu Ile Ser
            100                 105                 110

Ser Ala Lys Pro Tyr Leu Gly Asn Glu His Thr Pro Ile Asn Glu Phe
            115                 120                 125

His Pro Val Thr Arg Thr Thr Ser Val Asn Ile Lys Ser Ser Thr Asn
        130                 135                 140

Val Lys Ser Ser Ile Ile Leu Asn Leu Leu Val Leu Gly Ala Gly Pro
145                 150                 155                 160

Asp Ile Phe Glu Asn Tyr Ile Tyr Pro Val Arg Lys Leu Met Asp Ser
                165                 170                 175

Gly Gly Val Tyr Asp Pro Ser Ser Asp Gly Phe Gly Ser Ile Asn Ile
            180                 185                 190

Val Thr Phe Ser Pro Glu Tyr Lys Tyr Thr Phe Asn Asp Ile Ser Gly
            195                 200                 205

Gly Tyr Asn Ser Ser Thr Glu Ser Phe Ile Ala Asp Pro Ala Ile Ser
        210                 215                 220

Leu Ala His Glu Leu Ile His Ala Leu His Gly Leu Tyr Gly Ala Leu
225                 230                 235                 240

Gly Val Thr Cys Lys Glu Thr Ile Lys Val Lys Gln Ala Pro Leu Met
                245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
            275                 280                 285

Asn Leu Leu Ala Asn Tyr Glu Lys Ile Ala Thr Arg Leu Ser Arg Val
        290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Gly Asn Glu Ile Tyr Lys Lys Leu Tyr Ser Phe Thr
            340                 345                 350

Glu Ile Asp Leu Ala Asn Lys Leu Lys Val Lys Cys Arg Asn Thr Tyr
            355                 360                 365
```

```
Phe Ile Lys His Gly Phe Leu Lys Val Pro Asn Leu Leu Asp Asp Asp
    370             375             380

Ile Tyr Thr Val Ser Glu Gly Phe Asn Ile Gly His Leu Ala Val Asn
385             390             395             400

Asn Arg Gly Gln Asn Ile Lys Leu Asn Leu Lys Ile Ile Asp Ser Ile
            405             410             415

Pro Asp Lys Ala Trp Leu Arg Lys Ser
            420             425

<210> SEQ ID NO 25
<211> LENGTH: 425
<212> TYPE: PRT
<213> ORGANISM: Artificial Sequence
<220> FEATURE:
<223> OTHER INFORMATION: Synthetic

<400> SEQUENCE: 25

Met Pro Val Val Ile Asn Ser Phe Asn Tyr Asn Asp Pro Val Asn Asp
1               5               10              15

Asp Thr Ile Leu Tyr Met Gln Ile Pro Tyr Glu Glu Lys Ser Lys Lys
            20              25              30

Tyr Tyr Lys Ala Phe Glu Ile Met Arg Asn Val Trp Ile Ile Pro Glu
            35              40              45

Arg Asn Thr Ile Gly Thr Asp Pro Ser Asp Phe Asp Pro Pro Ala Ser
    50              55              60

Leu Asp Asn Gly Ser Ser Ala Tyr Tyr Asp Pro Asn Tyr Leu Thr Thr
65              70              75              80

Asp Ala Glu Lys Asp Arg Tyr Leu Lys Thr Thr Ile Lys Leu Phe Lys
            85              90              95

Arg Ile Asn Ser Asn Pro Ala Gly Glu Ala Leu Leu Gln Glu Ile Ser
            100             105             110

Tyr Ala Lys Pro Tyr Leu Gly Asn Glu His Thr Pro Ile Asn Glu Phe
            115             120             125

His Pro Val Thr Arg Thr Thr Ser Val Asn Ile Lys Ser Ser Thr Asn
    130             135             140

Val Lys Ser Ser Ile Ile Leu Asn Leu Leu Val Leu Gly Ala Gly Pro
145             150             155             160

Asp Ile Phe Glu Asn Tyr Ile Tyr Pro Val Arg Lys Leu Met Gly Ser
            165             170             175

Gly Gly Val Tyr Asp Pro Ser Lys Asp Gly Phe Gly Ser Ile Asn Ile
            180             185             190

Val Thr Phe Ser Pro Glu Tyr Gly Tyr Thr Phe Asn Asp Ile Ser Gly
            195             200             205

Gly Tyr Asn Ser Ser Thr Ile Ser Phe Ile Ala Asp Pro Ala Ile Ser
            210             215             220

Leu Ala His Glu Leu Ile His Ala Leu His Gly Leu Tyr Gly Ala Leu
225             230             235             240

Gly Val Thr Tyr Lys Glu Thr Ile Lys Val Lys Gln Ala Pro Leu Met
            245             250             255

Ile Ala Glu Lys Pro Ile Arg Leu Glu Glu Phe Leu Thr Phe Gly Gly
            260             265             270

Gln Asp Leu Asn Ile Ile Thr Ser Ala Met Lys Glu Lys Ile Tyr Asn
            275             280             285

Asn Leu Leu Ala Asn Tyr Glu Lys Ile Ala Thr Arg Leu Ser Arg Val
    290             295             300
```

-continued

```
Asn Ser Ala Pro Pro Glu Tyr Asp Ile Asn Glu Tyr Lys Asp Tyr Phe
305                 310             315             320

Gln Trp Lys Tyr Gly Ser Asp Lys Asn Ala Asp Gly Ser Tyr Thr Val
                325             330             335

Asn Glu Asn Lys Gly Asn Glu Ile Tyr Lys Lys Leu Tyr Ser Phe Thr
            340             345             350

Glu Ile Asp Leu Ala Asn Lys Leu Lys Val Lys Cys Arg Asn Thr Tyr
        355             360             365

Phe Ile Lys His Gly Phe Leu Lys Val Pro Asn Leu Leu Asp Asp Asp
    370             375             380

Ile Tyr Thr Val Ser Glu Gly Phe Asn Ile Gly His Leu Ala Val Asn
385             390             395             400

Asn Arg Gly Gln Asn Ile Lys Leu Asn Leu Lys Ile Ile Asp Ser Ile
            405             410             415

Pro Tyr Lys Ala Trp Leu Arg Lys Ser
            420             425

<210> SEQ ID NO 26
<211> LENGTH: 425
<212> TYPE: PRT
<213> ORGANISM: Artificial Sequence
<220> FEATURE:
<223> OTHER INFORMATION: Synthetic

<400> SEQUENCE: 26

Met Pro Val Val Ile Asn Ser Phe Asn Tyr Asn Asp Pro Val Asn Asp
1               5               10              15

Asp Thr Ile Leu Tyr Met Gln Ile Pro Tyr Glu Glu Lys Ser Lys Lys
            20              25              30

Tyr Tyr Lys Ala Phe Glu Ile Met Arg Asn Val Trp Ile Ile Pro Glu
        35              40              45

Arg Asn Thr Ile Gly Thr Asp Pro Ser Asp Phe Asp Pro Pro Ala Ser
    50              55              60

Leu Asp Asn Gly Ser Ser Ala Tyr Tyr Asp Pro Asn Tyr Leu Thr Thr
65              70              75              80

Asp Ala Glu Lys Asp Arg Tyr Leu Lys Thr Thr Ile Lys Leu Phe Lys
            85              90              95

Arg Ile Asn Ser Asn Pro Ala Gly Glu Ala Leu Leu Gln Glu Ile Ser
            100             105             110

Tyr Ala Lys Pro Tyr Leu Gly Asn Glu His Thr Pro Ile Asn Glu Phe
        115             120             125

His Pro Val Thr Arg Thr Thr Ser Val Asn Ile Lys Ser Ser Thr Asn
    130             135             140

Val Lys Ser Ser Ile Ile Leu Asn Leu Leu Val Leu Gly Ala Gly Pro
145             150             155             160

Asp Ile Phe Glu Asn Tyr Ile Tyr Pro Val Arg Lys Leu Met Gly Ser
            165             170             175

Gly Gly Val Tyr Asp Pro Ser Lys Asp Gly Phe Gly Ser Ile Asn Ile
            180             185             190

Val Thr Phe Ser Pro Glu Tyr Gly Tyr Thr Phe Asn Asp Ile Ser Gly
        195             200             205

Gly Tyr Asn Ser Ser Thr Ile Ser Phe Ile Ala Asp Pro Ala Ile Ser
    210             215             220

Leu Ala His Glu Leu Ile His Ala Leu His Gly Leu Tyr Gly Ala Phe
225             230             235             240
```

```
Gly Val Thr Tyr Lys Glu Thr Ile Lys Val Lys Gln Ala Pro Leu Met
            245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
            275                 280                 285

Asn Leu Leu Ala Asn Tyr Glu Lys Ile Ala Thr Arg Leu Ser Arg Val
            290                 295                 300

Asn Ser Ala Pro Pro Glu Tyr Asp Ile Asn Glu Tyr Lys Asp Tyr Phe
305                 310                 315                 320

Gln Trp Lys Tyr Gly Ser Asp Lys Asn Ala Asp Gly Ser Tyr Thr Val
            325                 330                 335

Asn Glu Asn Lys Gly Asn Glu Ile Tyr Lys Lys Leu Tyr Ser Phe Thr
            340                 345                 350

Glu Ile Asp Leu Ala Asn Lys Leu Lys Val Lys Cys Arg Asn Thr Tyr
            355                 360                 365

Phe Ile Lys His Gly Phe Leu Lys Val Pro Asn Leu Leu Asp Asp Asp
            370                 375                 380

Ile Tyr Thr Val Ser Glu Gly Phe Asn Ile Gly His Leu Ala Val Asn
385                 390                 395                 400

Asn Arg Gly Gln Asn Ile Lys Leu Asn Leu Lys Ile Ile Asp Ser Ile
            405                 410                 415

Pro Tyr Lys Ala Trp Leu Arg Lys Ser
            420                 425

<210> SEQ ID NO 27
<211> LENGTH: 425
<212> TYPE: PRT
<213> ORGANISM: Artificial Sequence
<220> FEATURE:
<223> OTHER INFORMATION: Synthetic

<400> SEQUENCE: 27

Met Pro Val Val Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
            20                  25                  30

Tyr Tyr Lys Ala Phe Glu Ile Met Arg Asn Val Trp Ile Ile Pro Glu
            35                  40                  45

Arg Asn Thr Ile Gly Thr Asp Pro Ser Asp Phe Asp Pro Pro Ala Ser
            50                  55                  60

Leu Glu Asn Gly Ser Ser Ala His Tyr Asp Pro Asn Tyr Leu Thr Thr
65                  70                  75                  80

Asp Ala Glu Lys Asp Arg Tyr Leu Lys Thr Thr Ile Lys Leu Phe Lys
            85                  90                  95

Arg Ile Ser Ser Asn Pro Ala Gly Glu Ala Leu Leu Gln Glu Ile Ser
            100                 105                 110

Tyr Ala Lys Pro Tyr Leu Gly Asn Glu His Thr Pro Ile Asn Glu Phe
            115                 120                 125

His Pro Gly Thr Arg Thr Thr Ser Val Asn Ile Lys Thr Ser Thr Asn
            130                 135                 140

Val Lys Ser Ser Ile Ile Leu Asn Leu Leu Val Leu Gly Ala Gly Pro
145                 150                 155                 160

Asp Ile Phe Glu Asn Tyr Ile Tyr Pro Val Arg Lys Leu Thr Asp Ser
            165                 170                 175
```

```
Gly Gly Val Tyr Asp Pro Ser Thr Asp Gly Phe Gly Ser Ile Asn Ile
        180                 185                 190

Met Thr Phe Ser Pro Glu Tyr Gly Tyr Thr Phe Asn Asp Ile Ser Gly
        195                 200                 205

Gly Tyr Asn Ser Ser Thr Ile Ser Phe Ile Ala Asp Pro Ala Ile Ser
        210                 215                 220

Leu Ala His Glu Leu Ile His Ala Leu His Gly Leu Tyr Gly Ala Leu
225                 230                 235                 240

Gly Val Thr Tyr Lys Glu Thr Ile Lys Val Lys Gln Ala Pro Leu Met
                245                 250                 255

Ile Ala Glu Lys Pro Ile Arg Leu Glu Glu Phe Leu Thr Phe Gly Gly
                260                 265                 270

Gln Asp Leu Asn Ile Ile Thr Ser Ala Met Lys Glu Lys Ile Tyr Asn
                275                 280                 285

Asn Leu Leu Ala Asn Tyr Glu Lys Ile Ala Thr Arg Leu Ser Arg Val
        290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Gly Asn Glu Ile Tyr Lys Lys Leu Tyr Ser Phe Thr
                340                 345                 350

Glu Ile Asp Leu Ala Asn Lys Leu Lys Val Lys Cys Arg Asn Thr Tyr
                355                 360                 365

Phe Ile Lys His Gly Phe Leu Lys Val Pro Asn Leu Leu Asp Asp Asp
        370                 375                 380

Ile Tyr Thr Val Ser Glu Gly Phe Asn Ile Gly His Leu Ala Val Asn
385                 390                 395                 400

Asn Arg Gly Gln Asn Ile Lys Leu Asn Leu Lys Ile Ile Asp Ser Ile
                405                 410                 415

Pro Asp Lys Ala Trp Leu Arg Lys Ser
                420                 425
```

```
<210> SEQ ID NO 28
<211> LENGTH: 425
<212> TYPE: PRT
<213> ORGANISM: Artificial Sequence
<220> FEATURE:
<223> OTHER INFORMATION: Synthetic

<400> SEQUENCE: 28
```

```
Met Pro Val Val Ile Asn Ser Phe Asn Tyr Asn Asp Pro Val Asn Asp
1                   5                   10                  15

Asp Thr Ile Leu Tyr Met Gln Ile Pro Tyr Glu Glu Lys Ser Lys Lys
                20                  25                  30

Tyr Tyr Lys Ala Phe Glu Ile Met Arg Asn Val Trp Ile Ile Pro Glu
        35                  40                  45

Arg Asn Thr Ile Gly Thr Asp Pro Ser Asp Phe Asp Pro Pro Ala Ser
        50                  55                  60

Leu Glu Asn Gly Ser Ser Ala His Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Ser Ser Asn Pro Ala Gly Glu Ala Leu Leu Gln Glu Ile Ser
        100                 105                 110
```

-continued

```
Tyr Ala Lys Pro Tyr Leu Gly Asn Glu His Thr Pro Ile Asn Glu Phe
        115                 120                 125

His Pro Gly Thr Arg Thr Thr Ser Val Asn Ile Lys Thr Ser Thr Asn
        130                 135                 140

Val Lys Ser Ser Ile Ile Leu Asn Leu Leu Val Leu Gly Ala Gly Pro
145                 150                 155                 160

Asp Ile Phe Glu Asn Tyr Ile Tyr Pro Val Arg Lys Leu Thr Asp Ser
                165                 170                 175

Gly Gly Val Tyr Asp Pro Ser Thr Asp Gly Phe Gly Ser Ile Asn Ile
                180                 185                 190

Met Thr Phe Ser Pro Glu Tyr Gly Tyr Thr Phe Asn Asp Ile Ser Gly
                195                 200                 205

Gly Tyr Asn Ser Ser Thr Ile Ser Phe Ile Ala Asp Pro Ala Ile Ser
        210                 215                 220

Leu Ala His Glu Leu Ile His Ala Leu His Gly Leu Tyr Gly Ala Phe
225                 230                 235                 240

Gly Val Thr Tyr Lys Glu Thr Ile Lys Val Lys Gln Ala Pro Leu Met
                245                 250                 255

Ile Ala Glu Lys Pro Ile Arg Leu Glu Glu Phe Leu Thr Phe Gly Gly
                260                 265                 270

Gln Asp Leu Asn Ile Ile Thr Ser Ala Met Lys Glu Lys Ile Tyr Asn
        275                 280                 285

Asn Leu Leu Ala Asn Tyr Glu Lys Ile Ala Thr Arg Leu Ser Arg Val
        290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Gly Asn Glu Ile Tyr Lys Lys Leu Tyr Ser Phe Thr
                340                 345                 350

Glu Ile Asp Leu Ala Asn Lys Leu Lys Val Lys Cys Arg Asn Thr Tyr
        355                 360                 365

Phe Ile Lys His Gly Phe Leu Lys Val Pro Asn Leu Leu Asp Asp Asp
        370                 375                 380

Ile Tyr Thr Val Ser Glu Gly Phe Asn Ile Gly His Leu Ala Val Asn
385                 390                 395                 400

Asn Arg Gly Gln Asn Ile Lys Leu Asn Leu Lys Ile Ile Asp Ser Ile
                405                 410                 415

Pro Asp Lys Ala Trp Leu Arg Lys Ser
                420                 425
```

```
<210> SEQ ID NO 29
<211> LENGTH: 425
<212> TYPE: PRT
<213> ORGANISM: Artificial Sequence
<220> FEATURE:
<223> OTHER INFORMATION: Synthetic

<400> SEQUENCE: 29

Met Pro Val Val Ile Asn Ser Phe Asn Tyr Asn Asp Pro Val Asn Asp
1                   5                   10                  15

Asp Thr Ile Leu Tyr Met Gln Ile Pro Tyr Glu Glu Lys Ser Lys Lys
                20                  25                  30

Tyr Tyr Lys Ala Phe Glu Ile Met Arg Asn Val Trp Ile Ile Pro Glu
        35                  40                  45
```

```
Arg Asn Thr Ile Gly Thr Asp Pro Ser Asp Phe Asp Pro Pro Ala Ser
    50              55                  60

Leu Glu Asn Gly Ser Ser Ala His Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Glu Ala Leu Leu Gln Glu Ile Ser
            100                 105                 110

Tyr Ala Lys Pro Tyr Leu Gly Asn Glu His Thr Pro Ile Asn Glu Phe
        115                 120                 125

His Pro Gly Thr Arg Thr Thr Ser Val Asn Ile Lys Thr Ser Thr Asn
    130                 135                 140

Val Lys Ser Ser Ile Ile Leu Asn Leu Leu Val Leu Gly Ala Gly Pro
145                 150                 155                 160

Asp Ile Phe Glu Asn Tyr Ile Tyr Pro Val Arg Lys Leu Met Thr Ser
                165                 170                 175

Gly Gly Val Tyr Asp Pro Ser Asn Asp Gly Phe Gly Ser Ile Asn Ile
            180                 185                 190

Val Thr Phe Ser Pro Glu Tyr Gly Tyr Thr Phe Asn Asp Ile Ser Gly
            195                 200                 205

Gly Tyr Asn Ser Ser Thr Glu Ser Phe Ile Ala Asp Pro Ala Ile Ile
    210                 215                 220

Leu Ala His Glu Leu Ile His Ala Leu His Gly Leu Tyr Gly Ala Leu
225                 230                 235                 240

Gly Val Thr Tyr Lys Glu Thr Ile Lys Val Lys Gln Ala Pro Leu Met
            245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285

Asn Leu Leu Ala Asn Tyr Glu Lys Ile Ala Thr Arg Leu Ser Arg Val
    290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
            325                 330                 335

Asn Glu Asn Lys Phe Asn Glu Ile Tyr Lys Lys Leu Tyr Gly Phe Thr
            340                 345                 350

Glu Ile Asp Leu Ala Asn Lys Leu Lys Val Lys Cys Arg Asn Thr Tyr
        355                 360                 365

Phe Ile Lys His Gly Phe Leu Lys Val Pro Asn Leu Leu Asp Asp Asp
    370                 375                 380

Ile Tyr Thr Val Ser Glu Gly Phe Asn Ile Gly His Leu Ala Val Asn
385                 390                 395                 400

Asn Arg Gly Gln Asn Ile Lys Leu Asn Leu Lys Ile Ile Asp Ser Ile
            405                 410                 415

Pro Asp Lys Ala Trp Leu Arg Lys Ser
            420                 425
```

<210> SEQ ID NO 30
<211> LENGTH: 425
<212> TYPE: PRT
<213> ORGANISM: Artificial Sequence
<220> FEATURE:

-continued

<223> OTHER INFORMATION: Synthetic

<400> SEQUENCE: 30

```
Met Pro Val Val Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
            20                  25                  30

Tyr Tyr Lys Ala Phe Glu Ile Met Arg Asn Val Trp Ile Ile Pro Glu
        35                  40                  45

Arg Asn Thr Ile Gly Thr Asp Pro Ser Asp Phe Asp Pro Pro Ala Ser
    50                  55                  60

Leu Glu Asn Gly Leu Ser Ala His Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Glu Ala Leu Leu Gln Glu Ile Ser
            100                 105                 110

Tyr Ala Lys Pro Tyr Leu Gly Asn Glu His Thr Pro Ile Asn Glu Phe
        115                 120                 125

His Pro Val Thr Arg Thr Thr Ser Val Asn Ile Lys Ser Ser Thr Asn
    130                 135                 140

Val Lys Ser Asn Ile Val Leu Asn Leu Leu Val Leu Gly Pro Gly Pro
145                 150                 155                 160

Asp Ile Phe Glu Asn Tyr Ile Tyr Pro Val Arg Lys Leu Met Met Ser
                165                 170                 175

Asp Gly Val Tyr Asp Pro Ser His Asp Gly Phe Gly Ser Ile Asn Ile
            180                 185                 190

Val Thr Phe Ser Pro Glu Tyr Gly Tyr Thr Phe Asn Asp Ile Ser Gly
            195                 200                 205

Gly Tyr Asn Ser Ser Thr Glu Ser Phe Ile Ala Asp Pro Ala Ile Ile
    210                 215                 220

Leu Ala His Glu Leu Ile His Ser Leu His Gly Leu Tyr Gly Ala Leu
225                 230                 235                 240

Gly Val Thr Tyr Lys Glu Thr Ile Lys Val Lys Gln Ala Pro Leu Met
                245                 250                 255

Ile Ala Glu Lys Pro Ile Arg Leu Glu Glu Phe Leu Thr Phe Gly Gly
                260                 265                 270

Gln Asp Leu Asn Ile Ile Thr Ser Ala Met Lys Glu Lys Ile Tyr Asn
            275                 280                 285

Asn Leu Leu Ala Asn Tyr Glu Lys Ile Ala Thr Arg Leu Ser Arg Val
    290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
            325                 330                 335

Asn Glu Asn Lys Phe Asn Glu Ile Tyr Lys Lys Leu Tyr Gly Phe Thr
            340                 345                 350

Glu Ile Asp Leu Ala Asn Lys Leu Lys Val Lys Cys Arg Asn Thr Tyr
            355                 360                 365

Phe Ile Lys Asn Gly Phe Leu Lys Val Pro Asn Leu Met Asp Asp Asp
    370                 375                 380

Ile Tyr Thr Val Ser Glu Gly Phe Asn Ile Gly His Leu Ala Val Asn
385                 390                 395                 400
```

-continued

```
Asn Arg Gly Gln Asn Ile Lys Leu Asn Leu Lys Ile Ile Asp Ser Ile
            405                 410                 415

Pro Asp Lys Ala Trp Leu Arg Lys Ser
            420                 425

<210> SEQ ID NO 31
<211> LENGTH: 425
<212> TYPE: PRT
<213> ORGANISM: Artificial Sequence
<220> FEATURE:
<223> OTHER INFORMATION: Synthetic

<400> SEQUENCE: 31

Met Pro Val Val Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Asn Lys
            20                  25                  30

Tyr Tyr Lys Ala Phe Glu Ile Met Arg Asn Val Trp Ile Ile Pro Glu
            35                  40                  45

Arg Asn Thr Ile Gly Thr Asp Pro Ser Asp Phe Asp Pro Pro Ala Ser
    50                  55                  60

Leu Glu Asn Gly Ser Ser Ala His Tyr Asp Pro Asn Tyr Leu Thr Thr
65                  70                  75                  80

Asp Ala Glu Lys Asp Arg Tyr Leu Lys Thr Thr Ile Lys Leu Phe Asn
            85                  90                  95

Arg Ile Asn Ser Asn Pro Ala Gly Glu Ala Leu Leu Gln Glu Ile Ser
            100                 105                 110

Tyr Ala Lys Pro Tyr Leu Gly Asn Glu His Thr Pro Ile Asn Glu Phe
            115                 120                 125

His Pro Phe Thr Arg Thr Thr Ser Val Asn Ile Lys Ser Ser Thr Asn
    130                 135                 140

Val Lys Ser Ser Ile Ile Leu Asn Leu Leu Val Leu Gly Ala Gly Pro
145                 150                 155                 160

Asp Ile Phe Glu Asn Tyr Leu Tyr Pro Val Arg Lys Leu Met Met Ser
            165                 170                 175

Gly Gly Val Tyr Asp Pro Ser Asn Asp Gly Phe Gly Ser Ile Asn Ile
            180                 185                 190

Val Thr Phe Ser Pro Glu Tyr Gly Tyr Thr Phe Asn Asp Ile Ser Gly
            195                 200                 205

Gly Tyr Asn Ser Ser Thr Glu Ser Phe Ile Ala Asp Pro Ala Ile Ile
    210                 215                 220

Leu Ala His Glu Leu Ile His Ala Leu His Gly Leu Tyr Gly Ala Leu
225                 230                 235                 240

Gly Val Thr Tyr Lys Glu Thr Ile Lys Val Lys Gln Ala Pro Leu Met
            245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Val Met Lys Glu Lys Ile Tyr Asn
            275                 280                 285

Asn Leu Leu Ala Asn Tyr Glu Lys Ile Ala Thr Arg Leu Ser His Val
    290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
            325                 330                 335
```

-continued

```
Asn Glu Asn Lys Phe Asn Glu Ile Tyr Lys Lys Leu Tyr Gly Phe Thr
            340                 345                 350

Glu Val Asp Leu Ala Asn Lys Leu Lys Val Lys Cys Arg Asn Thr Tyr
            355                 360                 365

Phe Ile Lys Pro Gly Phe Leu Lys Val Pro Asn Leu Leu Asp Asp Asp
            370                 375                 380

Ile Tyr Thr Val Ser Glu Gly Phe Asn Ile Gly His Leu Ala Val Asn
385                 390                 395                 400

Asn Arg Gly Gln Asn Ile Lys Leu Asn Leu Lys Asn Ile Asp Ser Ile
                405                 410                 415

Pro Asp Lys Ala Trp Leu Arg Lys Ser
            420                 425
```

```
<210> SEQ ID NO 32
<211> LENGTH: 116
<212> TYPE: PRT
<213> ORGANISM: Artificial Sequence
<220> FEATURE:
<223> OTHER INFORMATION: Synthetic

<400> SEQUENCE: 32
```

```
Met Ser Ala Pro Ala Gln Pro Pro Ala Glu Gly Thr Glu Gly Thr Ala
1               5                   10                  15

Pro Gly Gly Gly Pro Pro Gly Pro Pro Asn Met Thr Ser Asn Arg
            20                  25                  30

Arg Leu Gln Gln Thr Gln Ala Gln Val Glu Glu Val Val Asp Ile Ile
            35                  40                  45

Arg Val Asn Val Asp Lys Val Leu Glu Arg Asp Gln Lys Leu Ser Glu
            50                  55                  60

Leu Asp Asp Arg Ala Asp Ala Leu Gln Ala Gly Ala Ser Gln Phe Glu
65                  70                  75                  80

Ser Ser Ala Ala Lys Leu Lys Arg Lys Tyr Trp Trp Lys Asn Cys Lys
                85                  90                  95

Met Met Ile Met Leu Gly Ala Ile Cys Ala Ile Ile Val Val Val Ile
                100                 105                 110

Val Arg Arg Gly
        115
```

```
<210> SEQ ID NO 33
<211> LENGTH: 60
<212> TYPE: PRT
<213> ORGANISM: Artificial Sequence
<220> FEATURE:
<223> OTHER INFORMATION: Synthetic

<400> SEQUENCE: 33
```

```
Thr Ser Asn Arg Arg Leu Gln Gln Thr Gln Ala Gln Val Glu Glu Val
1               5                   10                  15

Val Asp Ile Ile Arg Val Asn Val Asp Lys Val Leu Glu Arg Asp Gln
            20                  25                  30

Lys Leu Ser Glu Leu Asp Asp Arg Ala Asp Ala Leu Gln Ala Gly Ala
            35                  40                  45

Ser Gln Phe Glu Ser Ser Ala Ala Lys Leu Lys Arg
        50                  55                  60
```

```
<210> SEQ ID NO 34
<211> LENGTH: 179
<212> TYPE: PRT
<213> ORGANISM: Artificial Sequence
```

<220> FEATURE:
<223> OTHER INFORMATION: Synthetic

<400> SEQUENCE: 34

```
Met Ala Ile Leu Phe Ala Val Val Ala Arg Gly Thr Thr Ile Leu Ala
1               5                   10                  15

Lys His Ala Trp Cys Gly Gly Asn Phe Leu Glu Asp Phe Glu Arg Ser
            20                  25                  30

Arg Ala Phe Asn Phe Leu Asn Glu Ile Lys Lys Arg Phe Gln Thr Thr
        35                  40                  45

Tyr Gly Ser Arg Ala Gln Thr Ala Leu Pro Tyr Ala Met Asn Ser Glu
    50                  55                  60

Phe Ser Ser Val Leu Ala Ala Gln Leu Lys His His Ser Glu Asn Lys
65                  70                  75                  80

Gly Leu Asp Lys Val Met Glu Thr Gln Ala Gln Val Asp Glu Leu Lys
                85                  90                  95

Gly Ile Met Val Arg Asn Ile Asp Leu Val Ala Gln Arg Gly Glu Arg
            100                 105                 110

Leu Glu Leu Leu Ile Asp Lys Thr Glu Asn Leu Val Asp Ser Ser Val
            115                 120                 125

Thr Phe Lys Thr Thr Ser Arg Asn Leu Ala Arg Ala Met Cys Met Lys
    130                 135                 140

Asn Leu Lys Leu Thr Ile Ile Ile Ile Ile Val Ser Ile Val Phe Ile
145                 150                 155                 160

Tyr Ile Ile Val Ser Pro Leu Cys Gly Gly Phe Thr Trp Pro Ser Cys
                165                 170                 175

Val Lys Lys
```

<210> SEQ ID NO 35
<211> LENGTH: 69
<212> TYPE: PRT
<213> ORGANISM: Artificial Sequence
<220> FEATURE:
<223> OTHER INFORMATION: Synthetic

<400> SEQUENCE: 35

```
Lys Gly Leu Asp Lys Val Met Glu Thr Gln Ala Gln Val Asp Glu Leu
1               5                   10                  15

Lys Gly Ile Met Val Arg Asn Ile Asp Leu Val Ala Gln Arg Gly Glu
            20                  25                  30

Arg Leu Glu Leu Leu Ile Asp Lys Thr Glu Asn Leu Val Asp Ser Ser
        35                  40                  45

Val Thr Phe Lys Thr Thr Ser Arg Asn Leu Ala Arg Gly Gly Ser Gly
    50                  55                  60

Gly Ser Gly Gly Ser
65
```

<210> SEQ ID NO 36
<211> LENGTH: 439
<212> TYPE: PRT
<213> ORGANISM: Artificial Sequence
<220> FEATURE:
<223> OTHER INFORMATION: Synthetic

<400> SEQUENCE: 36

```
Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
```

-continued

```
            20                    25                    30
Lys Gly Lys Gly Pro Phe Lys Ala Phe Gln Val Ile Lys Asn Ile Trp
            35                    40                    45
Ile Val Pro Glu Arg Tyr Asn Phe Thr Asn Asn Thr Asn Asp Leu Asn
        50                    55                    60
Ile Pro Ser Glu Pro Ile Met Glu Ala Asp Ala Ile Tyr Asn Pro Asn
65                    70                    75                    80
Tyr Leu Asn Thr Pro Ser Glu Lys Asp Glu Phe Leu Gln Gly Val Ile
                    85                    90                    95
Lys Gly Leu Glu Arg Ile Lys Ser Lys Pro Glu Gly Glu Lys Leu Leu
                100                   105                   110
Lys Leu Ile Ser Ser Ser Ile Pro Leu Pro Leu Val Ser Asn Gly Ala
                115                   120                   125
Leu Thr Leu Ser Asp Asn Glu Thr Ile Ala Tyr Gln Glu Asn Asn Asn
            130                   135                   140
Ile Val Ser Asn Leu Gln Ala Asn Leu Val Ile Tyr Gly Pro Gly Pro
145                   150                   155                   160
Asp Ile Ala Asn Asn Glu Thr Tyr Gly Leu Tyr Ser Thr Pro Ile Ser
                165                   170                   175
Asn Gly Glu Gly Thr Leu Ser Glu Val Ser Phe Ser Pro Phe Tyr Leu
                180                   185                   190
Lys Pro Phe Asp Glu Ser Tyr Gly Asn Tyr Arg Ser Leu Val Asn Ile
                195                   200                   205
Val Asn Lys Phe Val Lys Arg Glu Phe Ala Pro Asp Pro Ala Ser Thr
            210                   215                   220
Leu Met His Glu Leu Val His Val Thr His Asn Leu Tyr Gly Ile Ser
225                   230                   235                   240
Asn Arg Asn Phe Tyr Tyr Asn Phe Asp Thr Gly Lys Ile Glu Thr Ser
                245                   250                   255
Arg Gln Gln Asn Ser Leu Ile Phe Glu Glu Leu Leu Thr Phe Gly Gly
                260                   265                   270
Ile Asp Ser Lys Ala Ile Ser Leu Leu Ile Ile Lys Lys Ile Ile Glu
                275                   280                   285
Thr Ala Lys Asn Asn Tyr Thr Thr Leu Ile Ser Glu Arg Leu Asn Thr
        290                   295                   300
Val Thr Val Glu Asn Asp Leu Leu Lys Tyr Ile Lys Asn Lys Ile Pro
305                   310                   315                   320
Val Gln Gly Arg Leu Gly Asn Phe Lys Leu Asp Thr Ala Glu Phe Glu
                325                   330                   335
Lys Lys Leu Asn Thr Ile Leu Phe Val Leu Asn Glu Ser Asn Leu Ala
            340                   345                   350
Gln Arg Phe Ser Ile Leu Val Arg Lys His Tyr Leu Lys Glu Arg Pro
            355                   360                   365
Ile Asp Pro Ile Tyr Val Asn Ile Leu Asp Asp Asn Ser Tyr Ser Thr
        370                   375                   380
Leu Glu Gly Phe Asn Ile Ser Ser Gln Gly Ser Asn Asp Phe Gln Gly
385                   390                   395                   400
Gln Leu Leu Glu Ser Ser Tyr Phe Glu Lys Ile Glu Ser Asn Ala Leu
                405                   410                   415
Arg Ala Phe Ile Lys Ile Cys Pro Arg Asn Gly Leu Leu Tyr Asn Ala
                420                   425                   430
Ile Tyr Arg Asn Ser Lys Asn
                435
```

-continued

<210> SEQ ID NO 37
<211> LENGTH: 439
<212> TYPE: PRT
<213> ORGANISM: Artificial Sequence
<220> FEATURE:
<223> OTHER INFORMATION: Synthetic

<400> SEQUENCE: 37

```
Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
            20                  25                  30

Lys Gly Lys Gly Pro Phe Lys Ala Phe Gln Val Ile Lys Asn Ile Trp
        35                  40                  45

Ile Val Pro Glu Arg Tyr Asn Phe Thr Asn Asn Thr Asn Asp Leu Asn
    50                  55                  60

Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
                85                  90                  95

Lys Val Leu Glu Arg Ile Lys Ser Lys Pro Glu Gly Glu Lys Leu Leu
            100                 105                 110

Glu Leu Ile Ser Ser Ser Ile Pro Leu Pro Leu Val Ser Asn Gly Ala
            115                 120                 125

Leu Thr Leu Ser Asp Asn Glu Thr Ile Ala Tyr Gln Glu Asn Asn Asn
            130                 135                 140

Ile Val Ser Asn Leu Gln Ala Asn Leu Val Ile Tyr Gly Pro Gly Pro
145                 150                 155                 160

Asp Ile Ala Asn Asn Glu Thr Tyr Gly Leu Tyr Ser Thr Pro Ile Ser
                165                 170                 175

Asn Gly Glu Gly Thr Leu Ser Glu Val Ser Phe Ser Pro Phe Tyr Leu
            180                 185                 190

Lys Pro Phe Asp Glu Ser Tyr Gly Asn Tyr Arg Ser Leu Val Asn Ile
            195                 200                 205

Val Asn Lys Phe Val Lys Arg Glu Phe Ala Pro Asp Pro Ala Ser Thr
    210                 215                 220

Leu Met His Glu Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
                245                 250                 255

Arg Gln Gln Asn Ser Leu Ile Phe Glu Glu Leu Leu Thr Phe Gly Gly
            260                 265                 270

Ile Asp Ser Lys Ala Ile Ser Ser Leu Ile Ile Lys Lys Ile Ile Glu
            275                 280                 285

Thr Ala Lys Asn Asn Tyr Thr Thr Leu Ile Ser Glu Arg Leu Asn Thr
    290                 295                 300

Val Thr Val Glu Asn Asp Leu Leu Lys Tyr Ile Lys Asn Lys Ile Pro
305                 310                 315                 320

Val Gln Gly Arg Leu Gly Asn Phe Lys Leu Asp Thr Ala Glu Phe Glu
                325                 330                 335

Lys Lys Leu Asn Thr Ile Leu Phe Val Leu Asn Glu Ser Asn Leu Ala
            340                 345                 350

Gln Arg Phe Ser Ile Leu Val Arg Lys His Tyr Leu Lys Glu Arg Pro
            355                 360                 365
```

-continued

```
Ile Asp Pro Ile Tyr Val Asn Ile Leu Asp Asp Asn Ser Tyr Ser Thr
    370             375             380

Leu Glu Gly Phe Asn Ile Ser Ser Gln Gly Ser Asn Asp Phe Gln Gly
385             390             395             400

Gln Leu Leu Glu Ser Ser Tyr Phe Glu Lys Ile Glu Ser Asn Ala Leu
            405             410             415

Arg Ala Phe Ile Lys Ile Cys Pro Arg Asn Gly Leu Leu Tyr Asn Ala
            420             425             430

Ile Tyr Arg Asn Ser Lys Asn
    435

<210> SEQ ID NO 38
<211> LENGTH: 439
<212> TYPE: PRT
<213> ORGANISM: Artificial Sequence
<220> FEATURE:
<223> OTHER INFORMATION: Synthetic

<400> SEQUENCE: 38

Met Lys Leu Glu Ile Asn Lys Phe Asn Tyr Asn Asp Pro Ile Asp Gly
1               5               10              15

Ile Asn Val Ile Thr Met Arg Pro Pro Arg His Ser Asp Lys Ile Asn
                20              25              30

Lys Gly Lys Gly Pro Phe Lys Ala Phe Gln Val Ile Lys Asn Ile Trp
            35              40              45

Ile Val Pro Glu Arg Tyr Asn Phe Thr Asn Asn Thr Asn Asp Leu Asn
    50              55              60

Ile Pro Ser Glu Pro Ile Met Glu Ala Asp Ala Ile Tyr Asn Pro Asn
65              70              75              80

Tyr Leu Asn Thr Pro Ser Glu Lys Asp Glu Phe Leu Gln Gly Val Ile
                85              90              95

Lys Val Leu Glu Arg Ile Lys Ser Lys Pro Glu Gly Glu Lys Leu Leu
            100             105             110

Glu Leu Ile Ser Ser Ser Ile Pro Leu Pro Leu Val Ser Asn Gly Ala
            115             120             125

Leu Thr Leu Ser Asp Asn Glu Thr Ile Ala Tyr Gln Glu Asn Asn Asn
    130             135             140

Ile Val Ser Asn Leu Gln Ala Asn Leu Val Ile Tyr Gly Pro Gly Pro
145             150             155             160

Asp Ile Ala Asn Asn Glu Thr Tyr Gly Leu Tyr Ser Thr Pro Ile Ser
            165             170             175

Asn Gly Glu Gly Thr Leu Ser Glu Val Ser Phe Ser Pro Phe Tyr Leu
            180             185             190

Lys Pro Phe Asp Glu Ser Tyr Gly Asn Tyr Arg Ser Leu Val Asn Ile
            195             200             205

Val Asn Lys Phe Val Lys Arg Glu Phe Ala Pro Asp Pro Ala Ser Thr
    210             215             220

Leu Met His Glu Leu Val His Val Thr His Asn Leu Tyr Gly Ile Ser
225             230             235             240

Asn Arg Asn Phe Tyr Tyr Asn Phe Asp Thr Gly Lys Ile Glu Thr Ser
            245             250             255

Arg Gln Gln Asn Ser Leu Ile Phe Glu Glu Leu Leu Thr Phe Gly Gly
            260             265             270

Ile Asp Ser Lys Ala Ile Ser Ser Leu Ile Ile Lys Lys Ile Ile Glu
    275             280             285
```

-continued

```
Thr Ala Lys Asn Asn Tyr Thr Thr Leu Ile Ser Glu Arg Leu Asn Thr
    290             295             300

Val Thr Val Glu Asn Asp Leu Leu Lys Tyr Ile Lys Asn Lys Ile Pro
305             310             315             320

Val Gln Gly Arg Leu Gly Asn Phe Lys Leu Asp Thr Ala Glu Phe Glu
            325             330             335

Lys Lys Leu Asn Thr Ile Leu Phe Val Leu Asn Glu Ser Asn Leu Ala
            340             345             350

Gln Arg Phe Ser Ile Leu Val Arg Lys His Tyr Leu Lys Glu Arg Pro
            355             360             365

Ile Asp Pro Ile Tyr Val Asn Ile Leu Asp Asp Asn Ser Tyr Ser Thr
    370             375             380

Leu Glu Gly Phe Asn Ile Ser Ser Gln Gly Ser Asn Asp Phe Gln Gly
385             390             395             400

Gln Leu Leu Glu Leu Ser Tyr Phe Glu Lys Ile Glu Ser Asn Ala Leu
            405             410             415

Arg Ala Phe Ile Lys Ile Cys Pro Arg Asn Gly Leu Leu Tyr Asn Ala
            420             425             430

Ile Tyr Leu Asn Ser Lys Asn
            435
```

```
<210> SEQ ID NO 39
<211> LENGTH: 439
<212> TYPE: PRT
<213> ORGANISM: Artificial Sequence
<220> FEATURE:
<223> OTHER INFORMATION: Synthetic

<400> SEQUENCE: 39
```

```
Met Lys Leu Glu Ile Asn Lys Phe Asn Tyr Asn Asp Pro Ile Asp Gly
1               5               10              15

Ile Asn Val Ile Thr Met Arg Pro Pro Arg His Ser Asp Lys Ile Asn
            20              25              30

Lys Gly Lys Gly Pro Phe Lys Ala Phe Gln Val Ile Lys Asn Ile Trp
            35              40              45

Ile Val Pro Glu Arg Tyr Asn Phe Thr Asn Asn Thr Asn Asp Leu Asn
    50              55              60

Ile Pro Ser Ala Pro Ile Met Glu Ala Asp Ala Ile Tyr Asn Pro Asn
65              70              75              80

Tyr Leu Asn Thr Pro Ser Glu Lys Asp Glu Phe Leu Gln Gly Val Ile
            85              90              95

Lys Val Leu Glu Arg Ile Lys Ser Lys Pro Glu Gly Glu Lys Leu Leu
            100             105             110

Glu Leu Ile Ser Ser Ser Ile Pro Leu Pro Leu Val Ser Asn Gly Ala
            115             120             125

Leu Thr Leu Ser Asp Asn Glu Thr Ile Ala Tyr Gln Glu Asn Asn Asn
    130             135             140

Ile Val Ser Asn Leu Leu Ala Asn Leu Val Ile Tyr Gly Pro Gly Pro
145             150             155             160

Asp Ile Ala Asn Asn Glu Thr Tyr Gly Leu Tyr Ser Thr Pro Ile Ser
            165             170             175

Asn Gly Glu Gly Thr Leu Ser Glu Val Ser Phe Ser Pro Phe Tyr Leu
            180             185             190

Lys Pro Phe Asp Glu Ser Tyr Gly Asn Tyr Arg Ser Leu Val Asn Ile
            195             200             205
```

```
Val Asn Lys Phe Val Lys Arg Glu Phe Ala Pro Asp Pro Ala Ser Thr
    210             215             220

Leu Met His Glu Leu Val His Val Thr His Asn Leu Tyr Gly Ile Ser
225             230             235             240

Asn Arg Asn Phe Tyr Tyr Asn Phe Asp Thr Gly Lys Ile Glu Thr Ser
                245             250             255

Arg Gln Gln Asn Ser Leu Ile Phe Glu Glu Leu Leu Thr Phe Gly Gly
            260             265             270

Ile Asp Ser Lys Ala Ile Ser Ser Leu Ile Ile Lys Lys Ile Ile Glu
            275             280             285

Thr Ala Lys Asn Asn Tyr Thr Thr Leu Ile Ser Glu Arg Leu Asn Thr
    290             295             300

Val Thr Val Glu Asn Asp Leu Leu Lys Tyr Ile Lys Asn Lys Ile Pro
305             310             315             320

Val Gln Gly Arg Leu Gly Asn Phe Lys Leu Asp Thr Ala Glu Phe Glu
            325             330             335

Lys Lys Leu Asn Thr Ile Leu Phe Val Leu Asn Glu Ser Asn Leu Ala
            340             345             350

Gln Arg Phe Ser Ile Leu Val Arg Lys His Tyr Leu Lys Glu Arg Pro
            355             360             365

Ile Asp Pro Ile Tyr Val Asn Ile Leu Asp Asp Asn Ser Tyr Ser Thr
    370             375             380

Leu Glu Gly Phe Asn Ile Ser Ser Gln Gly Ser Asn Asp Phe Gln Gly
385             390             395             400

Gln Leu Leu Glu Ser Ser Tyr Phe Glu Lys Ile Glu Ser Asn Ala Leu
            405             410             415

Arg Ala Phe Ile Lys Ile Cys Pro Arg Asn Gly Leu Leu Tyr Asn Ala
            420             425             430

Ile Tyr Arg Asn Ser Lys Asn
        435

<210> SEQ ID NO 40
<211> LENGTH: 439
<212> TYPE: PRT
<213> ORGANISM: Artificial Sequence
<220> FEATURE:
<223> OTHER INFORMATION: Synthetic

<400> SEQUENCE: 40

Met Lys Leu Glu Ile Asn Lys Phe Asn Tyr Asn Asp Pro Ile Asp Gly
1               5               10              15

Ile Asn Val Ile Thr Met Arg Pro Pro Arg His Ser Asp Lys Ile Asn
            20              25              30

Lys Gly Lys Gly Pro Phe Lys Ala Phe Gln Val Ile Lys Asn Ile Trp
        35              40              45

Ile Val Pro Glu Arg Tyr Asn Phe Thr Asn Asn Thr Asn Asp Leu Asn
    50              55              60

Ile Pro Ser Glu Pro Ile Met Glu Ala Asp Ala Ile Tyr Asn Pro Asn
65              70              75              80

Tyr Leu Asn Thr Pro Ser Glu Lys Asp Glu Phe Leu Gln Gly Val Ile
                85              90              95

Lys Val Leu Glu Arg Ile Lys Ser Lys Pro Glu Gly Glu Lys Leu Leu
            100             105             110

Glu Leu Ile Ser Ser Ser Ile Pro Leu Pro Leu Val Ser Asn Gly Ala
            115             120             125
```

-continued

```
Leu Thr Leu Ser Asp Asn Glu Thr Ile Ala Tyr Gln Glu Asn Asn Asn
    130                 135                 140

Ile Val Ser Asn Leu Gln Ala Asn Leu Val Ile Tyr Gly Pro Gly Pro
145                 150                 155                 160

Asp Ile Ala Asn Asn Glu Thr Tyr Gly Leu Tyr Ser Thr Pro Ile Ser
                165                 170                 175

Asn Gly Glu Gly Thr Leu Ser Glu Val Ser Phe Ser Pro Phe Tyr Leu
                180                 185                 190

Lys Pro Phe Asp Glu Ser Tyr Gly Asn Tyr Arg Ser Leu Val Asn Ile
        195                 200                 205

Val Asn Lys Phe Val Lys Arg Glu Phe Ala Pro Asp Pro Ala Ser Thr
    210                 215                 220

Leu Met His Glu Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
                245                 250                 255

Arg Gln Gln Asn Ser Leu Ile Phe Glu Glu Leu Leu Thr Phe Gly Gly
                260                 265                 270

Ile Asp Ser Lys Ala Ile Ser Ser Leu Ile Ile Lys Lys Ile Ile Glu
        275                 280                 285

Thr Ala Lys Asn Asn Tyr Thr Thr Leu Ile Ser Glu Arg Leu Asn Thr
    290                 295                 300

Val Thr Val Glu Asn Asp Leu Leu Lys Tyr Ile Lys Asn Lys Ile Pro
305                 310                 315                 320

Val Gln Gly Arg Leu Gly Asn Phe Lys Leu Asp Thr Ala Glu Phe Glu
                325                 330                 335

Lys Lys Leu Asn Thr Ile Leu Phe Val Leu Asn Glu Ser Asn Leu Ala
                340                 345                 350

Gln Arg Phe Ser Ile Leu Val Arg Lys His Tyr Leu Lys Glu Arg Pro
        355                 360                 365

Ile Asp Pro Ile Tyr Val Asn Ile Leu Asp Asp Asn Ser Tyr Ser Thr
    370                 375                 380

Leu Glu Gly Phe Asn Ile Ser Ser Gln Gly Ser Asn Asp Phe Gln Gly
385                 390                 395                 400

Gln Leu Leu Glu Ser Ser Tyr Phe Glu Lys Ile Glu Ser Asn Ala Leu
                405                 410                 415

Arg Ala Phe Ile Lys Ile Cys Pro Arg Asn Gly Leu Leu Tyr Asn Ala
                420                 425                 430

Ile Tyr Arg Asn Ser Lys Asn
        435
```

```
<210> SEQ ID NO 41
<211> LENGTH: 439
<212> TYPE: PRT
<213> ORGANISM: Artificial Sequence
<220> FEATURE:
<223> OTHER INFORMATION: Synthetic

<400> SEQUENCE: 41
```

```
Met Lys Leu Glu Ile Asn Lys Phe Asn Tyr Asn Asp Pro Ile Asp Gly
1                   5                   10                  15

Ile Asn Val Ile Thr Met Arg Pro Pro Arg His Ser Asp Lys Ile Asn
                20                  25                  30

Lys Gly Lys Gly Pro Phe Lys Ala Phe Gln Val Ile Lys Asn Ile Trp
        35                  40                  45
```

-continued

```
Ile Val Pro Glu Arg Tyr Asn Phe Thr Asn Asn Thr Asn Asp Leu Asn
    50              55              60

Ile Pro Ser Glu Pro Ile Met Glu Ala Asp Ala Ile Tyr Asn Pro Asn
65              70              75              80

Tyr Leu Asn Thr Pro Ser Glu Lys Asp Glu Phe Leu Gln Gly Val Ile
            85              90              95

Lys Val Leu Glu Arg Ile Lys Ser Lys Pro Glu Gly Glu Lys Leu Leu
            100             105             110

Glu Leu Ile Ser Ser Ser Ile Pro Leu Pro Leu Val Ser Asn Gly Ala
            115             120             125

Leu Thr Leu Ser Asp Asn Glu Thr Ile Ala Tyr Gln Glu Asn Asn Asn
    130             135             140

Ile Val Ser Asn Leu Gln Ala Asn Leu Val Ile Tyr Gly Pro Gly Pro
145             150             155             160

Asp Ile Ala Asn Asn Glu Thr Tyr Gly Leu Tyr Ser Thr Pro Ile Ser
            165             170             175

Asn Gly Glu Gly Thr Leu Ser Glu Val Ser Phe Ser Pro Phe Tyr Leu
            180             185             190

Lys Pro Phe Asp Glu Ser Tyr Gly Asn Tyr Arg Ser Leu Val Asn Ile
            195             200             205

Val Asn Lys Phe Val Lys Arg Glu Phe Ala Pro Asp Pro Ala Ser Thr
    210             215             220

Leu Met His Glu Leu Val His Val Thr His Asn Leu Tyr Gly Ile Ser
225             230             235             240

Asn Arg Asn Phe Tyr Tyr Asn Phe Asp Thr Gly Lys Ile Glu Thr Ser
            245             250             255

Arg Gln Gln Asn Ser Leu Ile Phe Glu Glu Leu Leu Thr Phe Gly Gly
            260             265             270

Ile Asp Ser Lys Ala Ile Ser Ser Leu Ile Ile Lys Lys Ile Ile Glu
            275             280             285

Thr Ala Lys Asn Asn Tyr Thr Thr Leu Ile Ser Glu Arg Leu Asn Thr
    290             295             300

Val Thr Val Glu Asn Asp Leu Leu Lys Tyr Ile Lys Asn Lys Ile Pro
305             310             315             320

Val Gln Gly Arg Leu Gly Asn Phe Lys Leu Asp Thr Ala Glu Phe Glu
            325             330             335

Lys Lys Leu Asn Thr Ile Leu Phe Val Leu Asn Glu Ser Asn Leu Ala
            340             345             350

Gln Arg Phe Ser Ile Leu Val Arg Lys His Tyr Leu Lys Glu Arg Pro
            355             360             365

Ile Asp Pro Ile Tyr Val Asn Ile Leu Asp Asp Asn Ser Tyr Ser Thr
    370             375             380

Leu Glu Gly Phe Asn Ile Ser Ser Gln Gly Ser Asn Asp Phe Gln Gly
385             390             395             400

Gln Leu Leu Glu Ser Ser Tyr Phe Glu Lys Ile Glu Ser Asn Ala Leu
            405             410             415

Arg Ala Phe Ile Lys Ile Cys Pro Arg Asn Gly Leu Leu Tyr Asn Ala
            420             425             430

Ile Tyr Arg Asn Ser Lys Asn
            435
```

```
<210> SEQ ID NO 42
<211> LENGTH: 439
```

-continued

```
<212> TYPE: PRT
<213> ORGANISM: Artificial Sequence
<220> FEATURE:
<223> OTHER INFORMATION: Synthetic

<400> SEQUENCE: 42

Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
            20                  25                  30

Lys Gly Lys Gly Pro Phe Lys Ala Phe Gln Val Ile Lys Asn Ile Trp
        35                  40                  45

Ile Val Pro Glu Arg Tyr Asn Phe Thr Asn Asn Thr Asn Asp Leu Asn
    50                  55                  60

Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
                85                  90                  95

Lys Val Leu Glu Arg Ile Lys Ser Lys Pro Glu Gly Glu Lys Leu Leu
            100                 105                 110

Glu Leu Ile Ser Ser Ser Ile Pro Leu Pro Leu Val Ser Asn Gly Ala
            115                 120                 125

Leu Thr Leu Ser Asp Asn Glu Thr Ile Ala Tyr Gln Glu Asn Asn Asn
    130                 135                 140

Ile Val Ser Asn Leu Gln Ala Asn Leu Val Ile Tyr Gly Pro Gly Pro
145                 150                 155                 160

Asp Ile Ala Asn Asn Glu Thr Tyr Gly Leu Tyr Ser Thr Pro Ile Ser
                165                 170                 175

Asn Gly Glu Gly Thr Leu Ser Glu Val Ser Phe Ser Pro Phe Tyr Leu
            180                 185                 190

Lys Pro Phe Asp Glu Ser Tyr Gly Asn Tyr Arg Ser Leu Val Asn Ile
        195                 200                 205

Val Asn Lys Phe Val Lys Arg Glu Phe Ala Pro Asp Pro Ala Ser Thr
    210                 215                 220

Leu Met His Glu Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
                245                 250                 255

Arg Gln Gln Asn Ser Leu Ile Phe Glu Glu Leu Leu Thr Phe Gly Gly
            260                 265                 270

Ile Asp Ser Lys Ala Ile Ser Ser Leu Ile Ile Lys Lys Ile Ile Glu
        275                 280                 285

Thr Ala Lys Asn Asn Tyr Thr Thr Leu Ile Ser Glu Arg Leu Asn Thr
    290                 295                 300

Val Thr Val Glu Asn Asp Leu Leu Lys Tyr Ile Lys Asn Lys Ile Pro
305                 310                 315                 320

Val Gln Gly Arg Leu Gly Asn Phe Lys Leu Asp Thr Ala Glu Phe Glu
                325                 330                 335

Lys Lys Leu Asn Thr Ile Leu Phe Val Leu Asn Glu Ser Asn Leu Ala
            340                 345                 350

Gln Arg Phe Ser Ile Leu Val Arg Lys His Tyr Leu Lys Glu Arg Pro
        355                 360                 365

Ile Asp Pro Ile Tyr Val Asn Ile Leu Asp Asp Asn Ser Tyr Ser Thr
    370                 375                 380
```

-continued

```
Leu Glu Gly Phe Asn Ile Ser Ser Gln Gly Ser Asn Asp Phe Gln Gly
385                 390                 395                 400

Gln Leu Leu Glu Ser Ser Tyr Phe Glu Lys Ile Glu Ser Asn Ala Leu
                405                 410                 415

Arg Ala Phe Ile Lys Ile Cys Pro Arg Asn Gly Leu Leu Tyr Asn Ala
                420                 425                 430

Ile Tyr Leu Asn Ser Lys Asn
        435

<210> SEQ ID NO 43
<211> LENGTH: 439
<212> TYPE: PRT
<213> ORGANISM: Artificial Sequence
<220> FEATURE:
<223> OTHER INFORMATION: Synthetic

<400> SEQUENCE: 43

Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
                20                  25                  30

Lys Gly Lys Gly Pro Phe Lys Ala Phe Gln Val Ile Lys Asn Ile Trp
        35                  40                  45

Ile Val Pro Glu Arg Tyr Asn Phe Thr Asn Asn Thr Asn Asp Leu Asn
        50                  55                  60

Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
                85                  90                  95

Lys Gly Leu Glu Arg Ile Lys Ser Lys Pro Glu Gly Glu Lys Leu Leu
                100                 105                 110

Lys Leu Ile Ser Ser Ser Ile Pro Leu Pro Leu Val Ser Asn Gly Ala
        115                 120                 125

Leu Thr Leu Ser Asp Asn Glu Thr Ile Ala Tyr Gln Glu Asn Asn Asn
        130                 135                 140

Ile Val Ser Asn Leu Gln Ala Asn Leu Val Ile Tyr Gly Pro Gly Pro
145                 150                 155                 160

Asp Ile Ala Asn Asn Glu Thr Tyr Gly Leu Tyr Ser Thr Pro Ile Ser
                165                 170                 175

Asn Gly Glu Gly Thr Leu Ser Glu Val Ser Phe Ser Pro Phe Tyr Leu
                180                 185                 190

Lys Pro Phe Asp Glu Ser Tyr Gly Asn Tyr Arg Ser Leu Val Asn Ile
        195                 200                 205

Val Asn Lys Phe Val Lys Arg Glu Phe Ala Pro Asp Pro Ala Ser Thr
        210                 215                 220

Leu Met His Glu Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
                245                 250                 255

Arg Gln Gln Asn Ser Leu Ile Phe Glu Glu Leu Leu Thr Phe Gly Gly
        260                 265                 270

Ile Asp Ser Lys Ala Ile Ser Ser Leu Ile Ile Lys Lys Ile Ile Glu
        275                 280                 285

Thr Ala Lys Asn Asn Tyr Thr Thr Leu Ile Ser Glu Arg Leu Asn Thr
        290                 295                 300
```

```
Val Thr Val Glu Asn Asp Leu Leu Lys Tyr Ile Lys Asn Lys Ile Pro
305             310             315             320

Val Gln Gly Arg Leu Gly Asn Phe Lys Leu Asp Thr Ala Glu Phe Glu
            325             330             335

Lys Lys Leu Asn Thr Ile Leu Phe Val Leu Asn Glu Ser Asn Leu Ala
            340             345             350

Gln Arg Phe Ser Ile Leu Val Arg Lys His Tyr Leu Lys Glu Arg Pro
            355             360             365

Ile Asp Pro Ile Tyr Val Asn Ile Leu Asp Asp Asn Ser Tyr Ser Thr
        370             375             380

Leu Glu Gly Phe Asn Ile Ser Ser Gln Gly Ser Asn Asp Phe Gln Gly
385             390             395             400

Gln Leu Leu Glu Ser Ser Tyr Phe Glu Lys Ile Glu Ser Asn Ala Leu
            405             410             415

Arg Ala Phe Ile Lys Ile Cys Pro Arg Asn Gly Leu Leu Tyr Asn Ala
            420             425             430

Ile Tyr Leu Asn Ser Lys Asn
        435
```

```
<210> SEQ ID NO 44
<211> LENGTH: 15
<212> TYPE: PRT
<213> ORGANISM: Artificial Sequence
<220> FEATURE:
<223> OTHER INFORMATION: Synthetic

<400> SEQUENCE: 44

Gly Leu Val Glu Lys Ile Val Lys Phe Ala Trp Leu Arg Lys Ser
1               5               10              15
```

```
<210> SEQ ID NO 45
<211> LENGTH: 9
<212> TYPE: PRT
<213> ORGANISM: Artificial Sequence
<220> FEATURE:
<223> OTHER INFORMATION: Synthetic

<400> SEQUENCE: 45

Gly Leu Val Glu Lys Ile Val Lys Phe
1               5
```

```
<210> SEQ ID NO 46
<211> LENGTH: 6
<212> TYPE: PRT
<213> ORGANISM: Artificial Sequence
<220> FEATURE:
<223> OTHER INFORMATION: Synthetic

<400> SEQUENCE: 46

Ala Trp Leu Arg Lys Ser
1               5
```

```
<210> SEQ ID NO 47
<211> LENGTH: 7
<212> TYPE: PRT
<213> ORGANISM: Artificial Sequence
<220> FEATURE:
<223> OTHER INFORMATION: Synthetic

<400> SEQUENCE: 47

Val Ala Trp Leu Arg Lys Ser
1               5
```

US 12,655,182 B2

215                                                                              216

-continued

<210> SEQ ID NO 48
<211> LENGTH: 6
<212> TYPE: PRT
<213> ORGANISM: Artificial Sequence
<220> FEATURE:
<223> OTHER INFORMATION: Synthetic

<400> SEQUENCE: 48

Tyr Leu Asn Ser Lys Asn
1               5

<210> SEQ ID NO 49
<211> LENGTH: 18
<212> TYPE: PRT
<213> ORGANISM: Artificial Sequence
<220> FEATURE:
<223> OTHER INFORMATION: Synthetic

<400> SEQUENCE: 49

Thr Ala Thr Gln Lys Thr Asn Asn Gly Asp Phe Gln His Gly Leu Ala
1               5                   10                  15

Arg Pro

<210> SEQ ID NO 50
<211> LENGTH: 20
<212> TYPE: PRT
<213> ORGANISM: Artificial Sequence
<220> FEATURE:
<223> OTHER INFORMATION: Synthetic

<400> SEQUENCE: 50

Ala Phe Thr Ala Thr Gln Lys Ser Asn Asn Gly Asp Phe Gln His Gly
1               5                   10                  15

Leu Ala Gln Pro
            20

<210> SEQ ID NO 51
<211> LENGTH: 60
<212> TYPE: PRT
<213> ORGANISM: Artificial Sequence
<220> FEATURE:
<223> OTHER INFORMATION: Synthetic

<400> SEQUENCE: 51

Lys Gly Leu Asp Lys Val Met Glu Thr Gln Ala Gln Val Asp Glu Leu
1               5                   10                  15

Lys Gly Ile Met Val Arg Asn Ile Asp Leu Val Ala Gln Arg Gly Glu
            20                  25                  30

Arg Leu Glu Leu Leu Ile Asp Lys Thr Glu Asn Leu Val Asp Ser Ser
        35                  40                  45

Val Thr Phe Lys Thr Thr Ser Arg Asn Leu Ala Arg
        50                  55                  60

<210> SEQ ID NO 52
<211> LENGTH: 29
<212> TYPE: PRT
<213> ORGANISM: Artificial Sequence
<220> FEATURE:
<223> OTHER INFORMATION: Synthetic

<400> SEQUENCE: 52

Gly Ser Gly Gly Gly Ala Ser Gly Gly Ala Gly Glu Asn Leu Tyr Phe
1               5                   10                  15

```
Gln Ser Ala Gly Gly Ser Ala Gly Ser Gly Ala Gly Gly
        20                  25

<210> SEQ ID NO 53
<211> LENGTH: 60
<212> TYPE: PRT
<213> ORGANISM: Artificial Sequence
<220> FEATURE:
<223> OTHER INFORMATION: Synthetic

<400> SEQUENCE: 53

Thr Ser Asn Arg Arg Leu Gln Gln Thr Gln Ala Gln Val Asp Glu Val
1               5                   10                  15

Val Asp Ile Met Arg Val Asn Val Asp Lys Val Leu Glu Arg Asp Gln
            20                  25                  30

Lys Leu Ser Glu Leu Asp Asp Arg Ala Asp Ala Leu Gln Ala Gly Ala
        35                  40                  45

Ser Gln Phe Glu Thr Ser Ala Ala Lys Leu Lys Arg
    50                  55                  60

<210> SEQ ID NO 54
<211> LENGTH: 60
<212> TYPE: PRT
<213> ORGANISM: Artificial Sequence
<220> FEATURE:
<223> OTHER INFORMATION: Synthetic

<400> SEQUENCE: 54

Thr Ser Asn Arg Arg Leu Gln Gln Thr Gln Ala Gln Val Glu Glu Val
1               5                   10                  15

Val Asp Ile Ile Arg Val Asn Val Asp Lys Val Leu Glu Arg Gly Gln
            20                  25                  30

Lys Leu Ser Glu Leu Asp Asp Arg Ala Asp Ala Leu Gln Ala Gly Ala
        35                  40                  45

Ser Gln Phe Glu Ser Ser Ala Ala Lys Leu Lys Arg
    50                  55                  60

<210> SEQ ID NO 55
<211> LENGTH: 60
<212> TYPE: PRT
<213> ORGANISM: Artificial Sequence
<220> FEATURE:
<223> OTHER INFORMATION: Synthetic

<400> SEQUENCE: 55

Thr Ser Asn Arg Arg Leu Gln Gln Thr Gln Ala Gln Val Glu Glu Val
1               5                   10                  15

Val Asp Ile Ile Arg Val Asn Val Asp Lys Val Ala Glu Arg Gly Gln
            20                  25                  30

Lys Leu Ser Glu Leu Asp Asp Arg Ala Asp Ala Leu Gln Ala Gly Ala
        35                  40                  45

Ser Gln Phe Glu Ser Ser Ala Ala Lys Leu Lys Arg
    50                  55                  60

<210> SEQ ID NO 56
<211> LENGTH: 60
<212> TYPE: PRT
<213> ORGANISM: Artificial Sequence
<220> FEATURE:
<223> OTHER INFORMATION: Synthetic

<400> SEQUENCE: 56
```

-continued

```
Thr Ser Asn Arg Arg Leu Gln Gln Thr Gln Ala Gln Val Glu Glu Val
1               5                   10                  15

Val Asp Ile Ile Arg Val Asn Val Asp Lys Val Ala Glu Arg Gly Glu
            20                  25                  30

Lys Leu Ser Glu Leu Asp Asp Arg Ala Asp Ala Leu Gln Ala Gly Ala
        35                  40                  45

Ser Gln Phe Glu Ser Ser Ala Ala Lys Leu Lys Arg
    50                  55                  60

<210> SEQ ID NO 57
<211> LENGTH: 60
<212> TYPE: PRT
<213> ORGANISM: Artificial Sequence
<220> FEATURE:
<223> OTHER INFORMATION: Synthetic

<400> SEQUENCE: 57

Lys Gly Leu Asp Lys Val Gln Gln Thr Gln Ala Gln Val Glu Glu Val
1               5                   10                  15

Val Asp Ile Ile Arg Val Asn Val Asp Lys Val Ala Glu Arg Gly Glu
            20                  25                  30

Lys Leu Ser Glu Leu Asp Asp Arg Thr Glu Asn Leu Val Asp Ser Ser
        35                  40                  45

Val Thr Phe Lys Thr Thr Ser Arg Asn Leu Ala Arg
    50                  55                  60

<210> SEQ ID NO 58
<211> LENGTH: 60
<212> TYPE: PRT
<213> ORGANISM: Artificial Sequence
<220> FEATURE:
<223> OTHER INFORMATION: Synthetic

<400> SEQUENCE: 58

Lys Gly Leu Asp Lys Val Met Glu Thr Gln Ala Gln Val Asp Glu Leu
1               5                   10                  15

Lys Gly Ile Met Val Arg Asn Ile Asp Leu Val Ala Gln Arg Gly Glu
            20                  25                  30

Arg Leu Glu Leu Leu Ile Asp Lys Thr Glu Asn Leu Val Asp Ser Ser
        35                  40                  45

Val Thr Phe Lys Thr Thr Ser Arg Asn Leu Ala Arg
    50                  55                  60

<210> SEQ ID NO 59
<211> LENGTH: 60
<212> TYPE: PRT
<213> ORGANISM: Artificial Sequence
<220> FEATURE:
<223> OTHER INFORMATION: Synthetic

<400> SEQUENCE: 59

Thr Ser Asn Arg Arg Leu Gln Gln Thr Gln Ala Gln Val Glu Glu Val
1               5                   10                  15

Val Asp Ile Ile Arg Val Asn Val Asp Lys Val Leu Glu Arg Asp Gln
            20                  25                  30

Lys Leu Ser Glu Leu Asp Asp Arg Ala Asp Ala Leu Gln Ala Gly Ala
        35                  40                  45

Ser Gln Phe Glu Ser Ser Ala Ala Lys Leu Lys Arg
    50                  55                  60
```

```
<210> SEQ ID NO 60
<211> LENGTH: 60
<212> TYPE: PRT
<213> ORGANISM: Artificial Sequence
<220> FEATURE:
<223> OTHER INFORMATION: Synthetic

<400> SEQUENCE: 60

Gly Ser Asn Arg Arg Leu Gln Gln Thr Gln Asn Gln Val Asp Glu Val
1               5                   10                  15

Val Asp Ile Met Arg Val Asn Val Asp Lys Val Leu Glu Arg Asp Gln
            20                  25                  30

Lys Leu Ser Glu Leu Asp Asp Arg Ala Asp Ala Leu Gln Ala Gly Ala
        35                  40                  45

Ser Gln Phe Glu Thr Ser Ala Ala Lys Leu Lys Arg
    50                  55                  60

<210> SEQ ID NO 61
<211> LENGTH: 52
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (1)..(2)
<223> OTHER INFORMATION: Xaa can be any amino acid
<220> FEATURE:
<221> NAME/KEY: SITE
<222> LOCATION: (12)..(12)
<223> OTHER INFORMATION: Xaa can be any amino acid
<220> FEATURE:
<221> NAME/KEY: SITE
<222> LOCATION: (15)..(16)
<223> OTHER INFORMATION: Xaa can be any amino acid
<220> FEATURE:
<221> NAME/KEY: SITE
<222> LOCATION: (20)..(20)
<223> OTHER INFORMATION: Xaa can be any amino acid
<220> FEATURE:
<221> NAME/KEY: SITE
<222> LOCATION: (23)..(23)
<223> OTHER INFORMATION: Xaa can be any amino acid
<220> FEATURE:
<221> NAME/KEY: SITE
<222> LOCATION: (27)..(27)
<223> OTHER INFORMATION: Xaa can be any amino acid
<220> FEATURE:
<221> NAME/KEY: SITE
<222> LOCATION: (30)..(30)
<223> OTHER INFORMATION: Xaa can be any amino acid
<220> FEATURE:
<221> NAME/KEY: SITE
<222> LOCATION: (32)..(32)
<223> OTHER INFORMATION: Xaa can be any amino acid
<220> FEATURE:
<221> NAME/KEY: SITE
<222> LOCATION: (37)..(37)
<223> OTHER INFORMATION: Xaa can be any amino acid
<220> FEATURE:
<221> NAME/KEY: SITE
<222> LOCATION: (39)..(39)
<223> OTHER INFORMATION: Xaa can be any amino acid
<220> FEATURE:
<221> NAME/KEY: SITE
<222> LOCATION: (41)..(41)
<223> OTHER INFORMATION: Xaa can be any amino acid
<220> FEATURE:
<221> NAME/KEY: SITE
<222> LOCATION: (43)..(44)
<223> OTHER INFORMATION: Xaa can be any amino acid
<220> FEATURE:
<221> NAME/KEY: SITE
<222> LOCATION: (50)..(50)
```

<223> OTHER INFORMATION: Xaa can be any amino acid

<400> SEQUENCE: 61

```
Xaa Xaa Thr Gln Ala Gln Val Glu Glu Val Lys Xaa Ile Met Xaa Xaa
1               5                   10                  15

Asn Val Asp Xaa Val Leu Xaa Arg Gly Glu Xaa Leu Glu Xaa Leu Xaa
            20                  25                  30

Asp Lys Thr Glu Xaa Leu Xaa Ala Xaa Ser Xaa Xaa Phe Lys Thr Thr
        35                  40                  45

Ser Xaa Lys Leu
    50
```

<210> SEQ ID NO 62
<211> LENGTH: 52
<212> TYPE: PRT
<213> ORGANISM: Artificial Sequence
<220> FEATURE:
<223> OTHER INFORMATION: Synthetic

<400> SEQUENCE: 62

```
Gln Gln Thr Gln Ala Gln Val Glu Glu Val Val Asp Ile Ile Arg Val
1               5                   10                  15

Asn Val Asp Lys Val Leu Glu Arg Asp Gln Lys Leu Ser Glu Leu Asp
            20                  25                  30

Asp Arg Ala Asp Ala Leu Gln Ala Gly Ala Ser Gln Phe Glu Ser Ser
        35                  40                  45

Ala Ala Lys Leu
    50
```

<210> SEQ ID NO 63
<211> LENGTH: 52
<212> TYPE: PRT
<213> ORGANISM: Artificial Sequence
<220> FEATURE:
<223> OTHER INFORMATION: Synthetic

<400> SEQUENCE: 63

```
Met Glu Thr Gln Ala Gln Val Asp Glu Leu Lys Gly Ile Met Val Arg
1               5                   10                  15

Asn Ile Asp Leu Val Ala Gln Arg Gly Glu Arg Leu Glu Leu Leu Ile
            20                  25                  30

Asp Lys Thr Glu Asn Leu Val Asp Ser Ser Val Thr Phe Lys Thr Thr
        35                  40                  45

Ser Arg Asn Leu
    50
```

<210> SEQ ID NO 64
<211> LENGTH: 52
<212> TYPE: PRT
<213> ORGANISM: Artificial Sequence
<220> FEATURE:
<223> OTHER INFORMATION: Synthetic

<400> SEQUENCE: 64

```
Arg Asn Leu Gln Ser Glu Val Glu Gly Val Lys Asn Ile Met Thr Gln
1               5                   10                  15

Asn Val Glu Arg Ile Leu Ala Arg Gly Glu Asn Leu Glu His Leu Arg
            20                  25                  30

Asn Lys Thr Glu Asp Leu Glu Ala Thr Ser Glu His Phe Lys Thr Thr
        35                  40                  45
```

```
Ser Gln Lys Val
    50

<210> SEQ ID NO 65
<211> LENGTH: 60
<212> TYPE: PRT
<213> ORGANISM: Artificial Sequence
<220> FEATURE:
<223> OTHER INFORMATION: Synthetic

<400> SEQUENCE: 65

Gly Gly Asn Asp Arg Val Arg Asn Leu Gln Ser Glu Val Glu Gly Val
1               5                   10                  15

Lys Asn Ile Met Thr Gln Asn Val Glu Arg Ile Leu Ala Arg Gly Glu
            20                  25                  30

Asn Leu Glu His Leu Arg Asn Lys Thr Glu Asp Leu Glu Ala Thr Ser
        35                  40                  45

Glu His Phe Lys Thr Thr Ser Gln Lys Val Ala Arg
    50                  55                  60

<210> SEQ ID NO 66
<211> LENGTH: 57
<212> TYPE: PRT
<213> ORGANISM: Artificial Sequence
<220> FEATURE:
<223> OTHER INFORMATION: Synthetic

<400> SEQUENCE: 66

Arg Leu Gln Gln Thr Gln Ala Gln Val Glu Glu Val Val Asp Ile Ile
1               5                   10                  15

Arg Val Asn Val Asp Lys Val Leu Glu Arg Asp Gln Lys Leu Ser Glu
            20                  25                  30

Leu Asp Asp Arg Ala Asp Ala Leu Gln Ala Gly Ala Ser Gln Phe Glu
        35                  40                  45

Ser Ser Ala Ala Lys Leu Lys Arg Lys
    50                  55

<210> SEQ ID NO 67
<211> LENGTH: 57
<212> TYPE: PRT
<213> ORGANISM: Artificial Sequence
<220> FEATURE:
<223> OTHER INFORMATION: Synthetic

<400> SEQUENCE: 67

Lys Val Met Glu Thr Gln Ala Gln Val Asp Glu Leu Lys Gly Ile Met
1               5                   10                  15

Val Arg Asn Ile Asp Leu Val Ala Gln Arg Gly Glu Arg Leu Glu Leu
            20                  25                  30

Leu Ile Asp Lys Thr Glu Asn Leu Val Asp Ser Ser Val Thr Phe Lys
        35                  40                  45

Thr Thr Ser Arg Asn Leu Ala Arg Ala
    50                  55

<210> SEQ ID NO 68
<211> LENGTH: 59
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (1)..(1)
```

<223> OTHER INFORMATION: Xaa can be any amino acid
<220> FEATURE:
<221> NAME/KEY: SITE
<222> LOCATION: (8)..(8)
<223> OTHER INFORMATION: Xaa can be any amino acid
<220> FEATURE:
<221> NAME/KEY: SITE
<222> LOCATION: (10)..(12)
<223> OTHER INFORMATION: Xaa can be any amino acid
<220> FEATURE:
<221> NAME/KEY: SITE
<222> LOCATION: (14)..(16)
<223> OTHER INFORMATION: Xaa can be any amino acid
<220> FEATURE:
<221> NAME/KEY: SITE
<222> LOCATION: (18)..(18)
<223> OTHER INFORMATION: Xaa can be any amino acid
<220> FEATURE:
<221> NAME/KEY: SITE
<222> LOCATION: (20)..(20)
<223> OTHER INFORMATION: Xaa can be any amino acid
<220> FEATURE:
<221> NAME/KEY: SITE
<222> LOCATION: (22)..(22)
<223> OTHER INFORMATION: Xaa can be any amino acid
<220> FEATURE:
<221> NAME/KEY: SITE
<222> LOCATION: (25)..(25)
<223> OTHER INFORMATION: Xaa can be any amino acid
<220> FEATURE:
<221> NAME/KEY: SITE
<222> LOCATION: (27)..(27)
<223> OTHER INFORMATION: Xaa can be any amino acid
<220> FEATURE:
<221> NAME/KEY: SITE
<222> LOCATION: (29)..(30)
<223> OTHER INFORMATION: Xaa can be any amino acid
<220> FEATURE:
<221> NAME/KEY: SITE
<222> LOCATION: (32)..(32)
<223> OTHER INFORMATION: Xaa can be any amino acid
<220> FEATURE:
<221> NAME/KEY: SITE
<222> LOCATION: (34)..(37)
<223> OTHER INFORMATION: Xaa can be any amino acid
<220> FEATURE:
<221> NAME/KEY: SITE
<222> LOCATION: (39)..(44)
<223> OTHER INFORMATION: Xaa can be any amino acid
<220> FEATURE:
<221> NAME/KEY: SITE
<222> LOCATION: (46)..(51)
<223> OTHER INFORMATION: Xaa can be any amino acid
<220> FEATURE:
<221> NAME/KEY: SITE
<222> LOCATION: (53)..(53)
<223> OTHER INFORMATION: Xaa can be any amino acid
<220> FEATURE:
<221> NAME/KEY: SITE
<222> LOCATION: (55)..(58)
<223> OTHER INFORMATION: Xaa can be any amino acid

<400> SEQUENCE: 68

Xaa Glx Thr Gln Ala Gln Val Xaa Glu Xaa Xaa Xaa Ile Xaa Xaa Xaa
1               5                   10                  15

Asn Xaa Asp Xaa Val Xaa Glx Arg Xaa Glx Xaa Leu Xaa Xaa Leu Xaa
            20                  25                  30

Asp Xaa Xaa Xaa Xaa Leu Xaa Xaa Xaa Xaa Xaa Xaa Phe Xaa Xaa Xaa
        35                  40                  45

Xaa Xaa Xaa Leu Xaa Arg Xaa Xaa Xaa Xaa Lys
    50                  55

<210> SEQ ID NO 69
<211> LENGTH: 59

<212> TYPE: PRT
<213> ORGANISM: Artificial Sequence
<220> FEATURE:
<223> OTHER INFORMATION: Synthetic

<400> SEQUENCE: 69

Gln Gln Thr Gln Ala Gln Val Glu Glu Val Val Asp Ile Ile Arg Val
1               5                   10                  15

Asn Val Asp Lys Val Leu Glu Arg Asp Gln Lys Leu Ser Glu Leu Asp
            20                  25                  30

Asp Arg Ala Asp Ala Leu Gln Ala Gly Ala Ser Gln Phe Glu Ser Ser
        35                  40                  45

Ala Ala Lys Leu Lys Arg Lys Tyr Trp Trp Lys
    50                  55

<210> SEQ ID NO 70
<211> LENGTH: 59
<212> TYPE: PRT
<213> ORGANISM: Artificial Sequence
<220> FEATURE:
<223> OTHER INFORMATION: Synthetic

<400> SEQUENCE: 70

Met Glu Thr Gln Ala Gln Val Asp Glu Leu Lys Gly Ile Met Val Arg
1               5                   10                  15

Asn Ile Asp Leu Val Ala Gln Arg Gly Glu Arg Leu Glu Leu Leu Ile
            20                  25                  30

Asp Lys Thr Glu Asn Leu Val Asp Ser Ser Val Thr Phe Lys Thr Thr
        35                  40                  45

Ser Arg Asn Leu Ala Arg Ala Met Cys Met Lys
    50                  55

<210> SEQ ID NO 71
<211> LENGTH: 62
<212> TYPE: PRT
<213> ORGANISM: Artificial Sequence
<220> FEATURE:
<223> OTHER INFORMATION: Synthetic

<400> SEQUENCE: 71

Thr Ser Asn Arg Arg Leu Gln Gln Thr Gln Ala Gln Val Asp Glu Val
1               5                   10                  15

Val Asp Ile Met Arg Val Asn Val Asp Lys Val Leu Glu Arg Asp Gln
            20                  25                  30

Lys Leu Ser Glu Leu Asp Asp Arg Ala Asp Ala Leu Gln Ala Gly Ala
        35                  40                  45

Ser Gln Phe Glu Thr Ser Ala Ala Lys Leu Lys Arg Lys Tyr
    50                  55                  60

<210> SEQ ID NO 72
<211> LENGTH: 65
<212> TYPE: PRT
<213> ORGANISM: Artificial Sequence
<220> FEATURE:
<223> OTHER INFORMATION: Synthetic

<400> SEQUENCE: 72

Ser Glu Asn Lys Gly Leu Asp Lys Val Met Glu Thr Gln Ala Gln Val
1               5                   10                  15

Asp Glu Leu Lys Gly Ile Met Val Arg Asn Ile Asp Leu Val Ala Gln
            20                  25                  30

```
Arg Gly Glu Arg Leu Glu Leu Leu Ile Asp Lys Thr Glu Asn Leu Val
        35                  40                  45

Asp Ser Ser Val Thr Phe Lys Thr Thr Ser Arg Asn Leu Ala Arg Ala
    50                  55                  60

Met
65

<210> SEQ ID NO 73
<211> LENGTH: 57
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (1)..(3)
<223> OTHER INFORMATION: Xaa can be any amino acid
<220> FEATURE:
<221> NAME/KEY: SITE
<222> LOCATION: (10)..(10)
<223> OTHER INFORMATION: Xaa can be any amino acid
<220> FEATURE:
<221> NAME/KEY: SITE
<222> LOCATION: (12)..(14)
<223> OTHER INFORMATION: Xaa can be any amino acid
<220> FEATURE:
<221> NAME/KEY: SITE
<222> LOCATION: (16)..(18)
<223> OTHER INFORMATION: Xaa can be any amino acid
<220> FEATURE:
<221> NAME/KEY: SITE
<222> LOCATION: (20)..(20)
<223> OTHER INFORMATION: Xaa can be any amino acid
<220> FEATURE:
<221> NAME/KEY: SITE
<222> LOCATION: (22)..(22)
<223> OTHER INFORMATION: Xaa can be any amino acid
<220> FEATURE:
<221> NAME/KEY: SITE
<222> LOCATION: (24)..(24)
<223> OTHER INFORMATION: Xaa can be any amino acid
<220> FEATURE:
<221> NAME/KEY: SITE
<222> LOCATION: (27)..(27)
<223> OTHER INFORMATION: Xaa can be any amino acid
<220> FEATURE:
<221> NAME/KEY: SITE
<222> LOCATION: (29)..(29)
<223> OTHER INFORMATION: Xaa can be any amino acid
<220> FEATURE:
<221> NAME/KEY: SITE
<222> LOCATION: (31)..(32)
<223> OTHER INFORMATION: Xaa can be any amino acid
<220> FEATURE:
<221> NAME/KEY: SITE
<222> LOCATION: (34)..(34)
<223> OTHER INFORMATION: Xaa can be any amino acid
<220> FEATURE:
<221> NAME/KEY: SITE
<222> LOCATION: (36)..(39)
<223> OTHER INFORMATION: Xaa can be any amino acid
<220> FEATURE:
<221> NAME/KEY: SITE
<222> LOCATION: (41)..(46)
<223> OTHER INFORMATION: Xaa can be any amino acid
<220> FEATURE:
<221> NAME/KEY: SITE
<222> LOCATION: (48)..(53)
<223> OTHER INFORMATION: Xaa can be any amino acid
<220> FEATURE:
<221> NAME/KEY: SITE
<222> LOCATION: (55)..(55)
<223> OTHER INFORMATION: Xaa can be any amino acid
<220> FEATURE:
<221> NAME/KEY: SITE
<222> LOCATION: (57)..(57)
```

<223> OTHER INFORMATION: Xaa can be any amino acid

<400> SEQUENCE: 73

Xaa Xaa Xaa Glx Thr Gln Ala Gln Val Xaa Glu Xaa Xaa Xaa Ile Xaa
1               5                   10                  15

Xaa Xaa Asn Xaa Asp Xaa Val Xaa Glx Arg Xaa Glx Xaa Leu Xaa Xaa
            20              25                  30

Leu Xaa Asp Xaa Xaa Xaa Xaa Leu Xaa Xaa Xaa Xaa Xaa Phe Xaa
        35                  40                  45

Xaa Xaa Xaa Xaa Xaa Leu Xaa Arg Xaa
    50                  55

<210> SEQ ID NO 74
<211> LENGTH: 61
<212> TYPE: PRT
<213> ORGANISM: Artificial Sequence
<220> FEATURE:
<223> OTHER INFORMATION: Synthetic

<400> SEQUENCE: 74

Thr Ser Asn Arg Arg Leu Gln Gln Thr Gln Ala Gln Val Glu Glu Val
1               5                   10                  15

Val Asp Ile Ile Arg Val Asn Val Asp Lys Val Leu Glu Arg Asp Gln
            20              25                  30

Lys Leu Ser Glu Leu Asp Asp Arg Ala Asp Ala Leu Gln Ala Gly Ala
        35                  40                  45

Ser Gln Phe Glu Ser Ser Ala Ala Lys Leu Lys Arg Lys
    50                  55                  60

<210> SEQ ID NO 75
<211> LENGTH: 61
<212> TYPE: PRT
<213> ORGANISM: Artificial Sequence
<220> FEATURE:
<223> OTHER INFORMATION: Synthetic

<400> SEQUENCE: 75

Gly Gly Asn Asp Arg Val Arg Asn Leu Gln Ser Glu Val Glu Gly Val
1               5                   10                  15

Lys Asn Ile Met Thr Gln Asn Val Glu Arg Ile Leu Ala Arg Gly Glu
            20              25                  30

Asn Leu Glu His Leu Arg Asn Lys Thr Glu Asp Leu Glu Ala Thr Ser
        35                  40                  45

Glu His Phe Lys Thr Thr Ser Gln Lys Val Ala Arg Lys
    50                  55                  60

<210> SEQ ID NO 76
<211> LENGTH: 35
<212> TYPE: PRT
<213> ORGANISM: Artificial Sequence
<220> FEATURE:
<223> OTHER INFORMATION: Synthetic

<400> SEQUENCE: 76

Thr Gln Ala Gln Val Asp Glu Val Val Asp Ile Met Arg Val Asn Val
1               5                   10                  15

Asp Lys Val Leu Glu Arg Asp Gln Lys Leu Ser Glu Leu Asp Asp Arg
            20              25                  30

Ala Asp Ala
        35

<210> SEQ ID NO 77
<211> LENGTH: 35
<212> TYPE: PRT
<213> ORGANISM: Artificial Sequence
<220> FEATURE:
<223> OTHER INFORMATION: Synthetic

<400> SEQUENCE: 77

Thr Gln Ala Gln Val Asp Glu Leu Lys Gly Ile Met Val Arg Asn Ile
1               5                   10                  15

Asp Leu Val Ala Gln Arg Gly Glu Arg Leu Glu Leu Leu Ile Asp Lys
            20                  25                  30

Thr Glu Asn
        35

<210> SEQ ID NO 78
<211> LENGTH: 35
<212> TYPE: PRT
<213> ORGANISM: Artificial Sequence
<220> FEATURE:
<223> OTHER INFORMATION: Synthetic

<400> SEQUENCE: 78

Ile Met Val Arg Asn Ile Asp Leu Val Ala Gln Arg Gly Glu Arg Leu
1               5                   10                  15

Glu Leu Leu Ile Asp Lys Thr Glu Asn Leu Val Asp Ser Ser Val Thr
            20                  25                  30

Phe Lys Thr
        35

<210> SEQ ID NO 79
<211> LENGTH: 61
<212> TYPE: PRT
<213> ORGANISM: Artificial Sequence
<220> FEATURE:
<223> OTHER INFORMATION: Synthetic

<400> SEQUENCE: 79

Thr Ser Asn Arg Arg Leu Gln Gln Thr Gln Ala Gln Val Glu Glu Val
1               5                   10                  15

Val Asp Ile Ile Arg Val Asn Val Asp Lys Val Leu Glu Arg Gly Gln
            20                  25                  30

Lys Leu Ser Glu Leu Asp Asp Arg Ala Asp Ala Leu Gln Ala Gly Ala
        35                  40                  45

Ser Gln Phe Glu Ser Ser Ala Ala Lys Leu Lys Arg Lys
    50                  55                  60

<210> SEQ ID NO 80
<211> LENGTH: 61
<212> TYPE: PRT
<213> ORGANISM: Artificial Sequence
<220> FEATURE:
<223> OTHER INFORMATION: Synthetic

<400> SEQUENCE: 80

Thr Ser Asn Arg Arg Leu Gln Gln Thr Gln Ala Gln Val Glu Glu Val
1               5                   10                  15

Val Asp Ile Ile Arg Val Asn Val Asp Lys Val Ala Glu Arg Gly Gln
            20                  25                  30

Lys Leu Ser Glu Leu Asp Asp Arg Ala Asp Ala Leu Gln Ala Gly Ala
        35                  40                  45

Ser Gln Phe Glu Ser Ser Ala Ala Lys Leu Lys Arg Lys
    50                  55                  60

<210> SEQ ID NO 81
<211> LENGTH: 61
<212> TYPE: PRT
<213> ORGANISM: Artificial Sequence
<220> FEATURE:
<223> OTHER INFORMATION: Synthetic

<400> SEQUENCE: 81

Thr Ser Asn Arg Arg Leu Gln Gln Thr Gln Ala Gln Val Glu Glu Val
1               5                   10                  15

Val Asp Ile Ile Arg Val Asn Val Asp Lys Val Ala Glu Arg Gly Glu
                20                  25                  30

Lys Leu Ser Glu Leu Asp Asp Arg Ala Asp Ala Leu Gln Ala Gly Ala
        35                  40                  45

Ser Gln Phe Glu Ser Ser Ala Ala Lys Leu Lys Arg Lys
    50                  55                  60

<210> SEQ ID NO 82
<211> LENGTH: 61
<212> TYPE: PRT
<213> ORGANISM: Artificial Sequence
<220> FEATURE:
<223> OTHER INFORMATION: Synthetic

<400> SEQUENCE: 82

Thr Ser Asn Arg Arg Leu Gln Gln Thr Gln Ala Gln Val Glu Glu Val
1               5                   10                  15

Val Asp Ile Ile Arg Val Asn Val Asp Lys Val Ala Glu Arg Gly Glu
                20                  25                  30

Arg Leu Ser Glu Leu Asp Asp Arg Ala Asp Ala Leu Gln Ala Gly Ala
        35                  40                  45

Ser Gln Phe Glu Ser Ser Ala Ala Lys Leu Lys Arg Lys
    50                  55                  60

<210> SEQ ID NO 83
<211> LENGTH: 61
<212> TYPE: PRT
<213> ORGANISM: Artificial Sequence
<220> FEATURE:
<223> OTHER INFORMATION: Synthetic

<400> SEQUENCE: 83

Lys Gly Leu Asp Lys Val Gln Gln Thr Gln Ala Gln Val Glu Glu Val
1               5                   10                  15

Lys Asp Ile Ile Arg Val Asn Val Asp Leu Val Ala Glu Arg Gly Glu
                20                  25                  30

Arg Leu Ser Glu Leu Ile Asp Arg Thr Glu Asn Leu Val Asp Ser Ser
        35                  40                  45

Val Thr Phe Lys Thr Thr Ser Arg Asn Leu Ala Arg Ala
    50                  55                  60

<210> SEQ ID NO 84
<211> LENGTH: 61
<212> TYPE: PRT
<213> ORGANISM: Artificial Sequence
<220> FEATURE:
<223> OTHER INFORMATION: Synthetic

<400> SEQUENCE: 84

-continued

```
Lys Gly Leu Asp Lys Val Met Glu Thr Gln Ala Gln Val Asp Glu Leu
1               5                   10                  15

Lys Gly Ile Met Val Arg Asn Ile Asp Leu Val Ala Gln Arg Gly Glu
            20                  25                  30

Arg Leu Glu Leu Leu Ile Asp Lys Thr Glu Asn Leu Val Asp Ser Ser
        35                  40                  45

Val Thr Phe Lys Thr Thr Ser Arg Asn Leu Ala Arg Ala
    50                  55                  60

<210> SEQ ID NO 85
<211> LENGTH: 17
<212> TYPE: PRT
<213> ORGANISM: Artificial Sequence
<220> FEATURE:
<223> OTHER INFORMATION: Synthetic

<400> SEQUENCE: 85

Leu Glu Arg Gly Glu Lys Leu Asp Asp Leu Val Ser Lys Ser Glu Val
1               5                   10                  15

Leu

<210> SEQ ID NO 86
<211> LENGTH: 17
<212> TYPE: PRT
<213> ORGANISM: Artificial Sequence
<220> FEATURE:
<223> OTHER INFORMATION: Synthetic

<400> SEQUENCE: 86

Leu Glu Arg Asp Gln Lys Leu Ser Glu Leu Asp Asp Arg Ala Asp Ala
1               5                   10                  15

Leu

<210> SEQ ID NO 87
<211> LENGTH: 17
<212> TYPE: PRT
<213> ORGANISM: Artificial Sequence
<220> FEATURE:
<223> OTHER INFORMATION: Synthetic

<400> SEQUENCE: 87

Ile Glu Arg Gly Glu Arg Leu Asp Glu Leu Gln Asp Lys Ser Glu Ser
1               5                   10                  15

Leu

<210> SEQ ID NO 88
<211> LENGTH: 17
<212> TYPE: PRT
<213> ORGANISM: Artificial Sequence
<220> FEATURE:
<223> OTHER INFORMATION: Synthetic

<400> SEQUENCE: 88

Leu Glu Arg Gly Val Lys Leu Ala Glu Leu Gln Gln Arg Ser Asp Gln
1               5                   10                  15

Leu

<210> SEQ ID NO 89
<211> LENGTH: 6
<212> TYPE: PRT
<213> ORGANISM: Artificial Sequence
<220> FEATURE:
<223> OTHER INFORMATION: Synthetic
```

-continued

```
<400> SEQUENCE: 89

Tyr Arg Asn Ser Lys Asn
1               5

<210> SEQ ID NO 90
<211> LENGTH: 12
<212> TYPE: PRT
<213> ORGANISM: Artificial Sequence
<220> FEATURE:
<223> OTHER INFORMATION: Synthetic

<400> SEQUENCE: 90

Leu Leu Tyr Asn Ala Ile Tyr Arg Asn Ser Lys Asn
1               5                   10

<210> SEQ ID NO 91
<211> LENGTH: 24
<212> TYPE: PRT
<213> ORGANISM: Artificial Sequence
<220> FEATURE:
<223> OTHER INFORMATION: Synthetic

<400> SEQUENCE: 91

Cys Cys Ile Met Pro Phe Thr Ala Thr Gln Lys Thr Asn Asn Gly Asp
1               5                   10                  15

Phe Gln His Gly Leu Ala Gln Pro
            20

<210> SEQ ID NO 92
<211> LENGTH: 20
<212> TYPE: PRT
<213> ORGANISM: Artificial Sequence
<220> FEATURE:
<223> OTHER INFORMATION: Synthetic

<400> SEQUENCE: 92

Met Gly Asn Glu Ile Asp Thr Gln Asn Arg Gln Ile Asp Arg Ile Met
1               5                   10                  15

Glu Lys Ala Asp
            20

<210> SEQ ID NO 93
<211> LENGTH: 20
<212> TYPE: PRT
<213> ORGANISM: Artificial Sequence
<220> FEATURE:
<223> OTHER INFORMATION: Synthetic

<400> SEQUENCE: 93

Asn Gly Ser Leu Cys Asp Gln Glu Ile Asp Ser Ile Cys Ser Ile Glu
1               5                   10                  15

Arg Ala Asp Asn
            20

<210> SEQ ID NO 94
<211> LENGTH: 20
<212> TYPE: PRT
<213> ORGANISM: Artificial Sequence
<220> FEATURE:
<223> OTHER INFORMATION: Synthetic

<400> SEQUENCE: 94

Met Gly Asn Glu Ile Asp Thr Gln Asn Arg Gln Ile Asp Ser Ile Met
1               5                   10                  15
```

```
Glu Lys Ala Asp
          20

<210> SEQ ID NO 95
<211> LENGTH: 20
<212> TYPE: PRT
<213> ORGANISM: Artificial Sequence
<220> FEATURE:
<223> OTHER INFORMATION: Synthetic

<400> SEQUENCE: 95

Met Gly Asn Glu Ile Asp Thr Gln Asn Arg Gln Ile Cys Ser Ile Met
1               5                  10                  15

Glu Lys Ala Asp
          20

<210> SEQ ID NO 96
<211> LENGTH: 20
<212> TYPE: PRT
<213> ORGANISM: Artificial Sequence
<220> FEATURE:
<223> OTHER INFORMATION: Synthetic

<400> SEQUENCE: 96

Met Gly Ser Leu Cys Asp Thr Gln Asn Arg Gln Ile Cys Ser Ile Met
1               5                  10                  15

Glu Lys Ala Asp
          20

<210> SEQ ID NO 97
<211> LENGTH: 20
<212> TYPE: PRT
<213> ORGANISM: Artificial Sequence
<220> FEATURE:
<223> OTHER INFORMATION: Synthetic

<400> SEQUENCE: 97

Asn Gly Ser Leu Cys Asp Gln Glu Ile Asp Ser Ile Cys Ser Ile Glu
1               5                  10                  15

Glu Lys Ala Asp
          20

<210> SEQ ID NO 98
<211> LENGTH: 20
<212> TYPE: PRT
<213> ORGANISM: Artificial Sequence
<220> FEATURE:
<223> OTHER INFORMATION: Synthetic

<400> SEQUENCE: 98

Met Gly Asn Glu Ile Asp Thr Gln Asn Arg Gln Ile Cys Arg Ile Met
1               5                  10                  15

Glu Lys Ala Asp
          20
```